(12) United States Patent
Marcoux et al.

(10) Patent No.: US 10,435,369 B2
(45) Date of Patent: Oct. 8, 2019

(54) TRICYCLIC SULFONES AS ROR GAMMA MODULATORS

(71) Applicant: BRISTOL-MYERS SQUIBB COMPANY, Princeton, NJ (US)

(72) Inventors: David Marcoux, Pennington, NJ (US); Myra Beaudoin Bertrand, Lambertville, NJ (US); T. G. Murali Dhar, Newtown, PA (US); Michael G. Yang, Narbeth, PA (US); Zili Xiao, East Windsor, NJ (US); Hai-Yun Xiao, Belle Mead, NJ (US); Yeheng Zhu, Stockton, NJ (US); Carolyn A. Weigelt, Langhorne, PA (US); Douglas G. Batt, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/806,554

(22) Filed: Nov. 8, 2017

(65) Prior Publication Data

US 2018/0127368 A1     May 10, 2018

Related U.S. Application Data

(60) Provisional application No. 62/419,607, filed on Nov. 9, 2016.

(51) Int. Cl.
  *C07C 317/12*     (2006.01)
  *C07C 317/44*     (2006.01)
  (Continued)

(52) U.S. Cl.
  CPC ............ *C07D 211/48* (2013.01); *A61P 37/00* (2018.01); *C07C 317/20* (2013.01); *C07C 317/24* (2013.01); *C07C 317/30* (2013.01); *C07C 317/44* (2013.01); *C07D 205/04* (2013.01); *C07D 205/08* (2013.01); *C07D 207/09* (2013.01); *C07D 207/10* (2013.01); *C07D 207/16* (2013.01); *C07D 207/277* (2013.01); *C07D 207/28* (2013.01); *C07D 211/62* (2013.01); *C07D 211/78* (2013.01); *C07D 211/96* (2013.01); *C07D 213/40* (2013.01); *C07D 213/56* (2013.01); *C07D 213/75* (2013.01); *C07D 213/81* (2013.01); *C07D 215/36* (2013.01); *C07D 231/06* (2013.01); *C07D 231/08* (2013.01); *C07D 231/18* (2013.01); *C07D 233/64* (2013.01); *C07D 233/76* (2013.01); *C07D 233/78* (2013.01); *C07D 233/90* (2013.01); *C07D 241/08* (2013.01); *C07D 249/12* (2013.01); *C07D 257/04* (2013.01); *C07D 261/18* (2013.01); *C07D 263/20* (2013.01); *C07D 285/06* (2013.01); *C07D 295/16* (2013.01); *C07D 295/195* (2013.01); *C07D 305/08* (2013.01); *C07D 307/22* (2013.01); *C07D 309/10* (2013.01); *C07D 333/48* (2013.01); *C07D 335/02* (2013.01); *C07D 401/04* (2013.01); *C07D 401/12* (2013.01); *C07D 405/04* (2013.01); *C07D 405/12* (2013.01); *C07D 471/04* (2013.01); *C07D 471/10* (2013.01); *C07F 9/091* (2013.01); *C07B 2200/05* (2013.01); *C07B 2200/07* (2013.01); *C07C 2601/02* (2017.05); *C07C 2601/04* (2017.05);
  (Continued)

(58) Field of Classification Search
  CPC ... C07C 312/12; C07C 317/44; C07C 317/12; A61K 31/10
  USPC ............... 514/708, 709; 568/34, 31, 28, 27
  See application file for complete search history.

(56) References Cited

FOREIGN PATENT DOCUMENTS

WO   WO 2007/084595 A2    7/2007
WO   WO-2007084595 A2 *   7/2007   ........... C07C 317/14
(Continued)

OTHER PUBLICATIONS

Sheridan, Robert, "The Most Common Chemical Replacements in Drug-Like Compounds" J. Chem. Inf. Comp. Sci. (2002), 42: pp. 103-108. (Year: 2002).*

(Continued)

*Primary Examiner* — Matthew P Coughlin
*Assistant Examiner* — Sagar Patel
(74) *Attorney, Agent, or Firm* — Elliott Korsen

(57) ABSTRACT

There are described RORγ modulators of the formula (I),

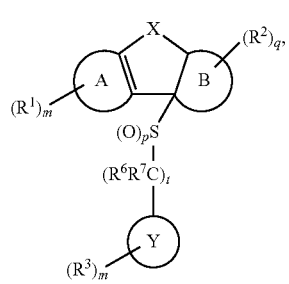

or stereoisomers, tautomers, pharmaceutically acceptable salts, solvates, or prodrugs thereof, wherein all substituents are defined herein. Also provided are pharmaceutical compositions comprising the same. Such compounds and compositions are useful in methods for modulating RORγ activity in a cell and methods for treating a subject suffering from a disease or disorder in which the subject would therapeutically benefit from modulation of RORγ activity, for example, autoimmune and/or inflammatory disorders.

6 Claims, No Drawings

(51) Int. Cl.

| | | |
|---|---|---|
| A61K 31/10 | (2006.01) | |
| C07D 211/48 | (2006.01) | |
| A61P 37/00 | (2006.01) | |
| C07D 205/04 | (2006.01) | |
| C07D 205/08 | (2006.01) | |
| C07D 207/10 | (2006.01) | |
| C07D 207/16 | (2006.01) | |
| C07D 207/277 | (2006.01) | |
| C07D 211/96 | (2006.01) | |
| C07D 213/40 | (2006.01) | |
| C07D 213/75 | (2006.01) | |
| C07D 231/08 | (2006.01) | |
| C07D 241/08 | (2006.01) | |
| C07D 257/04 | (2006.01) | |
| C07D 295/195 | (2006.01) | |
| C07D 307/22 | (2006.01) | |
| C07D 309/10 | (2006.01) | |
| C07D 333/48 | (2006.01) | |
| C07D 335/02 | (2006.01) | |
| C07D 471/04 | (2006.01) | |
| C07D 471/10 | (2006.01) | |
| C07D 213/81 | (2006.01) | |
| C07D 215/36 | (2006.01) | |
| C07D 231/06 | (2006.01) | |
| C07D 231/18 | (2006.01) | |
| C07D 233/64 | (2006.01) | |
| C07D 233/76 | (2006.01) | |
| C07D 233/78 | (2006.01) | |
| C07D 233/90 | (2006.01) | |
| C07D 401/04 | (2006.01) | |
| C07D 401/12 | (2006.01) | |
| C07D 405/04 | (2006.01) | |
| C07C 317/20 | (2006.01) | |
| C07C 317/24 | (2006.01) | |
| C07C 317/30 | (2006.01) | |
| C07D 405/12 | (2006.01) | |
| C07D 249/12 | (2006.01) | |
| C07D 261/18 | (2006.01) | |
| C07D 263/20 | (2006.01) | |
| C07D 207/09 | (2006.01) | |
| C07D 207/28 | (2006.01) | |
| C07D 285/06 | (2006.01) | |
| C07D 211/62 | (2006.01) | |
| C07D 295/16 | (2006.01) | |
| C07D 211/78 | (2006.01) | |
| C07D 213/56 | (2006.01) | |
| C07D 305/08 | (2006.01) | |
| C07F 9/09 | (2006.01) | |

(52) U.S. Cl.
CPC ...... C07C 2601/08 (2017.05); C07C 2601/14 (2017.05); C07C 2602/38 (2017.05); C07C 2602/44 (2017.05); C07C 2602/50 (2017.05); C07C 2603/08 (2017.05); C07C 2603/12 (2017.05); C07C 2603/16 (2017.05); C07C 2603/90 (2017.05)

(56) References Cited

FOREIGN PATENT DOCUMENTS

| WO | WO 2009/008980 A2 | 1/2009 |
|---|---|---|
| WO | WO 2009/011851 A1 | 1/2009 |
| WO | WO 2015/103507 A1 | 7/2015 |
| WO | WO 2015/103508 A1 | 7/2015 |
| WO | WO 2015/103509 A1 | 7/2015 |
| WO | WO 2015-103510 A1 | 7/2015 |
| WO | PCT/US2017/055687 | 10/2017 |
| WO | PCT/US2017/056257 | 10/2017 |

OTHER PUBLICATIONS

Ruo et al., "SAR of tricyclic sulfones as v-secretase inhibitors" Sci. China Chem. (2011), 54 (11), pp. 1688-1701. (Year: 2011).*

Alberti, Guido, et al., "Intramolecular Capture of a Cyclobutylthionium Ion for the Synthesis of New Strained Heterocycles BCD Ring Sequence of Penitrems", Synlett, 2006, No. 14, pp. 2241-2245.

Bernard, Angela M., et al., "Synthesis of New Heterocycles through a Cation-Driven Tandem Ring-Enlargement-Annulation Reaction", Organic Letters, 2002, vol. 4, No. 15, pp. 2565-2567.

Buggle, Katherine, et al., "Decomposition Products of Pyrazolines formed from 3-Alkyithioinden-1-ones and Diazomethane", Journal of the Chemical Society, Perkin Transactions 1, 1975, No. 6, pp. 572-575.

Buggle, Katherine, et al., Ring-expansion of 3-Arylinden-1-ones with Lithium Methylsulphinylmethanide, Journal of the Chemical Society, Perkin Transactions 1, 1983, pp. 2075-2076.

Campaigne, E., et al., "Cyclization of Ylidenemalononitriles. X. Synthesis of Benzazapropellane Derivatives from [alpha]-Cyano-[beta]-chloroalkylcinnamonitriles (1a)", Journal of Hetercyclic Chemistry, 1977, vol. 14, No. 8, pp. 1337-1345.

Kuck, Dietmar, et al., "Synthesis of Tribenzotriquinacene by Stereocontrolled Cyclization of Phenyl-Substituted $C_s$, -Diindans", 4bα, 9, 9aα, 10-Tetrahydroindeno[1,2-a]indenes), Chemische Berichte, 1994, vol. 127, pp. 151-164.

Müller, Paul, et al., "Aromatization of Tetrahydrocyclopropa[a]napthalenes: An alternative Synthesis of 1H-Cyclopropa[a]naphthalene", Helvetica Chimica Acta, 1989, vol. 72, No. 7, pp. 1627-1638.

Ruo, Xu, et al., "SAR of trycyclic sulfones as γ-secretase inhibitors", Science China Chemistry, SP Science China Press, 2011, vol. 54, No. 11, pp. 1688-1701.

U.S. Appl. No. 15/148,209, filed May 6, 2016, Granted U.S. Pat. No. 9,815,859.

U.S. Appl. No. 15/701,818, filed Sep. 12, 2017, Published US20180002358A1.

* cited by examiner

TRICYCLIC SULFONES AS ROR GAMMA MODULATORS

CROSS-REFERENCE TO RELATED APPLICATIONS

This application claims the benefit of U.S. Provisional Application No. 62/419,607 filed Nov. 9, 2016, the disclosure of which is incorporated herein by reference in its entirety.

FIELD OF THE INVENTION

This invention relates to modulators of the retinoid-related orphan receptor RORγ and methods for using said modulators. The compounds described herein can be particularly useful for diagnosing, preventing, or treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis and multiple sclerosis.

BACKGROUND OF THE INVENTION

The retinoid-related orphan receptors, RORα, RORβ, and RORγ, play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the Formula (I),

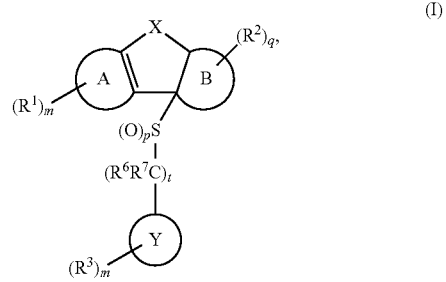

or a stereoisomer or pharmaceutically acceptable salt thereof, wherein

X is —$CR^4R^5$—, —$(CR^4R^5)_2$—, —$OCR^6R^7$—, —$S(O)_p$ $CR^6R^7$—, —$S(O)(NR^g)CR^6R^7$— or —$NR^6CR^6R^7$—;

A is a monocyclic 5- or 6-membered aromatic or heteroaromatic ring;

B is a monocyclic 3-, 4-, 5-, 6- or 7-membered carbocyclic ring;

Y is a 5 or 6-membered aromatic or heteroaromatic ring;

$R^1$ is, independently at each occurrence, selected from hydrogen, CD3, halo, $OCF_3$, CN, $S(O)_p(C_1-C_6)$alkyl, $S(O)$ $(NR^g)(C_1-C_6)$alkyl, —$S(O)_p(C_1-C_6)$alkyl-OH, $S(O)(NR^g)$ $(C_1-C_6)$alkyl-OH, -thioalkoxyalkoxy, $NR^{11}R^{11}$, $C_{1-6}$ alkyl substituted with 0-3 $R^{1a}$, O—$C_{1-6}$ alkyl substituted with 0-3 $R^{1a}$, —$(CR^{1b}R^{1c})_r$-3-14 membered carbocycle substituted with 0-3 $R^{1a}$ and —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^{1a}$;

$R^{11}$ is, independently at each occurrence, hydrogen, =O, halo, $CF_3$, $OCF_3$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, $(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, $(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-3 $R^a$;

$R^{1b}$ and $R^{1c}$ are, independently at each occurrence, hydrogen, halogen or $C_{1-6}$ alkyl;

$R^2$ is, independently at each occurrence, hydrogen, $C_{1-6}$ alkyl substituted with 0-3 $R^{2a}$, =$CR^{2a}R^{2a}$, $C_{2-6}$ alkenyl substituted with 0-3 $R^{2a}$, —$(CR^{2e}R^{2f})_rOR^{2b}$, —$(CR^{2e}R^{2f})_r$ $C(O)R^{2b}$, —$(CR^{2e}R^{2f})_rC(O)OR^{2b}$, —$(CR^{2e}R^{2f})_rOC(O)$ $OR^{2b}$, —$(CR^{2e}R^{2f})_rOC(O)NR^{11}R^{11}$, —$(CR^{2e}R^{2f})_rNR^{2b}C(O)NR^{11}R^{11}$, —$(CR^{2e}R^{2f})_rC(O)NR^{11}R^{11}$, —$(CR^{2e}R^{2f})_rS(O)_pR^c$, —$(CR^{2e}R^{2f})_rS(O)(NR^g)R^c$, —$(CR^{2e}R^{2f})_rS(O)_pNR^{11}R^{11}$, —$(CR^{2e}R^{2f})_rNR^{2b}C(O)R^{2c}$, —$(CR^{2e}R^{2f})_rNR^{2b}C(O)OR^{2c}$, —$(CR^{2e}R^{2f})_r$ $NR^{11}R^{11}$, —$(CR^{2e}R^{2f})_rNR^{2b}$ $S(O)_pR$, —$(CR^{2e}R^{2f})_rNR^{2b}S(O)_pNR^{11}R^{11}$, —$(CR^{2e}R^{2f})_r$-3-10 membered carbocycle substituted with 0-3 $R^{2a}$ or —$(CR^{2e}R^{2f})_r$-4-10 membered heterocycle comprising carbon atoms, and 1-4 heteroatoms selected from N, O, $S(O)_p$ and $S(O)(NR^g)$ substituted with 0-3 $R^{2a}$; or one $R^2$ together with an $R^2$ on an adjacent carbon combine to form a fused ring substituted with 0-3 $R^{2a}$, wherein the fused ring is selected from 3-10 membered carbocycle substituted with 0-3 $R^{2a}$, or 3-7 membered heterocycle comprising carbon atoms and 1-4 heteroatoms selected from N, O, P(O), $S(O)_p$ and $S(O)(NR^g)$, substituted with 0-3 $R^{2a}$;

$R^{2a}$ is, independently at each occurrence, hydrogen, =O, halo, $OCF_3$, CN, $NO_2$, —$(CR^{2e}R^{2f})_r$—$OR^b$, —$(CR^{2e}R^{2f})_r$—$S(O)_pR^b$, —$(CR^{2e}R^{2f})_r$—$S(O)(NR^g)R^b$, —$(CR^{2e}R^{2f})_r$—$C(O)R^b$, —$(CR^{2e}R^{2f})_r$—$C(O)OR^b$, —$(CR^{2e}R^{2f})_r$—$OC(O)R^b$, —$(CR^{2e}R^{2f})_r$—$OC(O)NR^{11}R^{11}$, —$(CR^{2e}R^{2f})_r$—$OC(O)OR^c$, —$(CR^{2e}R^{2f})_r$—$NR^{11}R^{11}$, —$(CR^{2e}R^{2f})_r$—$C(O)NR^{11}R^{11}$, $(CR^{2e}R^{2f})_r$—$NR^bC(O)R^c$, —$(CR^{2e}R^{2f})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{2e}R^{2f})_r$-3-14 membered carbocycle substituted with 0-3 $R^a$, or —$(CR^{2e}R^{2f})_r$-4-7 membered heterocycle comprising carbon atoms, and 1-4 heteroatoms selected from N, O, $S(O)_p$ and $S(O)(NR^g)$, substituted with 0-4 $R^a$;

$R^{2b}$ is, independently at each occurrence, hydrogen, $CF_3$, —$(CR^{2e}R^{2f})_qOR^b$, —$(CR^{2e}R^{2f})_qS(O)_pR^b$, —$(CR^{2e}R^{2f})_qS(O)(NR^g)R^b$, —$(CR^{2e}R^{2f})_r$—$C(O)R^c$, —$(CR^{2e}R^{2f})_r$—$C(O)$ $OR^b$, —$(CR^{2e}R^{2f})_qOC(O)R^b$, —$(CR^{2e}R^{2f})_qNR^{11}R^{11}$, —$(CR^{2e}R^{2f})_r$—$C(O)NR^{11}R^{11}$, —$(CR^{2e}R^{2f})_qNR^bC(O)R^c$, —$(CR^{2e}R^{2f})_qNR^bC(O)OR^c$, —$(CR^{2e}R^{2f})_qNR^bC(O)$ $NR^{11}R^{11}$, —$(CR^{2e}R^{2f})_qS(O)_2NR^{11}R^{11}$, —$(CR^{2e}R^{2f})_qNR^bS$ $(O)_2R^c$, $C_{1-6}$ alkyl substituted with 0-2 $R^a$, $C_{1-6}$ haloalkyl, —$(CR^{2e}R^{2f})_r$-3-14 membered carbocycle substituted with 0-3 $R^a$, or —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^{2e}$ and $R^{2f}$ are, independently at each occurrence, hydrogen, halogen or $C_{1-6}$ alkyl;

$R^3$ is, independently at each occurrence, selected from hydrogen, halo, $N_3$, CN, —$(CR^{1b}R^{1c})_r$—$OR^{3b}$, —$(CR^{1b}R^{1c})_r$—$NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, $S(O)_p$ and $S(O)(NR^g)$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O, $S(O)_p$ and $S(O)(NR^g)$, both optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$ —$OR^b$, —$(CR^{1b}R^{1c})_r$—$S(O)_pR^b$, —$(CR^{1b}R^{1c})_r$—$S(O)$ $(NR^g)R^b$, —$(CR^{1b}R^{1c})_r$—$C(O)R^b$, —$(CR^{1b}R^{1c})_r$—$C(O)$ $OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)$ $R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$;

$R^{3b}$ is, independently at each occurrence, hydrogen, $CF_3$, —$(CR^{1b}R^{1c})_qOR^b$, —$(CR^{1b}R^{1c})_qS(O)_pR^b$, —$(CR^{1b}R^{1c})_qS(O)(NR^g)R^b$, —$(CR^{1b}R^{1c})_r$—$C(O)R^{3d}$, —$(CR^{1b}R^{1c})_r$—$C(O)OR^b$, $(CR^{1b}R^{1c})_qOC(O)R^b$, —$(CR^{1b}R^{1c})_qNR^{11}R^{11}$, —$(CR^{1b}R^{1c})_r$—$C(O)NR^{11}R^{11}$, —$(CR^{1b}R^{1c})_qNR^bC(O)R^{3c}$, —$(CR^{1b}R^{1c})_qNR^bC(O)OR^c$, —$(CR^{1b}R^{1c})_qNR^bC(O)$ $NR^{11}R^{11}$, —$(CR^{1b}R^{1c})_qS(O)_2NR^{11}R^{11}$, —$(CR^{1b}R^{1c})_qNR^bS$ $(O)_2R^c$, $C_{1-6}$ alkyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, halo, C(=O)$C_{1-4}$ alkyl, C(=O)O$C_{1-4}$ alkyl, $C_{1-6}$ alkyl or $C_{1-6}$ haloalkyl, or $R^4$ and $R^5$ taken together are =O, or together with the carbon atom to which they are attached form a 3- to 6-membered spirocarbocyclyl ring or a spiroheterocyclyl ring;

$R^6$ and $R^7$ are independently hydrogen, C(=O)$C_{1-4}$ alkyl, C(=O)O$C_{1-4}$ alkyl, $C_{1-6}$ alkyl or $C_{1-6}$ haloalkyl; or $R^6$ and $R^7$ taken together are =O, or together with the carbon atom to which they are attached form a 3- to 6-membered spirocarbocyclyl ring or a spiroheterocyclyl ring;

$R^{11}$ is, independently at each occurrence, hydrogen, $C_{1-6}$ alkyl substituted with 0-3 $R^f$, $CF_3$, —$(CR^{1b}R^{1c})_r$—$C_{3-10}$ cycloalkyl substituted with 0-3 $R^f$, —$(CR^{1b}R^{1c})_r$-phenyl substituted with 0-3 $R^d$, or —$(CR^{1b}R^{1c})_r$-5-7 membered heterocycle comprising carbon atoms and 1-4 heteroatoms selected from N, O, S(O)$_p$ and S(O)(NR$^g$), substituted with 0-4 R$^d$;

or one R$^{11}$ and a second R$^{11}$, both attached to the same nitrogen atom, combine to form a heterocycle comprising carbon atoms and 1-4 heteroatoms selected from N, O, S(O)$_p$ and S(O)(NR$^g$), substituted with 0-4 R$^d$;

R$^d$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, (CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, (CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —(CR$^{1b}$R$^{1c}$)$_r$—O(CR$^{1b}$R$^{1c}$O)$_r$P(O)(OR$^b$)$_2$, —(CR$^{1b}$R$^{1c}$)$_r$—O(CR$^{1b}$R$^{1c}$O)$_r$S(O)$_2$OR$^b$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C(O)R$^e$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, SO(NR$^g$)R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), SO(NR$^g$)(C$_{1-6}$ alkyl), CO$_2$H, CO$_2$(C$_{1-6}$ alkyl), OH, C$_{3-6}$ cycloalkyl, CF$_3$, O(C$_{1-6}$ alkyl); or an optionally substituted —(CR$^{1b}$R$^{1c}$)$_r$-5-10 membered heterocycle comprising carbon atoms and 1-4 heteroatoms selected from N, O, S(O)$_p$ and S(O)(NR$^g$), phenyl or C$_{3-6}$ cycloalkyl, each group optionally substituted with halo, CN, CF$_3$, C$_{1-6}$ alkyl or O(C$_{1-6}$ alkyl);

R$^g$ is, independently at each occurrence, hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(O) and S(O)$_p$ substituted with 0-4 R$^f$;

m is 0, 1, 2 or 3;
p is, independently at each occurrence, 0, 1, or 2;
q is, independently at each occurrence, 2 or 3;
r is 0, 1, 2, 3, or 4; and
t is 0 or 1.

In a second aspect, the invention comprises compounds of formula Ia

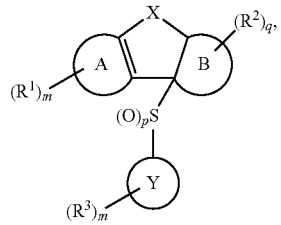

wherein
X is —CR$^4$R$^5$—, —(CR$^4$R$^5$)$_2$, —OCR$^6$R$^7$—, —S(O)$_p$CR$^6$R$^7$—, —S(O)(NR$^g$)CR$^6$R$^7$— or —NR$^6$CR$^6$R$^7$—;

A is a monocyclic 5- or 6-membered aromatic or heteroaromatic ring;

B is a monocyclic 3-, 4-, 5-, 6- or 7-membered carbocyclic ring;

Y is a 5 or 6-membered aromatic or heteroaromatic ring;

R$^1$ is, independently at each occurrence, selected from hydrogen, CD3, halo, OCF$_3$, CN, S(O)$_p$(C$_1$-C$_6$)alkyl, S(O)(NR$^g$)(C$_1$-C$_6$)alkyl, —S(O)$_p$(C$_1$-C$_6$)alkyl-OH, S(O)(NR$^g$)(C$_1$-C$_6$)alkyl-OH, -thioalkoxyalkoxy, NR$^{11}$R$^{11}$, C$_{1-6}$ alkyl substituted with 0-3 R$^{1a}$, O—C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{1b}$ and R$^{1c}$ are, independently at each occurrence, hydrogen, halogen or C$_{1-6}$ alkyl;

R$^2$ is, independently at each occurrence, hydrogen, C$_{1-6}$ alkyl substituted with 0-3 R$^{2a}$ =CR$^{2a}$R$^{2a}$, C$_{2-6}$ alkenyl substituted with 0-3 R$^{2a}$, —(CR$^{2e}$R$^{2f}$)$_r$OR$^{2b}$, —(CR$^{2e}$R$^{2f}$)$_r$C(O)R$^{2b}$, —(CR$^{2e}$R$^{2f}$)$_r$C(O)OR$^{2b}$, —(CR$^{2e}$R$^{2f}$)$_r$OC(O)OR$^{2b}$, —(CR$^{2e}$R$^{2f}$)$_r$OC(O)NR$^{11}$R$^{11}$, —(CR$^{2e}$R$^{2f}$)$_r$NR$^{2b}$C(O)NR$^{11}$R$^{11}$, —(CR$^{2e}$R$^{2f}$)$_r$C(O)NR$^{11}$R$^{11}$, —(CR$^{2e}$R$^{2f}$)$_r$S(O)$_p$R$^c$, —(CR$^{2e}$R$^{2f}$)$_r$S(O)(NR$^g$)R$^c$, —(CR$^{2e}$R$^{2f}$)$_r$S(O)$_p$NR$^{11}$R$^{11}$, —(CR$^{2e}$R$^{2f}$)$_r$NR$^{2b}$C(O)R$^{2c}$, —(CR$^{2e}$R$^{2f}$)$_r$NR$^{2b}$C(O)OR$^{2c}$, —(CR$^{2e}$R$^{2f}$)$_r$NR$^{11}$R$^{11}$, —(CR$^{2e}$R$^{2f}$)$_r$NR$^{2b}$S(O)$_p$R$^c$, —(CR$^{2e}$R$^{2f}$)$_r$NR$^{2b}$S(O)$_p$NR$^{11}$R$^{11}$, —(CR$^{2e}$R$^{2f}$)$_r$-3-10 membered carbocycle substituted with 0-3 R$^{2a}$ or —(CR$^{2e}$R$^{2f}$)$_r$-4-10 membered heterocycle comprising carbon atoms, and 1-4 heteroatoms selected from N, O, S(O)$_p$ and S(O)(NR$^g$) substituted with 0-3 R$^{2a}$; or one R$^2$ together with an R$^2$ on an adjacent carbon combine to form a fused ring substituted with 0-3 R$^{2a}$, wherein the fused ring is selected from 3-10 membered carbocycle substituted with 0-3 R$^{2a}$, or 3-7 membered heterocycle comprising carbon atoms and 1-4 heteroatoms selected from N, O, P(O), S(O)$_p$ and S(O)(NR$^g$), substituted with 0-3 R$^{2a}$;

$R^{2a}$ is, independently at each occurrence, hydrogen, =O, halo, $OCF_3$, CN, $NO_2$, —$(CR^{2e}R^{2f})_r$—$OR^b$, —$(CR^{2e}R^{2f})_r$—$S(O)_pR^b$, —$(CR^{2e}R^{2f})_r$—$S(O)(NR^g)R^b$, —$(CR^{2e}R^{2f})_r$—$C(O)R^b$, —$(CR^{2e}R^{2f})_r$—$C(O)OR^b$, —$(CR^{2e}R^{2f})_r$—$OC(O)R^b$, —$(CR^{2e}R^{2f})_r$—$OC(O)NR^{11}R^{11}$, —$(CR^{2e}R^{2f})_r$—$OC(O)$ $OR^c$, —$(CR^{2e}R^{2f})_r$—$NR^{11}R^{11}$, —$(CR^{2e}R^{2f})_r$—$C(O)$ $NR^{11}R^{11}$, —$(CR^{2e}R^{2f})_r$—$NR^bC(O)R^c$, —$(CR^{2e}R^{2f})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{2e}R^{2f})_r$-3-14 membered carbocycle substituted with 0-3 $R^a$, or —$(CR^{2e}R^{2f})_r$-4-7 membered heterocycle comprising carbon atoms, and 1-4 heteroatoms selected from N, O, $S(O)_p$ and $S(O)(NR^g)$, substituted with 0-4 $R^a$;

$R^{2b}$ is, independently at each occurrence, hydrogen, $CF_3$, —$(CR^{2e}R^{2f})_qOR^b$, —$(CR^{2e}R^{2f})_qS(O)_pR^b$, —$(CR^{2e}R^{2f})_qS(O)(NR^g)R^b$, —$(CR^{2e}R^{2f})_r$—$C(O)R^c$, —$(CR^{2e}R^{2f})_r$—$C(O)OR^b$, —$(CR^{2e}R^{2f})_qOC(O)R^b$, —$(CR^{2e}R^{2f})_qNR^{11}R^{11}$, —$(CR^{2e}R^{2f})_r$—$C(O)NR^{11}R^{11}$, —$(CR^{2e}R^{2f})_qNR^bC(O)R^c$, —$(CR^{2e}R^{2f})_qNR^bC(O)OR^c$, —$(CR^{2e}R^{2f})_qNR^bC(O)NR^{11}R^{11}$, —$(CR^{2e}R^{2f})_qS(O)_2NR^{11}R^{11}$, —$(CR^{2e}R^{2f})_qNR^bS(O)_2R^c$, $C_{1-6}$ alkyl substituted with 0-2 $R^a$, $C_{1-6}$ haloalkyl, —$(CR^{2e}R^{2f})_r$-3-14 membered carbocycle substituted with 0-3 $R^a$, or —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^{2e}$ and $R^{2f}$ are, independently at each occurrence, hydrogen, halogen or $C_{1-6}$ alkyl;

$R^3$ is, independently at each occurrence, selected from hydrogen, halo, $N_3$, CN, —$(CR^{1b}R^{1c})_r$—$OR^{3b}$, —$(CR^{1b}R^{1c})_r$—$NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, $S(O)_p$ and $S(O)(NR^g)$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O, $S(O)_p$ and $S(O)(NR^g)$, both optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$;

$R^{3b}$ is, independently at each occurrence, hydrogen, $CF_3$, —$(CR^{1b}R^{1c})_qOR^b$, —$(CR^{1b}R^{1c})_qS(O)_pR^b$, —$(CR^{1b}R^{1c})_qS(O)(NR^g)R^b$, —$(CR^{1b}R^{1c})_r$—$C(O)R^{3d}$, —$(CR^{1b}R^{1c})_r$—$C(O)OR^b$, —$(CR^{1b}R^{1c})_qOC(O)R^b$, —$(CR^{1b}R^{1c})_qNR^{11}R^{11}$, —$(CR^{1b}R^{1c})_r$—$C(O)NR^{11}R^{11}$, —$(CR^{1b}R^{1c})_qNR^bC(O)R^{3c}$, —$(CR^{1b}R^{1c})_qNR^bC(O)OR^c$, —$(CR^{1b}R^{1c})_qNR^bC(O)NR^{11}R^{11}$, —$(CR^{1b}R^{1c})_qS(O)_2NR^{11}R^{11}$, —$(CR^{1b}R^{1c})_qNR^bS(O)_2R^c$, $C_{1-6}$ alkyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, halo, $C(=O)C_{1-4}$ alkyl, $C(=O)OC_{1-4}$ alkyl, $C_{1-6}$ alkyl or $C_{1-6}$ haloalkyl, or $R^4$ and $R^5$ taken together are =O, or together with the carbon atom to which they are attached form a 3- to 6-membered spirocarbocyclyl ring or a spiroheterocyclyl ring;

$R^6$ and $R^7$ are independently hydrogen, $C(=O)C_{1-4}$ alkyl, $C(=O)OC_{1-4}$ alkyl, $C_{1-6}$ alkyl or $C_{1-6}$ haloalkyl; or $R^6$ and $R^7$ taken together are =O, or together with the carbon atom to which they are attached form a 3- to 6-membered spirocarbocyclyl ring or a spiroheterocyclyl ring;

$R^{11}$ is, independently at each occurrence, hydrogen, $C_{1-6}$ alkyl substituted with 0-3 $R^f$, $CF_3$, —$(CR^{1b}R^{1c})_r$—$C_{3-10}$ cycloalkyl substituted with 0-3 $R^f$, —$(CR^{1b}R^{1c})_r$-phenyl substituted with 0-3 $R^d$, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^d$;

or one $R^{11}$ and a second $R^{11}$, both attached to the same nitrogen atom, combine to form a heterocycle comprising carbon atoms and 1-4 heteroatoms selected from N, O, $S(O)_p$ and $S(O)(NR^g)$, substituted with 0-4 $R^d$;

$R^a$ is, independently at each occurrence, hydrogen, =O, halo, $OCF_3$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, $(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)$ $R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, —$(CR^{1b}R^{1c})_r$—$O(CR^{1b}R^{1c}O)_rP(O)(OR^b)_2$, —$(CR^{1b}R^{1c})_r$—$O(CR^{1b}R^{1c}O)_rS(O)_2OR^b$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$, or —$(CR^{1b}R^{1c})_r$-6-10 membered carbocycle substituted with 0-3 $R^d$;

$R^c$ is, independently at each occurrence, $C_{1-6}$ alkyl substituted with 0-3 $R^f$, —$(CR^{1b}R^{1c})_r$—$C_{3-6}$ cycloalkyl substituted with 0-3 $R^f$, or —$(CR^{1b}R^{1c})_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CR^{1b}R^{1c})_r$—$C(O)$ $R^c$, —$NR^eR^e$, —$NR^eC(O)OR^c$, $C(O)NR^eR^e$, —$NR^eC(O)R^c$, $CO_2H$, $CO_2R^c$, —$NR^eSO_2R^c$, $SO_2R^c$, $SO(NR^g)R^c$, $C_{1-6}$ alkyl substituted with 0-3 $R^f$, $C_{3-6}$ cycloalkyl substituted with 0-3 $R^f$, —$(CR^{1b}R^{1c})_r$-phenyl substituted with 0-3 $R^f$ or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or —(CR$^{1b}$R$^{1c}$)$_r$-phenyl substituted with 0-3 R$^f$ is, independently at each occurrence, hydrogen, =O, halo, CN, NH$_2$, NH(C$_{1-6}$ alkyl), N(C$_{1-6}$ alkyl)$_2$, SO$_2$ (C$_{1-6}$ alkyl), SO(NR$^g$)(C$_{1-6}$ alkyl), CO$_2$H, CO$_2$(C$_{1-6}$ alkyl), OH, C$_{3-6}$ cycloalkyl, CF$_3$, O(C$_{1-6}$ alkyl); or an optionally substituted —(CR$^{1b}$R$^{1c}$)$_r$-5-10 membered heterocycle comprising carbon atoms and 1-4 heteroatoms selected from N, O, S(O)$_p$ and S(O)(NR$^g$), phenyl or C$_{3-6}$ cycloalkyl, each group optionally substituted with halo, CN, CF$_3$, C$_{1-6}$ alkyl or O(C$_{1-6}$ alkyl);

R$^g$ is, independently at each occurrence, hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(O) and S(O)$_p$ substituted with 0-4 R$^f$;

m is 0, 1, 2 or 3;
p is, independently at each occurrence, 0, 1, or 2;
q is, independently at each occurrence, 2 or 3; and
r is 0, 1, 2, 3, or 4;
or a stereoisomer or pharmaceutically-acceptable salt thereof.

In a third aspect, the invention comprises compounds of the formula

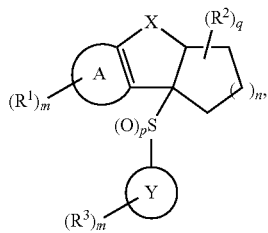

wherein
X is —CR$^4$R$^5$—, —(CR$^4$R$^5$)$_2$, —OCR$^6$R$^7$—, —S(O)$_p$CR$^6$R$^7$—, —S(O)(NR$^g$)CR$^6$R$^7$— or —NR$^6$CR$^6$R$^7$—;
A is a monocyclic 5- or 6-membered aromatic or heteroaromatic ring;
Y is a 5 or 6-membered aromatic or heteroaromatic ring;
R$^1$ is, independently at each occurrence, selected from hydrogen, CD3, halo, OCF$_3$, CN, S(O)$_p$(C$_1$-C$_6$)alkyl, S(O)(NR$^g$)(C$_1$-C$_6$)alkyl, —S(O)$_p$(C$_1$-C$_6$)alkyl-OH, S(O)(NR$^g$)(C$_1$-C$_6$)alkyl-OH, -thioalkoxyalkoxy, NR$^{11}$R$^{11}$, C$_{1-6}$ alkyl substituted with 0-3 R$^{1a}$, O—C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{1b}$ and R$^{1c}$ are, independently at each occurrence, hydrogen, halogen or C$_{1-6}$ alkyl;

R$^2$ is, independently at each occurrence, hydrogen, C$_{1-6}$ alkyl substituted with 0-3 R$^{2a}$, =CR$^{2a}$R$^{2a}$, C$_{2-6}$ alkenyl substituted with 0-3 R$^{2a}$, —(CR$^{2e}$R$^{2f}$)$_r$OR$^{2b}$, —(CR$^{2e}$R$^{2f}$)$_r$C(O)R$^{2b}$, —(CR$^{2e}$R$^{2f}$)$_r$C(O)OR$^{2b}$, —(CR$^{2e}$R$^{2f}$)$_r$OC(O)OR$^{2b}$, —(CR$^{2e}$R$^{2f}$)$_r$OC(O)NR$^{11}$R$^{11}$, —(CR$^{2e}$R$^{2f}$)$_r$NR$^{2b}$C(O)NR$^{11}$R$^{11}$, —(CR$^{2e}$R$^{2f}$)$_r$C(O)NR$^{11}$R$^{11}$, —(CR$^{2e}$R$^{2f}$)$_r$S(O)$_p$R$^c$, —(CR$^{2e}$R$^{2f}$)$_r$S(O)(NR$^g$)R$^c$, —(CR$^{2e}$R$^{2f}$)$_r$S(O)$_p$NR$^{11}$R$^{11}$, —(CR$^{2e}$R$^{2f}$)$_r$NR$^{2b}$C(O)R$^{2c}$, —(CR$^{2e}$R$^{2f}$)$_r$NR$^{2b}$C(O)OR$^{2c}$, —(CR$^{2e}$R$^{2f}$)$_r$NR$^{11}$R$^{11}$, —(CR$^{2e}$R$^{2f}$)$_r$NR$^{2b}$S(O)$_p$R$^c$, —(CR$^{2e}$R$^{2f}$)$_r$NR$^{2b}$S(O)$_p$NR$^{11}$R$^{11}$, —(CR$^{2e}$R$^{2f}$)$_r$-3-10 membered carbocycle substituted with 0-3 R$^{2a}$ or —(CR$^{2e}$R$^{2f}$)$_r$-4-10 membered heterocycle comprising carbon atoms, and 1-4 heteroatoms selected from N, O, S(O)$_p$ and S(O)(NR$^g$) substituted with 0-3 R$^{2a}$; or one R$^2$ together with an R$^2$ on an adjacent carbon combine to form a fused ring substituted with 0-3 R$^{2a}$, wherein the fused ring is selected from 3-10 membered carbocycle substituted with 0-3 R$^{2a}$, or 3-7 membered heterocycle comprising carbon atoms and 1-4 heteroatoms selected from N, O, P(O), S(O)$_p$ and S(O)(NR$^g$), substituted with 0-3 R$^{2a}$;

R$^{2a}$ is, independently at each occurrence, hydrogen, =O, halo, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—S(O)(NR$^g$)R$^b$, —(CR$^{2e}$R$^{2f}$)$_r$—C(O)R$^b$, —(CR$^{2e}$R$^{2f}$)$_r$—C(O)OR$^b$, —(CR$^{2e}$R$^{2f}$)$_r$—OC(O)R$^b$, —(CR$^{2e}$R$^{2f}$)$_r$—OC(O)NR$^{11}$R$^{11}$, —(CR$^{2e}$R$^{2f}$)$_r$—OC(O)OR$^c$, —(CR$^{2e}$R$^{2f}$)$_r$—NR$^{11}$R$^{11}$, —(CR$^{2e}$R$^{2f}$)$_r$—C(O)NR$^{11}$R$^{11}$, (CR$^{2e}$R$^{2f}$)$_r$—NR$^b$C(O)R$^c$, —(CR$^{2e}$R$^{2f}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)$_r$-3-14 membered carbocycle substituted with 0-3 R$^a$, or —(CR$^{2e}$R$^{2f}$)$_r$-4-7 membered heterocycle comprising carbon atoms, and 1-4 heteroatoms selected from N, O, S(O)$_p$ and S(O)(NR$^g$), substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)$_q$S(O)(NR$^g$)R$^b$, —(CR$^{2e}$R$^{2f}$)$_r$—C(O)R$^c$, —(CR$^{2e}$R$^{2f}$)$_r$—C(O)OR$^b$, —(CR$^{2e}$R$^{2f}$)$_r$—OC(O)R$^b$, —(CR$^{2e}$R$^{2f}$)$_q$NR$^{11}$R$^{11}$, —(CR$^{2e}$R$^{2f}$)$_r$—C(O)NR$^{11}$R$^{11}$, —(CR$^{2e}$R$^{2f}$)$_q$NR$^b$C(O)R$^c$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)$_r$-3-14 membered carbocycle substituted with 0-3 R$^a$, or —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, S(O)$_p$ and S(O)(NR$^g$), substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O, $S(O)_p$ and $S(O)(NR^g)$, both optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, $-(CR^{1b}R^{1c})_r-OR^b$, $-(CR^{1b}R^{1c})_r-S(O)_pR^b$, $-(CR^{1b}R^{1c})_r-S(O)(NR^g)R^b$, $-(CR^{1b}R^{1c})_r-C(O)R^b$, $-(CR^{1b}R^{1c})_r-C(O)OR^b$, $-(CR^{1b}R^{1c})_r-OC(O)R^b$, $-(CR^{1b}R^{1c})_r-NR^{11}R^{11}$, $-(CR^{1b}R^{1c})_r-C(O)NR^{11}R^{11}$, $-(CR^{1b}R^{1c})_r-NR^bC(O)R^c$, $-(CR^{1b}R^{1c})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CR^{1b}R^{1c})_r$-3-14 membered carbocycle substituted with 0-3 $R^a$, or $-(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$;

$R^{3b}$ is, independently at each occurrence, hydrogen, $CF_3$, $-(CR^{1b}R^{1c})_qOR^b$, $-(CR^{1b}R^{1c})_qS(O)_pR^b$, $-(CR^{1b}R^{1c})_qS(O)(NR^g)R^b$, $-(CR^{1b}R^{1c})_r-C(O)R^{3d}$, $-(CR^{1b}R^{1c})_r-C(O)OR^b$, $(CR^{1b}R^{1c})_qOC(O)R^b$, $-(CR^{1b}R^{1c})_qNR^{11}R^{11}$, $-(CR^{1b}R^{1c})_r-C(O)NR^{11}R^{11}$, $-(CR^{1b}R^{1c})_qNR^bC(O)R^{3c}$, $-(CR^{1b}R^{1c})_qNR^bC(O)OR^c$, $-(CR^{1b}R^{1c})_qNR^bC(O)NR^{11}R^{11}$, $-(CR^{1b}R^{1c})_qS(O)_2NR^{11}R^{11}$, $-(CR^{1b}R^{1c})_qNR^bS(O)_2R^c$, $C_{1-6}$ alkyl substituted with 0-3 $R^a$, $C_{1-6}$ haloalkyl, $-(CR^{1b}R^{1c})_r$-3-14 membered carbocycle substituted with 0-3 $R^a$, or $-(CR^{1b}R^{1c})_r$-5-7 membered heterocycle comprising carbon atoms and 1-4 heteroatoms selected from N, O, $S(O)_p$ and $S(O)(NR^g)$, substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, halo, $C(=O)C_{1-4}$ alkyl, $C(=O)OC_{1-4}$ alkyl, $C_{1-6}$ alkyl or $C_{1-6}$ haloalkyl, or $R^4$ and $R^5$ taken together are =O, or together with the carbon atom to which they are attached form a 3- to 6-membered spirocarbocyclyl ring or a spiroheterocyclyl ring;

$R^6$ and $R^7$ are independently hydrogen, $C(=O)C_{1-4}$ alkyl, $C(=O)OC_{1-4}$ alkyl, $C_{1-6}$ alkyl or $C_{1-6}$ haloalkyl; or $R^6$ and $R^7$ taken together are =O, or together with the carbon atom to which they are attached form a 3- to 6-membered spirocarbocyclyl ring or a spiroheterocyclyl ring;

$R^{11}$ is, independently at each occurrence, hydrogen, $C_{1-6}$ alkyl substituted with 0-3 $R^f$, $CF_3$, $-(CR^{1b}R^{1c})_r-C_{3-10}$ cycloalkyl substituted with 0-3 $R^f$, $-(CR^{1b}R^{1c})_r$-phenyl substituted with 0-3 $R^d$, or $-(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^d$;

or one $R^{11}$ and a second $R^{11}$, both attached to the same nitrogen atom, combine to form a heterocycle comprising carbon atoms and 1-4 heteroatoms selected from N, O, $S(O)_p$ and $S(O)(NR^g)$, substituted with 0-4 $R^d$;

$R^a$ is, independently at each occurrence, hydrogen, =O, halo, $OCF_3$, $CF_3$, $CHF_2$, CN, $NO_2$, $-(CR^{1b}R^{1c})_r-OR^b$, $-(CR^{1b}R^{1c})_r-S(O)_pR^b$, $-(CR^{1b}R^{1c})_r-S(O)(NR^g)R^b$, $-(CR^{1b}R^{1c})_r-C(O)R^b$, $(CR^{1b}R^{1c})_r-C(O)OR^b$, $-(CR^{1b}R^{1c})_r-OC(O)R^b$, $-(CR^{1b}R^{1c})_r-NR^{11}R^{11}$, $-(CR^{1b}R^{1c})_r-C(O)NR^{11}R^{11}$, $-(CR^{1b}R^{1c})_r-NR^bC(O)R^c$, $-(CR^{1b}R^{1c})_r-NR^bC(O)OR^c$, $-NR^bC(O)NR^{11}R^{11}$, $-S(O)_pNR^{11}R^{11}$, $NR^bS(O)_pR^c$, $-(CR^{1b}R^{1c})_r-O(CR^{1b}R^{1c}O)_tP(O)(OR^b)_2$, $-(CR^{1b}R^{1c})_r-O(CR^{1b}R^{1c}O)_tS(O)_2OR^b$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, $-(CR^{1b}R^{1c})_r$-3-14 membered carbocycle, or $-(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, $-(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$, or $-(CR^{1b}R^{1c})_r$-6-10 membered carbocycle substituted with 0-3 $R^d$;

$R^c$ is, independently at each occurrence, $C_{1-6}$ alkyl substituted with 0-3 $R^f$, $-(CR^{1b}R^{1c})_r-C_{3-6}$ cycloalkyl substituted with 0-3 $R^f$, or $-(CR^{1b}R^{1c})_r$-phenyl substituted with 0-3 $R^f$;

$R^d$ is, independently at each occurrence, hydrogen, =O, halo, $OCF_3$, $CF_3$, CN, $NO_2$, $-OR^e$, $-(CR^{1b}R^{1c})_r-C(O)R^c$, $-NR^eR^e$, $-NR^eC(O)OR^c$, $C(O)NR^eR^e$, $-NR^eC(O)R^c$, $CO_2H$, $CO_2R^c$, $-NR^eSO_2R^c$, $SO_2R^c$, $SO(NR^g)R^c$, $C_{1-6}$ alkyl substituted with 0-3 $R^f$, $C_{3-6}$ cycloalkyl substituted with 0-3 $R^f$, $-(CR^{1b}R^{1c})_r$-phenyl substituted with 0-3 $R^f$ or $-(CR^{1b}R^{1c})_r$-5-7 membered heterocycle comprising carbon atoms and 1-4 heteroatoms selected from N, O, $S(O)_p$ and $S(O)(NR^g)$, substituted with 0-4 $R^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or $-(CR^{1b}R^{1c})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl$)_2$, $SO_2(C_{1-6}$ alkyl), $SO(NR^g)(C_{1-6}$ alkyl), $CO_2H$, $CO_2(C_{1-6}$ alkyl), OH, $C_{3-6}$ cycloalkyl, $CF_3$, $O(C_{1-6}$ alkyl); or an optionally substituted $-(CR^{1b}R^{1c})_r$-5-10 membered heterocycle comprising carbon atoms and 1-4 heteroatoms selected from N, O, $S(O)_p$ and $S(O)(NR^g)$, phenyl or $C_{3-6}$ cycloalkyl, each group optionally substituted with halo, CN, $CF_3$, $C_{1-6}$ alkyl or $O(C_{1-6}$ alkyl);

$R^g$ is, independently at each occurrence, hydrogen, $C_{1-6}$ alkyl substituted with 0-3 $R^f$, $C_{1-6}$ haloalkyl, $-(CR^{1b}R^{1c})_r-C(O)R^b$, $-(CR^{1b}R^{1c})_r-C(O)OR^b$, $-(CR^{1b}R^{1c})_r-C(O)NR^{11}R^{11}$, $-(CR^{1b}R^{1c})_r$-3-14 membered carbocycle, or $-(CR^{1b}R^{1c})_r$-5-7 membered heterocycle comprising carbon atoms and 1-4 heteroatoms selected from N, O, P(O) and $S(O)_p$ substituted with 0-4 $R^f$;

m is 0, 1, 2 or 3;

n is 1 or 2;

p is, independently at each occurrence, 0, 1, or 2;

q is, independently at each occurrence, 2 or 3; and r is 0, 1, 2, 3, or 4;

or a stereoisomer or pharmaceutically-acceptable salt thereof.

In a 4$^{th}$ aspect, the invention comprises compounds of the formula

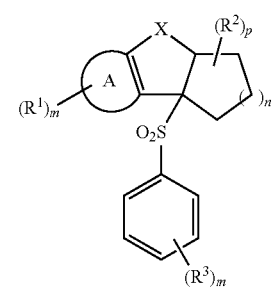

wherein

X is —CR$^4$R$^5$—, —(CR$^4$R$^5$)$_2$—, —OCR$^6$R$^7$—, —S(O)$_p$CR$^6$R$^7$—, —S(O)(NR$^g$)CR$^6$R$^7$— or —NR$^6$CR$^6$R$^7$—;

A is a monocyclic 5- or 6-membered aromatic or heteroaromatic ring;

R$^1$ is, independently at each occurrence, selected from hydrogen, CD3, halo, OCF$_3$, CN, S(O)$_p$(C$_1$-C$_6$)alkyl, S(O)(NR$^g$)(C$_1$-C$_6$)alkyl, —S(O)$_p$(C$_1$-C$_6$)alkyl-OH, S(O)(NR$^g$)(C$_1$-C$_6$)alkyl-OH, -thioalkoxyalkoxy, NR$^{11}$R$^{11}$, C$_{1-6}$ alkyl substituted with 0-3 R$^{1a}$, O—C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{1b}$ and R$^{1c}$ are, independently at each occurrence, hydrogen, halogen or C$_{1-6}$ alkyl;

R$^2$ is, independently at each occurrence, hydrogen, C$_{1-6}$ alkyl substituted with 0-3 R$^{2a}$, =CR$^{2a}$R$^{2a}$, C$_{2-6}$ alkenyl substituted with 0-3 R$^{2a}$, —(CR$^{2e}$R$^{2f}$)$_r$OR$^{2b}$, —(CR$^{2e}$R$^{2f}$)$_r$C(O)R$^{2b}$, —(CR$^{2e}$R$^{2f}$)$_r$C(O)OR$^{2b}$, —(CR$^{2e}$R$^{2f}$)$_r$OC(O)OR$^{2b}$, —(CR$^{2e}$R$^{2f}$)$_r$OC(O)NR$^{11}$R$^{11}$, —(CR$^{2e}$R$^{2f}$)$_r$NR$^{2b}$C(O)NR$^{11}$R$^{11}$, —(CR$^{2e}$R$^{2f}$)$_r$C(O)NR$^{11}$R$^{11}$, —(CR$^{2e}$R$^{2f}$)$_r$S(O)$_p$R$^c$, —(CR$^{2e}$R$^{2f}$)$_r$S(O)(NR$^g$)R$^c$, —(CR$^{2e}$R$^{2f}$)$_r$S(O)$_p$NR$^{11}$R$^{11}$, —(CR$^{2e}$R$^{2f}$)$_r$NR$^{2b}$C(O)R$^{2c}$, —(CR$^{2e}$R$^{2f}$)$_r$NR$^{2b}$C(O)OR$^{2c}$, —(CR$^{2e}$R$^{2f}$)$_r$NR$^{11}$R$^{11}$, —(CR$^{2e}$R$^{2f}$)$_r$NR$^{2b}$S(O)$_p$R$^c$, —(CR$^{2e}$R$^{2f}$)$_r$NR$^{2b}$S(O)$_p$NR$^{11}$R$^{11}$, —(CR$^{2e}$R$^{2f}$)$_r$-3-10 membered carbocycle substituted with 0-3 R$^{2a}$ or —(CR$^{2e}$R$^{2f}$)$_r$-4-10 membered heterocycle comprising carbon atoms, and 1-4 heteroatoms selected from N, O, S(O)$_p$ and S(O)(NR$^g$) substituted with 0-3 R$^{2a}$; or one R$^2$ together with an R$^2$ on an adjacent carbon combine to form a fused ring substituted with 0-3 R$^{2a}$, wherein the fused ring is selected from 3-10 membered carbocycle substituted with 0-3 R$^{2a}$, or 3-7 membered heterocycle comprising carbon atoms and 1-4 heteroatoms selected from N, O, P(O), S(O)$_p$ and S(O)(NR$^g$), substituted with 0-3 R$^{2a}$;

R$^{2a}$ is, independently at each occurrence, hydrogen, =O, halo, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^2$)$_r$—S(O)(NR$^g$)R$^b$, —(CR$^{2e}$R$^2$)$_r$—C(O)R$^b$, —(CR$^{2e}$R$^{2f}$)$_r$—C(O)OR$^b$, —(CR$^{2e}$R$^{2f}$)$_r$—OC(O)R$^b$, —(CR$^{2e}$R$^{2f}$)$_r$—OC(O)NR$^{11}$R$^{11}$, —(CR$^{2e}$R$^{2f}$)$_r$—OC(O)OR$^c$, —(CR$^{2e}$R$^{2f}$)$_r$—NR$^{11}$R$^{11}$, —(CR$^{2e}$R$^{2f}$)$_r$—C(O)NR$^{11}$R$^{11}$, —(CR$^{2e}$R$^{2f}$)$_r$—NR$^b$C(O)R$^c$, —(CR$^{2e}$R$^{2f}$)$_r$—NR$^b$C(O)OR$^c$, —NR$^b$C(O)NR$^{11}$R$^{11}$, —S(O)$_p$NR$^{11}$R$^{11}$, NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)$_r$-3-14 membered carbocycle substituted with 0-3 R$^a$, or —(CR$^{2e}$R$^{2f}$)$_r$-4-7 membered heterocycle comprising carbon atoms, and 1-4 heteroatoms selected from N, O, S(O)$_p$ and S(O)(NR$^g$), substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)$_q$S(O)(NR$^g$)R$^b$, —(CR$^{2e}$R$^{2f}$)$_r$—C(O)R$^c$, —(CR$^{2e}$R$^{2f}$)$_r$—C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)$_r$—C(O)NR$^{11}$R$^{11}$, —(CR$^{2e}$R$^{2f}$)$_q$NR$^b$C(O)R$^c$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)$_r$-3-14 membered carbocycle substituted with 0-3 R$^a$, or —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, S(O)$_p$ and S(O)(NR$^g$), substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O, S(O)$_p$ and S(O)(NR$^g$), both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$S(O)(NR$^g$)R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_r$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)NR$^{11}$R$^{11}$, —(CR$^{1b}$R$^{1c}$)$_q$S(O)$_2$NR$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, halo, C(=O)C$_{1-4}$ alkyl, C(=O)OC$_{1-4}$ alkyl, C$_{1-6}$ alkyl or C$_{1-6}$ haloalkyl, or R$^4$ and R$^5$ taken together are =O, or together with the carbon atom to which they are attached form a 3- to 6-membered spirocarbocyclyl ring or a spiroheterocyclyl ring;

R$^6$ and R$^7$ are independently hydrogen, C(=O)C$_{1-4}$ alkyl, C(=O)OC$_{1-4}$ alkyl, C$_{1-6}$ alkyl or C$_{1-6}$ haloalkyl; or R$^6$ and R$^7$ taken together are =O, or together with the carbon atom to which they are attached form a 3- to 6-membered spirocarbocyclyl ring or a spiroheterocyclyl ring;

R$^{11}$ is, independently at each occurrence, hydrogen, C$_{1-6}$ alkyl substituted with 0-3 R$^f$, CF$_3$, —(CR$^{1b}$R$^{1c}$)$_r$—C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^d$;

or one R$^{11}$ and a second R$^{11}$, both attached to the same nitrogen atom, combine to form a heterocycle comprising carbon atoms and 1-4 heteroatoms selected from N, O, S(O)$_p$ and S(O)(NR$^g$), substituted with 0-4 R$^d$;

R$^d$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, (CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —(CR$^{1b}$R$^{1c}$)$_r$—O(CR$^{1b}$R$^{1c}$O)$_t$P(O)(OR$^b$)$_2$, —(CR$^{1b}$R$^{1c}$)$_r$—O(CR$^{1b}$R$^{1c}$O)$_t$S(O)$_2$OR$^b$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, SO(NR$^g$)R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), SO(NR$^g$)(C$_{1-6}$ alkyl), CO$_2$H, CO$_2$(C$_{1-6}$ alkyl), OH, C$_{3-6}$ cycloalkyl, CF$_3$, O(C$_{1-6}$ alkyl); or an optionally substituted —(CR$^{1b}$R$^{1c}$)$_r$-5-10 membered heterocycle comprising carbon atoms and 1-4 heteroatoms selected from N, O, S(O)$_p$ and S(O)(NR$^g$), phenyl or C$_{3-6}$ cycloalkyl, each group optionally substituted with halo, CN, CF$_3$, C$_{1-6}$ alkyl or O(C$_{1-6}$ alkyl);

R$^g$ is, independently at each occurrence, hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(O) and S(O)$_p$ substituted with 0-4 R$^f$;

m is 0, 1, 2 or 3;
n is 1 or 2;
p is, independently at each occurrence, 0, 1, or 2;
q is, independently at each occurrence, 2 or 3; and
r is 0, 1, 2, 3, or 4;

or a stereoisomer or pharmaceutically-acceptable salt thereof.

In a 5$^{th}$ aspect, the invention comprises compounds of the formula

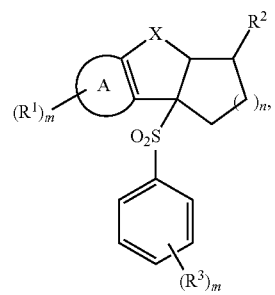

or a stereoisomer or pharmaceutically-acceptable salt thereof.

In a 6$^{th}$ aspect, the invention comprises compounds of the formula

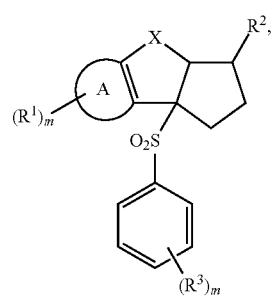

or a stereoisomer or pharmaceutically-acceptable salt thereof.

In a 7$^{th}$ aspect, the invention comprises compounds of the formula

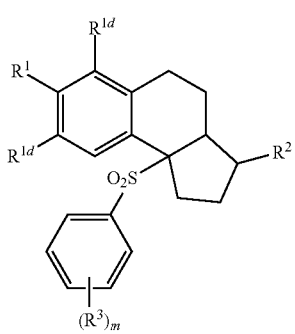

wherein R$^{1d}$ is, independently at each occurrence, hydrogen, CD$_3$, halo, CF$_3$, CN or C$_{1-4}$ alkyl;

or a stereoisomer or pharmaceutically-acceptable salt thereof.

In an 8th aspect, the invention comprises compounds of the formula

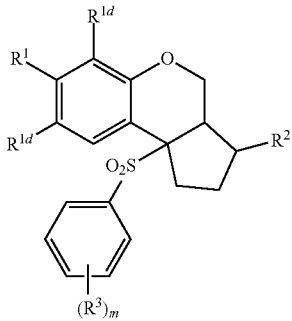

wherein $R^{1d}$ is, independently at each occurrence, hydrogen, $CD_3$, halo, $CF_3$, CN or $C_{1-4}$ alkyl;
or a stereoisomer or pharmaceutically-acceptable salt thereof.

In a 9th aspect, the invention comprises compounds of the formula

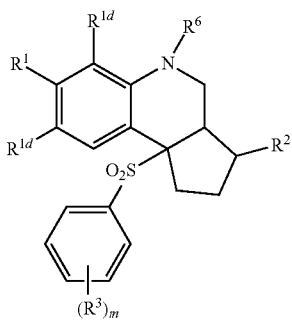

wherein $R^{1d}$ is, independently at each occurrence, hydrogen, $CD_3$, halo, $CF_3$, CN or $C_{1-4}$ alkyl;
or a stereoisomer or pharmaceutically-acceptable salt thereof.

In a 10th aspect, the invention comprises compounds within the 7th aspect, wherein $R^1$ is halo, phenyl substituted with 0-3 $R^{1a}$, $C_{1-6}$ alkyl substituted with 0-3 $R^{1a}$, or O—$C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, or —$(CR^{1b}R^{1c})_r$-phenyl substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, CN or $C_1$-$C_4$ alkyl;

$R^2$ is hydrogen, —$S(O)_2R^{2c}$, $C_{1-6}$ alkyl substituted with 0-3 $R^{2a}$, —$C(O)OR^{2b}$, —$C(O)R^{2b}$, —$C(O)NR^{11}R^{11}$, —$NR^{2b}C(O)NR^{11}R^{11}$, —$NR^{2b}C(O)R^{2c}$, $NR^{2b}C(O)OR^{2c}$, $NR^{11}R^{11}$, —$NR^{2b}S(O)_pR^c$, $NR^{2b}S(O)_pNR^{11}R^{11}$, or a 5-7 membered heterocycle comprising carbon atoms and 1-4 heteroatoms selected from N, O, P(O), $S(O)_p$ and $S(O)(NR^g)$, substituted with 0-4 $R^a$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2c}$ is $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, $N_3$, CN, $OR^{3b}$, —$NH_2$, —$NH(C_{1-6}$ alkyl), $N(C_{1-6}$ alkyl)$_2$, $C_{1-6}$ alkyl substituted with 0-3 $R^{3a}$, or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_rC(O)OR^b$, —$(CR^{1b}R^{1c})_r$—$OC(O)R^b$, —$(CR^{1b}R^{1c})_rNR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In an 11th aspect, the invention comprises compounds within the 8th aspect, wherein $R^1$ is halo, phenyl substituted with 0-3 $R^{1a}$, $C_{1-6}$ alkyl substituted with 0-3 $R^{1a}$, or O—$C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, or —$(CR^{1b}R^{1c})_r$-phenyl substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, CN or $C_1$-$C_4$ alkyl;

$R^2$ is hydrogen, —$S(O)_2R^{2c}$, $C_{1-6}$ alkyl substituted with 0-3 $R^{2a}$, —$C(O)OR^{2b}$, —$C(O)R^{2b}$, —$C(O)NR^{11}R^{11}$, —$NR^{2b}C(O)NR^{11}R^{11}$, —$NR^{2b}C(O)R^{2c}$, $NR^{2b}C(O)OR^{2c}$, $NR^{11}R^{11}$, —$NR^{2b}S(O)_pR^c$, $NR^{2b}S(O)_pNR^{11}R^{11}$, or a 5-7 membered heterocycle comprising carbon atoms and 1-4 heteroatoms selected from N, O, P(O), $S(O)_p$ and $S(O)(NR^g)$, substituted with 0-4 $R^a$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2c}$ is $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, $N_3$, CN, $OR^{3b}$, —$NH_2$, —$NH(C_{1-6}$ alkyl), $N(C_{1-6}$ alkyl)$_2$, $C_{1-6}$ alkyl substituted with 0-3 $R^{3a}$, or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $N_{O2}$, —$(CR^{1b}R^{1c})_r$—

$OR^b$, —$(CR^{1b}R^{1c})_r$—$S(O)_pR^b$, —$(CR^{1b}R^{1c})_r$—$S(O)(NR^g)$ $R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In a 12th aspect, the invention comprises compounds within the 9th aspect, wherein $R^1$ is halo, phenyl substituted with 0-3 $R^{1a}$, $C_{1-6}$ alkyl substituted with 0-3 $R^{1a}$, or O—$C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, or —$(CR^{1b}R^{1c})_r$-phenyl substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, CN or $C_1$-$C_4$ alkyl;

$R^2$ is hydrogen, —$S(O)_2R^{2c}$, $C_{1-6}$ alkyl substituted with 0-3 $R^{2a}$, —$C(O)OR^{2b}$, —$C(O)R^{2b}$, —$C(O)NR^{11}R^{11}$, —$NR^{2b}C(O)NR^{11}R^{11}$, —$NR^{2b}C(O)R^{2c}$, $NR^{2b}C(O)OR^{2c}$, $NR^{11}R^{11}$, —$NR^{2b}S(O)_pR^c$, $NR^{2b}S(O)_pNR^{11}R^{11}$, or a 5-7 membered heterocycle comprising carbon atoms and 1-4 heteroatoms selected from N, O, P(O), $S(O)_p$ and $S(O)(NR^g)$, substituted with 0-4 $R^a$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2c}$ is $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, $N_3$, CN, $OR^{3b}$, —$NH_2$, —$NH(C_{1-6}$ alkyl), $N(C_{1-6}$ alkyl$)_2$, $C_{1-6}$ alkyl substituted with 0-3 $R^{3a}$, or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$ —$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In a 13th aspect, the invention comprises compounds of the formula within the 10th aspect,

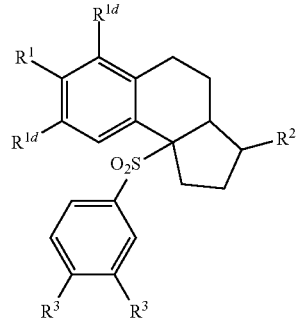

wherein $R^1$ is $C_{1-6}$ alkyl substituted with 0-3 $R^{1a}$ or O—$C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^{1d}$ is, independently at each occurrence, hydrogen, halo, or CN;

$R^2$ is $C_{1-6}$ alkyl substituted with 0-3 $R^{2a}$, —$C(O)OR^{2b}$, —$C(O)R^{2b}$, —$C(O)NR^{11}R^{11}$, —$NR^{2b}C(O)NR^{11}R^{11}$, —$NR^{2b}C(O)R^{2c}$, $NR^{2b}C(O)OR^{2c}$, $NR^{11}R^{11}$, —$NR^{2b}S(O)_pR^c$, or $NR^{2b}S(O)_pNR^{11}R^{11}$;

$R^{2a}$ is, independently at each occurrence, hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, $S(O)_p$ and $S(O)(NR^g)$, substituted with 0-4 $R^a$, or —$(CR^{2e}R^{2f})_r$-phenyl substituted with 0-3 $R^a$;

$R^{2c}$ is $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10 membered heterocycle containing 1-4 heteroatoms selected from N, O, $S(O)_p$ and $S(O)(NR^g)$, substituted with 0-4 $R^a$;

$R^3$ is, independently at each occurrence, hydrogen, halo, cyclopropyl or $C_{1-6}$ alkyl;

or a stereoisomer or pharmaceutically-acceptable salt thereof.

In a 14th aspect, the invention comprises compounds of the formula within the 11th aspect,

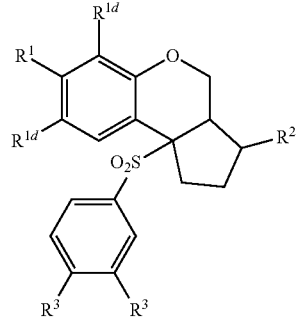

wherein

R$^1$ is C$_{1-6}$ alkyl substituted with 0-3 R$^{1a}$;

R$^{1a}$ is, independently at each occurrence, hydrogen, CF$_3$, halo or C$_{1-6}$ alkyl substituted with 0-3 R$^a$;

R$^{1d}$ is, independently at each occurrence, hydrogen, halo, or CN;

R$^2$ is C$_{1-6}$ alkyl substituted with 0-3 R$^{2a}$, —C(O)OR$^{2b}$, —C(O)R$^{2b}$, —C(O)NR$^{11}$R$^{11}$, —NR$^{2b}$C(O)NR$^{11}$R$^{11}$, —NR$^{2b}$C(O)R$^{2c}$, NR$^{2b}$C(O)OR$^{2c}$, NR$^{11}$R$^{11}$, —NR$^{2b}$S(O)$_p$R$^c$, or NR$^{2b}$S(O)$_p$NR$^{11}$R$^{11}$;

R$^{2a}$ is, independently at each occurrence, hydrogen or C$_{1-6}$ alkyl substituted with 0-3 R$^a$;

R$^{2b}$ is hydrogen, C$_{1-6}$ alkyl substituted with 0-2 R$^a$, C$_{3-6}$ cycloalkyl substituted with 0-3 R$^a$, —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$, or —(CR$^{2e}$R$^{2f}$)$_r$-phenyl substituted with 0-3 R$^a$;

R$^{2c}$ is C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;

R$^3$ is, independently at each occurrence, hydrogen, halo, cyclopropyl or C$_{1-6}$ alkyl;

or a stereoisomer or pharmaceutically-acceptable salt thereof.

In a 15th aspect, the invention comprises compounds of the formula within the 12$^{th}$ aspect,

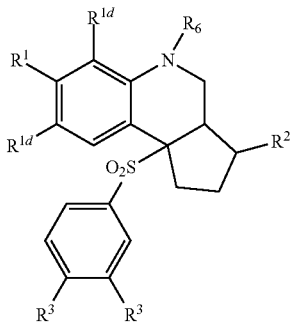

wherein

R$^1$ is C$_{1-6}$ alkyl substituted with 0-3 R$^{1a}$;

R$^{1a}$ is, independently at each occurrence, hydrogen, CF$_3$, halo or C$_{1-6}$ alkyl substituted with 0-3 R$^a$;

R$^{1d}$ is, independently at each occurrence, hydrogen, halo, or CN;

R$^2$ is C$_{1-6}$ alkyl substituted with 0-3 R$^{2a}$, —C(O)OR$^{2b}$, —C(O)R$^{2b}$, —C(O)NR$^{11}$R$^{11}$, —NR$^{2b}$C(O)NR$^{11}$R$^{11}$, —NR$^{2b}$C(O)R$^{2c}$, NR$^{2b}$C(O)OR$^{2c}$, NR$^{11}$R$^{11}$, —NR$^{2b}$S(O)$_p$R$^c$, or NR$^{2b}$S(O)$_p$NR$^{11}$R$^{11}$;

R$^{2a}$ is, independently at each occurrence, hydrogen or C$_{1-6}$ alkyl substituted with 0-3 R$^a$;

R$^{2b}$ is hydrogen, C$_{1-6}$ alkyl substituted with 0-2 R$^a$, C$_{3-6}$ cycloalkyl substituted with 0-3 R$^a$, —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$, or —(CR$^{2e}$R$^{2f}$)$_r$-phenyl substituted with 0-3 R$^a$;

R$^{2c}$ is C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;

R$^3$ is hydrogen, halo, cyclopropyl or C$_{1-6}$ alkyl;

or a stereoisomer or pharmaceutically-acceptable salt thereof.

In a 16$^{th}$ aspect, the invention comprises compounds of the formula within the 13$^{th}$ aspect,

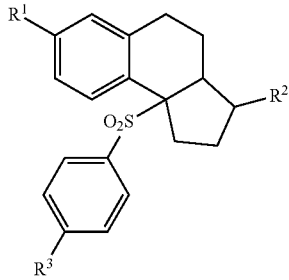

wherein

R$^1$ is C$_{1-6}$ alkyl substituted with 0-3 R$^{1a}$ or O—C$_{1-6}$ alkyl substituted with 0-3 R$^{1a}$;

R$^2$ is —C(O)NR$^{11}$R$^{11}$, —(CH$_2$)$_{0-1}$NHC(O)NR$^{11}$R$^{11}$ or —(CH$_2$)$_{0-1}$NHC(O)R$^{2c}$;

R$^{2c}$ is C$_{1-4}$ alkyl substituted with 0-3 R$^a$, C$_{3-6}$ cycloalkyl substituted with 0-3 R$^a$ or 5-10 membered heterocycle containing 1-2 heteroatoms selected from N, O and S(O)$_2$, substituted with 0-3 R$^a$;

R$^3$ is, independently at each occurrence, hydrogen or halo;

R$^{11}$ is, independently at each occurrence, hydrogen, C$_{1-6}$ alkyl substituted with 0-2 R$^f$, C$_{4-6}$ cycloalkyl substituted with 0-2 R$^f$, —CH$_2$—C$_{4-6}$ cycloalkyl substituted with 0-2 R$^f$, 5-6 membered heterocycle comprising carbon atoms and 1-2 heteroatoms selected from N, O and S(O)$_2$, substituted with 0-1 R$^d$, —CH$_2$-5-6 membered heterocycle comprising carbon atoms and 1-2 heteroatoms selected from N, O and S(O)$_2$, substituted with 0-2 R$^d$;

or one R$^{11}$ and a second R$^{11}$, both attached to the same nitrogen atom, combine to form a heterocycle comprising carbon atoms and 1-2 heteroatoms selected from N, O and S(O)$_2$, substituted with 0-2 R$^d$;

R$^a$ is, independently at each occurrence, hydrogen, =O, halo, CF$_3$, OH, CH$_2$OH, S(O)$_2$CH$_3$, —C(O)CH$_3$, NHC(O)CH$_3$, —OP(O)(OH)$_2$, C$_{1-2}$ alkyl substituted with 0-1 R$^f$ or pyridyl;

R$^d$ is, independently at each occurrence, hydrogen, —OH, —C(O)CH$_3$, CO$_2$H, CO$_2$R$^c$ or SO$_2$R$^c$;

R$^f$ is, independently at each occurrence, hydrogen, CO$_2$H, CN or OH;

or a stereoisomer or pharmaceutically-acceptable salt thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

Definitions

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group, for example, aryl or heteroaryl groups which are optionally substituted for example with alkyl, halo or haloalkyl. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of both straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

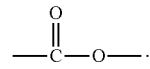

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Thus, examples of aryl groups include:

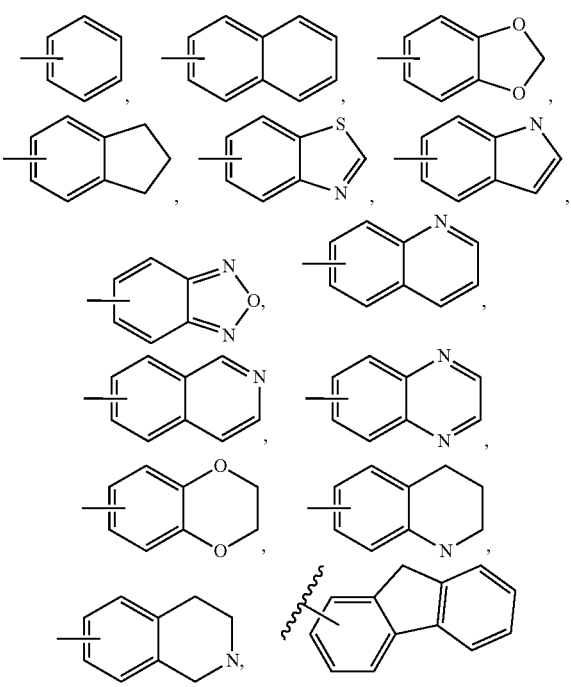

(fluorenyl) and the like, which optionally may be substituted at any available carbon or nitrogen atom. A preferred aryl group is optionally-substituted phenyl.

Accordingly, in compounds of Formula I, the term "cycloalkyl" includes cyclopropyl, cyclobutyl, cyclopentyl, cyclohexyl, cycloheptyl, bicyclooctyl, etc., as well as the following ring systems:

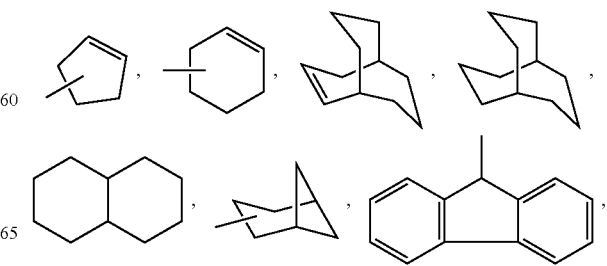

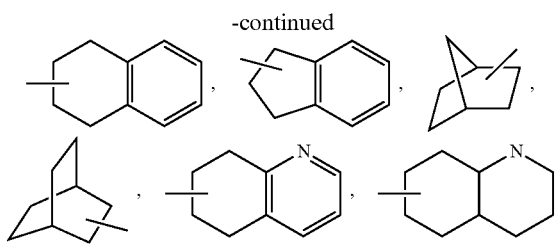
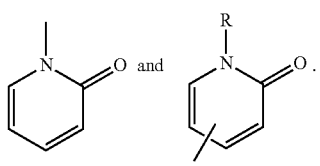

and the like, which optionally may be substituted at any available atoms of the ring(s).

Preferred cycloalkyl groups include cyclopropyl, cyclopentyl, cyclohexyl, and

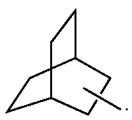

The term "halo" or "halogen" refers to chloro, bromo, fluoro and iodo.

The term "haloalkyl" means a substituted alkyl having one or more halo substituents. For example, "haloalkyl" includes mono, di, and trifluoromethyl.

The term "haloalkoxy" means an alkoxy group having one or more halo substituents. For example, "haloalkoxy" includes $OCF_3$.

The terms "heterocycle", "heterocycloalkyl", "heterocyclo", "heterocyclic", or

"heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrolinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The terms "carbocycle, carbocyclyl or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl.

The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of Formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of Formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the Formula I may be formed, for example, by reacting a compound of the Formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, hydrogen sulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-3-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogen sulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization. One enantiomer of a compound of Formula I may display superior activity compared with the other.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the Formula I, and/or a salt and/or solvate thereof. Any compound that will be converted in vivo to provide the bioactive agent (i.e., the compound for Formula I) is a prodrug within the scope and spirit of the invention. For example, compounds containing a carboxy group can form physiologically hydrolyzable esters which serve as prodrugs by being hydrolyzed in the body to yield Formula I compounds per se. Such prodrugs are preferably administered orally since hydrolysis in many instances occurs principally under the influence of the digestive enzymes. Parenteral administration may be used where the prodrug per se is active, or in those instances where hydrolysis occurs in the blood. Examples of physiologically hydrolyzable esters of compounds of Formula I containing a carboxy group include $C_{1-6}$-alkylbenzyl, 4-methoxybenzyl, indanyl, phthalyl, methoxymethyl, $C_{1-6}$-alkanoyloxy-$C_{1-6}$-alkyl, e.g., acetoxymethyl, pivaloyloxymethyl or propionyloxymethyl, $C_{1-6}$-alkoxycarbonyloxy-$C_{1-6}$-alkyl, e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Also, compounds containing a hydroxy group can form physiologically cleavable esters, acetals or ketals which serve as prodrugs by being hydrolyzed in the body to yield Formula I compounds per se. Examples of physiologically hydrolyzable esters, acetals and ketals of compounds of Formula I containing a hydroxy group include compounds where the hydrogen of the hydroxy group is replaced by acetyl, propionyl, butyryl, pivalyl, hydroxyacetyl, hydroxypropionyl, aminoacetyl, alanyl, β-alanyl, aspartyl, asparaginyl, glutamyl, glutaminyl, arginyl, lysyl, seryl, dihydroxyphosphoryl, hydroxysulfonyl, dihydroxyphosphoryloxymethyl, 1-dihydroxyphosphoryloxyethyl, hydroxysulfonyloxymethyl, 1-hydroxysulfonyloxyethyl, acetoxymethyl, 1-acetoxyethyl, optionally 2-substituted 2-aminoacyloxymethyl, and the like. Salt forms of such prodrugs are also contemplated, for example an acid addition salt (such as a hydrochloride) of an aminoacyl ester or aminoacyloxymethyl acetal, a mono- or disodium salt of a dihydroxyphosphoryl or dihydroxyphosphoryloxymethyl derivative, or a sodium salt of a hydroxysulfonyloxy or hydroxysulfonyloxymethyl derivative. Such esters, acetals and ketals may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the Formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Formulations/Compositions

Another aspect of the invention is a pharmaceutical composition including a compound, stereoisomeric form, pharmaceutical salt, solvate or hydrate as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

Utility

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to Formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol. Metab.* 2012, 23 (12): 619-627; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis.

In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.,* 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets,* 2012 April; 11(2): 159-68, which is hereby incorporated herein by reference in its entirety, as well as the references discussed in the Background section.

In other embodiments, the disease or disorder is inflammatory bowel disease. See, e.g., M. Leppkes et al., "RORgamma-expressing Th17 cells induce murine chronic intestinal inflammation via redundant effects of IL-17A and IL-17F," *Gastroenterology,* 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.,* 2012 August; 42(8):1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.,* 2012 Jun. 1; 122(6):2252-6; and S. P. Raychaudhuri, "Role of IL-17 in Psoriasis and Psoriatic Arthritis," Clin. Rev. Allergy Immunol., 2013; 44(2): 183-193, each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factor T-bet and RORγt in mice," *Blood,* 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.,* 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July: 18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, Greene's *Protective Groups in Organic Synthesis*, Fourth Edition, Wiley and Sons (2007).

Substituents shown in the schemes do not necessarily correspond to those used in the summary of the invention or in the claims.

A method for preparing compounds 8 is shown in Scheme 1. An appropriately functionalized carbonyl compound 1 (which is commercially available, or can be synthesized using various methods known in the literature; see, for example: *Eur. J. Med. Chem.* 2015, 90, 834; *Science of Synthesis* 2007, 31a, 1097; PCT Int. Appl. 2014/138484; *Bioorg. Med. Chem. Lett.* 2012, 22, 240; *Eur. J. Med. Chem.* 2013, 69, 490; or PCT Int. Appl. 2013/178322) can be reacted with an appropriate thiol in the presence of an acid such as HCl or $TiCl_4$ to provide a vinyl sulfide 2a, a thioketal 2b, or a mixture of 2a and 2b. Oxidation of sulfide 2a, thioketal 2b, or a mixture of 2a and 2b can be accomplished using a reagent such as m-chloroperoxybenzoic acid to provide sulfone 3. A protected carbinol 4 (where EWG is an electron-withdrawing group, for example, a carboxylic acid ester or $NO_2$, and PG is a suitable carbinol protecting group such as, for example, tert-butyldimethylsilyl) can be treated with a strong base such as lithium diisopropylamide or lithium bis(trimethylsilyl)amide to form the corresponding anion, which can react with sulfone 3 to provide a protected carbinol 5. The protecting group can be removed using suitable conditions (for example, if PG is tert-butyldimethylsilyl, by treatment with HCl) to provide carbinol 6. The carbinol of 6 can be converted to a suitable leaving group LG of compound 7, such as methanesulfonate, for example by treatment with methanesulfonyl chloride and triethylamine. Treatment of 7 with a base such as potassium tert-butoxide can provide a tricyclic compound 8.

SCHEME 1

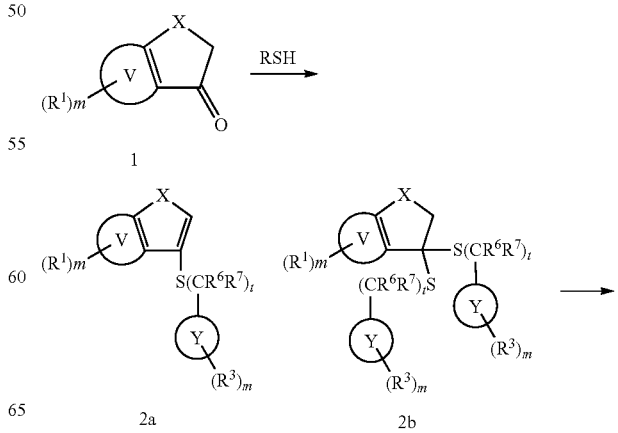

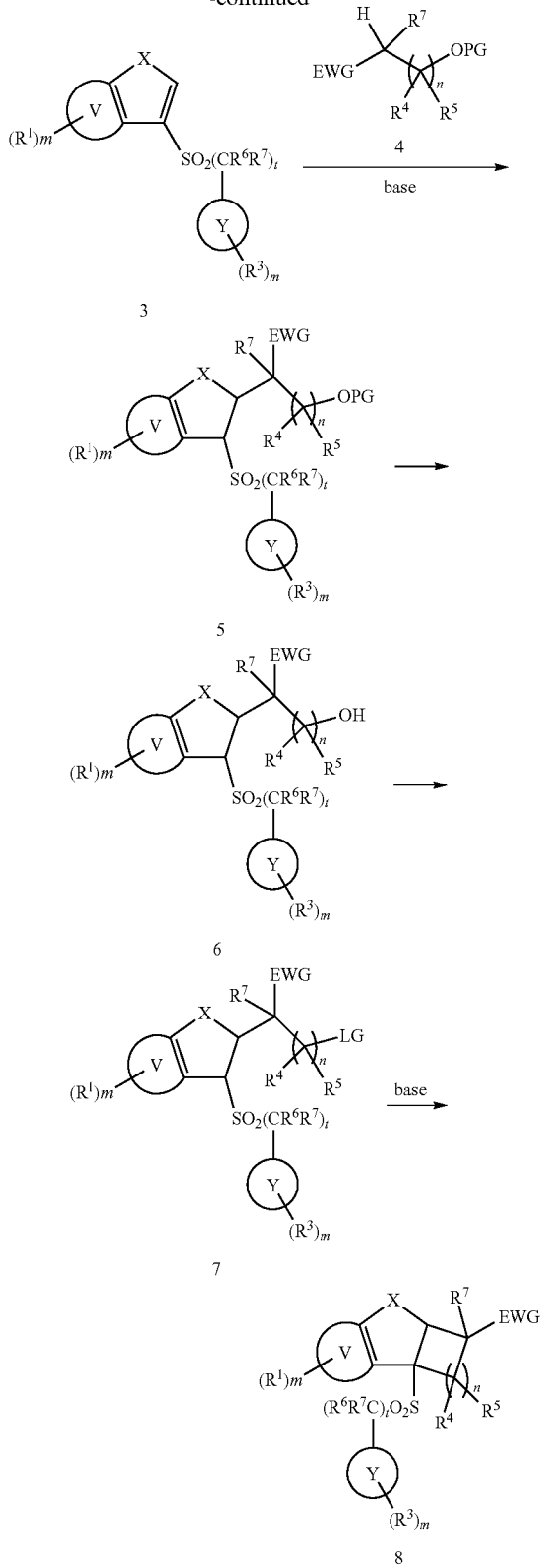

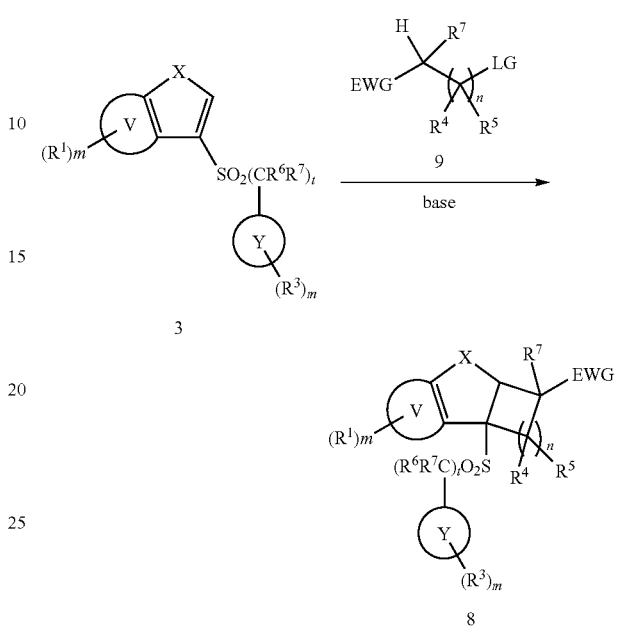

with sulfone 3 to directly provide the tricyclic compound 8 (see for example, *J. Org. Chem.* 2010, 75, 3251-3259).

Alternatively, as shown in Scheme 2, a compound 9 (where LG is an appropriate leaving group such as Cl) can be deprotonated with a strong base such as lithium diisopropylamide or lithium bis(trimethylsilyl)amide and reacted Conversion of certain compounds 8 into certain amide compounds of the present invention is illustrated in Scheme 3. Compound 8a, where R can be, for example, methyl, ethyl, tert-butyl, or benzyl, can be converted to acid 10 using standard methods. For example, if R is methyl or ethyl, treatment with lithium hydroxide or sodium hydroxide in the presence of water can provide 10, or if R is tert-butyl, treatment with a strong acid such as HCl or trifluoroacetic acid can provide 10, or if R is benzyl, treatment with hydrogen in the presence of a catalyst such as palladium on carbon can provide 10. Acid 10 can then be converted to an amide 11 using methods well known in the literature, for example by treatment with an amine in the presence of a suitable base and a coupling reagent such as (benzotriazol-1-yloxy)tris(dimethylamino)phosphonium hexafluorophosphate (BOP), O-(7-azabenzotriazol-1-yl)-1,1,3,3-tetramethyluronium hexafluorophosphate (HATU), benzotriazol-1-yl-oxytripyrrolidinophosphonium hexafluorophosphate (PyBOP), or a combination of 1-hydroxybenzotriazole (HOBT) and N-(3-dimethylaminopropyl)-NV-ethylcarbodiimide (EDC).

SCHEME 3

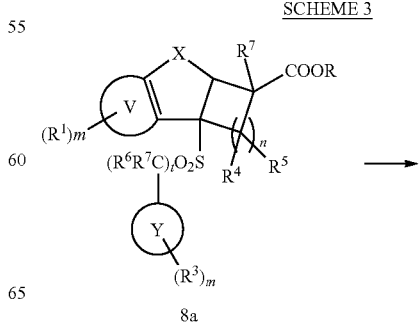

8a

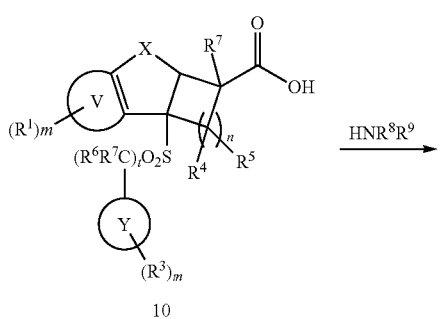

10 can be converted to an amine 13 using a variety of well-known methods, for example by treatment with diphenylphosphoryl azide in the presence of an alcohol such as tert-butanol or trimethylsilylethanol (known as the Curtius rearrangement, see for example *J. Am. Chem. Soc.* 1972, 94, 6203), to provide the corresponding carbamate 12. Treatment of the carbamate under appropriate conditions, for example by treatment with a strong acid such as trifluoroacetic acid if R is tert-butyl or trimethylsilylethyl, can give amine 13. Alternatively, a compound 8b (compound 8 where EWG is nitro) could be reduced to amine 13 by treatment with, for example, HCl and indium (*J. Org. Chem.* 2005, 70, 8140).

SCHEME 4

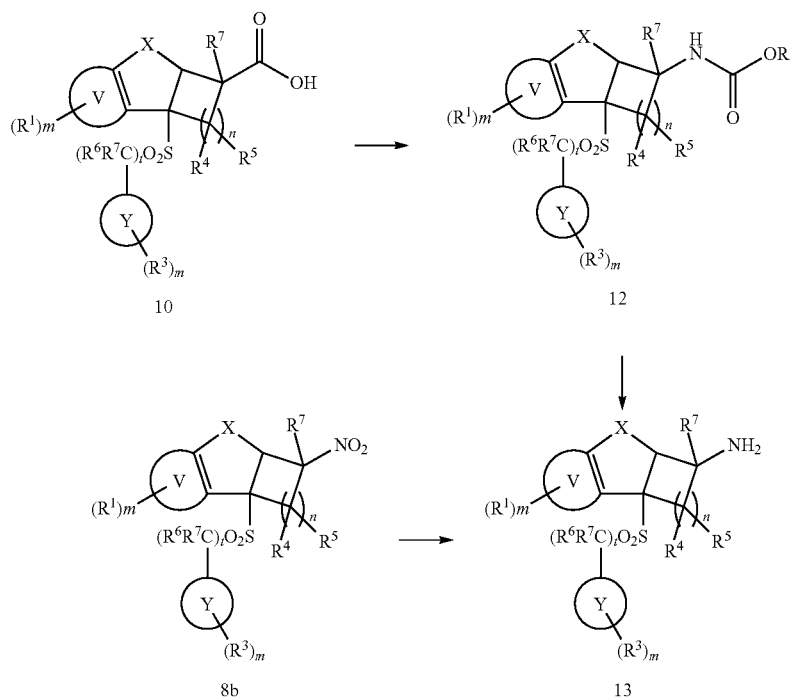

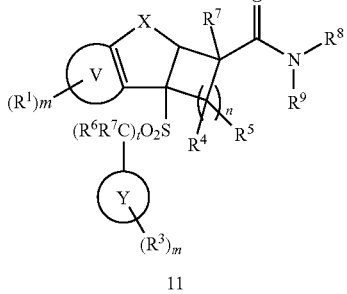

11

Methods for the preparation of certain amine compounds of the present invention are illustrated in Scheme 4. Acid 10

Alternative methods for the preparation of certain amine compounds of the present invention are illustrated in Scheme 5. An ester 8a (R=alkyl) can be reduced to a primary carbinol 14 using any of a number of methods known in the literature, for example by treatment with a reducing agent such as lithium aluminum hydride. The hydroxy group of 14 can be converted to a suitable leaving group such as a methanesulfonate or p-toluenesulfonate by treatment with a base and the appropriate sulfonyl chloride, followed by reaction with ammonia or a primary or secondary amine $HNR^8R^9$ to provide the amine 15. Alternatively, an acid 8a (R=H) can be converted to a ketone 16 using any of a number of methods known in the literature, for example by coupling with N,O-dimethylhydroxylamine in the presence of a suitable amide coupling reagent such as BOP or HATU to give the corresponding N,O-dimethylhydroxamide (known as a Weinreb amide), followed by treatment with an organometallic reagent such as an alkylmagnesium halide or an alkyllithium to provide 16. Treatment of the ketone with ammonia or a primary amine in the presence of a reducing agent such as sodium cyanoborohydride or sodium triacetoxyborohydride can then provide the amine 17.

SCHEME 5

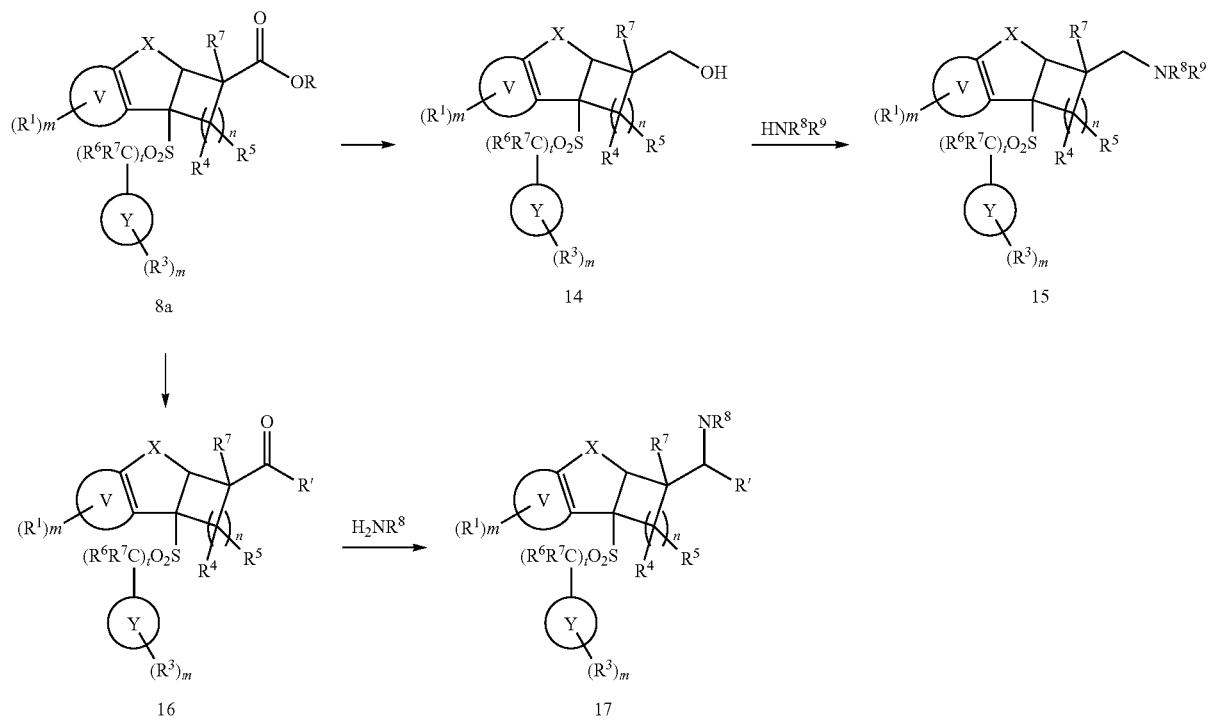

Methods for the preparation of certain amine compounds of the present invention are illustrated in Scheme 6. A sulfone 3 can be treated with a vinylic organometallic compound such as vinylmagnesium bromide or a vinyllithium, optionally in the presence of a copper reagent such as copper(I) bromide or copper(I) iodide, to provide olefin 18 (see, for example, *J. Organometallic Chem.* 2001, 624, 380; *Tetrahedron* 2000, 56, 7715; or *J. Org. Chem.* 2009, 74, 4188). The olefin can be converted to an epoxide 19, for example by treatment with an oxidizing reagent such as m-chloroperoxybenzoic acid, or by conversion to a bromohydrin, for example by treatment with a brominating agent such as N-bromosuccinimide in the presence of water, followed by treatment with a base such as potassium carbonate (see, for example, *J. Org. Chem.* 1986, 51, 5447). Treatment of the epoxide with a suitable base such as methylmagnesium bromide or potassium tert-butoxide can provide cyclopropyl carbinol 20, cyclobutanol 21, or a mixture of 20 and 21 (see, for example, PCT Int. Appl. 2010/068564). The carbinol 20 can be converted to an amine 22 using methods known in the literature, for example by conversion of the hydroxy to a leaving group such as a methanesulfonate by treatment with methanesulfonyl chloride and a base such as triethylamine, followed by treatment with an amine; or by oxidation of the carbinol to an aldehyde using a reagent such as pyridinium chlorochromate followed by treatment with an amine in the presence of a reducing agent such as sodium cyanoborohydride or sodium triacetoxyborohydride. Likewise, the carbinol 21 can be converted to the amine 23 using similar methods.

SCHEME 6

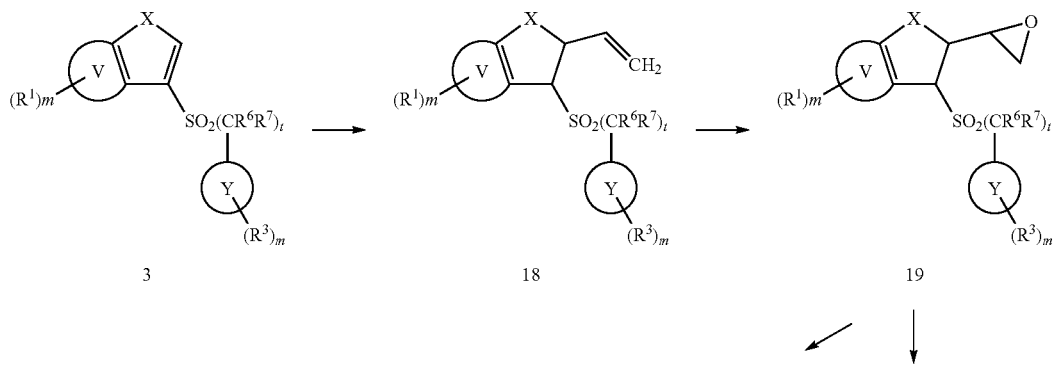

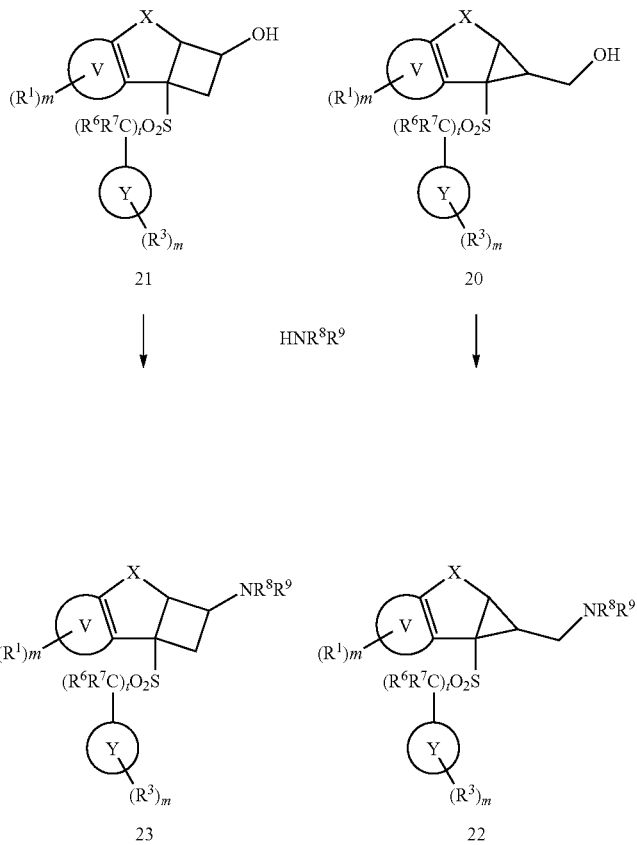

A variety of methods well known in the literature can be used for conversion of amines of the present invention to other compounds of the present invention. Some examples are shown in Scheme 7, starting from an amine 13 for illustrative purposes. An amine 13 can be treated with an acid anhydride (RC(=O))$_2$O or an acid chloride RC(=O)Cl in the presence of a base such as triethylamine or pyridine to provide an amide 24. Alternatively, an amine 13 can be treated with an acid RC(=O)OH in the presence of a suitable base and a coupling reagent such as (benzotriazol-1-yloxy)tris(dimethylamino)phosphonium hexafluorophosphate (BOP), O-(7-azabenzotriazol-1-yl)-1, 1,3,3-tetramethyluronium hexafluorophosphate (HATU), benzotriazol-1-yl-oxytripyrrolidinophosphonium hexafluorophosphate (PyBOP), or a combination of 1-hydroxybenzotriazole (HOBT) and N-(3-dimethylaminopropyl)-N'-ethylcarbodiimide (EDC) to provide an amide 24. An amine 13 can also be treated with a sulfonyl chloride RSO$_2$Cl in the presence of a suitable base to provide a sulfonamide 25. Amine 13 can also be treated with an isocyanate RN=C=O to provide a urea 26 (where R' is H), or with an aminocarbonyl chloride RN(R')C(=O)Cl to provide a urea 26. Alternatively, an amine 13 can be treated with phosgene or triphosgene to provide the intermediate N-chlorocarbonyl derivative, which can then be treated with an amine RN(R')H to provide a urea 26. An amine 13 can be treated with a sulfamyl chloride RN(R')SO$_2$Cl to provide a sulfamide 27. Alternatively, an amine 13 can be treated with sulfuric diamide to provide a sulfamide 27 where R and R' are both H. An amine 13 can be treated with an appropriate substituted or unsubstituted alkyl halide, cycloalkyl halide, or arylalkyl halide RC(R')(H)X' where X' is Br, I or Cl, or with a related alkyl group containing another leaving group X' such as methanesulfonate or trifluoromethanesulfonate, in the presence of a suitable base, to provide an alkylated amine 28. Alternatively, an amine 13 can be treated with an aldehyde RCHO or a ketone RC(=O)R', in the presence of a reducing agent such as sodium cyanoborohydride or sodium triacetoxyborohydride, to provide an alkylated amine 28 (where R' is H if an aldehyde is used). An amine 13 can be treated with an aryl or heteroaryl iodide ArI, an aryl or heteroaryl bromide ArBr, an aryl or heteroaryl chloride ArCl, or an aryl or heteroaryl trifluoromethanesulfonate ArOS(=O)$_2$CF$_3$ in the presence of a suitable palladium catalyst to provide an arylamine 29 (a reaction commonly known as the Buchwald-Hartwig coupling; see, for example, *Chem. Sci.* 2011, 2, 27; *Acc. Chem. Res.* 1998, 31, 805; *Angew. Chem. Int. Ed.* 2008, 47, 6338).

SCHEME 7
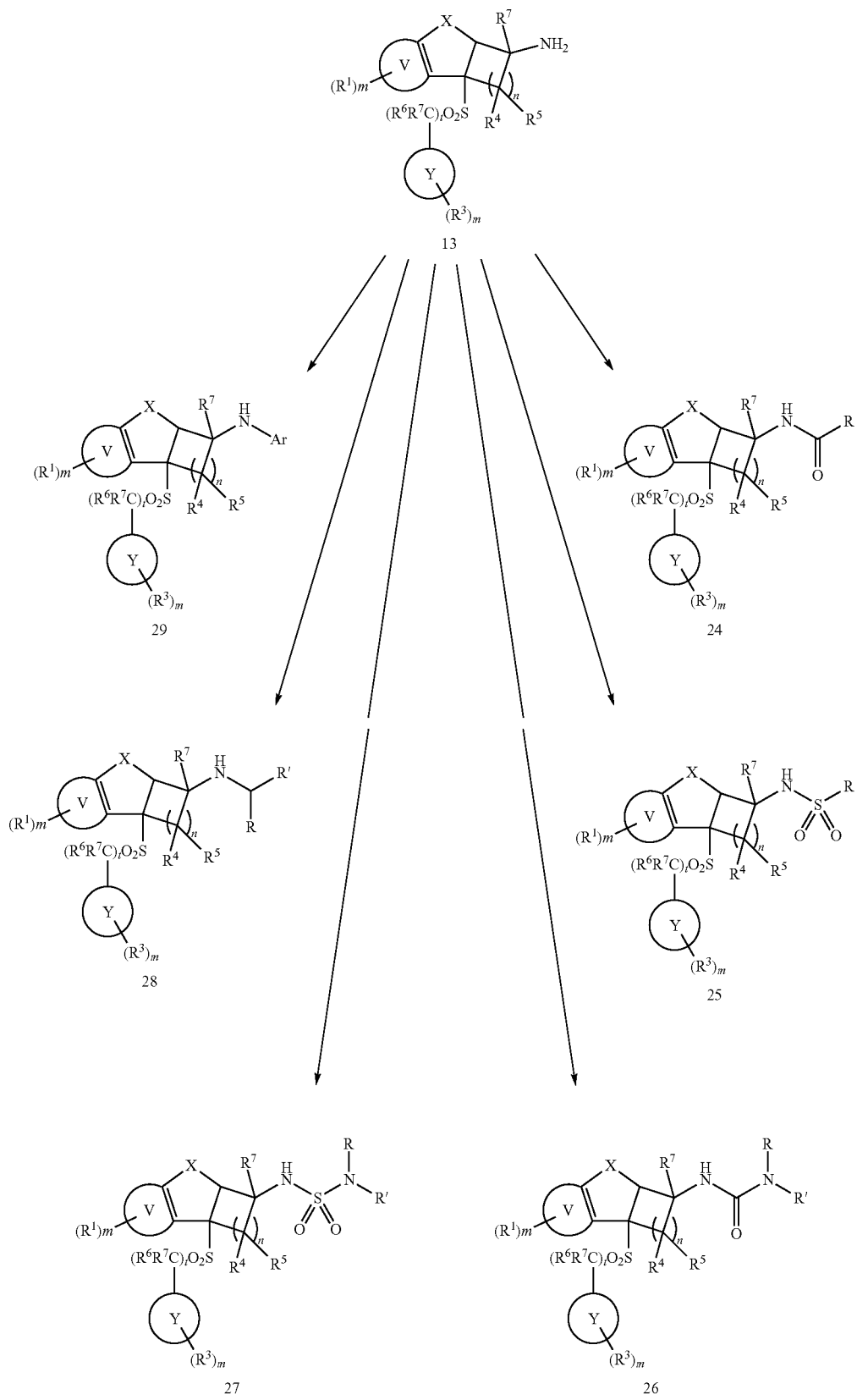

Many additional methods known in the literature can be used to modify intermediates or compounds of the present invention, converting them into other intermediates or compounds of the present invention. For example, by way of illustration, Scheme 8 shows some methods which can provide access to intermediates through modification of compounds 8. Compound 29, wherein $R^1$ is a halide such as Cl, Br or I, can be transformed into compounds 30, where $R^{1'}$ is a different substituent. Some examples, not intended to be limiting, are: (1) treatment with an aryl or alkenyl boronic acid or boronate ester in the presence of a suitable palladium catalyst, commonly known as the Suzuki coupling (see, for example, *Chem. Rev.* 1979, 95, 2457; *J. Organometallic Chem.* 1999, 576, 147), to give 30 where $R^{1'}$ can be aryl, heteroaryl or alkenyl (the latter of which can be further converted to the corresponding alkyl by catalytic reduction); (2) treatment with a zinc reagent such as zinc(II) cyanide or an alkyl- or cycloalkylzinc halide in the presence of a suitable palladium catalyst, commonly known as the Negishi coupling (see, for example, *Metal-Catalyzed Cross-Coupling Reactions* ($2^{nd}$ edition), 2004, 815), to give 30 where $R^{1'}$ can be, for example, alkyl, cycloalkyl or cyano; (3) treatment with an amine or amide in the presence of a suitable palladium catalyst, commonly known as the Buchwald-Hartwig coupling (see, for example, *Chem. Sci.* 2011, 2, 27; *Acc. Chem. Res.* 1998, 31, 805; *Angew. Chem. Int. Ed.* 2008, 47, 6338), to give 30 where $R^{1'}$ can be, for example, dialkylamino; (4) treatment with an organomagnesium halide in the presence of a suitable iron catalyst (see, for example, Org. React. 2014, 83, 1; *J. Am. Chem. Soc.*, 2002, 13856), to give 30 where $R^{1'}$ can be, for example, methyl or trideuteromethyl; (5) treatment with a fluorinated alkyl halide in the presence of a copper catalyst (see, for example, *Tetrahedron* 1969, 25, 5921; *Angew. Chem. Int. Ed.* 2011, 50, 3793), to give 30 where $R^{1'}$ can be, for example, trifluoromethyl, heptafluoropropyl, heptafluoroisopropyl, or the like; or (6) treatment with copper(I) halide to give 30 where $R^{1'}$ is a different halide from $R^1$ in 29; or (7) treatment with palladium catalyst in the presence of a base such as KOH (*J. Am. Chem. Soc.*, 2006, 128 10694) to yield a phenol which can be further derivatized for example with a substituted benzyl halide to give 30 where $R^{1'}$, for example, is OH or substituted or unsubstituted O-benzyl; or (8) treatment with an alkyllithium reagent to provide the corresponding aryllithium, followed by treatment with an aldehyde or ketone to give 30 where $R^{1'}$, for example, is a carbinol; or (9) treatment with a suitable reducing agent such as lithium tri-tert-butoxyaluminum hydride in the presence of a catalyst such as a nickel catalyst to give 30 where $R^{1'}$ is H. The same or similar methods can also be applied to a tricyclic 31 wherein $R^3$ is a halide such as Cl, Br or I to give the corresponding 32 where $R^{3'}$ is a different group, as described above.

SCHEME 8

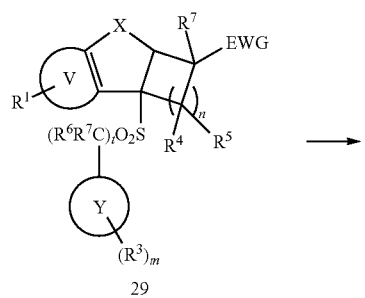

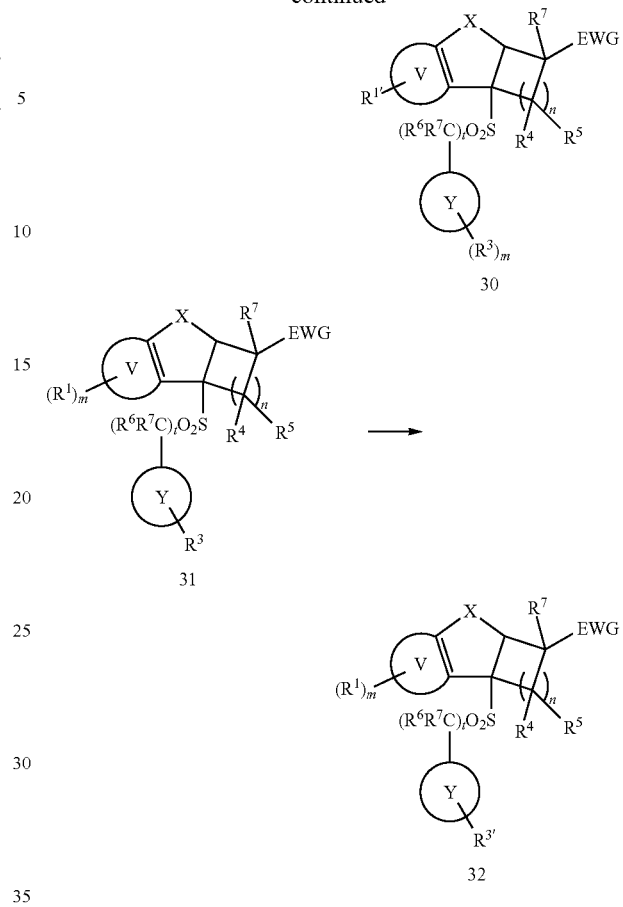

Many other simple functional group manipulations, well known to those skilled in the art of organic chemistry, can be used to convert an intermediate or compound of the present invention to a different intermediate or compound of the present invention. Examples include those methods described in Schemes 7 and 8, as well as others, including but not limited to: reduction of an ester or acid to a carbinol by treatment with a reagent such as lithium aluminum hydride or lithium borohydride; conversion of an ester to a tertiary carbinol by treatment with an organometallic reagent such as an alkylmagnesium halide or an alkyllithium; conversion of a carbinol to a fluoride by treatment with a reagent such as dimethylaminosulfur trifluoride (DAST); conversion of a carbinol to an ester by treatment with an acyl chloride or an acyl anhydride; conversion of a carbinol to a phosphate by treatment with a suitable phosphorus reagent such as dibenzyl diisopropylphorphoramidite in the presence of 5-methyl-1H-tetrazole followed by oxidation with hydrogen peroxide and subsequent reductive debenzylation; or alkylation on nitrogen by treatment with an olefin substituted with an electron-withdrawing group such as cyano or a carboxylate ester. Also, it will be appreciated by one skilled in the art of organic chemistry that various steps in a synthesis may be performed in an alternative sequence from that described in order to give a desired compound or compounds.

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common Intermediates are generally useful for the preparation of more than one Example and are identified sequentially by the Intermediate number and step in which they were prepared (e.g., Intermediate 1, Step A), or by the Intermediate number only where the compound is the title compound. Compounds of the Examples are identified by the Example number and step in which they were prepared (e.g., Example 1, Step A) if the compound is an intermediate, or by the Example number only where the compound is the title compound of the Example. In some instances alternative preparations of Intermediates or Examples are described. Frequently chemists skilled in the art of synthesis may devise alternative preparations which may be desirable based on one or more considerations such as shorter reaction time, less expensive starting materials, ease of operation or isolation, improved yield, suitability to catalysis, avoidance of toxic reagents, accessibility of specialized instrumentation, decreased number of linear steps, etc. The intent of describing alternative preparations is to further enable the preparation of the Examples of this invention. In some instances some functional groups in the outlined Examples and claims may be replaced by well-known bioisosteric replacements known in the art, for example, replacement of a carboxylic acid group with a tetrazole or a phosphate moiety. Starting materials and intermediates for which no preparation is explicitly shown are available commercially, are known in the literature, or may be prepared by analogy to similar compounds which are known in the literature.

Drying of organic solutions to remove residual water was done by allowing to stand over anhydrous sodium sulfate or anhydrous magnesium sulfate, followed by decantation or filtration. Solvent removal was performed by concentration under reduced pressure. Column chromatography was generally performed with pre-packed silica gel cartridges using a CombiFlash® automated chromatography apparatus (Teledyne Isco), eluting with the solvent or solvent mixture indicated. Analytical and preparative high performance liquid chromatography (HPLC) was generally performed using a reverse phase column of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chiral supercritical fluid chromatographic (SFC) separation of enantiomers or diastereomers was performed using conditions described for the individual cases. Mass spectral data were obtained by liquid chromatography mass spectroscopy (LCMS) using electrospray ionization.

Many Intermediates and Examples are homochiral (entirely or mostly a single enantiomer). If the absolute configuration at an asymmetric center of an Intermediate or Example is known, or that asymmetric center is derived from a precursor whose absolute configuration is known, this is explicitly shown in the structure of the Intermediate or Example. In some cases an Intermediate or Example is homochiral but the absolute configuration has not been proven at all asymmetric centers. In those cases, the stereochemistry at the unknown asymmetric center is not explicitly shown, and a text notation below the structure will indicate that the compound is homochiral and that the compound was obtained from the specified peak eluting during chiral SFC separation. For example, the structure 94 shown below indicates that, while the material is homochiral, the absolute configuration at two asymmetric centers of the material, which was derived from the first-eluting peak during SFC separation, is not known, but the material has one of the absolute configurations shown in 94a, 94b, 94c, or 94d.

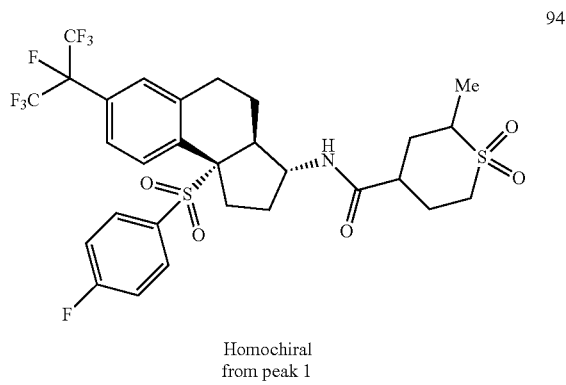

Homochiral from peak 1

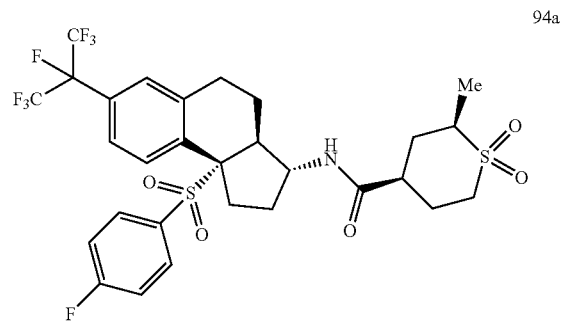

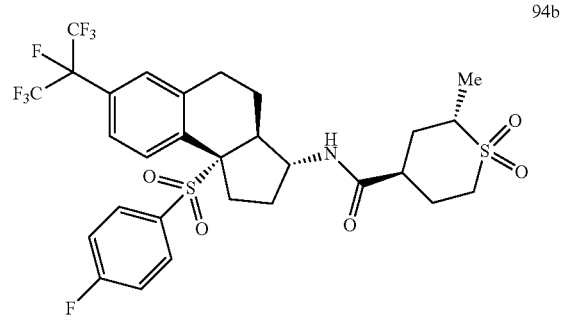

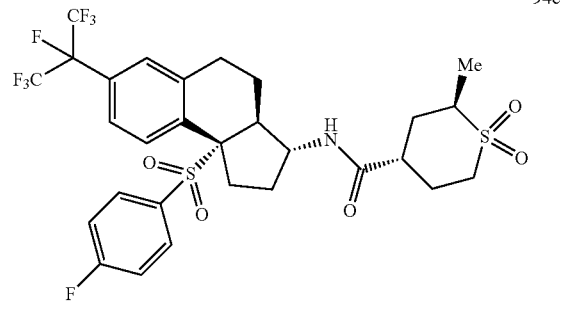

-continued

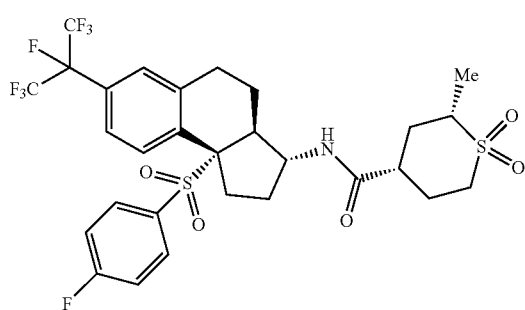

94d

In some cases an Intermediate or Example is a mixture of diastereomers with one, some, or all of the asymmetric centers being either of undefined absolute configuration or a mixture of both absolute configurations. In those cases a text notation below the structure will indicate that the compound is a mixture of diastereomers.

Chemical names were determined using ChemBioDraw Ultra, version 14.0.0.126 (PerkinElmer Inc.). The following abbreviations are used:

| ABBREVIATION | NAME |
| --- | --- |
| BINAP | 2,2'-bis(diphenylphosphino)-1,1'-binaphthalene |
| BOP | benzotriazole-1-yl-oxy-tris(dimethylamino)-phosphonium hexafluorophosphate |
| DAST | (diethylamino)sulfur trifluoride |
| DCM | dichloromethane |
| DIEA | diisopropylethylamine (Hunig's base) |
| DMF | N,N-dimethylformamide |
| DMSO | dimethyl sulfoxide |
| EDC | N-(3-dimethylaminopropyl)-N'-ethylcarbodiimide |
| EtOAc | ethyl acetate |
| h | hours |
| HATU | O-(7-azabenzotriazol-1-yl)-1,1,3,3-tetramethyluronium hexafluorophosphate |
| HOBT | 1-hydroxybenzotriazole |
| HPLC | high performance liquid chromatography |
| IPA | 2-propanol |
| LCMS | liquid chromatography - mass spectrometry |
| LDA | lithium diisopropylamide |
| mCPBA | m-chloroperoxybenzoic acid |
| MeCN | acetonitrile |
| MeOH | methanol |
| min | minutes |
| MsCl | methanesulfonyl chloride |
| rt | room temperature |
| SFC | super-critical fluid chromatography |
| TEA | triethylamine |
| TFA | trifluoroacetic acid |
| THF | tetrahydrofuran |
| $t_R$ | chromatographic retention time |

HPLC Methods

Method A: (Analytical)

Column: Acquity UPLC® BEH $C_{18}$ 2.1×50 mm, 1.7 μm (Waters Corp.); mobile phase A: water with 0.05% TFA; mobile phase B: MeCN with 0.05% TFA; temperature: 50° C.; flow rate 0.80 mL/min; gradient: 2-98% B over 1 min, then 0.5 min isocratic at 98% B.

Method B: (Analytical)

Column: Acquity UPLC® BEH $C_{18}$ 2.1×50 mm, 1.7 μm (Waters Corp.); mobile phase A: 5:95 MeCN-water with 10 mM ammonium acetate; mobile phase B: 95:5 MeCN-water with 10 mM ammonium acetate; temperature: 50° C.; flow rate 1.0 mL/min; gradient: 0-100% B over 3 min, then 0.75 min isocratic at 100% B.

Method C: (Analytical)

Column: Acquity UPLC® BEH $C_{18}$ 2.1×50 mm, 1.7 μm (Waters Corp.); mobile phase A: 5:95 MeCN-water with 0.1% TFA; mobile phase B: 95:5 MeCN-water with 0.1% TFA; temperature: 50° C.; flow rate 1.0 mL/min; gradient: 0-100% B over 3 min, then 0.75 min isocratic at 100% B.

Method D: (Analytical)

Column: Kinetex® $C_{18}$ 2.1×50 mm, 2.6 μm (Phenomenex Inc.); mobile phase A: 10:90 MeCN-water with 0.1% TFA; mobile phase B: 90:10 MeCN-water with 0.1% TFA; temperature: 40° C.; flow rate 1.0 mL/min; gradient: 0-100% B over 1.5 min, then isocratic at 100% B.

Method E: (Preparative)

Column: XBridge™ $C_{18}$ 19×200 mm, 5 μm (Waters Corp.); mobile phase A: 5:95 MeCN-water with 10 mM ammonium acetate; mobile phase B: 95:5 MeCN-water with 10 mM ammonium acetate; flow rate 20 mL/min; gradient: increasing B, then isocratic at 100% B.

Method F: (Preparative)

Column: XBridge™ $C_{18}$ 19×200 mm, 5 μm (Waters Corp.); mobile phase A: 5:95 MeCN-water with 0.1% TFA; mobile phase B: 95:5 MeCN-water with 0.1% TFA; flow rate 20 mL/min; gradient: increasing B, then isocratic at 100% B.

Method G: (Preparative)

Column: Sunfire™ $C_{18}$ 19×200 mm, 5 m (Waters Corp.); mobile phase A: 10:90 MeCN-water with 0.1% TFA; mobile phase B: 90:10 MeCN-water with 0.1% TFA; flow rate 20 mL/min; gradient: increasing B, then isocratic at 100% B.

Intermediates 1-4 ethyl 9b-((4-fluorophenyl)sulfonyl)-7-iodo-2,3,3a,4,5,9b-hexahydro-1H-cyclopenta[a]naphthalene-3-carboxylate (four single enantiomers)

Intermediate 1

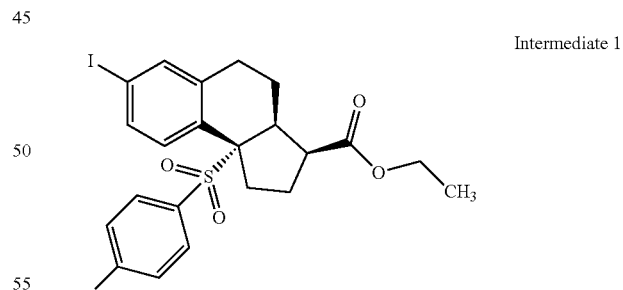

Intermediate 2

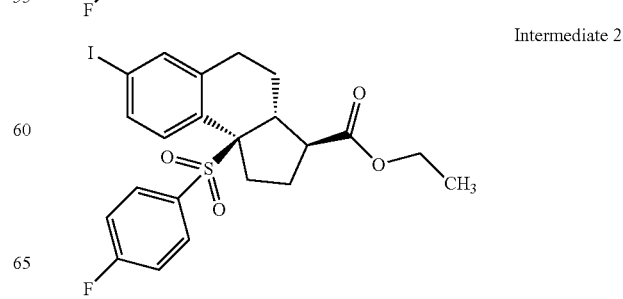

-continued

Intermediate 3

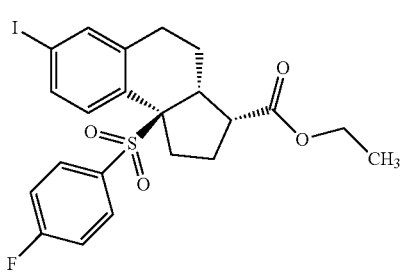

Intermediate 4

Step A: 4-((4-fluorophenyl)sulfonyl)-7-iodo-1,2-dihydronaphthalene

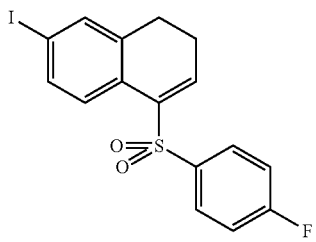 [SMILES: O=S(=O)(C1=CCCc2cc(I)ccc21)c1ccc(F)cc1]

A solution of 6-iodo-3,4-dihydronaphthalen-1(2H)-one (13.3 g, 48.9 mmol) and TiCl$_4$ (1 M in DCM; 48.9 mL, 48.9 mmol) in THF (326 mL) in an ice-water bath was treated with a solution of 4-fluorobenzenethiol (6.3 mL, 58.7 mmol) and Et$_3$N (13.6 mL, 98.0 mmol) in THF (25 mL) at a rate such that the temperature remained below 10° C. The solution was stirred at rt for 60 min, treated with water (200 mL) and concentrated to remove the bulk of the organic solvent. The aqueous residue was extracted with diethyl ether (2×250 mL). The combined organic layers were dried and concentrated to provide crude (4-fluorophenyl)(6-iodo-3,4-dihydronaphthalen-1-yl)sulfane (20 g) as a mixture with (6-iodo-1,2,3,4-tetrahydronaphthalene-1,1-diyl)bis((4-fluorophenyl)sulfane), which was used directly. HPLC $t_R$ 1.36 min (method B).

A solution of the mixture from the above reaction (18.7 g) in DCM (978 mL) was cooled on an ice-water bath and was treated portionwise with mCPBA (21.9 g, 98.0 mmol). The mixture was allowed to warm to rt and was stirred for 1 h, when LCMS showed consumption of the starting material and 4-((4-fluorophenyl)sulfinyl)-7-iodo-1,2-dihydronaphthalene as the major product. Additional mCPBA (11.0 g, 48.9 mmol) was added at rt. The mixture was stirred for 30 min, when LCMS showed very little sulfoxide ($t_R$ 1.00 min, method B). The mixture was washed twice with saturated aqueous NaHCO$_3$, and the organic phase was dried and concentrated. The residue was purified by column chromatography, eluting with EtOAc-hexanes (gradient from 0-10%). The resulting material was dissolved in EtOAc and washed twice with saturated aqueous NaHCO$_3$. The organic phase was dried and concentrated to provide 4-((4-fluorophenyl)sulfonyl)-7-iodo-1,2-dihydronaphthalene as a white amorphous solid (12.0 g, 59% yield over two steps). LCMS m/z 455.9 (M+H+MeCN)$^+$, HPLC $t_R$ 1.09 min (method A). $^1$H NMR (400 MHz, CDCl$_3$) δ 7.97-7.89 (m, 2H), 7.64 (d, J=8.8 Hz, 1H), 7.57-7.47 (m, 3H), 7.22-7.13 (m, 2H), 2.79-2.68 (m, 2H), 2.61-2.50 (m, 2H). $^{19}$F NMR (471 MHz, CDCl$_3$) δ −102.7 (s, 1F).

Alternative Procedure:

A solution of 6-iodo-3,4-dihydronaphthalen-1(2H)-one (5.0 g, 18.4 mmol), 4-fluorobenzenethiol (4.1 mL, 38.6 mmol) and absolute ethanol (20 mL) was cooled on an ice-water bath and bubbled with HCl gas until saturation was reached (observed by the formation of a white precipitate). The mixture was allowed to warm to rt and stirred overnight. The mixture was dissolved in diethyl ether (250 mL) and washed sequentially with water (2×125 mL), 0.5 M aqueous Na$_2$CO$_3$ (3×100 mL) and brine (100 mL). The organic layer was dried and concentrated to provide a solid (9.20 g) which was a mixture of (4-fluorophenyl)(6-iodo-3,4-dihydronaphthalen-1-yl)sulfane and (6-iodo-1,2,3,4-tetrahydronaphthalene-1,1-diyl)bis((4-fluorophenyl)sulfane).

The solid was dissolved in chloroform (150 mL) and cooled in an ice-water bath. A solution of mCPBA (35.0 g, 156 mmol) in DCM (200 mL) was washed with brine (50 mL), dried over Na$_2$SO$_4$, filtered, and the filter cake was washed with DCM (50 mL). The combined filtrates were added dropwise in portions to the chloroform solution of the mixture of (4-fluorophenyl)(6-iodo-3,4-dihydronaphthalen-1-yl)sulfane and (6-iodo-1,2,3,4-tetrahydronaphthalene-1,1-diyl)bis((4-fluorophenyl)sulfane) until the reaction was completed as judged by LCMS (175 mL of the mCPBA solution was needed). The mixture was cooled in an ice bath, filtered to remove the insoluble material, and the filtrate was stirred with 10% aqueous Na$_2$S$_2$O$_3$ (120 mL) for 5 min. The organic phase was separated, washed sequentially with 10% aqueous Na$_2$S$_2$O$_3$ (2×120 mL), 10% aqueous Na$_2$CO$_3$ (3×200 mL) and brine (150 mL), dried and concentrated. The residue was purified by column chromatography on silica gel, eluting with EtOAc-hexanes (gradient from 0-20%) to give 4-((4-fluorophenyl)sulfonyl)-7-iodo-1,2-dihydronaphthalene (5.3 g, 70% yield) as a white amorphous solid.

Step B: ethyl 9b-((4-fluorophenyl)sulfonyl)-7-iodo-2,3,3a,4,5,9b-hexahydro-1H-cyclopenta[a]naphthalene-3-carboxylate (four single enantiomers)

Intermediate 1

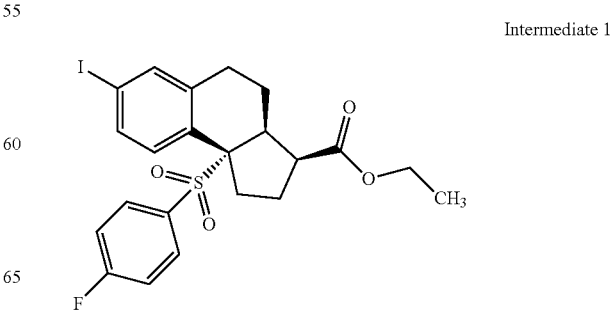

-continued

Intermediate 2

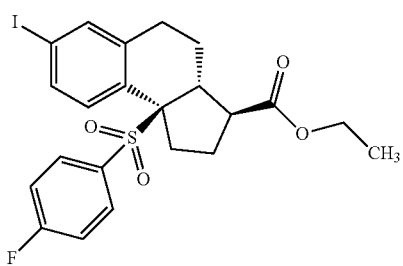

Intermediate 3

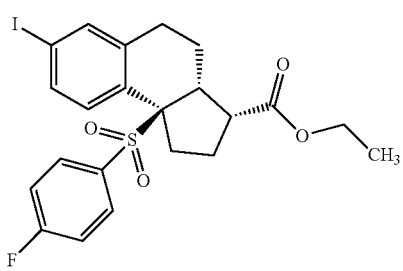

Intermediate 4

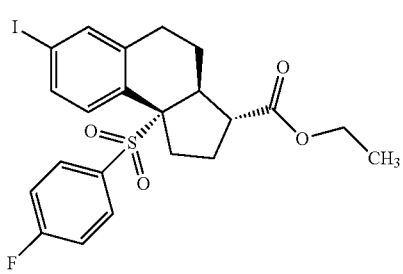

A solution of ethyl 4-chlorobutanoate (4.9 mL, 35 mmol) and 4-((4-fluorophenyl)sulfonyl)-7-iodo-1,2-dihydronaphthalene (4.8 g, 12.0 mmol) in THF (120 mL) was cooled to −78° C. and treated dropwise with LDA (1.0 M in THF; 35 mL, 35 mmol). The mixture was stirred at −78° C. for 45 min, then was treated with saturated aqueous NH$_4$Cl. The mixture was warmed to rt, diluted with EtOAc and washed with saturated aqueous NH$_4$Cl. The organic layer was dried and concentrated. The residue was subjected to column chromatography on silica gel, eluting with EtOAc-hexanes, to provide a mixture of diastereomers of ethyl 9b-((4-fluorophenyl)sulfonyl)-7-iodo-2,3,3a,4,5,9b-hexahydro-1H-cyclopenta[a]naphthalene-3-carboxylate (4.4 g, 72% yield). The material was separated by preparative chiral SFC on a Lux Cell-4 column (46×250 mm, 5 μm) at 35° C., eluting with CO$_2$-MeOH (80:20) at 100 bars, to provide 4 homochiral products:

Peak 1: ethyl (3S,3aS,9bS)-9b-((4-fluorophenyl)sulfonyl)-7-iodo-2,3,3a,4,5,9b-hexahydro-1H-cyclopenta[a]naphthalene-3-carboxylate (Intermediate 1, 789 mg). LCMS m/z 529.1 (M+H)$^+$; HPLC t$_R$ 1.16 min (Method B). $^1$H NMR (400 MHz, CDCl$_3$) δ 7.66-7.58 (m, 1H), 7.37 (br d, J=8.5 Hz, 1H), 7.32-7.25 (m, 3H), 7.12-6.98 (m, 2H), 4.26-4.11 (m, 2H), 3.52 (dt, J=11.5, 7.3 Hz, 1H), 3.15-3.02 (m, 2H), 2.49-2.41 (m, 1H), 2.39-2.32 (m, 1H), 2.25-2.11 (m, 1H), 2.11-1.91 (m, 1H), 1.81-1.68 (m, 1H), 1.60-1.45 (m, 1H), 1.35-1.23 (m, 3H), 1.23-1.09 (m, 1H). $^{19}$F NMR (471 MHz, CDCl$_3$) δ −103.1 (s, 1F). The absolute configuration was determined by single crystal X-ray analysis of Example 21, from the anomalous dispersion signal using the Flack method (*Acta Cryst.* B, 2013, 69, 249.)

Peak 2: ethyl (3S,3aR,9bR)-9b-((4-fluorophenyl)sulfonyl)-7-iodo-2,3,3a,4,5,9b-hexahydro-1H-cyclopenta[a]naphthalene-3-carboxylate (Intermediate 2, 1.9 g). LCMS m/z 529.1 (M+H)$^+$; HPLC t$_R$ 1.16 min (Method A). $^1$H NMR (499 MHz, CDCl$_3$) δ 7.54 (dd, J=8.2, 1.4 Hz, 1H), 7.40-7.33 (m, 3H), 7.09-7.02 (m, 3H), 4.27-4.09 (m, 2H), 3.36 (ddd, J=10.0, 8.4, 6.5 Hz, 1H), 3.18 (ddd, J=13.9, 7.2, 2.5 Hz, 1H), 2.62 (dt, J=10.3, 8.0 Hz, 1H), 2.47-2.33 (m, 2H), 2.19-2.11 (m, 2H), 2.09-2.01 (m, 1H), 1.93 (ddd, J=15.6, 11.7, 3.9 Hz, 1H), 1.34-1.13 (m, 3H), 1.11-1.01 (m, 1H). $^{19}$F NMR (471 MHz, CDCl$_3$) δ −103.1 (s, 1F). The absolute configuration was determined by single crystal X-ray analysis of Example 2, from the anomalous dispersion signal using the Flack method.

Peak 3: ethyl (3R,3aR,9bR)-9b-((4-fluorophenyl)sulfonyl)-7-iodo-2,3,3a,4,5,9b-hexahydro-1H-cyclopenta[a]naphthalene-3-carboxylate (Intermediate 3, 286 mg). LCMS m/z 529.1 (M+H)$^+$; HPLC t$_R$ 1.16 min (Method B). $^1$H NMR (499 MHz, CDCl$_3$) δ 7.66-7.58 (m, 1H), 7.37 (br d, J=8.5 Hz, 1H), 7.32-7.25 (m, 3H), 7.12-6.98 (m, 2H), 4.26-4.11 (m, 2H), 3.52 (dt, J=11.5, 7.3 Hz, 1H), 3.15-3.02 (m, 2H), 2.49-2.41 (m, 1H), 2.39-2.32 (m, 1H), 2.25-2.11 (m, 1H), 2.11-1.91 (m, 1H), 1.81-1.68 (m, 1H), 1.60-1.45 (m, 1H), 1.35-1.23 (m, 3H), 1.23-1.09 (m, 1H). $^{19}$F NMR (471 MHz, CDCl$_3$) δ −103.1 (s, 1F). The absolute configuration was determined by single crystal X-ray analysis of Example 9, from the anomalous dispersion signal using the Flack method.

Peak 4: ethyl (3R,3aS,9bS)-9b-((4-fluorophenyl)sulfonyl)-7-iodo-2,3,3a,4,5,9b-hexahydro-1H-cyclopenta[a]naphthalene-3-carboxylate (Intermediate 4, 1.8 g). LCMS m/z 529.1 (M+H)$^+$; HPLC t$_R$ 1.16 min (Method B). $^1$H NMR (499 MHz, CDCl$_3$) δ 7.54 (dd, J=8.2, 1.4 Hz, 1H), 7.40-7.33 (m, 3H), 7.09-7.02 (m, 3H), 4.27-4.09 (m, 2H), 3.36 (ddd, J=10.0, 8.4, 6.5 Hz, 1H), 3.18 (ddd, J=13.9, 7.2, 2.5 Hz, 1H), 2.62 (dt, J=10.3, 8.0 Hz, 1H), 2.47-2.33 (m, 2H), 2.19-2.11 (m, 2H), 2.09-2.01 (m, 1H), 1.93 (ddd, J=15.6, 11.7, 3.9 Hz, 1H), 1.34-1.13 (m, 3H), 1.11-1.01 (m, 1H). $^{19}$F NMR (471 MHz, CDCl$_3$) δ −103.1 (s, 1F). The absolute configuration was determined by single crystal X-ray analysis of Example 14, from the anomalous dispersion signal using the Flack method.

Intermediate 5

5-(tert-butyl) 3-ethyl (3R,3aR,9bS)-7-bromo-9b-((4-fluorophenyl)sulfonyl)-1,2,3,3a,4,9b-hexahydro-5H-cyclopenta[c]quinoline-3,5-dicarboxylate

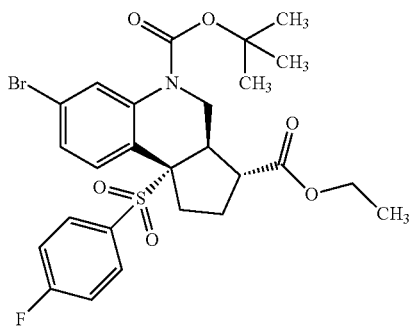 [SMILES: CCOC(=O)[C@@H]1CC[C@@]2(S(=O)(=O)c3ccc(F)cc3)c3ccc(Br)cc3N(C(=O)OC(C)(C)C)C[C@@H]12]

Step A: tert-butyl 7-bromo-4-((4-fluorophenyl)sulfonyl)quinoline-1(2H)-carboxylate

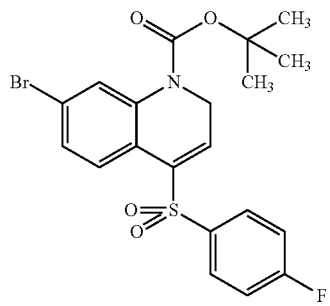 [SMILES: CC(C)(C)OC(=O)N1CC=C(S(=O)(=O)c2ccc(F)cc2)c2ccc(Br)cc21]

A solution of 7-bromo-2,3-dihydroquinolin-4(1H)-one (8.0 g, 35 mmol) and 4-fluorobenzenethiol (7.9 mL, 74 mmol) in ethanol (44 mL) was cooled on an ice-water bath. HCl gas was bubbled through the mixture until saturation was reached (as indicated by the formation of a white precipitate). The mixture was stirred on the ice-water bath for 1 h and at rt for 1 h more. The mixture was concentrated and the resulting oil was dissolved in DCM (250 mL), washed with 1 M aqueous NaOH, dried and concentrated to give crude 7-bromo-4,4-bis((4-fluorophenyl)thio)-1,2,3,4-tetrahydroquinoline as a solid (16.4 g, quantitative yield). HPLC $t_R$ 1.27 min (method B).

This material was dissolved in 1,4-dioxane (180 mL) and treated with 4-dimethylaminopyridine (13 g, 106 mmol) and di-tert-butyl dicarbonate (25 mL, 106 mmol). The mixture was stirred at rt for 16 h, then was diluted with EtOAc and washed twice with 1 M aqueous HCl. The organic phase was dried and concentrated to provide tert-butyl 7-bromo-4,4-bis((4-fluorophenyl)thio)-3,4-dihydroquinoline-1(2H)-carboxylate (20 g, quantitative yield). HPLC $t_R$ 1.37 min (method B).

This material was dissolved in DCM (350 mL) and cooled on an ice-water bath. mCPBA (22 g, 172 mmol) was added and the mixture was stirred for 1 h. Additional mCPBA (22 g, 172 mmol) was added, and stirring was continued for 1 h more. The mixture was filtered, and the filtrate was treated with 10% aqueous $Na_2S_2O_3$ (120 mL) and stirred for 5 min. The organic phase was separated, washed sequentially with 10% aqueous $Na_2S_2O_3$ (2×120 mL), 10% aqueous $Na_2CO_3$ (3×200 mL) and brine (150 mL), dried over $Na_2SO_4$ and concentrated to give crude tert-butyl 7-bromo-4-((4-fluorophenyl)sulfonyl)quinoline-1(2H)-carboxylate (17 g, quantitative yield) which was used without further purification. LCMS m/z 468.0 (M+H+MeCN)$^+$; HPLC $t_R$ 1.16 min (method B).

Step B: 5-(tert-butyl) 3-ethyl (3R,3aR,9bS)-7-bromo-9b-((4-fluorophenyl)sulfonyl)-1,2,3,3a,4,9b-hexahydro-5H-cyclopenta[c]quinoline-3,5-dicarboxylate

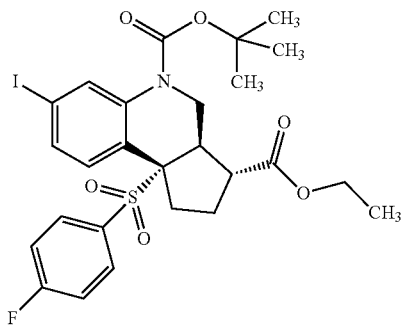 [SMILES: CCOC(=O)[C@@H]1CC[C@@]2(S(=O)(=O)c3ccc(F)cc3)c3ccc(I)cc3N(C(=O)OC(C)(C)C)C[C@@H]12]

A solution of ethyl 4-chlorobutanoate (6 mL, 43 mmol) and tert-butyl 7-bromo-4-((4-fluorophenyl)sulfonyl)quinoline-1(2H)-carboxylate (13 g, 28 mmol) in THF (240 mL) was cooled to −78° C. and treated dropwise with LDA (1 M in THF; 36 mL, 36 mmol). The mixture was stirred at −78° C. for 45 min, then was treated with saturated aqueous $NH_4Cl$. The aqueous phase was extracted twice with EtOAc, and the combined organic phases were dried and concentrated. The residue was subjected to column chromatography on silica gel, eluting with EtOAc-hexanes, to provide a mixture of diastereomers of 5-(tert-butyl) 3-ethyl 7-bromo-9b-((4-fluorophenyl)sulfonyl)-1,2,3,3a,4,9b-hexahydro-5H-cyclopenta[c]quinoline-3,5-dicarboxylate (8 g, 48% yield). This material was separated by preparative chiral SFC on a Chiralcel® IC column (46×250 mm, 5 μm; Chiral Technologies Inc.) at 35° C., eluting with $CO_2$-MeOH (81:19) at 320 mL/min and 140 bars. The fourth peak to elute ($t_R$ 7.11 min) provided 5-(tert-butyl) 3-ethyl (3R,3aR,9bS)-7-bromo-9b-((4-fluorophenyl)sulfonyl)-1,2,3,3a,4,9b-hexahydro-5H-cyclopenta[c]quinoline-3,5-dicarboxylate (2.4 g). LCMS m/z 366.0 (M-($C_6H_4FSO_2$+tBu)+H)$^+$, HPLC $t_R$ 1.11 min (method B). The absolute configuration was determined by single crystal X-ray analysis of Example 216, Step A, from the anomalous dispersion signal using the Flack method.

Intermediate 6 ethyl (3S,3aR,9bR)-9b-((4-fluorophenyl)sulfonyl)-7-(perfluoropropan-2-yl)-2,3,3a,4,5,9b-hexahydro-1H-cyclopenta[a]naphthalene-3-carboxylate

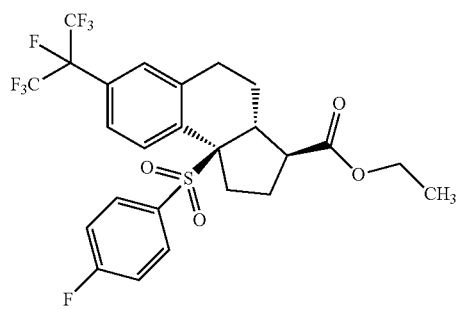 [SMILES: CCOC(=O)[C@H]1CC[C@]2(S(=O)(=O)c3ccc(F)cc3)c3ccc(C(F)(C(F)(F)F)C(F)(F)F)cc3CC[C@H]12]

Activated copper was prepared by adding zinc dust (24.6 g, 376 mmol) portionwise with stirring to a solution of $CuSO_4$ pentahydrate (45.1 g, 283 mmol) in water (250 mL) over 10 min. The mixture was stirred 10 min longer, then the supernatant was decanted from the red precipitate. This was washed twice with water by decantation, then was stirred with 1 M aqueous HCl (400 mL) for 2.5 h. The supernatant was decanted and the precipitate was washed repeatedly by decantation after stirring with fresh water until the pH of the supernatant was about 7. The solid was stored under water and an inert atmosphere (nitrogen or argon). For use the solid was washed twice by decantation from MeOH, then twice by decantation from diethyl ether, and dried under vacuum.

Dried activated copper (240 mg, 3.8 mmol) under nitrogen in a vial was purged of air by evacuation and back-filling with nitrogen. A solution of ethyl (3S,3aR,9bR)-9b-((4-fluorophenyl)sulfonyl)-7-iodo-2,3,3a,4,5,9b-hexahydro-1H-cyclopenta[a]naphthalene-3-carboxylate (Intermediate 2; 200 mg, 0.38 mmol) in DMF (1.9 mL) was added, followed by 1,1,1,2,3,3,3-heptafluoro-2-iodopropane (270

μL, 1.9 mmol). The vial was sealed under a nitrogen atmosphere and heated to 120° C. for 4 h. The mixture was cooled to rt, diluted with EtOAc and filtered through Celite. The solids were washed with EtOAc and the combined filtrates were washed 4 times with brine, dried and concentrated. The residue was subjected to column chromatography on silica gel, eluting with EtOAc-hexanes, to provide ethyl (3S,3aR,9bR)-9b-((4-fluorophenyl)sulfonyl)-7-(perfluoropropan-2-yl)-2,3,3a,4,5,9b-hexahydro-1H-cyclopenta[a]naphthalene-3-carboxylate (150 mg, 70% yield). LCMS m/z 571.1 (M+H)$^+$; HPLC t$_R$ 1.20 min (Method B). $^1$H NMR (500 MHz, DMSO-d$_6$) δ 7.47 (d, J=8.1 Hz, 1H), 7.43-7.33 (m, 2H), 7.25 (d, J=7.0 Hz, 4H), 4.14 (q, J=7.0 Hz, 2H), 3.28-3.20 (m, 1H), 3.04 (br dd, J=14.2, 5.6 Hz, 1H), 2.86-2.71 (m, 1H), 2.68-2.54 (m, 1H), 2.37-2.21 (m, 1H), 2.16 (br d, J=6.4 Hz, 1H), 2.13-2.04 (m, 1H), 2.01-1.94 (m, 2H), 1.28-1.18 (m, 4H). $^{19}$F NMR (471 MHz, CDCl$_3$) δ −103.1 (s, 1F), −75.1 (m, 6F), −75.0 (m, 1F).

The Intermediates in Table 1 were prepared using the procedures used to prepare Intermediate 6, or similar procedures, from the appropriate precursors.

TABLE 1

| Intermediate number | Structure | LCMS m/z observed | HPLC t$_R$ (min) | HPLC method |
|---|---|---|---|---|
| 7 | 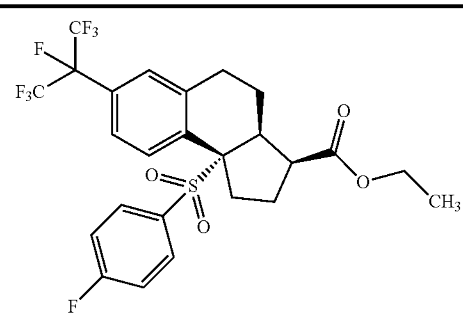 | 571.2 (M + H)$^+$ | 1.20 | B |
| 8 | 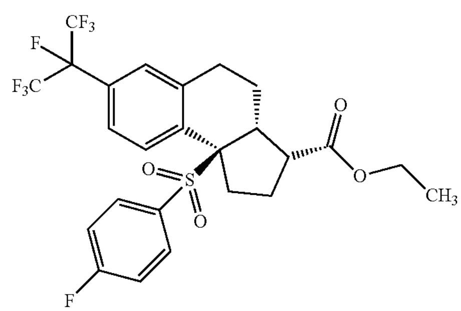 | 571.2 (M + H)$^+$ | 1.20 | B |
| 9 | 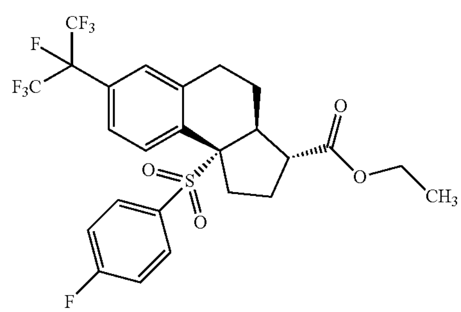 [SMILES: CCOC(=O)[C@@H]1CC[C@@]2(S(=O)(=O)c3ccc(F)cc3)c3ccc(C(F)(C(F)(F)F)C(F)(F)F)cc3CC[C@@H]12] | 571.2 (M + H)$^+$ | 1.20 | B |
| 10 | 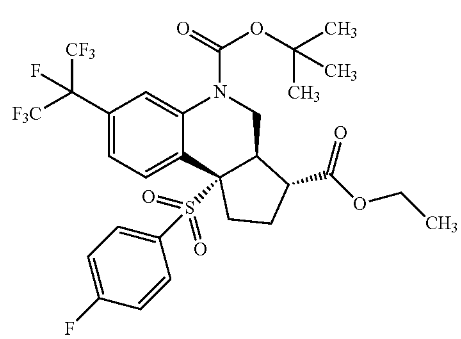 [SMILES: CCOC(=O)[C@@H]1CC[C@@]2(S(=O)(=O)c3ccc(F)cc3)c3ccc(C(F)(C(F)(F)F)C(F)(F)F)cc3N(C(=O)OC(C)(C)C)C[C@@H]12] | 616.0 (M + H − C$_4$H$_8$)$^+$ | 1.23 | A |

Intermediate 11

(3S,3aR,9bR)-9b-((4-fluorophenyl)sulfonyl)-7-(perfluoropropan-2-yl)-2,3,3a,4,5,9b-hexahydro-1H-cyclopenta[a]naphthalene-3-carboxylic acid

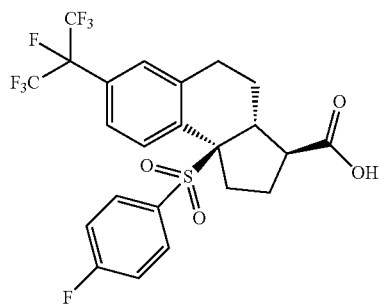 [SMILES: O=C(O)[C@H]1CC[C@]2(S(=O)(=O)c3ccc(F)cc3)c3ccc(C(F)(C(F)(F)F)C(F)(F)F)cc3CC[C@H]12]

A solution of ethyl (3S,3aR,9bR)-9b-((4-fluorophenyl)sulfonyl)-7-iodo-2,3,3a,4,5,9b-hexahydro-1H-cyclopenta[a]naphthalene-3-carboxylate (Intermediate 6; 140 mg, 0.25 mmol) in a mixture of THF (2.5 mL) and water (1.2 mL) was treated with LiOH hydrate (59 mg, 2.5 mmol). The reaction was heated to 65° C. and stirred for 1 h. The mixture was cooled to rt, diluted with EtOAc and washed with 1 M aqueous HCl. The organic layer was dried and concentrated to provide (3S,3aR,9bR)-9b-((4-fluorophenyl)sulfonyl)-7-(perfluoropropan-2-yl)-2,3,3a,4,5,9b-hexahydro-1H-cyclopenta[a]naphthalene-3-carboxylic acid (133 mg, 99% yield), used without further purification. LCMS m/z 543.1 (M+H)$^+$; HPLC $t_R$ 1.08 min (Method B). $^1$H NMR (500 MHz, DMSO-d$_6$) δ 7.47-7.37 (m, 2H), 7.37-7.25 (m, 5H), 3.04-2.91 (m, 2H), 2.64 (br d, J=16.2 Hz, 1H), 2.51-2.48 (m, 1H), 2.32-2.14 (m, 2H), 1.99-1.88 (m, 2H), 1.87-1.67 (m, 1H), 1.27-1.10 (m, 1H). $^{19}$F NMR (471 MHz, DMSO-d$_6$) δ −103.1 (s, 1F), −75.1 (m, 6F), −75.0 (m, 1F).

The Intermediates in Table 2 were prepared using the procedures used to prepare Intermediate 11, or similar procedures, from the appropriate precursors.

TABLE 2

| Intermediate number | Structure | LCMS m/z observed | HPLC $t_R$ (min) | HPLC method |
|---|---|---|---|---|
| 12 | 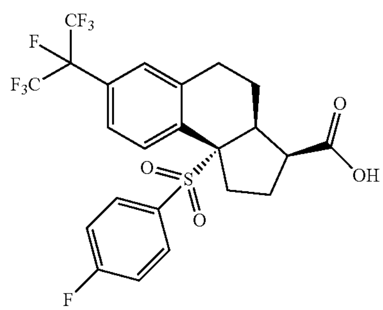 [SMILES: O=C(O)[C@H]1CC[C@@]2(S(=O)(=O)c3ccc(F)cc3)c3ccc(C(F)(C(F)(F)F)C(F)(F)F)cc3CC[C@@H]12] | 543.1 (M + H)$^+$ | 1.08 | B |
| 13 | 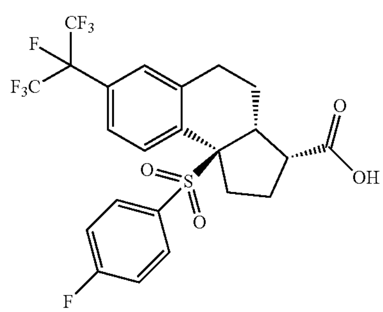 [SMILES: O=C(O)[C@@H]1CC[C@]2(S(=O)(=O)c3ccc(F)cc3)c3ccc(C(F)(C(F)(F)F)C(F)(F)F)cc3CC[C@H]12] | 543.1 (M + H)$^+$ | 1.08 | B |
| 14 | 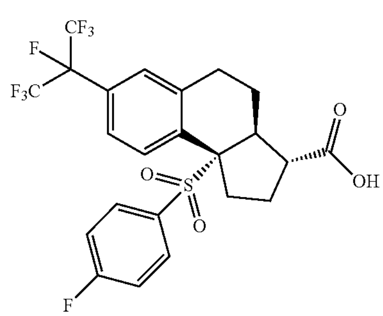 [SMILES: O=C(O)[C@@H]1CC[C@@]2(S(=O)(=O)c3ccc(F)cc3)c3ccc(C(F)(C(F)(F)F)C(F)(F)F)cc3CC[C@@H]12] | 543.1 (M + H)$^+$ | 1.08 | B |

TABLE 2-continued

| Intermediate number | Structure | LCMS m/z observed | HPLC $t_R$ (min) | HPLC method |
|---|---|---|---|---|
| 15 | 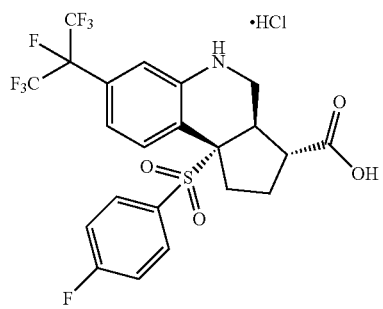 [SMILES: O=C(O)[C@@H]1CC[C@@]2(S(=O)(=O)c3ccc(F)cc3)c3ccc(C(F)(C(F)(F)F)C(F)(F)F)cc3NC[C@@H]12 ; Cl] | 588.0 $(M + H - C_4H_8)^+$ | 1.14 | A |

Intermediate 16

(3R,3aR,9bS)-9b-((4-fluorophenyl)sulfonyl)-7-(perfluoropropan-2-yl)-2,3,3a,4,5,9b-hexahydro-1H-cyclopenta[c]quinoline-3-carboxylic acid hydrochloride

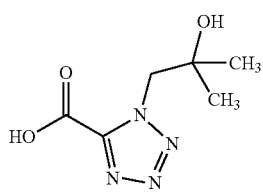

(3R,3aR,9bS)-5-(tert-butoxycarbonyl)-9b-((4-fluorophenyl)sulfonyl)-7-(perfluoropropan-2-yl)-2,3,3a,4,5,9b-hexahydro-1H-cyclopenta[c]quinoline-3-carboxylic acid (Intermediate 15; 400 mg, 0.62 mmol) was dissolved in HCl (4 M in 1,4-dioxane; 10 mL). After 2 h, the solvent was removed under reduced pressure to provide (3R,3aR,9bS)-9b-((4-fluorophenyl)sulfonyl)-7-(perfluoropropan-2-yl)-2,3,3a,4,5,9b-hexahydro-1H-cyclopenta[c]quinoline-3-carboxylic acid hydrochloride (360 mg, 100% yield). LCMS m/z 544.0 (M+H)$^+$; HPLC $t_R$ 1.02 min (Method A).

Intermediate 17

1-(2-hydroxy-2-methylpropyl)-1H-tetrazole-5-carboxylic acid

A mixture of ethyl 1H-tetrazole-5-carboxylate (300 mg, 2.11 mmol), 2,2-dimethyloxirane (152 mg, 2.11 mmol) and K$_2$CO$_3$ (583 mg, 4.22 mmol) in tert-butanol (2 mL) was heated in a sealed vial at 100° C. overnight. The mixture was cooled to rt and concentrated, and the residue was suspended in THF (3 mL) and MeOH (1 mL). This mixture was treated with a solution of LiOH hydrate (266 mg, 6.33 mmol) in water (1 mL) and stirred at rt for 2 h. The mixture was concentrated and the residue was acidified to pH 1 with 1 M aqueous HCl. This mixture was frozen at −78° C. and lyophilized overnight to provide 1-(2-hydroxy-2-methylpropyl)-1H-tetrazole-5-carboxylic acid as a mixture with LiCl and KCl. The mixture was used without further purification. LCMS m/z 187.0 (M+H)$^+$, HPLC $t_R$ 0.39 min (method A).

Intermediate 18

(S)-1-(2-cyanoethyl)-5-oxopyrrolidine-2-carboxylic acid

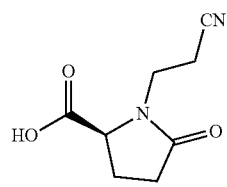 [SMILES: N#CCCN1C(=O)CC[C@H]1C(=O)O]

A solution of NaOH (2.72 g, 68.0 mmol) in water (11.3 mL) was stirred at rt and treated with L-glutamic acid (5.00 g, 34.0 mmol), gradually forming a solution. Acrylonitrile (2.68 mL, 40.8 mmol) was added and the mixture was heated at 50° C. overnight. After 20 h, the mixture was cooled in an ice-water bath and treated slowly with concentrated aqueous HCl (5.2 mL, 64.6 mmol). The solution was concentrated and the residue was suspended in acetone (40 mL) and heated at reflux overnight. After 20 h the mixture was cooled to rt. A white precipitate was removed by filtration and the filtrate was concentrated to afford a colorless oil. This material was purified by preparative SFC on a Princeton Cyano column (30×250 mm, 5 µm) at 40° C., eluting with CO$_2$-MeOH (80:20) at 160 mL/min and 100 bar. (S)-1-(2-cyanoethyl)-5-oxopyrrolidine-2-carboxylic acid was isolated as a white solid (3.72 g, 60% yield). LCMS m/z 183.1 (M+H)$^+$, HPLC $t_R$ 0.39 min (method A). $^1$H NMR (499 MHz, DMSO-d$_6$) δ 13.06 (br. s., 1H), 4.35-4.29 (m, 1H), 3.75 (dt, J=14.0, 7.0 Hz, 1H), 3.21-3.13 (m, 1H), 2.73 (t, J=6.8 Hz, 2H), 2.35-2.22 (m, 3H), 2.02-1.96 (m, 1H).

Intermediate 19

(2S,4R)-4-fluoro-1-(methyl-d$_3$)-5-oxopyrrolidine-2-carboxylic acid

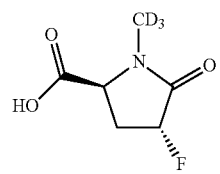

Step A: 1-(tert-butyl) 2-methyl (2S,4R)-4-fluoropyrrolidine-1,2-dicarboxylate

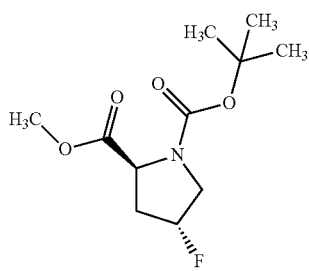 [SMILES: COC(=O)[C@@H]1C[C@@H](F)CN1C(=O)OC(C)(C)C]

A solution of (2S,4S)-1-tert-butyl 2-methyl 4-hydroxypyrrolidine-1,2-dicarboxylate (10.0 g, 40.8 mmol) in DCM (204 mL) was cooled in an ice-water bath and treated slowly with DAST (6.5 mL, 48.9 mmol). The mixture was stirred at rt for 5.5 h, then was partitioned between water and additional DCM. The organic phase was washed with brine, dried and concentrated to afford 1-(tert-butyl) 2-methyl (2S,4R)-4-fluoropyrrolidine-1,2-dicarboxylate as a light yellow syrup (10.6 g, 94% yield, 90% estimated purity). LCMS m/z 270.2 (M+Na)$^+$; HPLC t$_R$ 0.80 min (method A).

Step B: 1-(tert-butyl) 2-methyl (2S,4R)-4-fluoro-5-oxopyrrolidine-1, 2-dicarboxylate

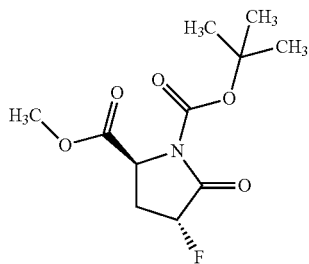 [SMILES: COC(=O)[C@@H]1C[C@@H](F)C(=O)N1C(=O)OC(C)(C)C]

A solution of sodium periodate (44.6 g, 209 mmol) in water (435 mL) was treated with RuCl$_3$ hydrate (7.84 g, 34.8 mmol), forming a dark red solution. This was treated slowly with a solution of crude (2S,4R)-1-tert-butyl 2-methyl 4-fluoropyrrolidine-1,2-dicarboxylate (9.55 g, 34.8 mmol) in EtOAc (145 mL). The mixture was stirred at rt for 17 h, then was treated with IPA (80 mL) and stirred at rt for 3 h.

The mixture was filtered through Celite and the solids were washed with water and EtOAc. The combined filtrates were diluted with additional EtOAc and water. The organic phase was separated, washed with brine, dried and concentrated. The residue was purified by column chromatography on silica gel (120 g), eluting with EtOAc-hexanes (10-50%), to provide 1-(tert-butyl) 2-methyl (2S,4R)-4-fluoro-5-oxopyrrolidine-1,2-dicarboxylate as a light yellow oil (67% yield). LCMS m/z 284.0 (M+Na)$^+$; HPLC t$_R$ 0.76 min (method A). $^1$H NMR (400 MHz, CDCl$_3$) δ 5.30-5.11 (m, 1H), 4.68 (dd, J=9.5, 2.0 Hz, 1H), 3.81 (s, 3H), 2.61-2.40 (m, 2H), 1.53 (s, 9H).

Step C: methyl (2S,4R)-4-fluoro-5-oxopyrrolidine-2-carboxylate

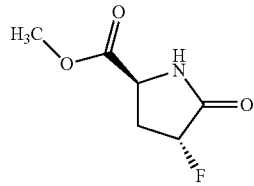

A solution of (2S,4R)-1-tert-butyl 2-methyl 4-fluoro-5-oxopyrrolidine-1,2-dicarboxylate (7.75 g, 25.8 mmol) in DCM (32 mL) was cooled in an ice-water bath and treated with TFA (12 mL). The mixture was stirred at rt for 2 h, then was concentrated and the residue was partitioned between water and EtOAc. The organic phase was washed sequentially with 1.5 M aqueous K$_2$HPO$_4$ and brine, dried and concentrated. The aqueous phase was extracted with chloroform-IPA (3:1) to provide additional product. The two portions were combined to provide methyl (2S,4R)-4-fluoro-5-oxopyrrolidine-2-carboxylate as a dark yellow syrup (3.38 g, 81% yield), used without further purification. LCMS m/z 162.0 (M+H)$^+$; HPLC t$_R$ 0.41 min (method A). $^1$H NMR (400 MHz, CDCl$_3$) δ 6.86 (br. s., 1H), 5.23-5.03 (m, 1H), 4.47-4.34 (m, 1H), 3.82-3.78 (m, 3H), 2.69-2.58 (m, 2H).

Step D: methyl (2S,4R)-4-fluoro-1-(methyl-d$_3$)-5-oxopyrrolidine-2-carboxylate

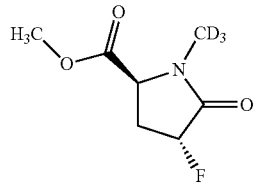

A mixture of (2S,4R)-methyl 4-fluoro-5-oxopyrrolidine-2-carboxylate (0.48 g, 2.98 mmol) and Cs$_2$CO$_3$ (2.43 g, 7.45 mmol) in MeCN (16.6 mL) was treated with iodomethane-d$_3$ (927 μL, 14.9 mmol) and heated in a sealed vial at 45° C. overnight. After 18 h, the mixture was cooled to rt, filtered and concentrated to provide methyl (2S,4R)-4-fluoro-1-(methyl-d$_3$)-5-oxopyrrolidine-2-carboxylate as a light yellow solid (0.53 g, quantitative yield), used without further purification. LCMS m/z 179.1 (M+H)$^+$; HPLC t$_R$ 0.46 min (method A).

Step E: (2S,4R)-4-fluoro-1-(methyl-d₃)-5-oxopyrrolidine-2-carboxylic acid

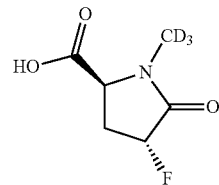

A mixture of methyl (2S,4R)-4-fluoro-1-(methyl-d₃)-5-oxopyrrolidine-2-carboxylate (530 mg, 2.97 mmol) and LiOH monohydrate (221 mg, 9.22 mmol) in THF-MeOH-water (3:1:1) (29.7 mL) was stirred at rt for 18 h. The mixture was concentrated, the residue was treated with HCl (4 M in 1,4-dioxane; 2.4 mL, 9.6 mmol), and the mixture was concentrated again to dryness. The crude mixture containing (2S,4R)-4-fluoro-1-(methyl-d₃)-5-oxopyrrolidine-2-carboxylic acid and LiCl was used without further purification. LCMS m/z 165.0 (M+H)⁺; HPLC $t_R$ 0.35 min (method A).

Intermediate 20

(2S,4R)-4-fluoro-5-oxopyrrolidine-2-carboxylic acid

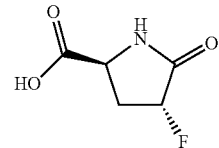

A solution of methyl (2S,4R)-4-fluoro-5-oxopyrrolidine-2-carboxylate (Intermediate 19, Step C; 1.01 g, 6.27 mmol) in THF (30 mL) and MeOH (10 mL) was treated with a solution of LiOH monohydrate (407 mg, 9.70 mmol) in water (10 mL). The mixture was stirred at rt for 2 h, then was acidified with 1 M aqueous HCl (9.8 mL) and concentrated under vacuum to remove the organic solvents. The aqueous residue was frozen at −78° C. and lyophilized to provide (2S,4R)-4-fluoro-5-oxopyrrolidine-2-carboxylic acid as a sticky yellow-tan amorphous solid (1.55 g) containing LiCl and residual water (estimated purity 60%) which was used without further purification. LCMS m/z 189.4 (M+H+MeCN)⁺; HPLC $t_R$ 0.29 min (method A).

Intermediate 21

(2S,4R)-4-hydroxy-1-(methyl-d₃)-5-oxopyrrolidine-2-carboxylic acid

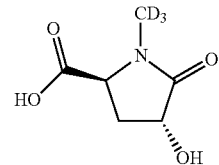 [SMILES: [2H]C([2H])([2H])N1C(=O)[C@H](O)C[C@H]1C(=O)O]

Step A: 1-(tert-butyl) 2-methyl (2S,4R)-4-((tert-butyldimethylsilyl)oxy)pyrrolidine-1,2-dicarboxylate

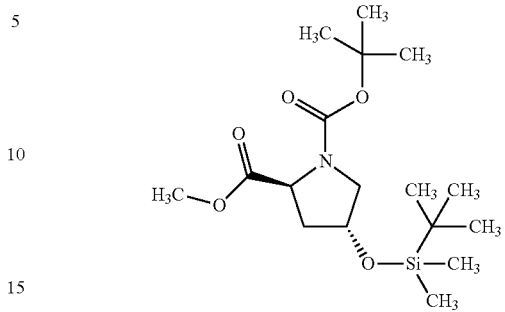

A solution of (2S,4R)-1-tert-butyl 2-methyl 4-hydroxy-pyrrolidine-1,2-dicarboxylate (2.00 g, 8.15 mmol) in THF (48 mL), cooled in an ice-water bath, was treated slowly with a solution of tert-butylchlorodimethylsilane (1.97 g, 13.1 mmol) in THF (6 mL), then with imidazole (1.22 g, 17.9 mmol). The mixture was stirred at rt overnight. After 18 h, the mixture was heated at 50° C. for 6 h, then stirred at rt for 3 days. The mixture was concentrated and the residue was partitioned between EtOAc and water. The organic phase was washed sequentially with 0.3 M aqueous HCl, saturated aqueous NaHCO₃ and brine, dried and concentrated to provide 1-(tert-butyl) 2-methyl (2S,4R)-4-((tert-butyldimethylsilyl)oxy)pyrrolidine-1,2-dicarboxylate as a nearly colorless oil (3.22 g, quantitative yield). LCMS m/z 260.2 (M+H—C₄H₈)⁺, 741.3 (2M+Na)⁺; HPLC $t_R$ 1.16 min (method B). ¹H NMR (400 MHz, CDCl₃) δ 4.47-4.30 (m, 2H), 3.76-3.72 (m, 3H), 3.65-3.54 (m, 1H), 3.45-3.28 (m, 1H), 2.24-2.12 (m, 1H), 2.07-1.97 (m, 1H), 1.48-1.40 (m, 9H), 0.88 (s, 9H), 0.07 (s, 6H).

Step B: 1-(tert-butyl) 2-methyl (2S,4R)-4-((tert-butyldimethylsilyl)oxy)-5-oxopyrrolidine-1,2-dicarboxylate

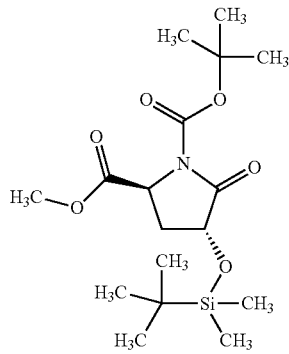 [SMILES: COC(=O)[C@@H]1C[C@@H](O[Si](C)(C)C(C)(C)C)C(=O)N1C(=O)OC(C)(C)C]

A solution of sodium periodate (4.39 g, 20.5 mmol) in water (78 mL) was treated with RuO₂ hydrate (271 mg, 1.79 mmol) and stirred at rt for 5 min. This mixture was then treated with a solution of (2S,4R)-1-tert-butyl 2-methyl 4-((tert-butyldimethylsilyl)oxy)pyrrolidine-1,2-dicarboxylate (3.22 g, 8.15 mmol) in EtOAc (58 mL) and stirred at rt. After 5 h, the mixture was diluted with EtOAc, filtered through Celite, and the solids were washed with water and EtOAc. The combined filtrates were partitioned between water and EtOAc. The organic phase was washed sequentially with 10% aqueous Na₂S₂O₃, saturated aqueous NaHCO₃ and brine, dried and concentrated to provide 1-(tert-butyl) 2-methyl (2S,4R)-4-((tert-butyldimethylsilyl)oxy)-5-oxopyrrolidine-1,2-dicarboxylate as a colorless oil (3.16 g, 86% yield, about 83% pure), used without further purification. LCMS m/z 274.2 (M+H—C₄H₈)⁺, 769.3 (2M+Na)⁺.

Step C: methyl (2S,4R)-4-hydroxy-5-oxopyrrolidine-2-carboxylate

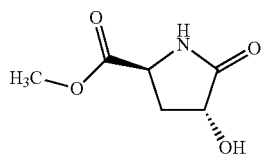

A solution of 1-tert-butyl 2-methyl (2S,4R)-4-((tert-butyldimethylsilyl)oxy)-5-oxopyrrolidine-1,2-dicarboxylate (3.16 g, 7.02 mmol) in DCM (9 mL) was cooled in an ice-water bath and treated with TFA (1.9 mL). The mixture was warmed to rt and stirred overnight, then was concentrated to provide crude methyl (2S,4R)-4-hydroxy-5-oxopyrrolidine-2-carboxylate as a yellow syrup (2.08 g), used without further purification. LCMS m/z 160.1 (M+H)⁺; HPLC $t_R$ 0.32 min (method B).

Step D: (2S,4R)-4-hydroxy-1-(methyl-d₃)-5-oxopyrrolidine-2-carboxylic acid

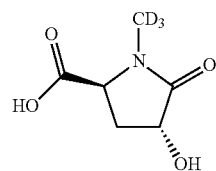 [SMILES: [2H]C([2H])([2H])N1C(=O)[C@H](O)C[C@H]1C(=O)O]

Following the procedures used in Steps D and E of the preparation of Intermediate 19, methyl (2S,4R)-4-hydroxy-5-oxopyrrolidine-2-carboxylate was converted into (2S,4R)-4-hydroxy-1-(methyl-d₃)-5-oxopyrrolidine-2-carboxylic acid. LCMS m/z 163.0 (M+H)⁺; HPLC $t_R$ 0.26 min (method B).

Intermediate 22

(2RS,4RS)-2-methyltetrahydro-2H-thiopyran-4-carboxylic acid 1,1-dioxide

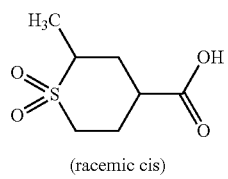

(racemic cis)

Step A: 4-((benzyloxy)methyl)tetrahydro-2H-thiopyran

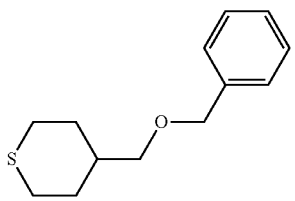 [SMILES: c1ccc(COCC2CCSCC2)cc1]

A suspension of NaH (60% in mineral oil; 1.234 g, 30.9 mmol) in DMF (50 mL) at 0° C. was treated portionwise with a solution of (tetrahydro-2H-thiopyran-4-yl)methanol (3.4 g, 25.7 mmol) in DMF (2 mL) and the mixture was stirred for 15 min. Benzyl bromide (3.4 mL, 28.3 mmol) was added dropwise over 2 min, and the mixture was allowed to warm to rt. After 1.5 h, the mixture was treated with saturated aqueous NH₄Cl (20 mL), diluted with water (50 mL) and extracted with EtOAc (75 mL). The organic phase was washed sequentially with 10% aqueous LiCl (3×30 mL) and brine (30 mL), dried and concentrated. The residue was purified by column chromatography on silica gel (120 g), eluting with EtOAc-hexanes (gradient from 0-10%), to give 4-((benzyloxy)methyl)tetrahydro-2H-thiopyran as a colorless oil (3.4 g, 60% yield). ¹H NMR (400 MHz, CDCl₃) δ 7.43-7.27 (m, 5H), 4.50 (s, 2H), 3.31 (d, J=6.4 Hz, 2H), 2.75-2.66 (m, 2H), 2.66-2.57 (m, 2H), 2.16-2.07 (m, 2H), 1.79-1.62 (m, 1H), 1.51-1.34 (m, 2H).

Step B: 4-((benzyloxy)methyl)tetrahydro-2H-thiopyran 1,1-dioxide

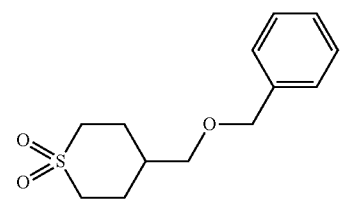 [SMILES: O=S1(=O)CCC(COCc2ccccc2)CC1]

A solution of 4-((benzyloxy)methyl)tetrahydro-2H-thiopyran (4.7 g, 21.1 mmol) in DCM (125 mL) at 0° C. was treated portionwise with mCPBA (77%; 9.95 g, 44.4 mmol) and the ice bath was removed to allow the mixture to warm to rt. After 2 h, the mixture was cooled to 0° C. and filtered, and the filtrate was stirred at rt for 10 min with 10% aqueous Na₂S₂O₃ (120 mL). The organic phase was separated and washed with 10% aqueous K₂CO₃ (2×150 mL), dried over Na₂SO₄ and concentrated. The residue was purified by column chromatography on silica gel (120 g), eluting with EtOAc-hexanes (gradient from 0-60%), to give 4-((benzyloxy)methyl)tetrahydro-2H-thiopyran 1,1-dioxide as a white solid (4.9 g, 91% yield). ¹H NMR (400 MHz, CDCl₃) δ 7.42-7.28 (m, 5H), 4.51 (s, 2H), 3.43-3.30 (m, 2H), 3.14-2.87 (m, 4H), 2.20 (d, J=11.9 Hz, 2H), 2.00-1.76 (m, 3H).

Step C: (2RS,4RS)-4-((benzyloxy)methyl)-2-methyltetrahydro-2H-thiopyran 1,1-dioxide

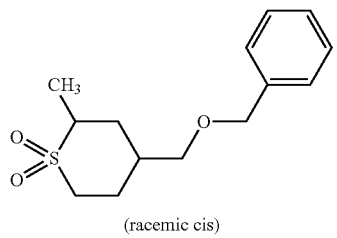 [SMILES: CC1CC(COCc2ccccc2)CCS1(=O)=O]

(racemic cis)

A solution of diisopropylamine (579 μL, 4.13 mmol) in THF (12 mL) under nitrogen was cooled to −78° C. and treated dropwise with n-butyllithium (2.4 M in hexanes; 1.556 mL, 3.74 mmol) and the mixture was stirred for 30 min, then at rt for 15 min. The mixture was cooled to −78° C., treated over 3 min with a solution of 4-((benzyloxy)methyl)tetrahydro-2H-thiopyran 1,1-dioxide (1.00 g, 3.93 mmol) in THF (5 mL) and stirred for 1 h. The mixture was then treated with a solution of iodomethane (257 μL, 4.13 mmol) in THF (0.5 mL). After 45 min, the cooling bath was removed and the mixture was allowed to warm to rt, then was stirred for 1 h. The mixture was treated with saturated aqueous $NH_4Cl$ (50 mL) and extracted with EtOAc (2×50 mL). The combined organic phases were washed with brine, dried over $Na_2SO_4$ and concentrated. The residue was purified by column chromatography on silica gel (80 g), eluting with EtOAc-hexanes (gradient from 0-35%), to give racemic cis-4-((benzyloxy)methyl)-2-methyltetrahydro-2H-thiopyran 1,1-dioxide as a white solid (450 mg, 43% yield). LCMS m/z 290.8 (M+Na)$^+$; HPLC $t_R$ 0.81 min (method B). $^1$H NMR (400 MHz, $CDCl_3$) δ 7.41-7.28 (m, 5H), 4.51 (s, 2H), 3.33 (d, J=6.2 Hz, 2H), 3.12 (dt, J=14.3, 3.4 Hz, 1H), 3.04-2.87 (m, 2H), 2.23-2.12 (m, 1H), 2.11-2.03 (m, 1H), 2.00-1.76 (m, 2H), 1.69-1.59 (m, 1H), 1.35 (d, J=6.8 Hz, 3H). The dimethylated side product (2R,4r,6S)-4-((benzyloxy)methyl)-2,6-dimethyltetrahydro-2H-thiopyran 1,1-dioxide was also isolated in 75% purity (250 mg, 23% yield). LCMS m/z 283.1 (M+H)$^+$; HPLC $t_R$ 0.88 min (method B).

Step D: (2RS,4RS)-4-(hydroxymethyl)-2-methyltetrahydro-2H-thiopyran 1,1-dioxide

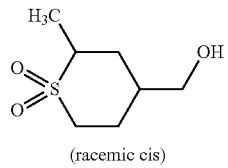

(racemic cis)

A solution of (2RS,4RS)-4-((benzyloxy)methyl)-2-methyltetrahydro-2H-thiopyran 1,1-dioxide (450 mg, 1.68 mmol) in MeOH (2 mL) and ethanol (10 mL) was treated with palladium on carbon (160 mg, 0.075 mmol) and stirred under a hydrogen atmosphere (balloon pressure) for 1.5 h. The mixture was filtered to remove the catalyst and the filtrate was concentrated to give (2RS,4RS)-4-(hydroxymethyl)-2-methyltetrahydro-2H-thiopyran 1,1-dioxide as a white solid (280 mg, 94% yield). $^1$H NMR (400 MHz, $CDCl_3$) δ 3.53 (d, J=5.7 Hz, 1H), 3.20-3.09 (m, 1H), 3.06-2.85 (m, 2H), 2.24-2.12 (m, 1H), 2.10-2.00 (m, 2H), 1.92-1.73 (m, 2H), 1.67-1.52 (m, 1H), 1.36 (d, J=6.8 Hz, 3H).

Step E: (2RS,4RS)-2-methyltetrahydro-2H-thiopyran-4-carboxylic acid 1,1-dioxide

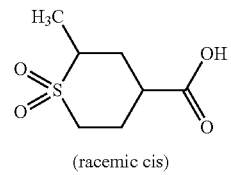

(racemic cis)

A solution of (2RS,4RS)-4-(hydroxymethyl)-2-methyltetrahydro-2H-thiopyran 1,1-dioxide (275 mg, 1.54 mmol) in MeCN (0.9 mL) and $CCl_4$ (0.9 mL) was treated with a solution of sodium periodate (1.35 g, 6.33 mmol) in water (1.3 mL), then with $RuCl_3$ hydrate (14 mg, 0.062 mmol), and the mixture was stirred at rt. After 30 min, the mixture was a yellow emulsion, and stirring was continued at rt for 30 min more with occasional sonication. An additional portion of $RuCl_3$ hydrate (14 mg, 0.062 mmol) was added, and stirring was continued for 1 h with occasional sonication. The mixture was diluted with EtOAc (125 mL), the organic phase was separated and washed with water (25 mL), dried over $Na_2SO_4$ and concentrated. The residue was treated with EtOAc (125 mL) and MeOH (10 mL), filtered and concentrated to give (2RS,4RS)-2-methyltetrahydro-2H-thiopyran-4-carboxylic acid 1,1-dioxide as a gray solid (165 mg, 56% yield), used without further purification. $^1$H NMR (400 MHz, MeOH-$d_4$) δ 3.28-3.04 (m, 3H), 2.69 (tt, J=12.4, 3.3 Hz, 1H), 2.37 (d quin, J=14.1, 3.5 Hz, 1H), 2.28 (dq, J=14.2, 3.2 Hz, 1H), 2.18-2.03 (m, 1H), 1.86 (dt, J=14.3, 12.5 Hz, 1H), 1.29 (d, J=6.8 Hz, 3H).

Intermediate 23

2-(3-hydroxy-1,1-dioxidotetrahydrothiophen-3-yl)acetic acid (racemic)

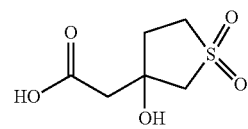 [SMILES: O=C(O)CC1(O)CCS(=O)(=O)C1]

Step A: tert-butyl 2-(3-hydroxytetrahydrothiophen-3-yl)acetate (racemic)

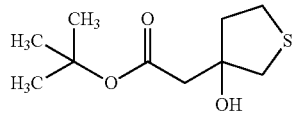

A solution of tert-butyl acetate (3.1 mL, 23.4 mmol) in THF (50 mL) at −78° C. was treated slowly with lithium bis(trimethylsilyl)amide (1.0 M in THF; 22.2 mL, 22.2 mmol). The mixture was stirred for 45 min, then was treated slowly with a solution of tetrahydrothiophen-3-one (2.00 mL, 23.4 mmol) in THF (5 mL). The mixture was stirred at −78° C. for 20 min, then was treated slowly with 2 M aqueous HCl (12.3 mL). The cooling bath was removed and the mixture was warmed to rt, then was extracted twice with EtOAc. The combined organic phases were washed sequentially with 1.5 M aqueous $K_2HPO_4$ and brine, dried and concentrated to provide crude racemic tert-butyl 2-(3-hydroxytetrahydrothiophen-3-yl)acetate as a colorless oil, used without purification. LCMS m/z 163.0 (M+H-tBu)+; HPLC $t_R$ 0.81 min (method A).

Step B: tert-butyl 2-(3-hydroxy-1,1-dioxidotetrahydrothiophen-3-yl)acetate

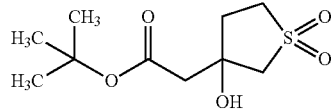 [SMILES: CC(C)(C)OC(=O)CC1(O)CCS(=O)(=O)C1]

A solution of crude racemic tert-butyl 2-(3-hydroxytetrahydrothiophen-3-yl)acetate (4.80 g, 22.0 mmol) in DCM (75 mL) at 0° C. was treated portionwise with mCPBA (70%, 17.3 g, 77.0 mmol). After 50 min, additional mCPBA (3.79 g) was added. After a total of 2 h, the mixture was filtered through Celite and the solids were washed with DCM. The combined filtrates were washed sequentially with saturated aqueous $NaHCO_3$ and brine, dried and concentrated to provide racemic tert-butyl 2-(3-hydroxy-1,1-dioxidotetrahydrothiophen-3-yl)acetate as a white solid (5.55 g, quantitative yield). $^1$H NMR (499 MHz, DMSO-$d_6$) δ 5.48 (s, 1H), 3.26-3.12 (m, 4H), 2.67-2.54 (m, 2H), 2.31-2.12 (m, 2H), 1.41 (s, 9H).

Step C: 2-(3-hydroxy-1,1-dioxidotetrahydrothiophen-3-yl)acetic acid (racemic)

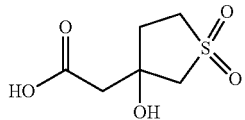

A solution of racemic tert-butyl 2-(3-hydroxy-1,1-dioxidotetrahydrothiophen-3-yl)acetate (5.55 g, 22.2 mmol) in DCM (60 mL) at rt was treated with TFA (12 mL, 156 mmol). After 2 h the solution was concentrated and dried in vacuo to provide racemic 2-(3-hydroxy-1,1-dioxidotetrahydrothiophen-3-yl)acetic acid as a white solid (4.21 g, 98% yield), used without further purification. $^1$H NMR (499 MHz, DMSO-$d_6$) δ 3.30-3.13 (m, 4H), 2.70-2.57 (m, 2H), 2.31-2.15 (m, 2H).

Intermediate 24

(1R,2S,4R)-4-(methoxycarbonyl)-2-methylcyclohexane-1-carboxylic acid

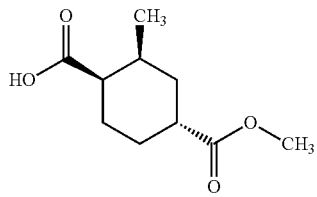

Step A: tert-butyl 2-acetyl-5-oxohexanoate (racemic)

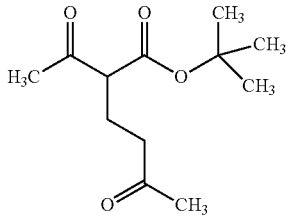 [SMILES: CC(=O)CCC(C(C)=O)C(=O)OC(C)(C)C]

A mixture of methyl vinyl ketone (116 mL, 1.43 mol), tert-butyl acetoacetate (248 mL, 1.50 mol), and TEA (994 µL, 7.13 mmol) was cooled to 12° C. in an acetone-dry ice bath. $LiClO_4$ (15.2 g, 143 mmol) was added portionwise over 30 min, then the mixture was warmed to 25° C. and stirred for 22 h. Diethyl ether (5 L) and added and the resulting mixture was washed sequentially with water (75 mL) and brine (75 mL), dried and concentrated. The residue, a cloudy oil (331.8 g), was redissolved in ether, filtered, and the filtrate was concentrated to give racemic tert-butyl 2-acetyl-5-oxohexanoate as a colorless oil (330.5 g, quantitative yield). $^1$H NMR (400 MHz, $CDCl_3$) δ 3.40-3.40 (m, 1H), 2.54-2.45 (m, 2H), 2.25-2.21 (m, 3H), 2.15 (s, 3H), 2.12-2.01 (m, 2H), 1.48-1.45 (m, 9H).

Step B: tert-butyl (R)-2-methyl-4-oxocyclohex-2-ene-1-carboxylate

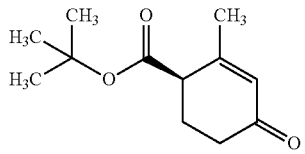

A mixture of tert-butyl 2-acetyl-5-oxohexanoate (57.5 g, 252 mmol), THF (331 mL), acetic acid (13.7 mL, 239 mmol) and piperidine (20.0 mL, 202 mmol) was heated to 60° C. and stirred for 44 h. EtOAc (670 mL) was added, followed by 1 N aqueous HCl (200 mL). The mixture was stirred for 10 minutes, then the layers were separated. The organic phase was washed sequentially with saturated aqueous $NaHCO_3$ (2×200 mL) and brine (200 mL), dried and concentrated. The residue was subjected to column chromatography, and the resulting racemic product was separated by preparative SFC to give tert-butyl (R)-2-methyl-4-oxocyclohex-2-ene-1-carboxylate (18.0 g, 34% yield). ¹H NMR (499 MHz, CDCl₃) δ 6.09-5.75 (m, 1H), 3.36-3.05 (m, 1H), 2.68-2.47 (m, 1H), 2.41-2.27 (m, 2H), 2.26-2.13 (m, 1H), 2.09-2.00 (m, 3H), 1.50 (s, 9H).

Step C: tert-butyl (1R, 2S)-2-methyl-4-oxocyclohexane-1-carboxylate

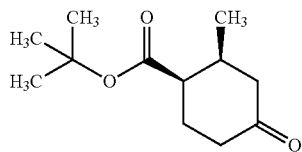

A solution of tert-butyl (R)-2-methyl-4-oxocyclohex-2-enecarboxylate (20.5 g, 97 mmol) in THF (195 mL) was bubbled with N₂ for several minutes. Wet 10% Pd on carbon (2 g, 1.88 mmol) was added and the mixture was stirred under a hydrogen atmosphere (balloon pressure) for 14 h. The mixture was filtered through Celite and the solids were rinsed with THF (500 mL). The combined filtrates were concentrated to give tert-butyl (1R, 2S)-2-methyl-4-oxocyclohexanecarboxylate (22.9 g, quantitative yield). ¹H NMR (400 MHz, CDCl3) δ 2.85-2.69 (m, 1H), 2.61-2.38 (m, 4H), 2.36-1.93 (m, 3H), 1.54-1.42 (m, 9H), 1.04-0.92 (m, 3H).

Step D: tert-butyl (1R, 6S)-6-methyl-4-(((trifluoromethyl)sulfonyl)oxy)cyclohex-3-ene-1-carboxylate

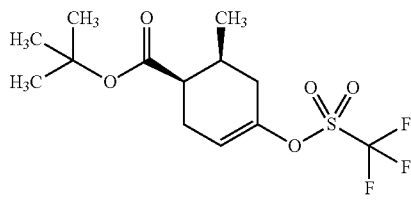 [SMILES: C[C@H]1CC(OS(=O)(=O)C(F)(F)F)=CC[C@H]1C(=O)OC(C)(C)C]

A mixture of N,N-bis(trifluoromethylsulfonyl)aniline (50.1 g, 140 mmol) and tert-butyl (1R,2S)-2-methyl-4-oxocyclohexanecarboxylate (22.9 g, 108 mmol) in anhydrous THF (330 mL) was cooled to −70° C. on an acetone-dry ice bath. Potassium bis(trimethylsilyl)amide (1.0 M in THF; 140 mL, 140 mmol) was added dropwise with stirring over 1 h. After 1 h more, the mixture was treated with water (500 mL) and warmed to 0° C. The mixture was extracted with EtOAc (500 mL), and the organic phase was washed sequentially with water (500 mL) and brine (500 mL), and dried and concentrated. The residue (41 g) was subjected to column chromatography on silica gel to give tert-butyl (1R,2S)-2-methyl-4-(((trifluoromethyl)sulfonyl)oxy)cyclohex-3-enecarboxylate (30.2 g, 81% yield). ¹H NMR (499 MHz, CDCl₃) δ 5.76 (td, J=5.4, 1.9 Hz, 1H), 2.99-2.09 (m, 5H), 2.02-1.86 (m, 1H), 1.48 (d, J=3.5 Hz, 9H), 1.05-0.99 (m, 3H).

Step E: 4-(tert-butyl) 1-methyl (4R, 5S)-5-methyl-cyclohex-1-ene-1, 4-dicarboxylate

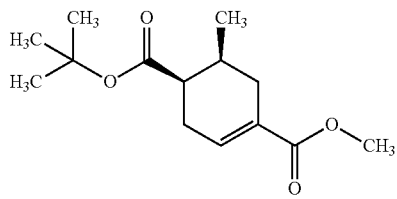 [SMILES: COC(=O)C1=CC[C@@H](C(=O)OC(C)(C)C)[C@@H](C)C1]

A solution of tert-butyl (1R, 6S)-6-methyl-4-(((trifluoromethyl)sulfonyl)oxy)-cyclohex-3-enecarboxylate (29.6 g, 86 mmol) in anhydrous DMF (215 mL) and MeOH (215 mL) was bubbled with nitrogen for 5 min. Palladium acetate (1.93 g, 8.59 mmol), 1,1'-bis(diphenylphosphino)ferrocene (4.76 g, 8.59 mmol) and TEA (35.9 mL, 258 mmol) were added. The mixture was then bubbled with carbon monoxide for 10 min and stirred at rt under a carbon monoxide atmosphere (balloon pressure) for 18 h. The mixture was diluted with EtOAc (500 mL), washed sequentially with 10% aqueous LiCl (3×500 mL) and brine (500 mL), dried and concentrated. The residue was subjected to column chromatography to give 4-tert-butyl 1-methyl (4R,5S)-5-methylcyclohex-1-ene-1,4-dicarboxylate (14.1 g, 65% yield). ¹H NMR (499 MHz, CDCl₃) δ 6.97-6.89 (m, 1H), 3.74 (s, 3H), 2.88-1.75 (m, 6H), 1.47 (d, J=3.8 Hz, 9H), 1.01 (d, J=7.2 Hz, 2H), 0.92 (d, J=6.8 Hz, 1H).

Step F: 1-(tert-butyl) 4-methyl (1R, 2S, 4R)-2-methylcyclohexane-1,4-dicarboxylate

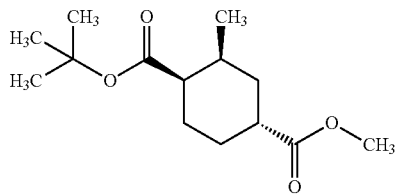 [SMILES: COC(=O)[C@@H]1CC[C@@H](C(=O)OC(C)(C)C)[C@@H](C)C1]

A solution of 4-tert-butyl 1-methyl (4R, 5S)-5-methylcyclohex-1-ene-1,4-dicarboxylate (14.09 g, 55.4 mmol) in DCM (554 mL) was bubbled with nitrogen for 10 min. (1,5-cyclooctadiene)-pyridine(tricyclohexylphosphine) iridium(1) hexafluorophosphate (Crabtree's catalyst; 1.12 g, 1.39 mmol) was added and the mixture was evacuated and purged 3 times with hydrogen. The mixture was stirred under a hydrogen atmosphere (balloon pressure) for 17 h. The solution was concentrated and the residue was subjected to column chromatography on silica gel to give 1-tert-butyl 4-methyl (1R,2S,4R)-2-methylcyclohexane-1,4-dicarboxylate as a colorless oil (14.1 g, 99% yield). ¹H NMR (400 MHz, CDCl₃) δ 3.66 (s, 3H), 2.54-2.34 (m, 3H), 2.00 (ddd, J=13.2, 3.7, 1.7 Hz, 1H), 1.89-1.80 (m, 1H), 1.78-1.56 (m, 3H), 1.46-1.38 (m, 10H), 0.92 (d, J=7.1 Hz, 3H).

Step G: (1R, 2S, 4R)-4-(methoxycarbonyl)-2-methylcyclohexane-1-carboxylic acid

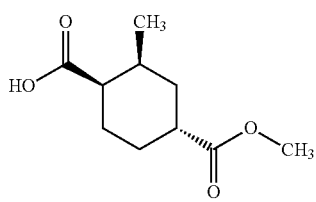

A solution of 1-tert-butyl 4-methyl (1R,2S,4R)-2-methylcyclohexane-1,4-dicarboxylate (27.5 g, 107 mmol) in DCM (37.2 mL) was treated with TFA (37.2 mL, 483 mmol) and stirred at rt. After 9 h, the mixture was concentrated, and the residue was treated with heptane (100 mL) and concentrated again. The residue was treated with heptane twice more (2×20 mL) and concentrated under high vacuum. The residue was crystallized from 5% tert-butyl methyl ether-heptane to give (1R,2S,4R)-4-(methoxycarbonyl)-2-methylcyclohexanecarboxylic acid as a white solid (17.3 g, 80% yield). $^1$H NMR (499 MHz, CDCl$_3$) δ 3.68 (s, 3H), 2.57-2.46 (m, 3H), 2.04 (dqd, J=13.3, 3.8, 1.8 Hz, 1H), 1.93-1.87 (m, 1H), 1.83 (dq, J=14.0, 3.9 Hz, 1H), 1.78-1.63 (m, 2H), 1.52-1.39 (m, 1H), 0.98 (d, J=7.0 Hz, 3H). $^{13}$C NMR (126 MHz, CDCl$_3$) δ 179.7, 176.3, 51.7, 45.1, 37.0, 34.8, 29.5, 27.6, 21.1, 13.9.

Intermediate 25

(1s,4s)-4-(ethoxycarbonyl)-1-fluorocyclohexane-1-carboxylic acid

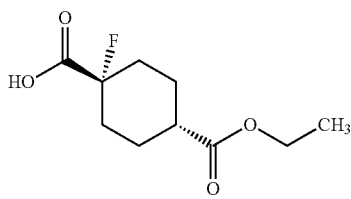

Step A: mixture of ethyl (3r,6r)-1-oxaspiro[2.5]octane-6-carboxylate and ethyl (3s,6r)-1-oxaspiro[2.5]octane-6-carboxylate

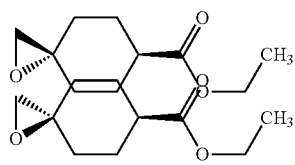

A suspension of potassium tert-butoxide (5.03 g, 44.8 mmol) in dry THF (100 mL) was treated with trimethylsulfoxonium iodide (10.2 g, 46.4 mmol) and the mixture was stirred at reflux under nitrogen for 2 h. The mixture was cooled to rt, treated dropwise over 2 min with a solution of ethyl 4-oxocyclohexanecarboxylate (5.3 g, 31.1 mmol) in THF (30 mL), then heated at reflux for 2.5 h. The mixture was cooled to rt, partitioned between EtOAc (250 mL) and water (150 mL) and the aqueous phase was extracted with EtOAc (2×50 mL). The combined organic phases were dried and concentrated. The residue was purified by column chromatography on silica gel (80 g), eluting with EtOAc-hexanes (gradient from 0-15%), to give a mixture of ethyl (3r,6r)-1-oxaspiro[2.5]octane-6-carboxylate and ethyl (3s, 6r)-1-oxaspiro[2.5]octane-6-carboxylate (3.8 g, 66% yield). $^1$H NMR (400 MHz, CDCl$_3$) δ 4.13 (q, J=7.2 Hz, 2.2H), 2.63 (s, 2H), 2.60 (s, 0.2H), 2.47-2.29 (m, 1.2H), 2.13-2.04 (m, 0.2H), 2.02-1.94 (m, 1.2H), 1.93-1.89 (m, 0.2H), 1.89-1.81 (m, 9.6H), 1.81-1.78 (m, 1.6H), 1.77-1.70 (m, 0.4H), 1.56-1.45 (m, 0.2H), 1.42-1.33 (m, 2H), 1.25 (t, J=7.2 Hz, 3.2H).

Step B: ethyl (1 s,4s)-4-fluoro-4-(hydroxymethyl)cyclohexane-1-carboxylate

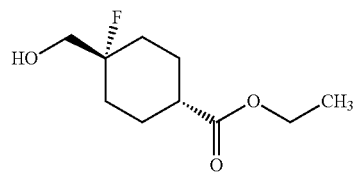

Hydrogen fluoride (70% in pyridine; 5 mL, 5.43 mmol) was cooled to −78° C. in a polypropylene vial and treated with a solution of the mixture of ethyl (3r,6r)-1-oxaspiro[2.5]octane-6-carboxylate and ethyl (3s,6r)-1-oxaspiro[2.5]octane-6-carboxylate from Step A (1.0 g, 5.43 mmol) in DCM (5 mL). The mixture was stirred at −78° C. for 4.5 h, then was poured into ice-cold 2 M aqueous NH$_4$OH (25 mL) and DCM (25 mL). The mixture was adjusted to pH 8 using concentrated aqueous NH$_4$OH and extracted with DCM (2×50 mL). The combined organic phases were washed sequentially with 1 M aqueous HCl (50 mL) and brine (50 mL), dried and concentrated. The residue was purified by column chromatography on silica gel (24 g), eluting with EtOAc-hexanes (gradient from 0-30%), to give (1s,4s)-ethyl 4-fluoro-4-(hydroxymethyl)cyclohexanecarboxylate as a solid (390 mg, 35% yield). $^1$H NMR (400 MHz, CDCl$_3$) δ 4.21-4.07 (m, 2H), 3.57 (dd, J=19.6, 5.7 Hz, 2H), 2.36-2.20 (m, 1H), 2.05 (dd, J=12.4, 9.4 Hz, 2H), 1.96-1.86 (m, 2H), 1.86-1.73 (m, 2H), 1.47-1.28 (m, 2H), 1.26 (t, J=7.2 Hz, 3H). (1s,4r)-ethyl 4-fluoro-4-(hydroxymethyl)cyclohexanecarboxylate was also isolated. $^1$H NMR (400 MHz, CDCl$_3$) δ 4.14 (q, J=7.1 Hz, 2H), 3.72-3.55 (m, 2H), 2.62-2.46 (m, 1H), 1.99-1.87 (m, 2H), 1.85-1.72 (m, 6H), 1.26 (t, J=7.2 Hz, 3H).

Step C: (1s,4s)-4-(ethoxycarbonyl)-1-fluorocyclohexane-1-carboxylic acid

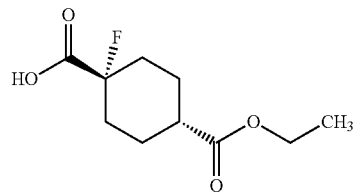

A solution of (1s,4s)-ethyl 4-fluoro-4-(hydroxymethyl)cyclohexanecarboxylate (760 mg, 3.72 mmol) in MeCN (8 mL) and tetrachloromethane (8.00 mL) was treated with a solution of periodic acid (3.48 g, 15.26 mmol) in water (12.00 mL), then with RuCl$_3$ hydrate (34 mg, 0.149 mmol). The mixture was stirred at rt for 1.5 h, then was diluted with diethyl ether (60 mL) and stirred at rt for 10 min. The mixture was filtered and the phases were separated, and the aqueous phase was extracted with diethyl ether (2×20 mL). The combined organic phases were washed with brine (2×30 mL), dried over $Na_2SO_4$ and concentrated to give crude (1s,4s)-4-(ethoxycarbonyl)-1-fluorocyclohexanecarboxylic acid as a solid (740 mg, 91% yield), used without further purification. $^1H$ NMR (400 MHz, $CDCl_3$) δ 4.16 (q, J=7.3 Hz, 2H), 2.45-2.31 (m, 1H), 2.23-2.11 (m, 2H), 2.04-1.94 (m, 3H), 1.94-1.72 (m, 3H), 1.27 (t, J=7.2 Hz, 3H).

Intermediates 26 and 27

8b-((4-fluorophenyl)sulfonyl)-6-iodo-2a,3,4,8b-tetrahydrocyclobuta[a]naphthalen-2(1H)-one (racemic) and 7b-((4-fluorophenyl)sulfonyl)-5-iodo-1a,2,3,7b-tetrahydro-1H-cyclopropa[a]naphthalene-1-carbaldehyde (mixture of diastereomers)

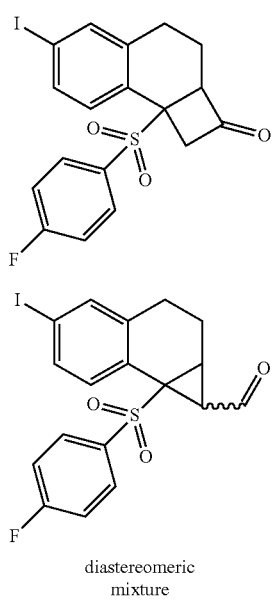

Intermediate 26

Intermediate 27 diastereomeric mixture

Step A: 1-((4-fluorophenyl)sulfonyl)-6-iodo-2-vinyl-1,2,3,4-tetrahydronaphthalene (mixture of diastereomers)

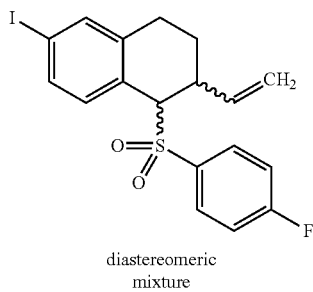 [SMILES: C=CC1CCc2cc(I)ccc2C1S(=O)(=O)c1ccc(F)cc1]

diastereomeric mixture

A solution of 4-((4-fluorophenyl)sulfonyl)-7-iodo-1,2-dihydronaphthalene (Intermediate 1, Step A; 2.00 g, 4.83 mmol) in THF (40 mL) was stirred on a dry ice-acetone bath and treated dropwise over 10 min with vinylmagnesium bromide (1.0 M in THF; 7.0 mL, 7.00 mmol) over 10 min. The solution was stirred at −78° C. for 70 min, then was allowed to warm to rt. After 80 min more, the mixture was treated with saturated aqueous $NH_4Cl$. The mixture was diluted with water and extracted twice with EtOAc. The combined organic phases were washed with brine, dried and concentrated. The residue was subjected to column chromatography on silica gel (220 g), eluting with EtOAc-hexanes (gradient from 0-22%), to provide a mixture of diastereomers of 1-((4-fluorophenyl)sulfonyl)-6-iodo-2-vinyl-1,2,3,4-tetrahydronaphthalene as a white solid (1.55 g, 72%). LCMS m/z 906.9 $(2M+Na)^+$; HPLC $t_R$ 1.08 min (method A). $^1H$ NMR (400 MHz, $CDCl_3$) δ 7.70-7.60 (m, 2H), 7.58-7.48 (m, 1H), 7.47-7.25 (m, 2H), 7.24-7.12 (m, 2H), 6.77 (d, J=8.1 Hz, 0.6H), 6.41 (d, J=8.1 Hz, 0.4H), 6.38-6.25 (m, 0.4H), 5.76 (ddd, J=17.2, 10.4, 6.9 Hz, 0.6H), 5.17-4.99 (m, 2H), 4.33 (d, J=3.5 Hz, 0.4H), 4.20 (d, J=3.1 Hz, 0.6H), 3.13-2.17 (m, 4H).

Step B: 2-(1-((4-fluorophenyl)sulfonyl)-6-iodo-1,2,34-tetrahydronaphthalen-2-yl)oxirane (mixture of diastereomers)

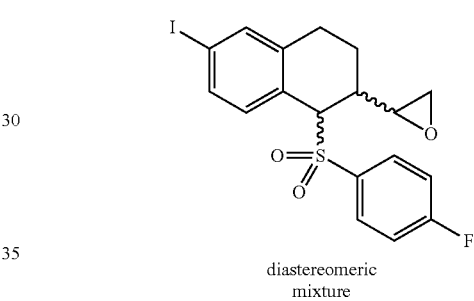

diastereomeric mixture

A solution of 1-((4-fluorophenyl)sulfonyl)-6-iodo-2-vinyl-1,2,3,4-tetrahydronaphthalene (1.50 g, 3.39 mmol) in THF (40 mL) was stirred on an ice-water bath and treated with water until cloudy (about 22 mL). The mixture was treated in portions with N-bromosuccinimide (0.724 g, 4.07 mmol) over about 5 min, and the mixture was kept in the dark at 0° C. overnight. After 20 h, the mixture was warmed to rt while still protecting from light. After 2.5 h more, the mixture was diluted with water and extracted twice with EtOAc. The combined organic phases were washed with brine, dried and concentrated. The residue was dissolved in MeOH (16 mL), stirred on an ice-water bath and treated with $K_2CO_3$ (0.656 g, 4.75 mmol). After 6.25 h, the mixture was concentrated and the residue was partitioned between EtOAc and water. The aqueous phase was extracted with EtOAc, and the combined organic phases were washed with brine, dried and concentrated. The residue was subjected to column chromatography on silica gel (120 g), eluting with EtOAc-hexanes (gradient from 10-40%), to provide a mixture of diastereomers of 2-(1-((4-fluorophenyl)sulfonyl)-6-iodo-1,2,3,4-tetrahydronaphthalen-2-yl)oxirane (744 mg, 48% yield) as an off-white amorphous solid. LCMS m/z 459.3 $(M+H)^+$, 939.0 $(2M+Na)^+$; HPLC $t_R$ 1.06 min (method A). $^1H$ NMR (400 MHz, $CDCl_3$) δ 7.70-7.41 (m, 4H), 7.23-7.12 (m, 2H), 6.84-6.62 (2d, 1H), 4.32-4.18 (2d, 1H), 3.04-2.75 (4m, 3H), 2.74-2.52 (2m, 3H), 2.44-2.13 (2m, 2H).

Also obtained was a mixture of diastereomers of the intermediate bromohydrin, 2-bromo-2-(1-((4-fluorophenyl)

sulfonyl)-6-iodo-1,2,3,4-tetrahydronaphthalen-2-yl)ethan-1-ol, as an off-white amorphous solid (166 mg, 9% yield), which could be converted to additional 2-(1-((4-fluorophenyl)sulfonyl)-6-iodo-1,2,3,4-tetrahydronaphthalen-2-yl)oxirane, as a mixture of diastereomers, by treatment with $K_2CO_3$ in MeOH as described above. LCMS m/z 538.8, 540.8 (M+H)$^+$; HPLC $t_R$ 1.08 min (method A). $^1$H NMR (499 MHz, CDCl$_3$) δ ppm 7.42-7.51 (m, 4H), 7.09-7.17 (m, 2H), 6.83 (d, J=8.2 Hz, 1H), 4.51-4.61 (m, 1H), 4.38 (d, J=4.9 Hz, 1H), 3.99 (dd, J=12.1, 6.3 Hz, 1H), 3.87 (dd, J=12.1, 7.2 Hz, 1H), 3.06-3.18 (m, 1H), 2.50 (dt, J=15.1, 3.2 Hz, 1H), 2.02-2.16 (m, 2H), 1.45-1.57 (m, 1H).

Step C: mixture of (7b-((4-fluorophenyl)sulfonyl)-5-iodo-1a,2,3,7b-tetrahydro-1H-cyclopropa[a]naphthalen-1-yl)methanol and 8b-((4-fluorophenyl)sulfonyl)-6-iodo-1,2,2a,3,4,8b-hexahydrocyclobuta[a]naphthalen-2-ol (mixtures of diastereomers)

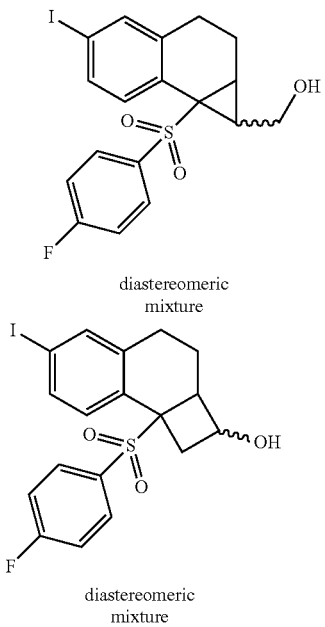

diastereomeric
mixture

A solution of a mixture of diastereomers of 2-(1-((4-fluorophenyl)sulfonyl)-6-iodo-1,2,3,4-tetrahydronaphthalen-2-yl)oxirane (277 mg, 0.574 mmol) in THF (12 mL) was stirred on a dry ice-acetone bath and treated with methylmagnesium bromide (3 M in diethyl ether; 574 µL, 1.72 mmol) over about 1 min. The resulting solution was stirred at −78° C. for 30 min, then allowed to warm to rt over 50 min. The mixture was treated with saturated aqueous NH$_4$Cl, extracted twice with EtOAc, and the combined organic phases were dried and concentrated. The residue was subjected to column chromatography on silica gel (24 g), eluting with EtOAc-hexanes (gradient from 0-60%), to provide a mixture of (7b-((4-fluorophenyl)sulfonyl)-5-iodo-1a,2,3,7b-tetrahydro-1H-cyclopropa[a]naphthalen-1-yl)methanol and 8b-((4-fluorophenyl)sulfonyl)-6-iodo-1,2,2a,3,4,8b-hexahydrocyclobuta[a]naphthalen-2-ol (as mixtures of diastereomers) as a white amorphous solid (202 mg, 77% yield), used without further purification. LCMS m/z 440.9 (M+H−H$_2$O)$^+$, 521.9 (M+Na+MeCN)$^+$; HPLC $t_R$ 0.93, 0.94 min (method A).

Step D: 8b-((4-fluorophenyl)sulfonyl)-6-iodo-2a,3,4,8b-tetrahydrocyclobuta[a]naphthalen-2(1H)-one (racemic) and 7b-((4-fluorophenyl)sulfonyl)-5-iodo-1a,2,3,7b-tetrahydro-1H-cyclopropa[a]naphthalene-1-carbaldehyde (mixture of diastereomers)

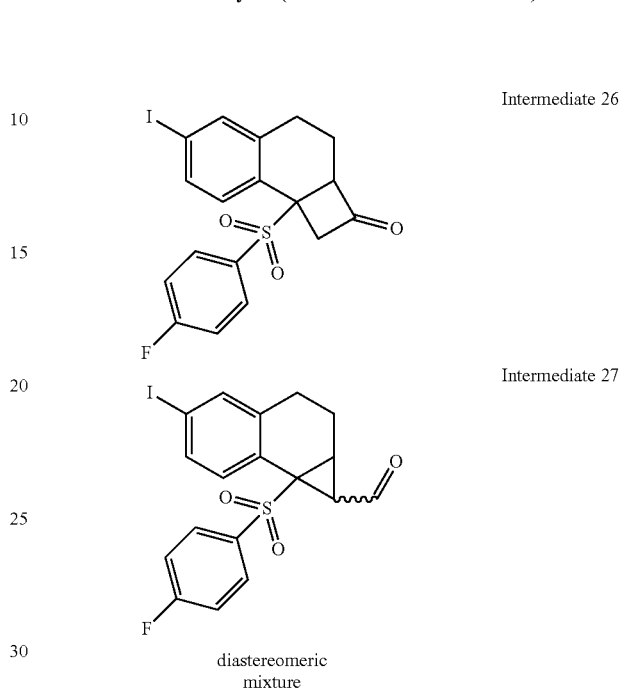

A solution of a mixture of (7b-((4-fluorophenyl)sulfonyl)-5-iodo-1a,2,3,7b-tetrahydro-1H-cyclopropa[a]naphthalen-1-yl)methanol and 8b-((4-fluorophenyl)sulfonyl)-6-iodo-1,2,2a,3,4,8b-hexahydrocyclobuta[a]naphthalen-2-ol (as mixtures of diastereomers; 199 mg, 0.434 mmol) in DCM (5 mL) was treated with Celite (500 mg, 0.434 mmol), then with pyridinium chlorochromate (206 mg, 0.955 mmol) and stirred at rt. After 3.5 h the mixture was diluted with ether, sonicated and stirred at rt for 45 min. The mixture was filtered through a pad of Florisil® and the solids were washed thoroughly with ether. The filtrate was concentrated under vacuum, and the residue was subjected to column chromatography on silica gel (24 g), eluting with EtOAc-hexanes (gradient from 0-40%), to provide two products.

The first product to elute was racemic 8b-((4-fluorophenyl)sulfonyl)-6-iodo-2a,3,4,8b-tetrahydrocyclobuta[a]naphthalen-2(1H)-one as an off-white amorphous solid (51 mg, 26% yield). LCMS m/z 519.8 (M+Na+MeCN)$^+$, 935.0 (2M+Na)$^+$; HPLC $t_R$ 0.97 min (method A). $^1$H NMR (400 MHz, CDCl$_3$) δ 7.62 (dd, J=8.1, 1.1 Hz, 1H), 7.50-7.41 (m, 3H), 7.13 (t, J=8.6 Hz, 2H), 7.03 (d, J=8.1 Hz, 1H), 4.48-4.33 (m, 2H), 3.41-3.31 (m, 1H), 2.44 (dt, J=15.0, 3.4 Hz, 1H), 2.13 (ddt, J=13.1, 9.6, 3.6 Hz, 1H), 1.85-1.69 (m, 1H), 1.60 (m, 1H).

The second product to elute was a mixture of diastereomers of 7b-((4-fluorophenyl)sulfonyl)-5-iodo-1a,2,3,7b-tetrahydro-1H-cyclopropa[a]naphthalene-1-carbaldehyde as a white amorphous solid (87 mg, 44% yield). LCMS m/z 478.9 (M+Na)$^+$, 519.9 (M+Na+MeCN)$^+$, 935.0 (2M+Na)$^+$; HPLC $t_R$ 0.96-1.01 min (method A). $^1$H NMR (400 MHz, CDCl$_3$) δ 9.88 (d, J=5.9 Hz, 0.4H), 9.14 (d, J=4.8 Hz, 0.6H), 7.69-7.33 (m, 5H), 7.11 (t, J=8.6 Hz, 2H), 3.28 (dd, J=9.8, 5.0 Hz, 0.6H), 3.17 (dt, J=8.8, 6.4 Hz, 0.4H), 2.69 (td, J=9.6, 7.0 Hz, 0.6H), 2.63-2.52 (m, 0.4H), 2.38-2.18 (m, 2H), 2.04-1.85 (m, 1H), 1.84-1.71 (m, 0.6H), 1.39-1.32 (m, 0.4H).

Intermediate 28

(7b-((4-fluorophenyl)sulfonyl)-5-iodo-1a,2,3,7b-tetrahydro-1H-cyclopropa[a]naphthalen-1-yl)methanamine hydrochloride (mixture of diastereomers)

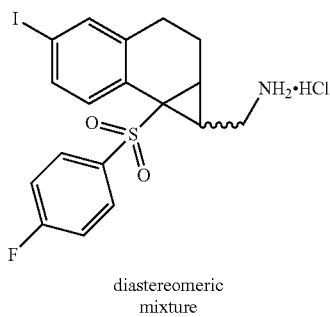

diastereomeric mixture

Step A: tert-butyl ((7b-((4-fluorophenyl)sulfonyl)-5-iodo-1a,2,3,7b-tetrahydro-1H-cyclopropa[a]naphthalen-1-yl)methyl)(4-methoxybenzyl)carbamate (mixture of diastereomers)

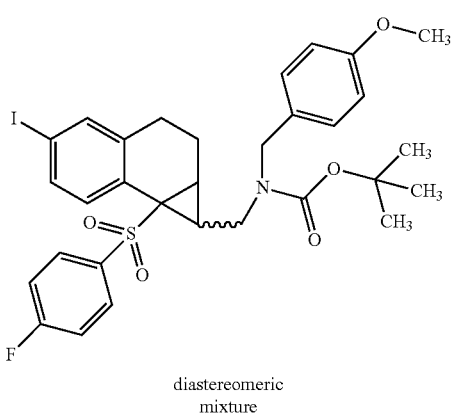 [SMILES: COc1ccc(CN(CC2C3CCc4cc(I)ccc4C32S(=O)(=O)c2ccc(F)cc2)C(=O)OC(C)(C)C)cc1]

diastereomeric mixture

A mixture of 7b-((4-fluorophenyl)sulfonyl)-5-iodo-1a,2,3,7b-tetrahydro-1H-cyclopropa[a]naphthalene-1-carbaldehyde (Intermediate 27; 316 mg, 0.693 mmol) and powdered activated molecular sieves (1.3 g) in 1,2-dichloroethane (6 mL) was stirred at rt and treated with (4-methoxyphenyl)methanamine (109 µL, 0.831 mmol) and acetic acid (59 µL, 1.04 mmol). After 15.5 h, the solution was treated with sodium triacetoxyborohydride (323 mg, 1.52 mmol) and stirring was continued at rt. After 7 h, the mixture was filtered and the solids were washed with EtOAc. The combined filtrates were washed sequentially with 1.5 M aqueous Na$_2$HPO$_4$, water and brine, dried and concentrated to provide a mixture of diastereomers of crude 1-(7b-((4-fluorophenyl)sulfonyl)-5-iodo-1a,2,3,7b-tetrahydro-1H-cyclopropa[a]naphthalen-1-yl)-N-(4-methoxybenzyl)methanamine as a brown gum, used without further purification. LCMS m/z 578.1 (M+H)$^+$; HPLC t$_R$ 0.86 and 0.88 min (method A). This material was dissolved in DCM (5 mL) and treated with TEA (338 µL, 2.42 mmol) and di-tert-butyl dicarbonate (529 mg, 2.42 mmol). The mixture was stirred at rt for 4 days, then was diluted with additional DCM, washed with saturated aqueous NaHCO$_3$, dried and concentrated. The residue was subjected to column chromatography on silica gel (40 g), eluting with EtOAc-hexanes (5-50%), to provide a mixture of diastereomers of tert-butyl ((7b-((4-fluorophenyl)sulfonyl)-5-iodo-1a,2,3,7b-tetrahydro-1H-cyclopropa[a]naphthalen-1-yl)methyl)(4-methoxybenzyl)carbamate as an off-white glassy solid (188 mg, 40% yield, purity about 85%), used without further purification. LCMS m/z 578.0 (M+H-Boc)$^+$, 1377.6 (2M+Na)$^+$; HPLC t$_R$ 1.24 min (method A).

Step B: tert-butyl ((7b-((4-fluorophenyl)sulfonyl)-5-iodo-1a,2,3,7b-tetrahydro-1H-cyclopropa[a]naphthalen-1-yl)methyl)carbamate (mixture of diastereomers)

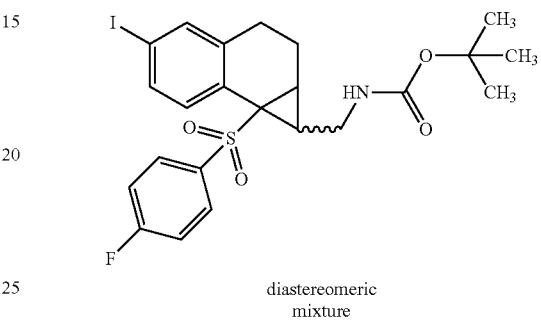

diastereomeric mixture

A solution of a mixture of diastereomers of tert-butyl ((7b-((4-fluorophenyl)sulfonyl)-5-iodo-1a,2,3,7b-tetrahydro-1H-cyclopropa[a]naphthalen-1-yl)methyl)(4-methoxybenzyl)carbamate (about 85% pure; 50 mg, 0.074 mmol) in MeCN (0.6 mL) was stirred on an ice-water bath, treated with a solution of ceric ammonium nitrate (121 mg, 0.221 mmol) in water (0.3 mL) over about 3 min, and stirred at 0° C. After 1 h, the mixture was diluted with water and extracted twice with EtOAc. The combined organic phases were dried and concentrated. The residue was subjected to column chromatography on silica gel (4 g), eluting with EtOAc-hexanes (gradient from 5-40%), to provide a mixture of diastereomers of tert-butyl ((7b-((4-fluorophenyl)sulfonyl)-5-iodo-1a,2,3,7b-tetrahydro-1H-cyclopropa[a]naphthalen-1-yl)methyl)carbamate as an off-white amorphous solid (31.9 mg, 78% yield.) LCMS m/z 457.9 (M+H-Boc)$^+$; HPLC t$_R$ 1.12 min (method A). $^1$H NMR (499 MHz, CDCl$_3$) δ 7.62 (dd, J=8.5, 1.5 Hz, 1H), 7.54-7.48 (m, 2H), 7.45 (d, J=8.1 Hz, 1H), 7.35 (s, 1H), 7.08 (t, J=8.5 Hz, 2H), 4.55 (br s, 1H), 2.97-2.79 (m, 2H), 2.71-2.63 (m, 1H), 2.37-2.13 (m, 3H), 1.84-1.70 (m, 1H), 1.50-1.43 (2s, 9H), 1.40-1.31 (m, 1H).

Step C: (7b-((4-fluorophenyl)sulfonyl)-5-iodo-1a,2,3,7b-tetrahydro-1H-cyclopropa[a]naphthalen-1-yl)methanamine hydrochloride (mixture of diastereomers)

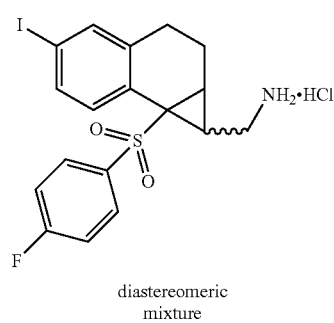

diastereomeric mixture

A solution of tert-butyl ((7b-((4-fluorophenyl)sulfonyl)-5-iodo-1a,2,3,7b-tetrahydro-1H-cyclopropa[a]naphthalen-1-yl)methyl)carbamate (29 mg, 0.052 mmol) in EtOAc (1 mL) was treated with HCl (4 M in 1,4-dioxane; 1 mL, 4.00 mmol) and allowed to stand at rt. After 75 min, the solution was concentrated to provide a crude mixture of diastereomers of (7b-((4-fluorophenyl)sulfonyl)-5-iodo-1a,2,3,7b-tetrahydro-1H-cyclopropa[a]naphthalen-1-yl)methanamine hydrochloride as a pale yellow amorphous solid (31.8 mg), used without further purification. LCMS m/z 458.0 (M+H)$^+$, 498.9 (M+H+MeCN)$^+$, 915.0 (2M+H)$^+$, 937.0 (2M+Na)$^+$; HPLC t$_R$ 0.77, 0.79 min (method A). $^1$H NMR (499 MHz, MeOH-d$_4$) δ 7.72 (dd, J=8.1, 1.1 Hz, 1H), 7.64-7.59 (m, 2H), 7.54 (d, J=8.1 Hz, 1H), 7.48 (s, 1H), 7.24 (t, J=8.7 Hz, 2H), 3.79-3.73 (m, 1H), 2.98 (dd, J=13.7, 4.6 Hz, 1H), 2.74-2.65 (m, 1H), 2.54 (td, J=9.4, 7.3 Hz, 1H), 2.40 (dd, J=13.8, 9.5 Hz, 1H), 2.37-2.24 (m, 2H), 1.79 (td, J=14.2, 4.1 Hz, 1H).

Intermediate 29

8b-((4-fluorophenyl)sulfonyl)-6-iodo-1,2,2a,3,4,8b-hexahydrocyclobuta[a]naphthalen-2-amine hydrochloride (mixture of diastereomers)

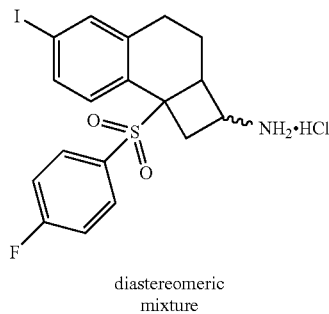

diastereomeric mixture

Following the procedures used to prepare Intermediate 28, racemic 8b-((4-fluorophenyl)sulfonyl)-6-iodo-2a,3,4,8b-tetrahydrocyclobuta[a]naphthalen-2(1H)-one (Intermediate 26; 178 mg, 0.390 mmol) was converted into a crude mixture of diastereomers of 8b-((4-fluorophenyl)sulfonyl)-6-iodo-1,2,2a,3,4,8b-hexahydrocyclobuta[a]naphthalen-2-amine hydrochloride (35 mg, 9% yield, about 50% purity), which was used without further purification. LCMS m/z 458.0 (M+H)$^+$, 498.9 (M+H+MeCN)$^+$, 915.7 (2M+H)$^+$; HPLC t$_R$ 0.76 min (method A).

Intermediate 30

2-(1-(aminomethyl)-7b-((4-fluorophenyl)sulfonyl)-1a,2,3,7b-tetrahydro-1H-cyclopropa[a]naphthalen-5-yl)-1,1,1,3,3,3-hexafluoropropan-2-ol hydrochloride (mixture of diastereomers)

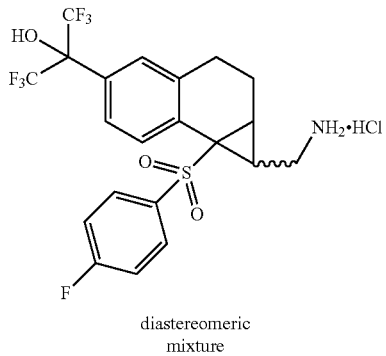

diastereomeric mixture

Step A: tert-butyl ((7b-((4-fluorophenyl)sulfonyl)-5-(1,1,1,3,3,3-hexafluoro-2-hydroxypropan-2-yl)-1a,2,3,7b-tetrahydro-1H-cyclopropa[a]naphthalen-1-yl)methyl)(4-methoxybenzyl)carbamate (mixture of diastereomers)

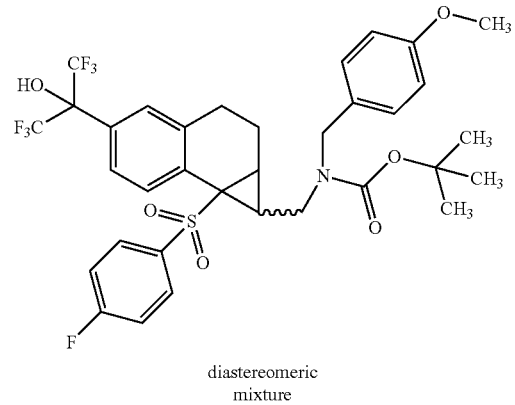 [SMILES: COc1ccc(CN(CC2C3CCc4cc(C(O)(C(F)(F)F)C(F)(F)F)ccc4C32S(=O)(=O)c2ccc(F)cc2)C(=O)OC(C)(C)C)cc1]

diastereomeric mixture

A solution of tert-butyl ((7b-((4-fluorophenyl)sulfonyl)-5-iodo-1a,2,3,7b-tetrahydro-1H-cyclopropa[a]naphthalen-1-yl)methyl)(4-methoxybenzyl)carbamate (Intermediate 27; 106 mg, 0.156 mmol) in diethyl ether (2 mL) was stirred on a dry ice-acetone bath and treated dropwise with tert-butyllithium (1.7 M in pentane; 202 μL, 0.344 mmol) over about 30 sec, forming a yellow-brown color. After 10 min, hexafluoroacetone was introduced via a needle above the surface of the solution for about 25 sec, causing rapid lightening of the color. (About 0.25-0.5 g of hexafluoroacetone was added.) The mixture was stirred at −78° C. for 1 h, then allowed to warm to rt and stirred for 25 min. The mixture was treated with saturated aqueous NH$_4$Cl, diluted with EtOAc and water, and the layers mixed and separated. The organic phase was washed with brine, dried and concentrated. The residue was subjected to column chromatography on silica gel (12 g), eluting with EtOAc-hexanes (gradient from 0-50%), to provide a mixture of diastereomers of tert-butyl ((7b-((4-fluorophenyl)sulfonyl)-5-(1,1,1,3,3,3-hexafluoro-2-hydroxypropan-2-yl)-1a,2,3,7b-tetrahydro-1H-cyclopropa[a]naphthalen-1-yl)methyl)(4-methoxybenzyl)carbamate as a white amorphous solid (37.5 mg, 33% yield), used without further purification. LCMS m/z 618.2 (M+H−Boc)$^+$, 662.3 (M+H−C$_4$H$_8$)$^+$, 1457 (2M+Na)$^+$; HPLC t$_R$ 1.15 min (method A).

Step B: 2-(1-(aminomethyl)-7b-((4-fluorophenyl)sulfonyl)-1a,2,3,7b-tetrahydro-1H-cyclopropa[a]naphthalen-5-yl)-1,1,1,3,3,3-hexafluoropropan-2-ol hydrochloride (mixture of diastereomers)

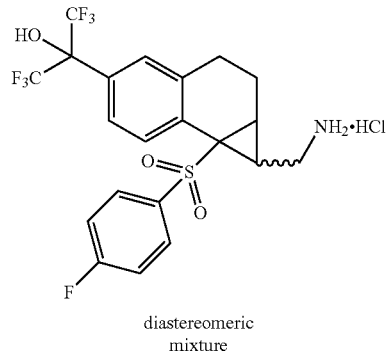

diastereomeric mixture

Following the procedure used to prepare Intermediate 28, a mixture of diastereomers of tert-butyl (((7b-((4-fluorophenyl)sulfonyl)-5-(1,1,1,3,3,3-hexafluoro-2-hydroxypropan-2-yl)-1a,2,3,7b-tetrahydro-H-cyclopropa[a]naphthalen-1-yl)methyl)(4-methoxybenzyl)carbamate (32.4 mg, 0.045 mmol) was converted into a mixture of diastereomers of 2-(1-(aminomethyl)-7b-((4-fluorophenyl)sulfonyl)-1a,2,3,7b-tetrahydro-1H-cyclopropa[a]naphthalen-5-yl)-1,1,1,3,3,3-hexafluoropropan-2-ol hydrochloride as a colorless amorphous solid (15.6 mg, 48% yield), used without further purification. LCMS m/z 498.1 (M+H)$^+$, 539.3 (M+H+MeCN)$^+$; 995.2 (2M+H)$^+$; HPLC $t_R$ 0.77 min (method A).

Example 1

((3S,3aR,9bR)-9b-((4-fluorophenyl)sulfonyl)-7-(perfluoropropan-2-yl)-2,3,3a,4,5,9b-hexahydro-1H-cyclopenta[a]naphthalen-3-yl)(4-hydroxy-4-methylpiperidin-1-yl)methanone

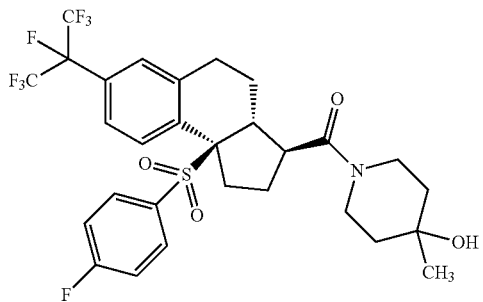 [SMILES: CC1(O)CCN(C(=O)[C@H]2CC[C@]3(S(=O)(=O)c4ccc(F)cc4)c4ccc(C(F)(C(F)(F)F)C(F)(F)F)cc4CC[C@H]23)CC1]

A solution of (3S,3aR,9bR)-9b-((4-fluorophenyl)sulfonyl)-7-(perfluoropropan-2-yl)-2,3,3a,4,5,9b-hexahydro-1H-cyclopenta[a]naphthalene-3-carboxylic acid (Intermediate 11; 20 mg, 0.037 mmol) in DMF (370 µL) was treated with 4-methylpiperidin-4-ol (13 mg, 0.11 mmol), DIEA (32 µL, 0.184 mmol) and HATU (21 mg, 0.055 mmol). The mixture was stirred at rt for 30 min, then was purified by preparative HPLC (Method E, gradient 45-90% B, 20 min) to provide ((3S,3aR,9bR)-9b-((4-fluorophenyl)sulfonyl)-7-(perfluoropropan-2-yl)-2,3,3a,4,5,9b-hexahydro-1H-cyclopenta[a]naphthalen-3-yl)(4-hydroxy-4-methylpiperidin-1-yl)methanone (11.5 mg, 49% yield). LCMS m/z 640.2 (M+H)$^+$; HPLC $t_R$ 1.03 min (Method A). $^1$H NMR (500 MHz, DMSO-d$_6$) δ 7.46-7.36 (m, 2H), 7.36-7.24 (m, 5H), 4.51 (s, 1H), 3.94 (br s, 1H), 3.61-3.54 (m, 1H), 3.31 (br t, J=12.5 Hz, 1H), 3.17 (d, J=5.2 Hz, 1H), 3.14-3.04 (m, 1H), 3.03-2.90 (m, 2H), 2.73-2.54 (m, 1H), 2.41-2.22 (m, 1H), 2.18 (br d, J=10.7 Hz, 1H), 1.92 (br s, 2H), 1.86-1.66 (m, 1H), 1.44 (br s, 2H), 1.33 (br t, J=10.1 Hz, 2H), 1.18-1.06 (m, 4H). $^{19}$F NMR (471 MHz, DMSO-d$_6$) δ −103.1 (s, 1F), −75.1 (m, 6F), −75.0 (m, 1F).

The Examples in Table 3 were prepared using the procedures used to prepare Example 1, or similar procedures, from the appropriate carboxylic acid and amine starting materials.

TABLE 3

| Ex. number | Structure | LCMS m/z observed | HPLC $t_R$ (min) | HPLC method |
|---|---|---|---|---|
| 2 | (structure) | 633.2 (M + H)$^+$ | 0.91 | B |
| 3 | (structure) | 653.3 (M + H)$^+$ | 1.00 | A |

TABLE 3-continued

| Ex. number | Structure | LCMS m/z observed | HPLC t$_R$ (min) | HPLC method |
|---|---|---|---|---|
| 4 | 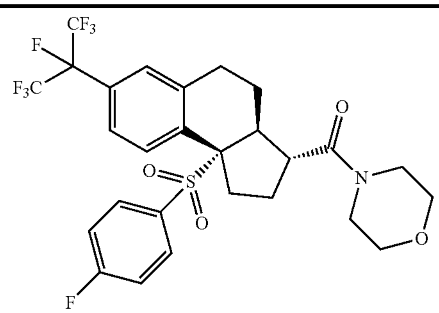 | 612.2 (M + H)$^+$ | 1.05 | A |
| 5 | 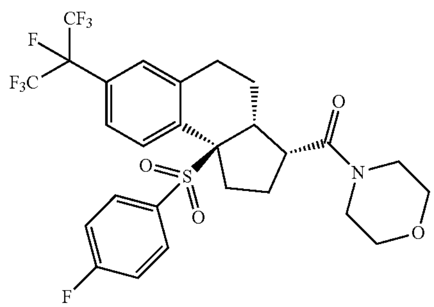 [SMILES: O=C([C@@H]1CC[C@]2(S(=O)(=O)c3ccc(F)cc3)c3ccc(C(F)(C(F)(F)F)C(F)(F)F)cc3CC[C@H]12)N1CCOCC1] | 612.2 (M + H)$^+$ | 1.06 | A |
| 6 | 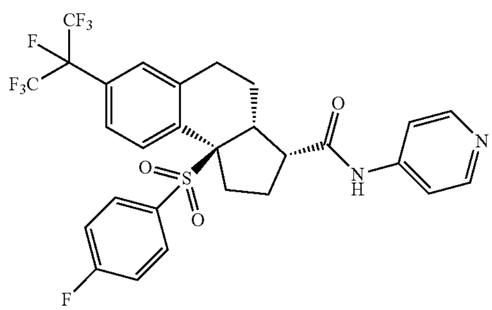 [SMILES: O=C(Nc1ccncc1)[C@@H]1CC[C@]2(S(=O)(=O)c3ccc(F)cc3)c3ccc(C(F)(C(F)(F)F)C(F)(F)F)cc3CC[C@H]12] | 619.1 (M + H)$^+$ | 0.91 | A |
| 7 | 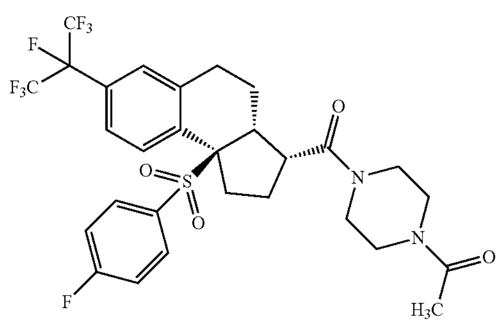 [SMILES: CC(=O)N1CCN(C(=O)[C@@H]2CC[C@]3(S(=O)(=O)c4ccc(F)cc4)c4ccc(C(F)(C(F)(F)F)C(F)(F)F)cc4CC[C@H]23)CC1] | 653.1 (M + H)$^+$ | 2.15 | C |
| 8 | 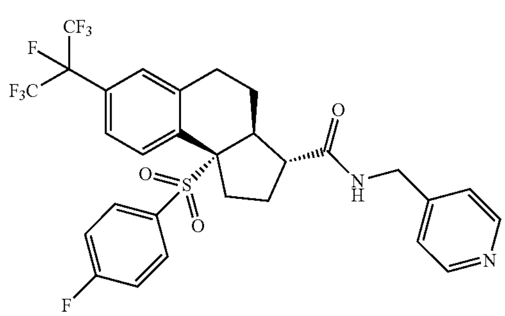 [SMILES: O=C(NCc1ccncc1)[C@@H]1CC[C@@]2(S(=O)(=O)c3ccc(F)cc3)c3ccc(C(F)(C(F)(F)F)C(F)(F)F)cc3CC[C@@H]12] | 633.2 (M + H)$^+$ | 0.91 | B |

TABLE 3-continued

| Ex. number | Structure | LCMS m/z observed | HPLC $t_R$ (min) | HPLC method |
|---|---|---|---|---|
| 9 | 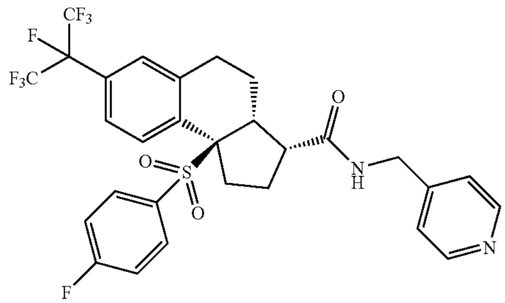 [SMILES: O=C(NCc1ccncc1)[C@@H]1CC[C@]2(S(=O)(=O)c3ccc(F)cc3)c3ccc(C(F)(C(F)(F)F)C(F)(F)F)cc3CC[C@H]12] | 633.2 (M + H)+ | 0.87 | A |
| 10 | 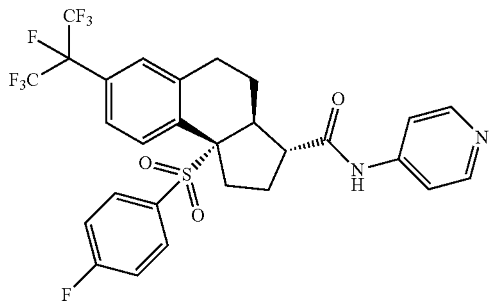 [SMILES: O=C(Nc1ccncc1)[C@@H]1CC[C@@]2(S(=O)(=O)c3ccc(F)cc3)c3ccc(C(F)(C(F)(F)F)C(F)(F)F)cc3CC[C@@H]12] | 619.1 (M + H)+ | 0.94 | B |
| 11 | 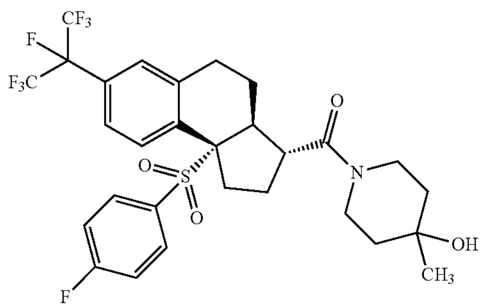 [SMILES: CC1(O)CCN(C(=O)[C@@H]2CC[C@@]3(S(=O)(=O)c4ccc(F)cc4)c4ccc(C(F)(C(F)(F)F)C(F)(F)F)cc4CC[C@@H]23)CC1] | 640.2 (M + H)+ | 1.07 | B |
| 12 | Diastereomeric mixture | 660.1 (M + H)+ | 1.01 | A |
| 13 | 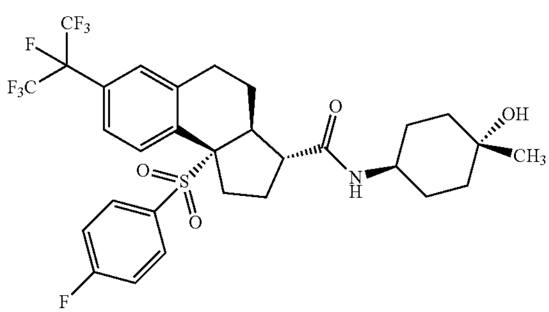 [SMILES: C[C@]1(O)CC[C@H](NC(=O)[C@@H]2CC[C@@]3(S(=O)(=O)c4ccc(F)cc4)c4ccc(C(F)(C(F)(F)F)C(F)(F)F)cc4CC[C@@H]23)CC1] | 654.2 (M + H)+ | 1.03 | A |

TABLE 3-continued

| Ex. number | Structure | LCMS m/z observed | HPLC t$_R$ (min) | HPLC method |
|---|---|---|---|---|
| 14 | 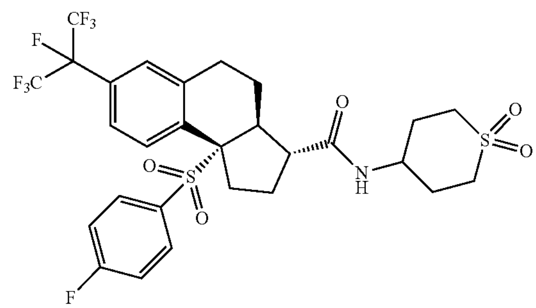 [SMILES: O=C(NC1CCS(=O)(=O)CC1)[C@@H]1CC[C@@]2(S(=O)(=O)c3ccc(F)cc3)c3ccc(C(F)(C(F)(F)F)C(F)(F)F)cc3CC[C@@H]12] | 674.1 (M + H)$^+$ | 1.01 | A |
| 15 | Diastereomeric mixture | 674.2 (M + H)$^+$ | 1.01 | A |
| 16 | 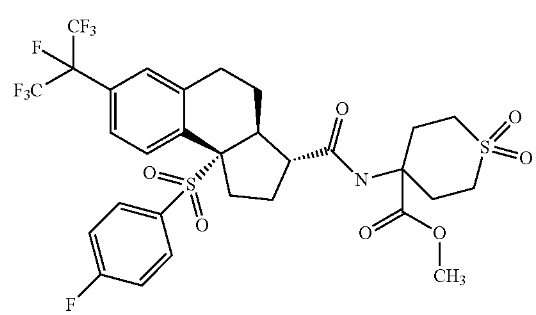 [SMILES: COC(=O)C1(NC(=O)[C@@H]2CC[C@@]3(S(=O)(=O)c4ccc(F)cc4)c4ccc(C(F)(C(F)(F)F)C(F)(F)F)cc4CC[C@@H]23)CCS(=O)(=O)CC1] | 732.1 (M + H)$^+$ | 1.05 | A |
| 17 | 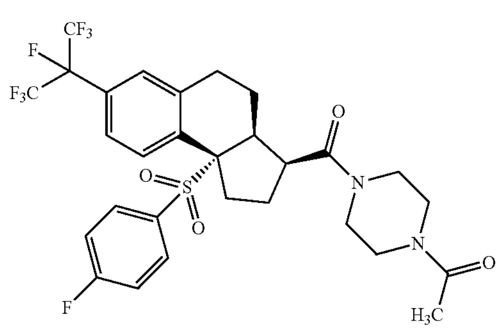 [SMILES: CC(=O)N1CCN(C(=O)[C@H]2CC[C@@]3(S(=O)(=O)c4ccc(F)cc4)c4ccc(C(F)(C(F)(F)F)C(F)(F)F)cc4CC[C@@H]23)CC1] | 653.2 (M + H)$^+$ | 1.01 | A |

TABLE 3-continued

| Ex. number | Structure | LCMS m/z observed | HPLC t_R (min) | HPLC method |
|---|---|---|---|---|
| 18 | 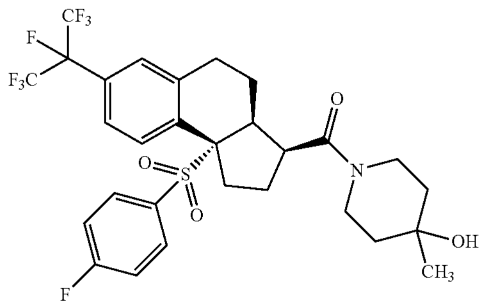 [SMILES: CC1(O)CCN(C(=O)[C@H]2CC[C@@]3(S(=O)(=O)c4ccc(F)cc4)c4ccc(C(F)(C(F)(F)F)C(F)(F)F)cc4CC[C@@H]23)CC1] | 640.2 (M + H)+ | 1.04 | A |
| 19 | 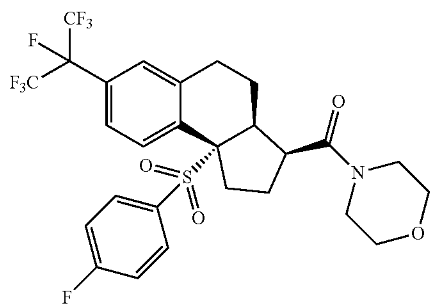 [SMILES: O=C([C@H]1CC[C@@]2(S(=O)(=O)c3ccc(F)cc3)c3ccc(C(F)(C(F)(F)F)C(F)(F)F)cc3CC[C@@H]12)N1CCOCC1] | 612.2 (M + H)+ | 1.06 | A |
| 20 | 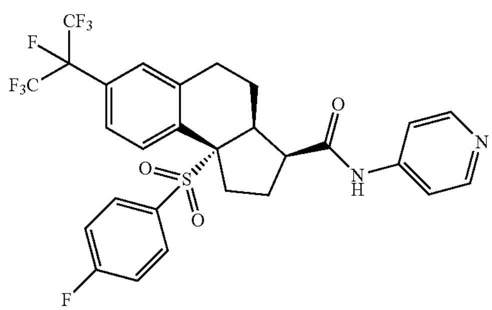 [SMILES: O=C(Nc1ccncc1)[C@H]1CC[C@@]2(S(=O)(=O)c3ccc(F)cc3)c3ccc(C(F)(C(F)(F)F)C(F)(F)F)cc3CC[C@@H]12] | 619.2 (M + H)+ | 0.91 | A |
| 21 | 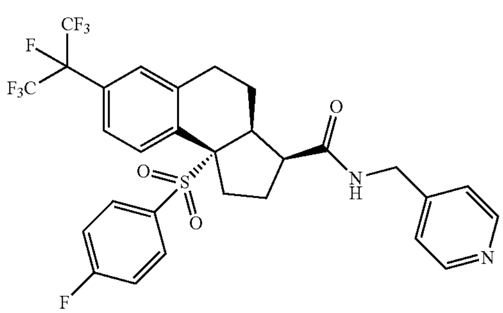 [SMILES: O=C(NCc1ccncc1)[C@H]1CC[C@@]2(S(=O)(=O)c3ccc(F)cc3)c3ccc(C(F)(C(F)(F)F)C(F)(F)F)cc3CC[C@@H]12] | 633.2 (M + H)+ | 0.87 | A |
| 22 | 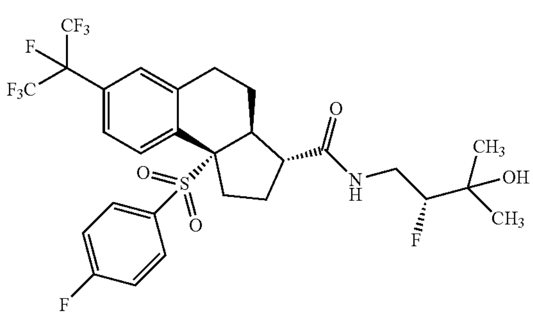 [SMILES: CC(C)(O)[C@H](F)CNC(=O)[C@@H]1CC[C@@]2(S(=O)(=O)c3ccc(F)cc3)c3ccc(C(F)(C(F)(F)F)C(F)(F)F)cc3CC[C@@H]12] | 646.2 (M + H)+ | 1.06 | B |

TABLE 3-continued

| Ex. number | Structure | LCMS m/z observed | HPLC $t_R$ (min) | HPLC method |
|---|---|---|---|---|
| 23 | (structure) Diastereomeric mixture | 644.2 (M + H)+ | 1.00 | B |
| 24 | (structure) | 612.2 (M + H)+ | 1.01 | B |
| 25 | (structure) | 608.2 (M + H)+ | 1.14 | B |
| 26 | (structure) | 542.1 (M + H)+ | 1.03 | B |
| 27 | (structure) | 659.2 (M + H)+ | 1.04 | B |

TABLE 3-continued

| Ex. number | Structure | LCMS m/z observed | HPLC $t_R$ (min) | HPLC method |
|---|---|---|---|---|
| 28 | 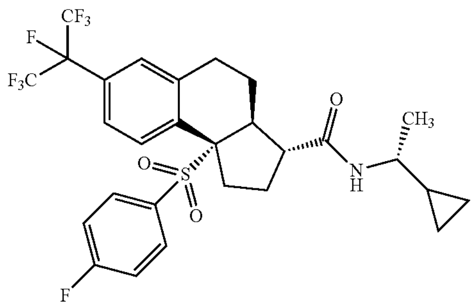 [SMILES: C[C@@H](NC(=O)[C@@H]1CC[C@@]2(S(=O)(=O)c3ccc(F)cc3)c3ccc(C(F)(C(F)(F)F)C(F)(F)F)cc3CC[C@@H]12)C1CC1] | 610.2 (M + H)+ | 1.14 | B |
| 29 | 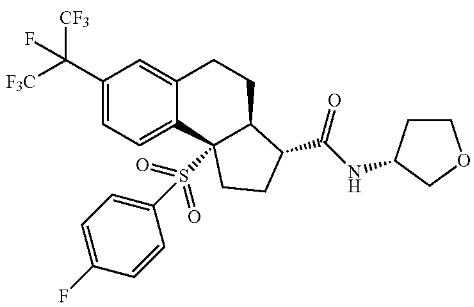 [SMILES: O=C(N[C@@H]1CCOC1)[C@@H]1CC[C@@]2(S(=O)(=O)c3ccc(F)cc3)c3ccc(C(F)(C(F)(F)F)C(F)(F)F)cc3CC[C@@H]12] | 612.2 (M + H)+ | 1.05 | B |
| 30 | 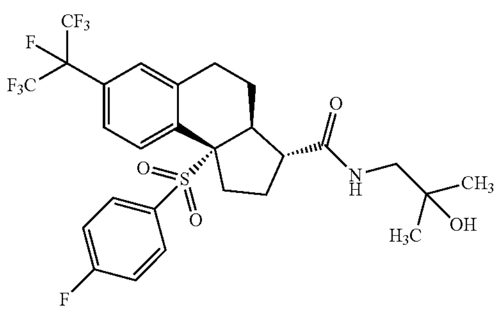 [SMILES: CC(C)(O)CNC(=O)[C@@H]1CC[C@@]2(S(=O)(=O)c3ccc(F)cc3)c3ccc(C(F)(C(F)(F)F)C(F)(F)F)cc3CC[C@@H]12] | 614.2 (M + H)+ | 1.04 | B |
| 31 | 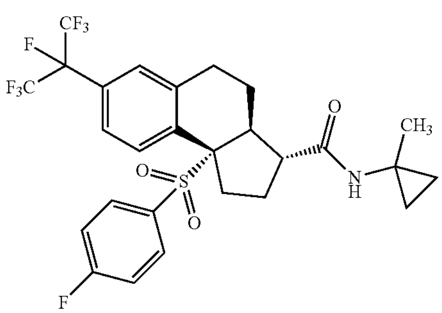 | 596.2 (M + H)+ | 1.11 | B |
| 32 | 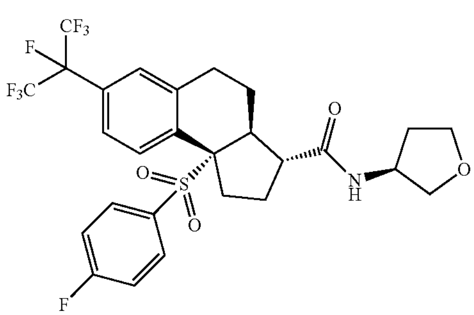 [SMILES: O=C(N[C@H]1CCOC1)[C@@H]1CC[C@@]2(S(=O)(=O)c3ccc(F)cc3)c3ccc(C(F)(C(F)(F)F)C(F)(F)F)cc3CC[C@@H]12] | 612.2 (M + H)+ | 1.05 | B |

TABLE 3-continued
| Ex. number | Structure | LCMS m/z observed | HPLC $t_R$ (min) | HPLC method |
|---|---|---|---|---|
| 33 | 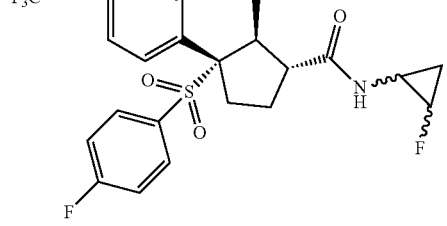 Diastereomeric mixture | 600.1 (M + H)+ | 1.07 | B |
| 34 | 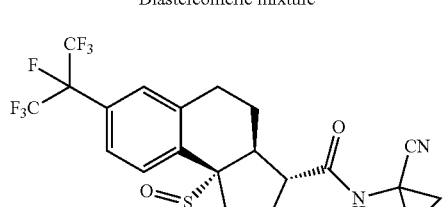 | 607.1 (M + H)+ | 1.07 | B |
| 35 | 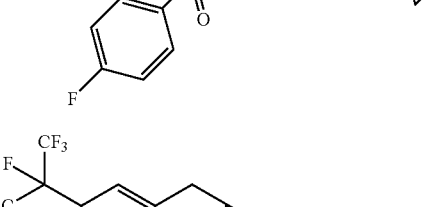 | 632.1 (M + H)+ | 1.11 | B |
| 36 | 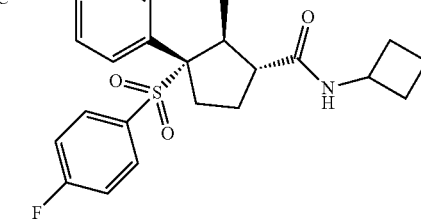 | 640.3 (M + H)+ | 1.03 | B |
| 37 | 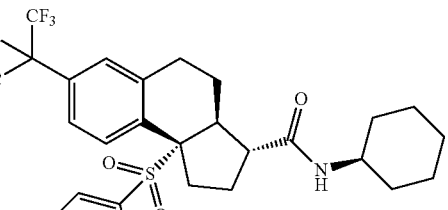 | 559.1 (M + H)+ | 1.05 | B |

TABLE 3-continued

| Ex. number | Structure | LCMS m/z observed | HPLC t$_R$ (min) | HPLC method |
|---|---|---|---|---|
| 38 | 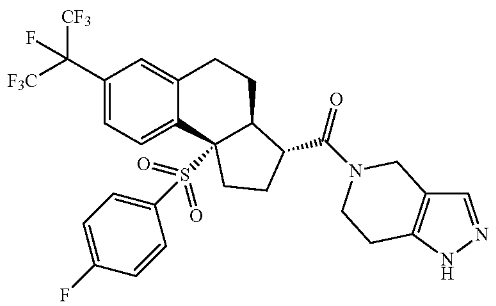 [SMILES: O=C([C@@H]1CC[C@@]2(S(=O)(=O)c3ccc(F)cc3)c3ccc(C(F)(C(F)(F)F)C(F)(F)F)cc3CC[C@@H]12)N1CCc2[nH]ncc2C1] | 648.2 (M + H)⁺ | 1.00 | B |
| 39 | Diastereomeric mixture | 639.1 (M + H)⁺ | 1.01 | B |
| 40 | 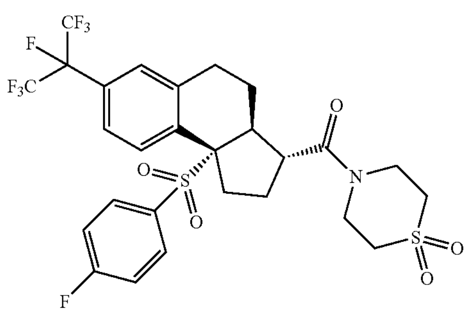 [SMILES: O=C([C@@H]1CC[C@@]2(S(=O)(=O)c3ccc(F)cc3)c3ccc(C(F)(C(F)(F)F)C(F)(F)F)cc3CC[C@@H]12)N1CCS(=O)(=O)CC1] | 660.1 (M + H)⁺ | 1.05 | B |
| 41 | 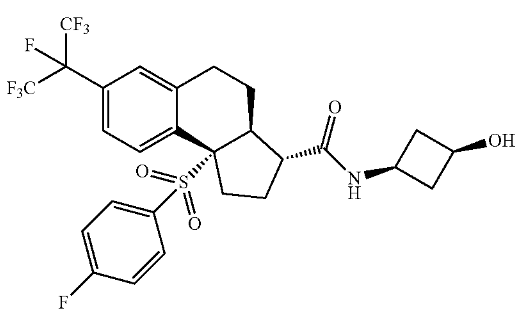 [SMILES: O=C(N[C@H]1C[C@@H](O)C1)[C@@H]1CC[C@@]2(S(=O)(=O)c3ccc(F)cc3)c3ccc(C(F)(C(F)(F)F)C(F)(F)F)cc3CC[C@@H]12] | 612.2 (M + H)⁺ | 1.01 | B |

TABLE 3-continued

| Ex. number | Structure | LCMS m/z observed | HPLC t$_R$ (min) | HPLC method |
|---|---|---|---|---|
| 42 | 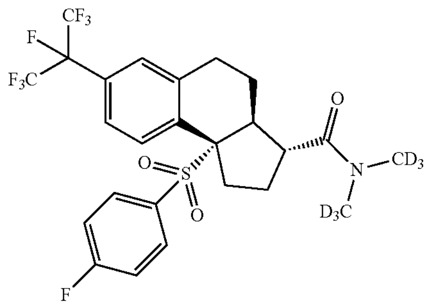 [SMILES: [2H]C([2H])([2H])N(C(=O)[C@@H]1CC[C@@]2(S(=O)(=O)c3ccc(F)cc3)c3ccc(C(F)(C(F)(F)F)C(F)(F)F)cc3CC[C@@H]12)C([2H])([2H])[2H]] | 576.2 (M + H)$^+$ | 1.08 | A |
| 43 | 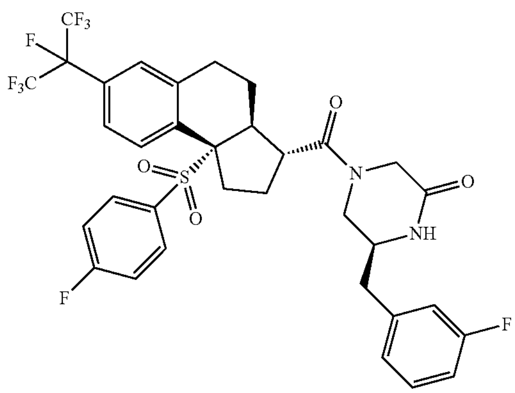 [SMILES: O=C1CN(C(=O)[C@@H]2CC[C@@]3(S(=O)(=O)c4ccc(F)cc4)c4ccc(C(F)(C(F)(F)F)C(F)(F)F)cc4CC[C@@H]23)C[C@H](Cc2cccc(F)c2)N1] | 733.2 (M + H)$^+$ | 1.10 | B |
| 44 | 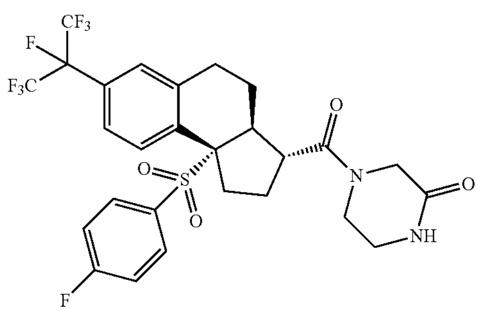 [SMILES: O=C1CN(C(=O)[C@@H]2CC[C@@]3(S(=O)(=O)c4ccc(F)cc4)c4ccc(C(F)(C(F)(F)F)C(F)(F)F)cc4CC[C@@H]23)CCN1] | 625.2 (M + H)$^+$ | 1.00 | B |
| 45 | 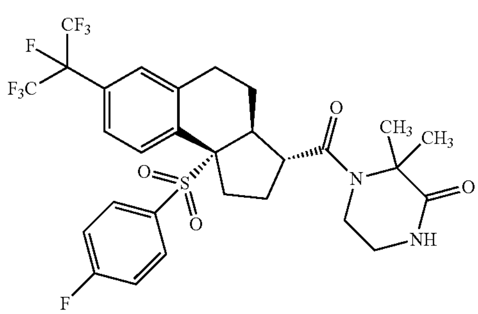 [SMILES: CC1(C)C(=O)NCCN1C(=O)[C@@H]1CC[C@@]2(S(=O)(=O)c3ccc(F)cc3)c3ccc(C(F)(C(F)(F)F)C(F)(F)F)cc3CC[C@@H]12] | 653.2 (M + H)$^+$ | 1.05 | B |

TABLE 3-continued

| Ex. number | Structure | LCMS m/z observed | HPLC $t_R$ (min) | HPLC method |
|---|---|---|---|---|
| 46 | 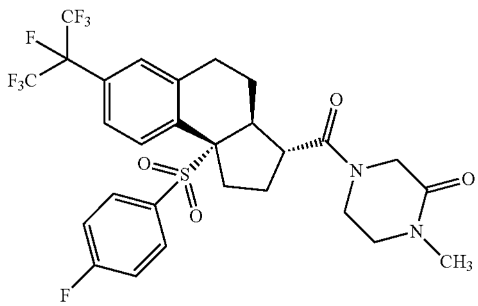 [SMILES: CN1CCN(C(=O)[C@@H]2CC[C@@]3(S(=O)(=O)c4ccc(F)cc4)c4ccc(C(F)(C(F)(F)F)C(F)(F)F)cc4CC[C@@H]23)CC1=O] | 639.1 (M + H)⁺ | 1.02 | B |
| 47 | Diastereomeric mixture | 639.1 (M + H)⁺ | 1.01 | B |
| 48 | 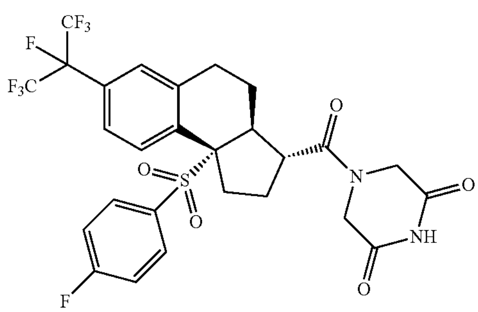 [SMILES: O=C1CN(C(=O)[C@@H]2CC[C@@]3(S(=O)(=O)c4ccc(F)cc4)c4ccc(C(F)(C(F)(F)F)C(F)(F)F)cc4CC[C@@H]23)CC(=O)N1] | 639.0 (M + H)⁺ | 1.04 | B |
| 49 | Diastereomeric mixture | 618.2 (M + H)⁺ | 1.10 | B |

TABLE 3-continued

| Ex. number | Structure | LCMS m/z observed | HPLC t_R (min) | HPLC method |
|---|---|---|---|---|
| 50 | 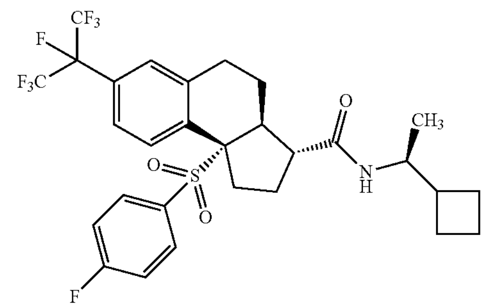 [SMILES: C[C@H](NC(=O)[C@@H]1CC[C@@]2(S(=O)(=O)c3ccc(F)cc3)c3ccc(C(F)(C(F)(F)F)C(F)(F)F)cc3CC[C@@H]12)C1CCC1] | 624.2 (M + H)+ | 1.16 | B |
| 51 | 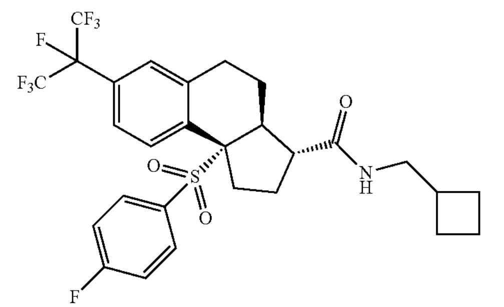 [SMILES: O=C(NCC1CCC1)[C@@H]1CC[C@@]2(S(=O)(=O)c3ccc(F)cc3)c3ccc(C(F)(C(F)(F)F)C(F)(F)F)cc3CC[C@@H]12] | 610.2 (M + H)+ | 1.15 | B |
| 52 | 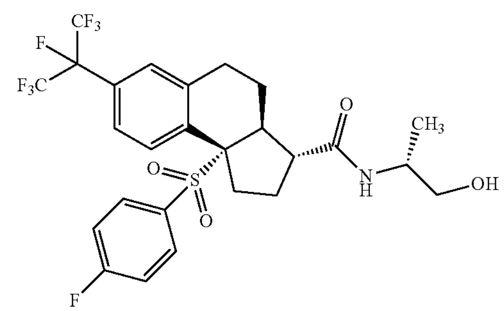 [SMILES: C[C@H](CO)NC(=O)[C@@H]1CC[C@@]2(S(=O)(=O)c3ccc(F)cc3)c3ccc(C(F)(C(F)(F)F)C(F)(F)F)cc3CC[C@@H]12] | 600.2 (M + H)+ | 1.02 | B |
| 53 | 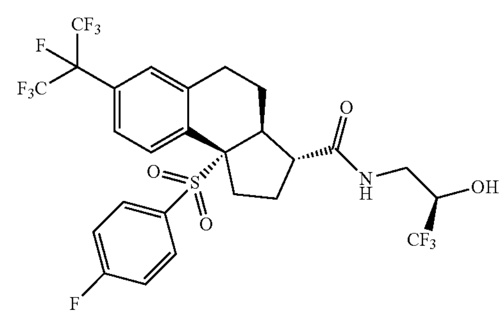 [SMILES: O=C(NC[C@@H](O)C(F)(F)F)[C@@H]1CC[C@@]2(S(=O)(=O)c3ccc(F)cc3)c3ccc(C(F)(C(F)(F)F)C(F)(F)F)cc3CC[C@@H]12] | 654.2 (M + H)+ | 1.07 | B |
| 54 | 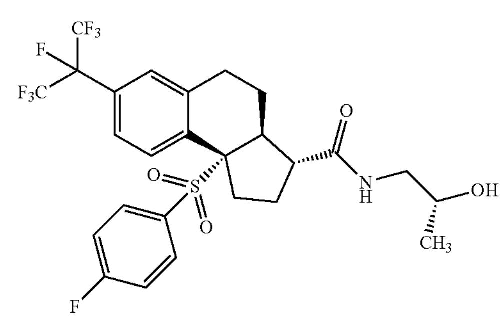 [SMILES: C[C@@H](O)CNC(=O)[C@@H]1CC[C@@]2(S(=O)(=O)c3ccc(F)cc3)c3ccc(C(F)(C(F)(F)F)C(F)(F)F)cc3CC[C@@H]12] | 600.2 (M + H)+ | 1.02 | B |

TABLE 3-continued

| Ex. number | Structure | LCMS m/z observed | HPLC t$_R$ (min) | HPLC method |
|---|---|---|---|---|
| 55 | 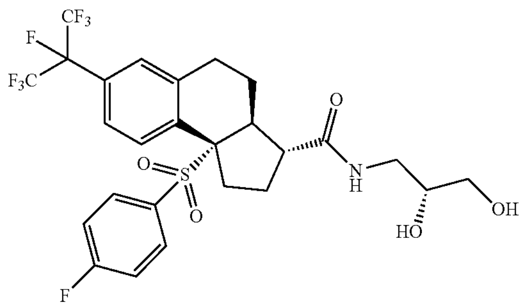 [SMILES: O=C(NC[C@@H](O)CO)[C@@H]1CC[C@@]2(S(=O)(=O)c3ccc(F)cc3)c3ccc(C(F)(C(F)(F)F)C(F)(F)F)cc3CC[C@@H]12] | 616.2 (M + H)$^+$ | 0.97 | B |
| 56 | 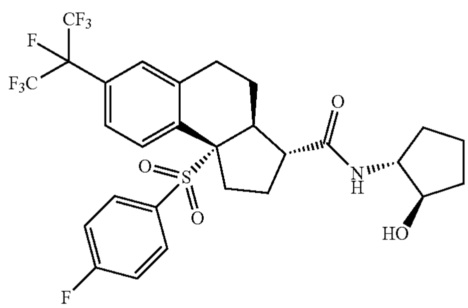 [SMILES: O=C(N[C@@H]1CCC[C@H]1O)[C@@H]1CC[C@@]2(S(=O)(=O)c3ccc(F)cc3)c3ccc(C(F)(C(F)(F)F)C(F)(F)F)cc3CC[C@@H]12] | 626.2 (M + H)$^+$ | 1.06 | B |
| 57 | 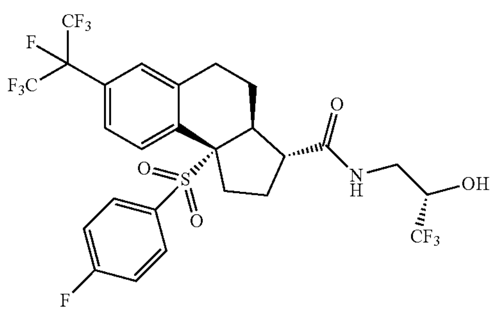 [SMILES: O=C(NC[C@H](O)C(F)(F)F)[C@@H]1CC[C@@]2(S(=O)(=O)c3ccc(F)cc3)c3ccc(C(F)(C(F)(F)F)C(F)(F)F)cc3CC[C@@H]12] | 654.2 (M + H)$^+$ | 1.07 | B |
| 58 | 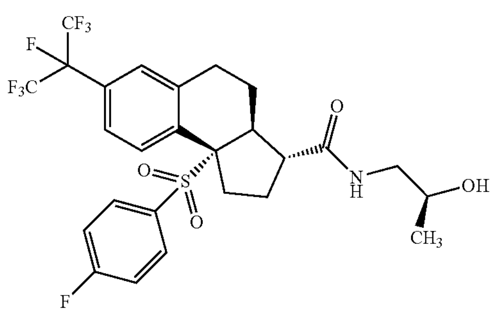 [SMILES: C[C@H](O)CNC(=O)[C@@H]1CC[C@@]2(S(=O)(=O)c3ccc(F)cc3)c3ccc(C(F)(C(F)(F)F)C(F)(F)F)cc3CC[C@@H]12] | 600.2 (M + H)$^+$ | 1.02 | B |
| 59 | 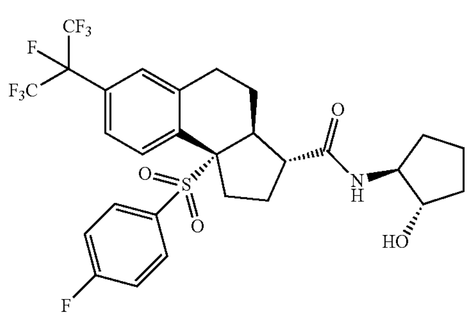 [SMILES: O=C(N[C@H]1CCC[C@@H]1O)[C@@H]1CC[C@@]2(S(=O)(=O)c3ccc(F)cc3)c3ccc(C(F)(C(F)(F)F)C(F)(F)F)cc3CC[C@@H]12] | 626.2 (M + H)$^+$ | 1.06 | B |

TABLE 3-continued

| Ex. number | Structure | LCMS m/z observed | HPLC t_R (min) | HPLC method |
|---|---|---|---|---|
| 60 | (structure) | 600.2 (M + H)⁺ | 1.02 | B |
| 61 | (structure) | 610.2 (M + H)⁺ | 1.14 | B |
| 62 | (structure) | 586.1 (M + H)⁺ | 1.00 | A |
| 63 | (structure) | 668.0 (M + H)⁺ | 1.16 | A |
| 64 | (structure) | 662.0 (M + H)⁺ | 1.08 | A |

TABLE 3-continued

| Ex. number | Structure | LCMS m/z observed | HPLC t$_R$ (min) | HPLC method |
|---|---|---|---|---|
| 65 | 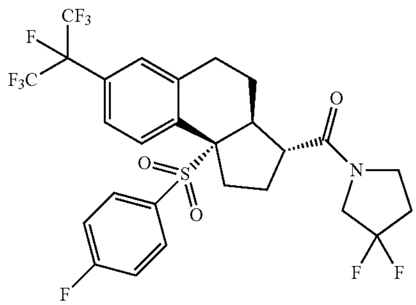 [SMILES: O=C([C@@H]1CC[C@@]2(S(=O)(=O)c3ccc(F)cc3)c3ccc(C(F)(C(F)(F)F)C(F)(F)F)cc3CC[C@@H]12)N1CCC(F)(F)C1] | 632.0 (M + H)$^+$ | 1.13 | A |
| 66 | 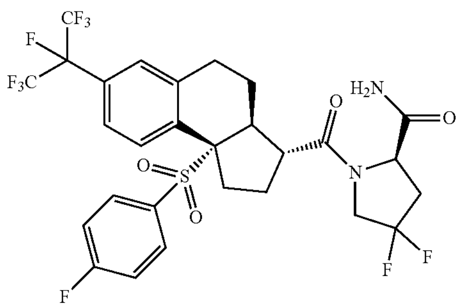 [SMILES: NC(=O)[C@H]1CC(F)(F)CN1C(=O)[C@@H]1CC[C@@]2(S(=O)(=O)c3ccc(F)cc3)c3ccc(C(F)(C(F)(F)F)C(F)(F)F)cc3CC[C@@H]12] | 675.0 (M + H)$^+$ | 1.04 | A |
| 67 | 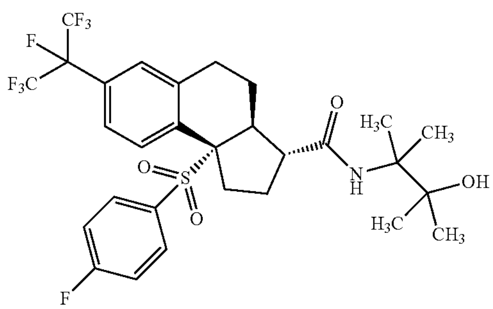 [SMILES: CC(C)(O)C(C)(C)NC(=O)[C@@H]1CC[C@@]2(S(=O)(=O)c3ccc(F)cc3)c3ccc(C(F)(C(F)(F)F)C(F)(F)F)cc3CC[C@@H]12] | 642.1 (M + H)$^+$ | 1.12 | A |
| 68 | Homochiral from peak 1 | 646.1 (M + H)$^+$ | 1.13 | A |
| 69 | Homochiral from peak 2 | 646.1 (M + H)$^+$ | 1.13 | A |

TABLE 3-continued

| Ex. number | Structure | LCMS m/z observed | HPLC t_R (min) | HPLC method |
|---|---|---|---|---|
| 70 | 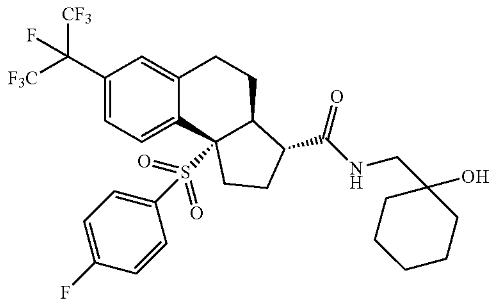 [SMILES: O=C(NCC1(O)CCCCC1)[C@@H]1CC[C@@]2(S(=O)(=O)c3ccc(F)cc3)c3ccc(C(F)(C(F)(F)F)C(F)(F)F)cc3CC[C@@H]12] | 654.2 (M + H)+ | 1.08 | B |
| 71 | 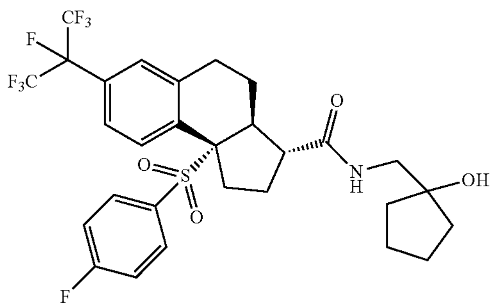 [SMILES: O=C(NCC1(O)CCCC1)[C@@H]1CC[C@@]2(S(=O)(=O)c3ccc(F)cc3)c3ccc(C(F)(C(F)(F)F)C(F)(F)F)cc3CC[C@@H]12] | 640.2 (M + H)+ | 1.05 | B |
| 72 | 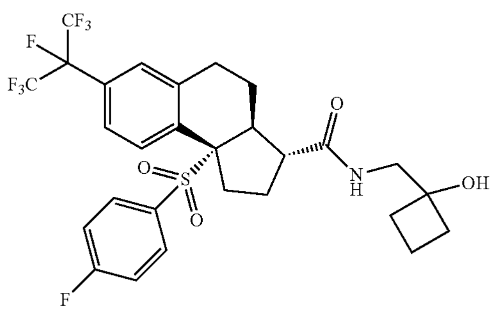 [SMILES: O=C(NCC1(O)CCC1)[C@@H]1CC[C@@]2(S(=O)(=O)c3ccc(F)cc3)c3ccc(C(F)(C(F)(F)F)C(F)(F)F)cc3CC[C@@H]12] | 626.2 (M + H)+ | 1.04 | B |
| 73 | 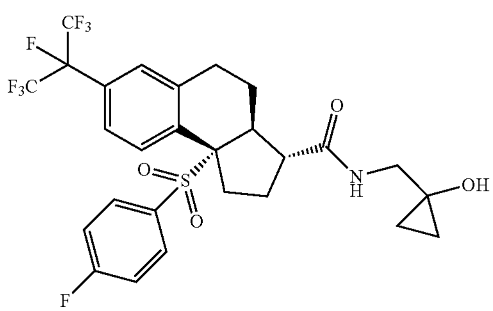 [SMILES: O=C(NCC1(O)CC1)[C@@H]1CC[C@@]2(S(=O)(=O)c3ccc(F)cc3)c3ccc(C(F)(C(F)(F)F)C(F)(F)F)cc3CC[C@@H]12] | 612.2 (M + H)+ | 1.01 | B |
| 74 | 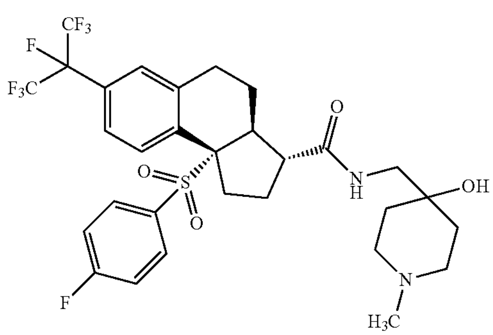 [SMILES: CN1CCC(O)(CNC(=O)[C@@H]2CC[C@@]3(S(=O)(=O)c4ccc(F)cc4)c4ccc(C(F)(C(F)(F)F)C(F)(F)F)cc4CC[C@@H]23)CC1] | 669.2 (M + H)+ | 0.84 | B |

TABLE 3-continued

| Ex. number | Structure | LCMS m/z observed | HPLC $t_R$ (min) | HPLC method |
|---|---|---|---|---|
| 75 | 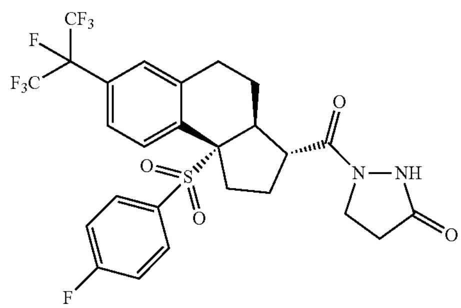 [SMILES: O=C1CCN(C(=O)[C@@H]2CC[C@@]3(S(=O)(=O)c4ccc(F)cc4)c4ccc(C(F)(C(F)(F)F)C(F)(F)F)cc4CC[C@@H]23)N1] | 611.0 (M + H)⁺ | 1.00 | B |
| 76 | 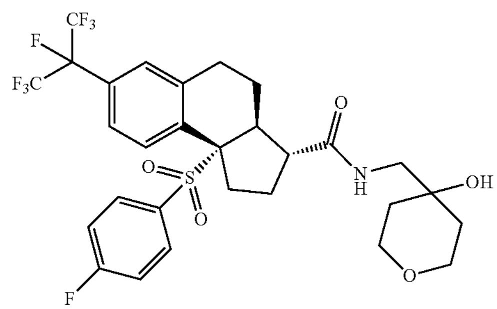 | 656.1 (M + H)⁺ | 1.05 | A |
| 77 | 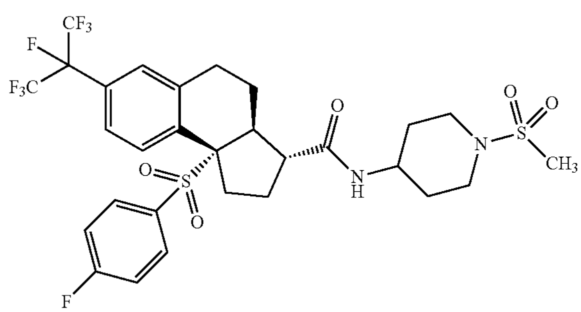 [SMILES: CS(=O)(=O)N1CCC(NC(=O)[C@@H]2CC[C@@]3(S(=O)(=O)c4ccc(F)cc4)c4ccc(C(F)(C(F)(F)F)C(F)(F)F)cc4CC[C@@H]23)CC1] | 702.9 (M + H)⁺ | 2.22 | A |
| 78 | 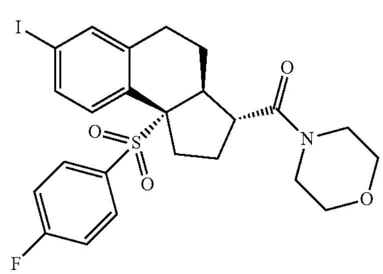 [SMILES: O=C([C@@H]1CC[C@@]2(S(=O)(=O)c3ccc(F)cc3)c3ccc(I)cc3CC[C@@H]12)N1CCOCC1] | 570.0 (M + H)⁺ | 1.99 | A |
| 79 | 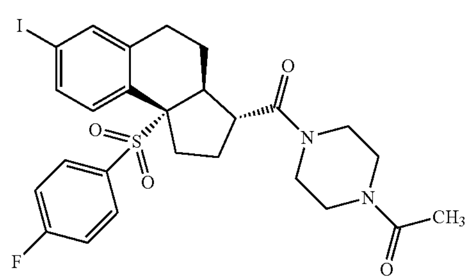 [SMILES: CC(=O)N1CCN(C(=O)[C@@H]2CC[C@@]3(S(=O)(=O)c4ccc(F)cc4)c4ccc(I)cc4CC[C@@H]23)CC1] | 611.3 (M + H)⁺ | 1.81 | A |

TABLE 3-continued

| Ex. number | Structure | LCMS m/z observed | HPLC $t_R$ (min) | HPLC method |
|---|---|---|---|---|
| 80 | 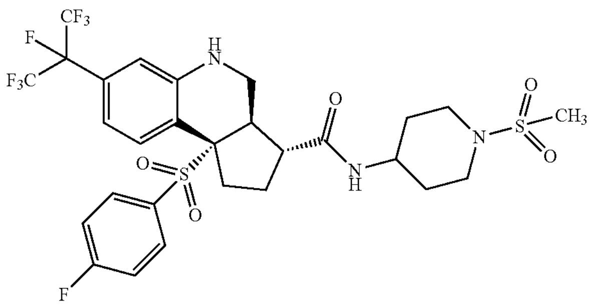 [SMILES: CS(=O)(=O)N1CCC(NC(=O)[C@@H]2CC[C@@]3(S(=O)(=O)c4ccc(F)cc4)c4ccc(C(F)(C(F)(F)F)C(F)(F)F)cc4NC[C@@H]23)CC1] | 704.0 (M + H)+ | 1.01 | A |
| 81 | 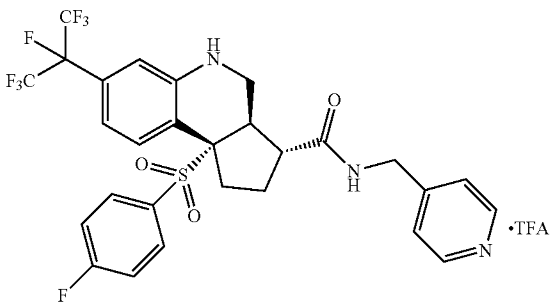 [SMILES: O=C(NCc1ccncc1)[C@@H]1CC[C@@]2(S(=O)(=O)c3ccc(F)cc3)c3ccc(C(F)(C(F)(F)F)C(F)(F)F)cc3NC[C@@H]12] | 634.0 (M + H)+ | 0.87 | A |
| 82 | 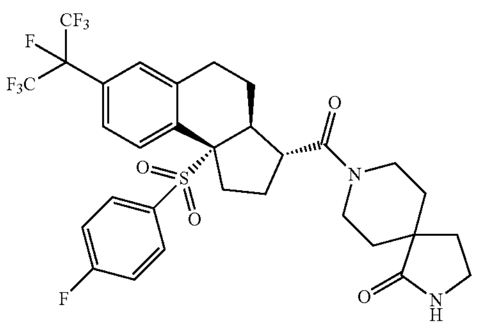 [SMILES: O=C([C@@H]1CC[C@@]2(S(=O)(=O)c3ccc(F)cc3)c3ccc(C(F)(C(F)(F)F)C(F)(F)F)cc3CC[C@@H]12)N1CCC2(CCNC2=O)CC1] | 679.0 (M + H)+ | 2.08 | C |
| 83 | 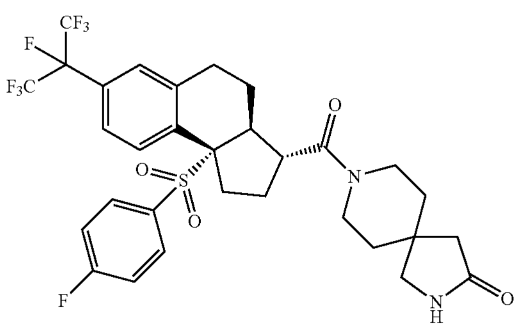 [SMILES: O=C1CC2(CCN(C(=O)[C@@H]3CC[C@@]4(S(=O)(=O)c5ccc(F)cc5)c5ccc(C(F)(C(F)(F)F)C(F)(F)F)cc5CC[C@@H]34)CC2)CN1] | 679.2 (M + H)+ | 2.03 | C |
| 84 | 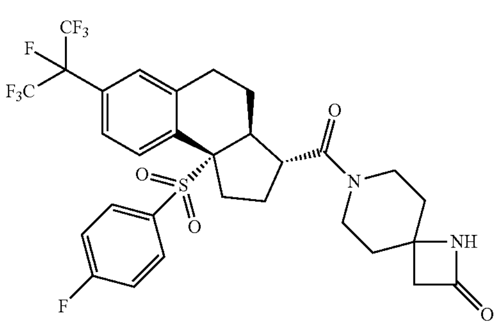 [SMILES: O=C1CC2(CCN(C(=O)[C@@H]3CC[C@@]4(S(=O)(=O)c5ccc(F)cc5)c5ccc(C(F)(C(F)(F)F)C(F)(F)F)cc5CC[C@@H]34)CC2)N1] | 665.2 (M + H)+ | 2.11 | C |

| Ex. number | Structure | LCMS m/z observed | HPLC $t_R$ (min) | HPLC method |
|---|---|---|---|---|
| 85 | 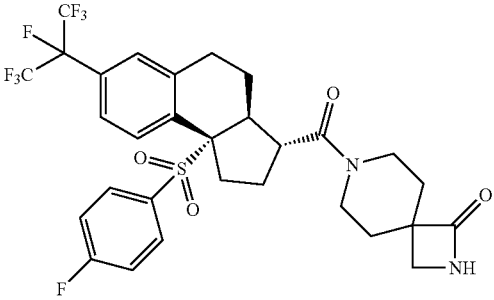 [SMILES: O=C([C@@H]1CC[C@@]2(S(=O)(=O)c3ccc(F)cc3)c3ccc(C(F)(C(F)(F)F)C(F)(F)F)cc3CC[C@@H]12)N1CCC2(CC1)CNC2=O] | 664.7 (M + H)+ | 2.18 | C |

Examples 86 and 87

3-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxamido)methyl)cyclobutane-1-carboxylic acid (two single geometric isomers)

Example 86

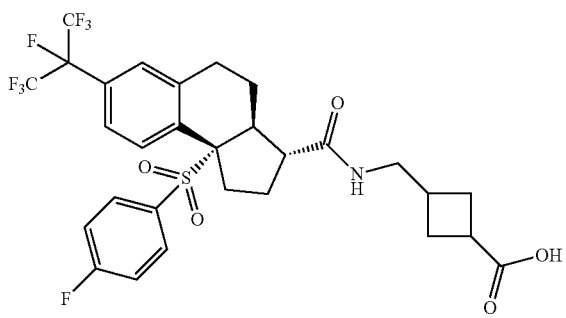

Homochiral from peak 1

Example 87

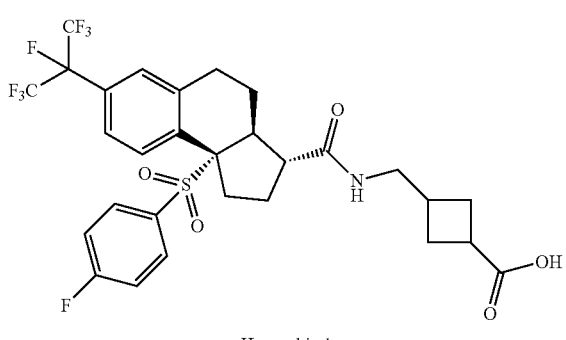

Homochiral from peak 2

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxylic acid (Intermediate 60 mg, 0.11 mmol) in DMF (1.1 mL) was treated with methyl 3-(aminomethyl)cyclobutane-carboxylate (32 mg, 0.22 mmol), DIEA (77 µL, 0.44 mmol) and HATU (63 mg, 0.17 mmol). The mixture was stirred at rt for 30 min, then was diluted with EtOAc and washed sequentially with 1 M aqueous HCl, 1 M aqueous NaOH and brine. The organic layer was dried and concentrated to provide methyl 3-(((3R, 3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxamido)methyl)cyclobutanecarboxylate (74 mg, 100%) as a mixture of cis and trans isomers. LCMS m/z 668.2 (M+1)+; HPLC $t_R$ 1.10 min (Method A).

This material was separated by preparative chiral SFC on a Chiralcel® OD-H column (50×250 mm, 5 µm; Chiral Technologies Inc.) at 35° C., eluting with CO$_2$-MeOH (90:10) at 300 mL/min and 100 bars. The separated geometric isomers were isolated from two peaks: Peak 1 eluted with $t_R$ 2.45 min, and Peak 2 eluted with $t_R$ 3.55 min A solution of the material from Peak 1 (30 mg, 0.045 mmol) in THF (450 µL) was treated with LiOH hydrate (22 mg, 0.90 mmol) and water (0.5 mL). The mixture was stirred at rt for 2 h, then was purified via preparative HPLC (Method E, gradient 45-90% B, 20 min) to provide a single geometric isomer of 3-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxamido)methyl)cyclobutanecarboxylic acid (Example 86; 13 mg, 43% yield). LCMS m/z 654.2 (M+1)+; HPLC $t_R$ 1.02 min (Method A). $^1$H NMR (500 MHz, DMSO-d$_6$) δ 7.96-7.78 (m, 1H), 7.53-7.24 (m, 6H), 3.66-3.49 (m, 1H), 3.26-3.08 (m, 2H), 3.07-2.85 (m, 3H), 2.81-2.59 (m, 1H), 2.43-2.27 (m, 2H), 2.27-2.06 (m, 3H), 2.03-1.74 (m, 4H), 1.35-1.14 (m, 2H), 1.04-0.94 (m, 2H).

Using the same procedure, the material from Peak 2 (30 mg, 0.045 mmol) was converted to the other geometric isomer of 3-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxamido)methyl)cyclobutanecarboxylic acid (Example 87; 18.6 mg, 63% yield). LCMS m/z 654.2 (M+1)+; HPLC $t_R$ 1.02 min (Method A).

The absolute configurations (cis or trans) on the cyclobutane ring were not assigned.

The Examples in Table 4 were prepared using the procedures used to prepare Examples 86 and 87, or similar procedures, from the appropriate carboxylic acid and amine starting materials.

TABLE 4

| Ex. number | Structure | LCMS m/z observed | HPLC $t_R$ (min) | HPLC method |
|---|---|---|---|---|
| 88 | 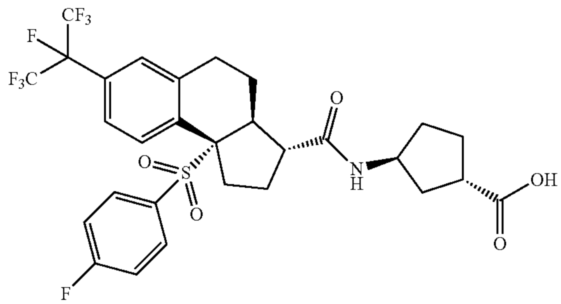 [SMILES: O=C(O)[C@H]1CC[C@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1] | 654.1 (M + H)⁺ | 1.01 | B |
| 89 | 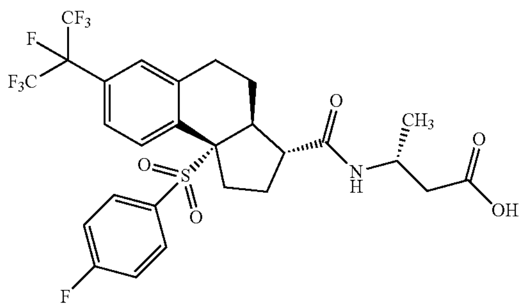 [SMILES: C[C@H](CC(=O)O)NC(=O)[C@@H]1CC[C@@]2(S(=O)(=O)c3ccc(F)cc3)c3ccc(C(F)(C(F)(F)F)C(F)(F)F)cc3CC[C@@H]12] | 628.2 (M + H)⁺ | 1.02 | A |
| 90 | 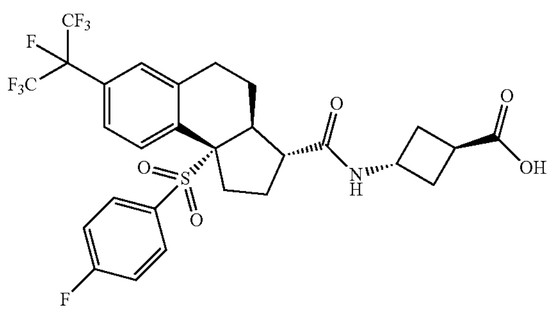 [SMILES: O=C(N[C@H]1C[C@H](C(=O)O)C1)[C@@H]1CC[C@@]2(S(=O)(=O)c3ccc(F)cc3)c3ccc(C(F)(C(F)(F)F)C(F)(F)F)cc3CC[C@@H]12] | 640.2 (M + H)⁺ | 1.03 | A |
| 91 | Homochiral from peak 2 | 640.3 (M + H)⁺ | 1.03 | A |

TABLE 4-continued
| Ex. number | Structure | LCMS m/z observed | HPLC $t_R$ (min) | HPLC method |
|---|---|---|---|---|
| 92 | 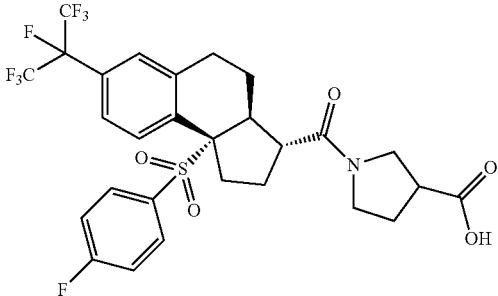 Homochiral from peak 1 | 640.2 (M + H)+ | 1.03 | A |
| 93 | 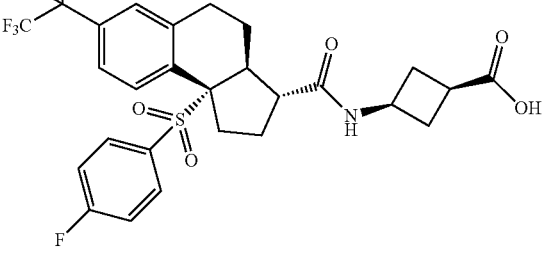 | 640.2 (M + H)+ | 1.02 | A |
| 94 | 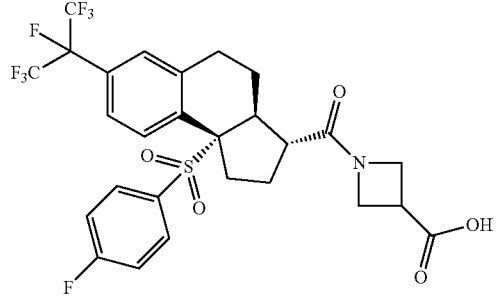 [SMILES: O=C(O)C1CN(C(=O)[C@@H]2CC[C@@]3(S(=O)(=O)c4ccc(F)cc4)c4ccc(C(F)(C(F)(F)F)C(F)(F)F)cc4CC[C@@H]23)C1] | 626.1 (M + H)+ | 1.01 | A |
| 95 | 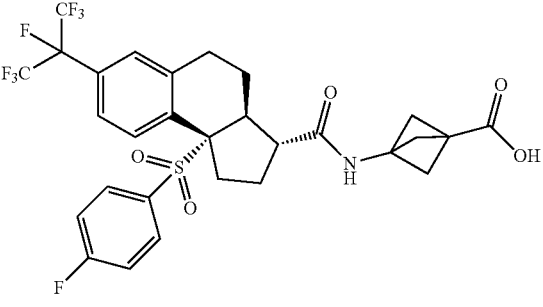 [SMILES: O=C(NC12CC(C(=O)O)(C1)C2)[C@@H]1CC[C@@]2(S(=O)(=O)c3ccc(F)cc3)c3ccc(C(F)(C(F)(F)F)C(F)(F)F)cc3CC[C@@H]12] | 652.2 (M + H)+ | 1.04 | A |

TABLE 4-continued

| Ex. number | Structure | LCMS m/z observed | HPLC $t_R$ (min) | HPLC method |
|---|---|---|---|---|
| 96 | 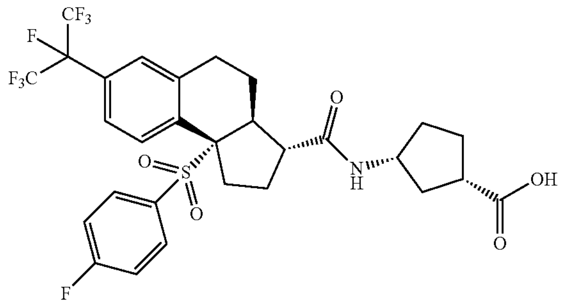 [SMILES: O=C(O)[C@H]1CC[C@@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1] | 654.1 (M + H)+ | 1.01 | B |
| 97 | 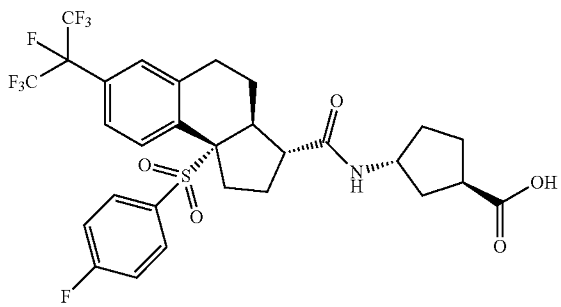 [SMILES: O=C(O)[C@@H]1CC[C@@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1] | 654.1 (M + H)+ | 1.01 | B |
| 98 | Homochiral from peak 1 | 668.1 (M + H)+ | 1.03 | B |
| 99 | Homochiral from peak 2 | 668.1 (M + H)+ | 1.03 | B |

TABLE 4-continued
| Ex. number | Structure | LCMS m/z observed | HPLC $t_R$ (min) | HPLC method |
|---|---|---|---|---|
| 100 | 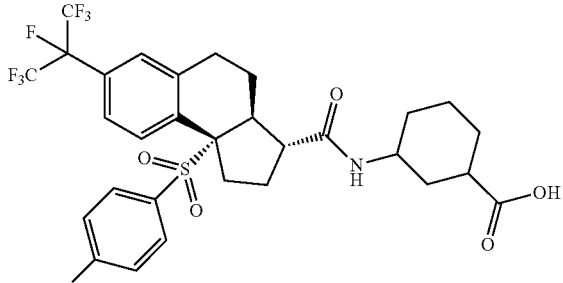 Homochiral from peak 3 | 668.1 (M + H)+ | 1.03 | B |
| 101 | 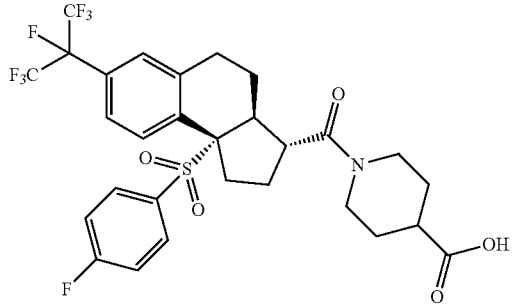 [SMILES: O=C(O)C1CCN(C(=O)[C@@H]2CC[C@@]3(S(=O)(=O)c4ccc(F)cc4)c4ccc(C(F)(C(F)(F)F)C(F)(F)F)cc4CC[C@@H]23)CC1] | 654.0 (M + H)+ | 2.18 | C |
| 102 | 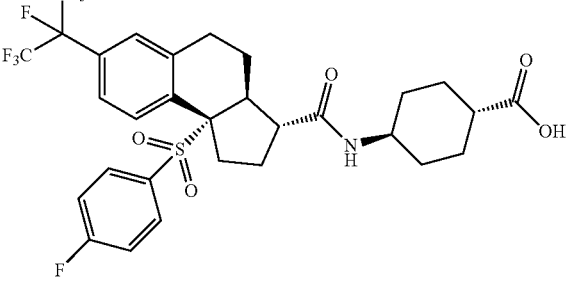 | 668.4 (M + H)+ | 2.18 | C |
| 103 | 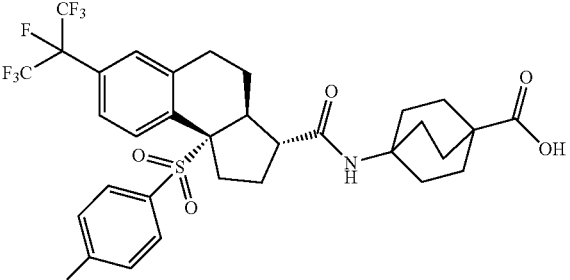 | 694.5 (M + H)+ | 2.28 | C |

TABLE 4-continued

| Ex. number | Structure | LCMS m/z observed | HPLC $t_R$ (min) | HPLC method |
|---|---|---|---|---|
| 104 | 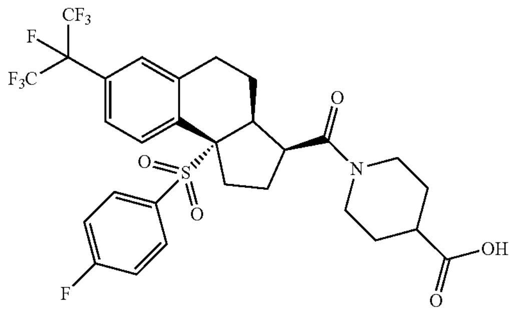 [SMILES: O=C(O)C1CCN(C(=O)[C@H]2CC[C@@]3(S(=O)(=O)c4ccc(F)cc4)c4ccc(C(F)(C(F)(F)F)C(F)(F)F)cc4CC[C@@H]23)CC1] | 654.4 (M + H)⁺ | 2.22 | C |
| 105 | 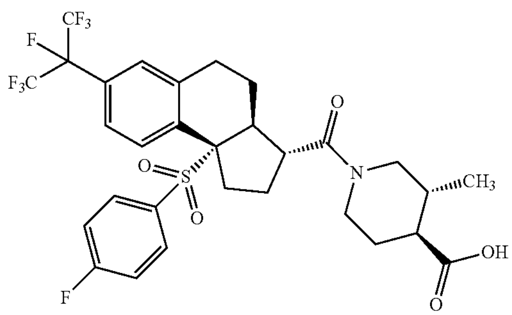 [SMILES: C[C@H]1CN(C(=O)[C@@H]2CC[C@@]3(S(=O)(=O)c4ccc(F)cc4)c4ccc(C(F)(C(F)(F)F)C(F)(F)F)cc4CC[C@@H]23)CC[C@@H]1C(=O)O] | 668.1 (M + H)⁺ | 2.21 | C |

Example 106

((3R,3aS,9bS)-9b-((4-fluorophenyl)sulfon)-7-(perfluoropropan-2-yl)-2)-23a,4,5,9b-hexahydro-1H-cyclopenta[a]naphthalene-3-carbonyl)glycine

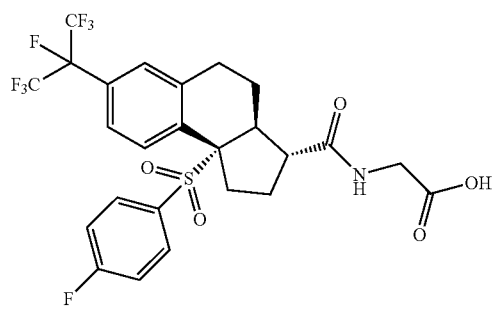 [SMILES: O=C(O)CNC(=O)[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxylic acid (Intermediate 14; 25 mg, 0.046 mmol) in DMF (460 µL) was treated with tert-butyl 2-aminoacetate (12 mg, 0.092 mmol), DIEA (32 µL, 0.18 mmol) and HATU (26 mg, 0.069 mmol) and the mixture was stirred at rt for 30 min. The mixture was diluted with EtOAc and washed sequentially with 1 M aqueous HCl, 1 M aqueous NaOH and brine, and dried and concentrated. The residue was dissolved in TFA (1 mL) and the mixture was stirred at rt for 1 h, then was concentrated and the residue was purified by preparative HPLC (Method E, gradient 45-90% B, 20 min) to provide ((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carbonyl)glycine (14 mg, 49% yield). LCMS m/z 600.1 (M+1)⁺; HPLC $t_R$ 1.01 min (Method A). ¹H NMR (500 MHz, DMSO-$d_6$) δ 8.26-8.11 (m, 1H), 7.52-7.44 (m, 1H), 7.44-7.38 (m, 2H), 7.38-7.24 (m, 4H), 3.87-3.65 (m, 2H), 3.28-3.12 (m, 1H), 3.07-2.92 (m, 1H), 2.81-2.69 (m, 1H), 2.61-2.54 (m, 1H), 2.33-2.16 (m, 2H), 2.09-1.78 (m, 3H), 1.38-1.22 (m, 1H).

The Examples in Table 5 were prepared using the procedures used to prepare Example 106, or similar procedures, from the appropriate carboxylic acid and amine starting materials.

TABLE 5

| Ex. number | Structure | LCMS m/z observed | HPLC $t_R$ (min) | HPLC method |
|---|---|---|---|---|
| 107 | 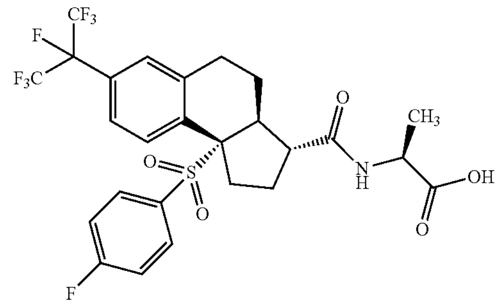 [SMILES: C[C@H](NC(=O)[C@@H]1CC[C@@]2(S(=O)(=O)c3ccc(F)cc3)c3ccc(C(F)(C(F)(F)F)C(F)(F)F)cc3CC[C@@H]12)C(=O)O] | 614.2 (M + H)⁺ | 1.03 | A |
| 108 | 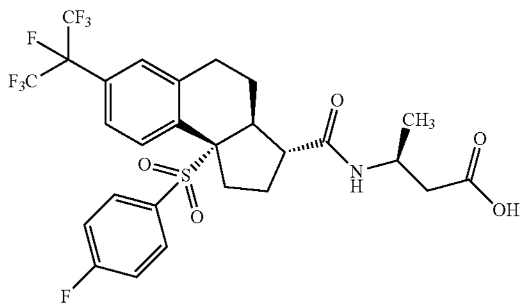 [SMILES: C[C@@H](CC(=O)O)NC(=O)[C@@H]1CC[C@@]2(S(=O)(=O)c3ccc(F)cc3)c3ccc(C(F)(C(F)(F)F)C(F)(F)F)cc3CC[C@@H]12] | 628.2 (M + H)⁺ | 1.03 | A |
| 109 | 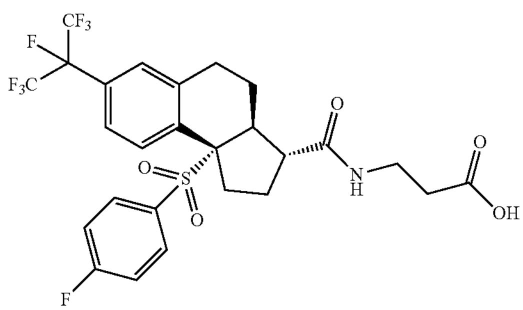 [SMILES: O=C(O)CCNC(=O)[C@@H]1CC[C@@]2(S(=O)(=O)c3ccc(F)cc3)c3ccc(C(F)(C(F)(F)F)C(F)(F)F)cc3CC[C@@H]12] | 614.1 (M + H)⁺ | 1.01 | A |

Example 110

(perfluoropropan-2-yl)-2,3,3a,5,9b-hexahydro-1H-cyclopenta[a]naphthalene-3-carboxamide hydrochloride

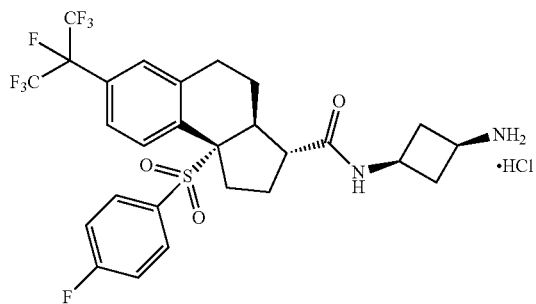 [SMILES: N[C@H]1C[C@@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1 ; Cl]

A solution of (3R,3aS,9b S)-9b-((4-fluorophenyl)sulfonyl)-7-(perfluoropropan-1-yl)-2,3,3a,4,5,9b-hexahydro-H-cyclopenta[a]naphthalene-3-carboxylic acid (Intermediate 14; 100 mg, 0.18 mmol) in DMF (1.8 mL) was treated with tert-butyl ((1s,3s)-3-aminocyclobutyl)carbamate (69 mg, 0.37 mmol), DIEA (130 µL, 0.74 mmol) and HATU (105 mg, 0.28 mmol). The mixture was stirred at rt for 30 min, then was diluted with EtOAc and washed sequentially with 1 M aqueous HCl, 1 M aqueous NaOH and brine. The organic layer was dried and concentrated to provide tert-butyl ((1S,3s)-3-((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxamido)cyclobutyl) carbamate (130 mg, 100%), used without further purification. LCMS m/z 711.2 (M+1)⁺; HPLC $t_R$ 1.12 min (Method A). This material was dissolved in HCl (4 M in 1,4-dioxane; 1.8 mL, 7.4 mmol) and the mixture was stirred at rt. After 30 min, the mixture was concentrated to provide (3R,3aS,9bS)—N-((1s,3S)-3-aminocyclobutyl)-9b-((4-fluorophenyl)sulfonyl)-7-(perfluoropropan-2-yl)-2,3,3a,4,5,9b-hexahydro-1H-cyclopenta[a]naphthalene-3-carboxamide (110 mg, 95% yield). LCMS m/z 611.1 (M+1)⁺; HPLC $t_R$ 0.85 min (Method B). ¹H NMR (500 MHz, DMSO-d₆) δ 8.25-8.05 (m, 1H), 7.52-7.41 (m, 1H), 7.41-7.31 (m, 2H), 7.31-7.14 (m, 3H), 3.91-3.61 (m, 3H), 3.26-3.11 (m, 2H), 3.05-2.89 (m, 1H), 2.75-2.59 (m, 1H), 2.46-2.33 (m, 1H), 2.29-2.08 (m, 2H), 2.02-1.90 (m, 1H), 1.90-1.76 (m, 2H), 1.76-1.54 (m, 2H), 1.32-1.12 (m, 2H).

The Examples in Table 6 were prepared using the procedures used to prepare Example 110, or similar procedures, from the appropriate carboxylic acid and amine starting materials.

TABLE 6

| Ex. number | Structure | LCMS m/z observed | HPLC $t_R$ (min) | HPLC method |
|---|---|---|---|---|
| 111 | 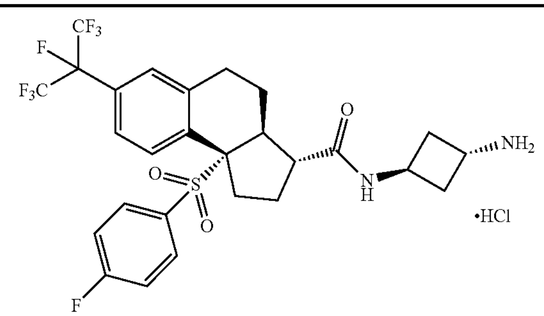 | 611.1 (M + H)+ | 0.90 | A |
| 112 | Homochiral from peak 1 | 625.2 (M + H)+ | 0.90 | A |
| 113 | Homochiral from peak 2 | 625.2 (M + H)+ | 0.85 | B |

Example 114

(3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine

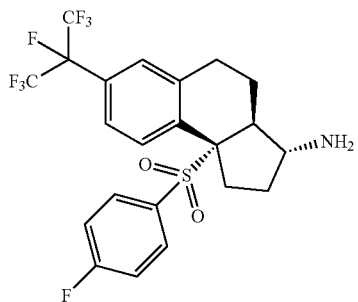 [SMILES: N[C@@H]1CC[C@@]2(S(=O)(=O)c3ccc(F)cc3)c3ccc(C(F)(C(F)(F)F)C(F)(F)F)cc3CC[C@@H]12]

A suspension of (3R,3aS)-9b-((4-fluorophenyl)sulfonyl)-7-(perfluoropropan-2-yl)-2,3,3a,4,5,9b-hexahydro-1H-cyclopenta[a]naphthalene-3-carboxylic acid (Intermediate 14; 200 mg, 0.369 mmol) in toluene (6 mL) was cooled on an ice/water bath and treated with TEA (154 μL, 1.11 mmol). The resulting solution was stirred at 0° C. for 5 min, then was treated with diphenyl phosphorazidate (254 μL, 1.11 mmol) and warmed to rt. After being stirred for 1 h, the mixture was treated with water and extracted with EtOAc. The organic layer was washed with brine, dried and concentrated under reduced pressure. The residue was suspended in 2-(trimethylsilyl)ethanol (3 mL, 20.9 mmol) and the mixture was warmed to 80° C. After 1.5 h, the mixture was concentrated under reduced pressure. Water and EtOAc were added, and the organic layer was separated, washed with brine, dried and concentrated. The resulting oil was subjected to column chromatography on silica gel (24 g), eluting with EtOAc-hexanes (gradient from 0-50%). The resulting colorless oil (680 mg) was dissolved in DCM (5 mL) and treated with TFA (1 mL). After 1 h, the mixture was concentrated and the residue was dissolved in EtOAc, washed with brine, dried and concentrated to provide crude (3S,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (trifluoroacetate) as a yellow oil (373 mg). A portion of this (23.2 mg) was purified by preparative HPLC (Method E, gradient 30-70% B, 20 min) to provide (3S,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (5.3 mg, 28% yield). LCMS m/z 514.3 (M+H)$^+$; HPLC $t_R$ 1.78 min (Method C). $^1$H NMR (499 MHz, DMSO-$d_6$) δ 8.37-8.05 (m, 1H), 7.49 (br d, J=9.0 Hz, 1H), 7.43-7.35 (m, 2H), 7.34-7.19 (m, 3H), 5.30-4.31 (m, 2H), 3.51-3.35 (m, 1H), 3.19-2.98 (m, 2H), 2.77-2.61 (m, 1H), 2.40-2.28 (m, 1H), 2.28-2.18 (m, 1H), 2.17-2.02 (m, 2H), 1.99-1.86 (m, 1H), 1.41 (br d, J=2.6 Hz, 1H). $^{19}$F NMR (470 MHz, DMSO-$d_6$) δ −181.78 (br d, J=8.5 Hz, 3F), −103.20 (br s, 1F), −75.06 (m, 6F), −74.33 (s, 1F).

The Examples in Table 7 were prepared using the procedures used to prepare Example 114, or similar procedures, from the appropriate carboxylic acid starting material.

Example 118

(S)-1-(2-cyanoethyl)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-oxopyrrolidine-2-carboxamide

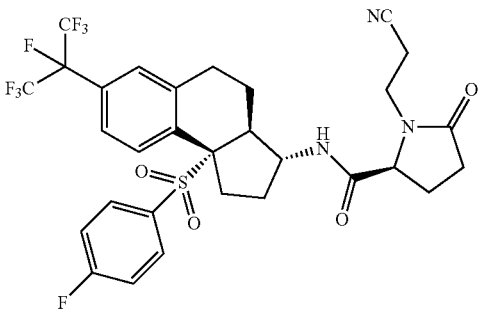 [SMILES: N#CCCN1C(=O)CC[C@H]1C(=O)N[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114; 23 mg, 0.037 mmol) in DMF (1 mL) was treated with (S)-1-(2-cyanoethyl)-5-oxopyrrolidine-2-carboxylic acid (Intermediate 18; 20 mg, 0.111 mmol), DIEA (97 µL, 0.554

TABLE 7

| Ex. number | Structure | LCMS m/z observed | HPLC $t_R$ (min) | HPLC method |
|---|---|---|---|---|
| 115 | 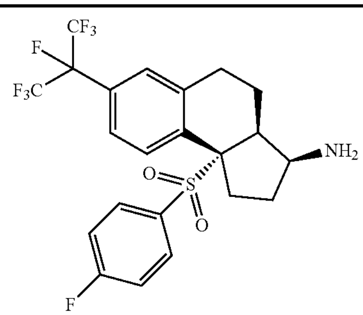 | 514.1 (M + H)$^+$ | 0.87 | B |
| 116 | 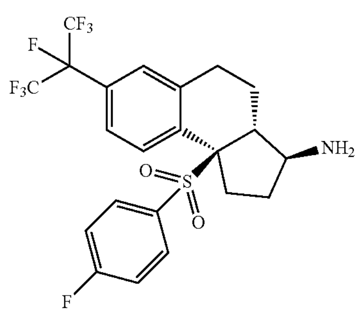 | 514.1 (M + H)$^+$ | 0.87 | B |
| 117 | | 514.1 (M + H)$^+$ | 0.87 | B | mmol) and HATU (42 mg, 0.111 mmol). The mixture was stirred at rt for 30 min, then was purified by preparative HPLC (Method E, gradient 45-90% B over 20 min) to provide (S)-1-(2-cyanoethyl)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-oxopyrrolidine-2-carboxamide (13.1 mg, 52% yield). LCMS m/z 678.2 (M+H)$^+$; HPLC $t_R$ 1.01 min (Method A). $^1$H NMR (500 MHz, DMSO-d$_6$) δ 8.55 (d, J=7.6 Hz, 1H), 7.50-7.39 (m, 2H), 7.34 (s, 1H), 7.25 (d, J=7.0 Hz, 4H), 4.32-4.18 (m, 1H), 4.01-3.91 (m, 1H), 3.75 (dt, J=13.8, 7.0 Hz, 1H), 3.50 (br d, J=8.5 Hz, 1H), 3.03 (br dd, J=13.6, 6.6 Hz, 2H), 2.94-2.84 (m, 1H), 2.81-2.61 (m, 3H), 2.41-2.20 (m, 3H), 2.12-1.94 (m, 3H), 1.94-1.80 (m, 2H), 1.25 (br d, J=10.1 Hz, 1H); $^{19}$F NMR (471 MHz, DMSO-d$_6$) δ -103.3 (s, 1F), -75.1 (m, 6F), -75.0 (m, 1F).

Example 119

N-((3R,3aS,9bS)-9b-((4-fluorophenyl)sulfonyl)-7-(perfluoropropan-2-yl)-2,3,3a4,5,9b-hexahydro-1H-cyclopenta[a]naphthalen-3-yl)acetamide-2,2,2-d$_3$

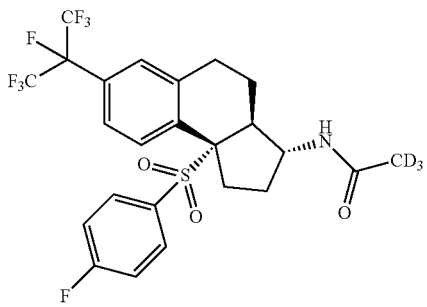 [SMILES: CC(=O)N[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114; 25 mg, 0.040 mmol) in DMF (1 mL) was treated with acetic anhydride-d$_6$ (20 μL, 0.199 mmol) and DIEA (84 μL, 0.478 mmol). The mixture was stirred at rt for 2 h, then was purified by preparative HPLC (Method E, gradient 45-90% B, 20 min) to provide N-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)acetamide-2,2,2-d$_3$ (12.4 mg, 56% yield). LCMS m/z 558.9 (M+H)$^+$; HPLC $t_R$ 2.16 min (Method B). $^1$H NMR (500 MHz, DMSO-d$_6$) δ 8.11 (br d, J=7.9 Hz, 1H), 7.52-7.44 (m, 2H), 7.35 (s, 1H), 7.32-7.24 (m, 4H), 3.98-3.87 (m, 1H), 3.07-2.97 (m, 1H), 2.84-2.74 (m, 1H), 2.65 (br d, J=14.6 Hz, 1H), 2.27-2.15 (m, 1H), 2.08-1.89 (m, 3H), 1.86-1.73 (m, 1H), 1.34-1.18 (m, 1H).

Example 120

N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)acetamide

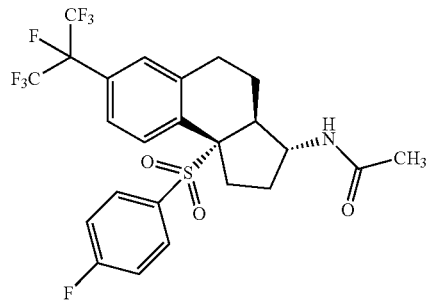

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 40 mg, 0.078 mmol) in DCM (2 mL) was treated with acetyl chloride (8 mg, 0.101 mmol) and triethylamine (11 μL, 0.078 mmol) and stirred at rt. After 2 h the mixture was diluted with water and saturated aqueous NaHCO$_3$ and extracted with EtOAc. The organic layer was dried and concentrated, and the residue was purified by preparative HPLC (Method E, gradient 40-80% B, 20 min) to provide N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)acetamide (11.2 mg, 26% yield). LCMS m/z 556.1 (M+H)$^+$; HPLC $t_R$ 1.08 min (Analytical HPLC Method A); $^1$H NMR (500 MHz, DMSO-d$_6$) δ 8.14-8.09 (m, 1H), 7.53-7.46 (m, 2H), 7.39-7.25 (m, 6H), 3.97-3.90 (m, 1H), 3.07-2.98 (m, 1H), 2.83-2.76 (m, 1H), 2.70-2.62 (m, 1H), 2.26-2.18 (m, 1H), 2.05-1.93 (m, 3H), 1.88-1.85 (m, 3H), 1.85-1.78 (m, 1H), 1.33-1.24 (m, 2H).

The Examples in Table 8 were prepared using the procedures used to prepare Examples 118 through 120, or similar procedures, from the appropriate amine and carboxylic acid, carboxylic acid chloride, or carboxylic acid anhydride starting materials.

TABLE 8

| Ex. number | Structure | LCMS m/z observed | HPLC $t_R$ (min) | HPLC method |
|---|---|---|---|---|
| 121 | (structure shown) | 633.1 (M + H)$^+$ | 0.92 | B |

TABLE 8-continued

| Ex. number | Structure | LCMS m/z observed | HPLC $t_R$ (min) | HPLC method |
|---|---|---|---|---|
| 122 | 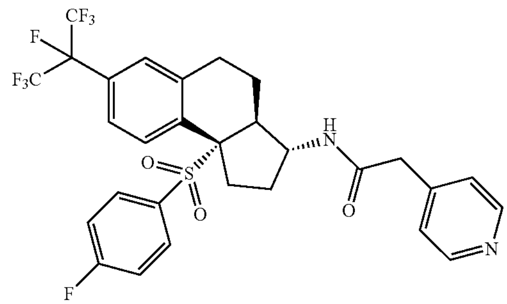 [SMILES: O=C(Cc1ccncc1)N[C@@H]1CC[C@@]2(S(=O)(=O)c3ccc(F)cc3)c3ccc(C(F)(C(F)(F)F)C(F)(F)F)cc3CC[C@@H]12] | 633.1 (M + H)+ | 0.92 | B |
| 123 | 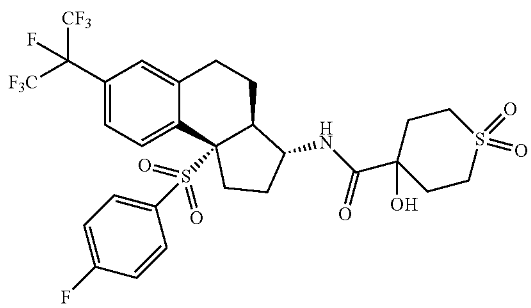 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)C1(O)CCS(=O)(=O)CC1] | 690.2 (M + H)+ | 1.03 | B |
| 124 | 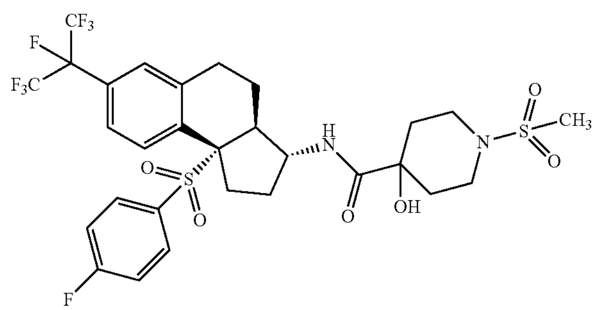 [SMILES: CS(=O)(=O)N1CCC(O)(C(=O)N[C@@H]2CC[C@@]3(S(=O)(=O)c4ccc(F)cc4)c4ccc(C(F)(C(F)(F)F)C(F)(F)F)cc4CC[C@@H]23)CC1] | 719.2 (M + H)+ | 1.02 | B |
| 125 | 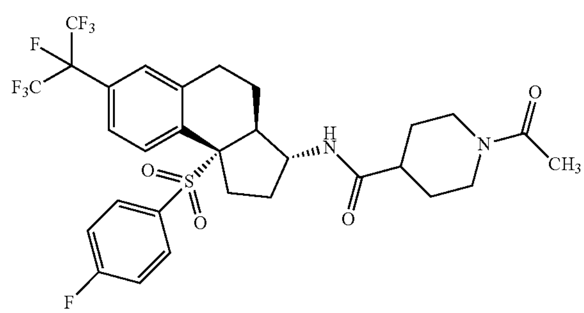 [SMILES: CC(=O)N1CCC(C(=O)N[C@@H]2CC[C@@]3(S(=O)(=O)c4ccc(F)cc4)c4ccc(C(F)(C(F)(F)F)C(F)(F)F)cc4CC[C@@H]23)CC1] | 667.2 (M + H)+ | 1.01 | A |
| 126 | 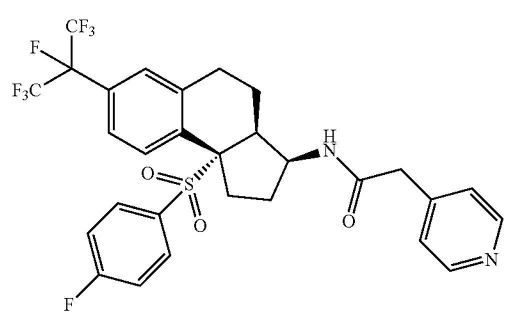 [SMILES: O=C(Cc1ccncc1)N[C@H]1CC[C@@]2(S(=O)(=O)c3ccc(F)cc3)c3ccc(C(F)(C(F)(F)F)C(F)(F)F)cc3CC[C@@H]12] | 633.2 (M + H)+ | 0.91 | A |

TABLE 8-continued

| Ex. number | Structure | LCMS m/z observed | HPLC $t_R$ (min) | HPLC method |
|---|---|---|---|---|
| 127 | 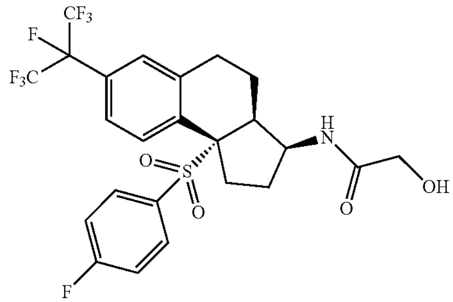 [SMILES: O=C(CO)N[C@H]1CC[C@@]2(S(=O)(=O)c3ccc(F)cc3)c3ccc(C(F)(C(F)(F)F)C(F)(F)F)cc3CC[C@@H]12] | 572.1 (M + H)+ | 0.98 | A |
| 128 | 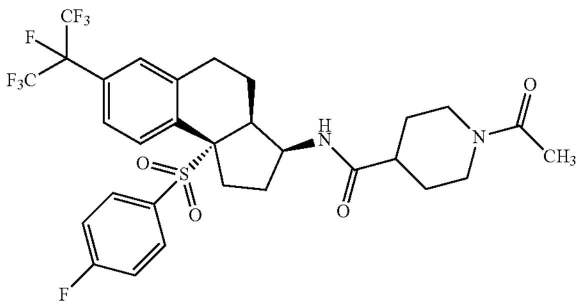 [SMILES: CC(=O)N1CCC(C(=O)N[C@H]2CC[C@@]3(S(=O)(=O)c4ccc(F)cc4)c4ccc(C(F)(C(F)(F)F)C(F)(F)F)cc4CC[C@@H]23)CC1] | 667.1 (M + H)+ | 1.00 | A |
| 129 | 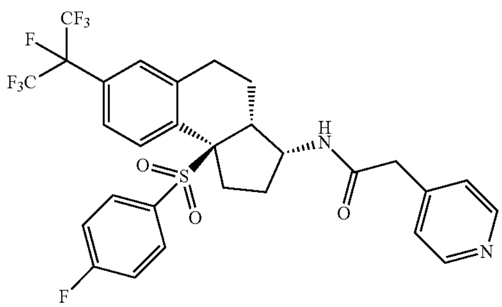 [SMILES: O=C(Cc1ccncc1)N[C@@H]1CC[C@]2(S(=O)(=O)c3ccc(F)cc3)c3ccc(C(F)(C(F)(F)F)C(F)(F)F)cc3CC[C@H]12] | 633.2 (M + H)+ | 0.91 | B |
| 130 | 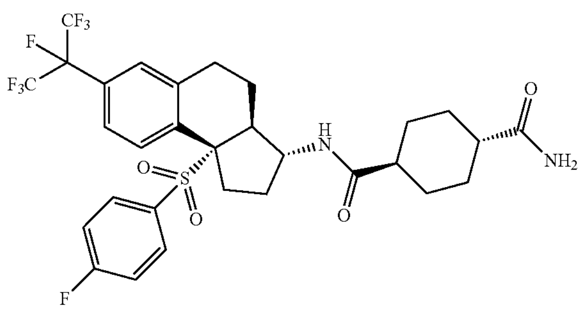 [SMILES: NC(=O)[C@H]1CC[C@H](C(=O)N[C@@H]2CC[C@@]3(S(=O)(=O)c4ccc(F)cc4)c4ccc(C(F)(C(F)(F)F)C(F)(F)F)cc4CC[C@@H]23)CC1] | 667.1 (M + H)+ | 1.01 | B |
| 131 | 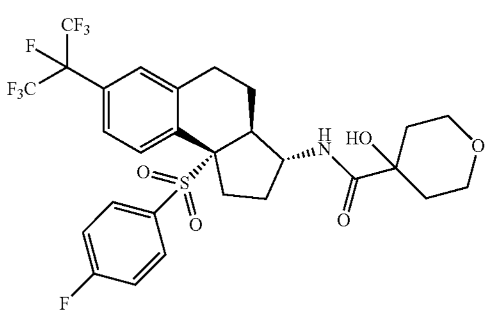 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)C1(O)CCOCC1] | 642.2 (M + H)+ | 1.04 | B |

TABLE 8-continued

| Ex. number | Structure | LCMS m/z observed | HPLC $t_R$ (min) | HPLC method |
|---|---|---|---|---|
| 132 | 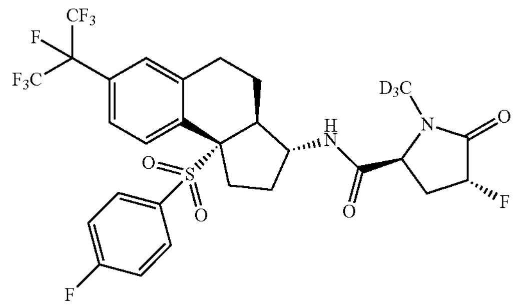 [SMILES: [2H]C([2H])([2H])N1C(=O)[C@H](F)C[C@H]1C(=O)N[C@@H]1CC[C@@]2(S(=O)(=O)c3ccc(F)cc3)c3ccc(C(F)(C(F)(F)F)C(F)(F)F)cc3CC[C@@H]12] | 660.1 (M + H)+ | 1.02 | A |
| 133 | 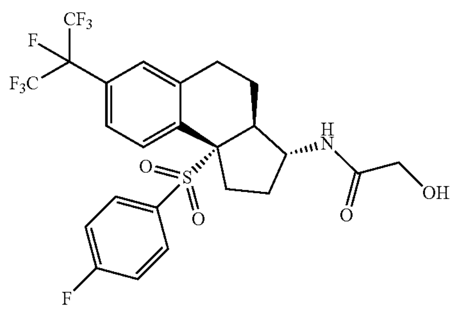 | 572.0 (M + H)+ | 1.02 | B |
| 134 | 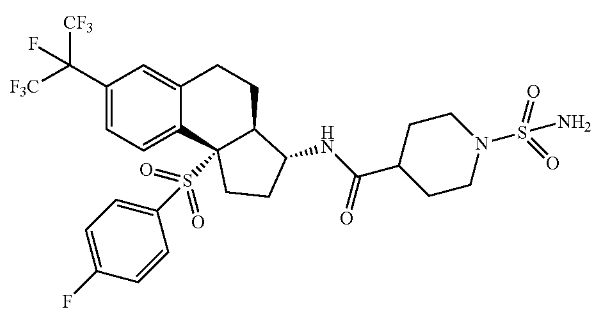 [SMILES: NS(=O)(=O)N1CCC(C(=O)N[C@@H]2CC[C@@]3(S(=O)(=O)c4ccc(F)cc4)c4ccc(C(F)(C(F)(F)F)C(F)(F)F)cc4CC[C@@H]23)CC1] | 704.1 (M + H)+ | 1.01 | A |
| 135 | Homochiral from peak 1 | 688.2 (M + H)+ | 1.05 | B |

TABLE 8-continued
| Ex. number | Structure | LCMS m/z observed | HPLC $t_R$ (min) | HPLC method |
|---|---|---|---|---|
| 136 | 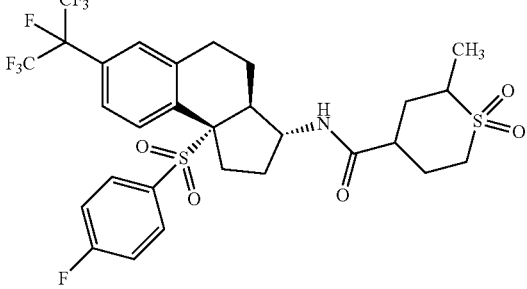<br>Homochiral from peak 3 | 688.2 (M + H)⁺ | 1.05 | B |
| 137 | 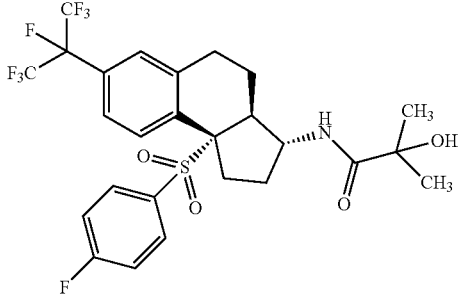 [SMILES: CC(C)(O)C(=O)N[C@@H]1CC[C@@]2(S(=O)(=O)c3ccc(F)cc3)c3ccc(C(F)(C(F)(F)F)C(F)(F)F)cc3CC[C@@H]12] | 600.0 (M + H)⁺ | 1.06 | B |
| 138 | 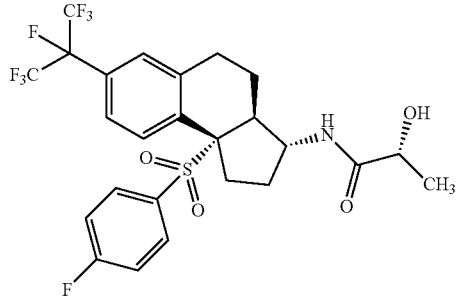 [SMILES: C[C@@H](O)C(=O)N[C@@H]1CC[C@@]2(S(=O)(=O)c3ccc(F)cc3)c3ccc(C(F)(C(F)(F)F)C(F)(F)F)cc3CC[C@@H]12] | 586.1 (M + H)⁺ | 1.04 | B |
| 139 | 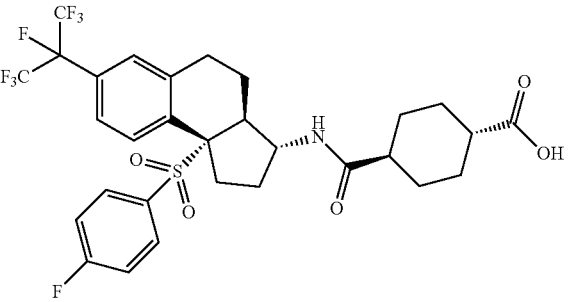 [SMILES: O=C(O)[C@H]1CC[C@H](C(=O)N[C@@H]2CC[C@@]3(S(=O)(=O)c4ccc(F)cc4)c4ccc(C(F)(C(F)(F)F)C(F)(F)F)cc4CC[C@@H]23)CC1] | 668.6 (M + H)⁺ | 2.18 | A |

TABLE 8-continued

| Ex. number | Structure | LCMS m/z observed | HPLC $t_R$ (min) | HPLC method |
|---|---|---|---|---|
| 140 | 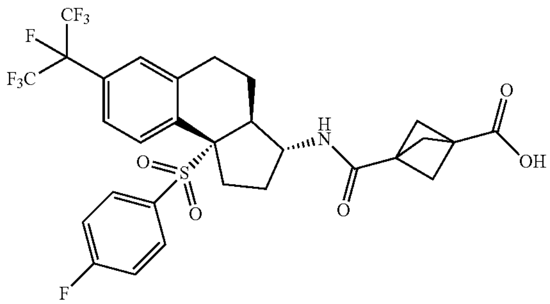 [SMILES: O=C(O)C12CC(C(=O)N[C@@H]3CC[C@@]4(S(=O)(=O)c5ccc(F)cc5)c5ccc(C(F)(C(F)(F)F)C(F)(F)F)cc5CC[C@@H]34)(C1)C2] | 652.4 (M + H)+ | 2.16 | A |
| 141 | Diasteromeric mixture | 680.1 (M + H)+ | 2.30 | A |
| 142 | Homochiral from peak 2 | 688.2 (M + H)+ | 2.17 | A |
| 143 | Homochiral from peak 4 | 688.3 (M + H)+ | 2.17 | A |

TABLE 8-continued

| Ex. number | Structure | LCMS m/z observed | HPLC $t_R$ (min) | HPLC method |
|---|---|---|---|---|
| 144 | 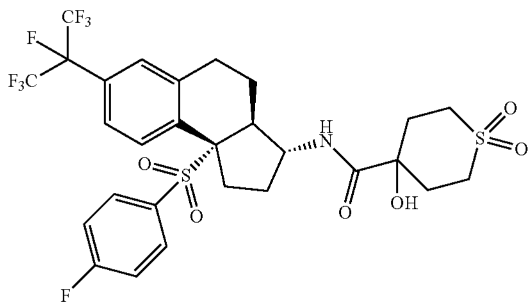 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)C1(O)CCS(=O)(=O)CC1] | 690.9 (M + H)+ | 1.98 | A |
| 145 | 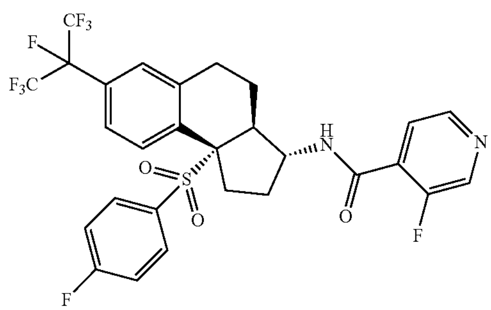 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)c1ccncc1F] | 690.9 (M + H)+ | 2.00 | A |
| 146 | 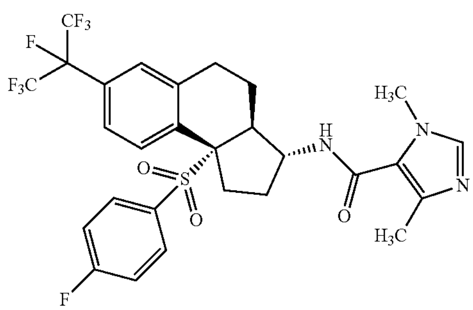 [SMILES: Cc1ncn(C)c1C(=O)N[C@@H]1CC[C@@]2(S(=O)(=O)c3ccc(F)cc3)c3ccc(C(F)(C(F)(F)F)C(F)(F)F)cc3CC[C@@H]12] | 636.1 (M + H)+ | 1.93 | A |
| 147 | 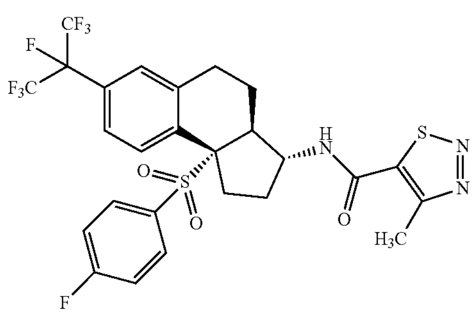 [SMILES: Cc1nnsc1C(=O)N[C@@H]1CC[C@@]2(S(=O)(=O)c3ccc(F)cc3)c3ccc(C(F)(C(F)(F)F)C(F)(F)F)cc3CC[C@@H]12] | 639.9 (M + H)+ | 2.35 | A |
| 148 | 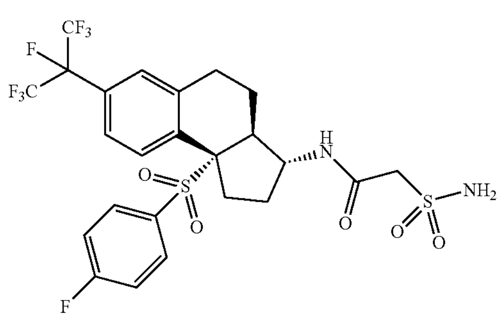 [SMILES: NS(=O)(=O)CC(=O)N[C@@H]1CC[C@@]2(S(=O)(=O)c3ccc(F)cc3)c3ccc(C(F)(C(F)(F)F)C(F)(F)F)cc3CC[C@@H]12] | 634.9 (M + H)+ | 1.99 | A |

TABLE 8-continued

| Ex. number | Structure | LCMS m/z observed | HPLC t$_R$ (min) | HPLC method |
|---|---|---|---|---|
| 149 | 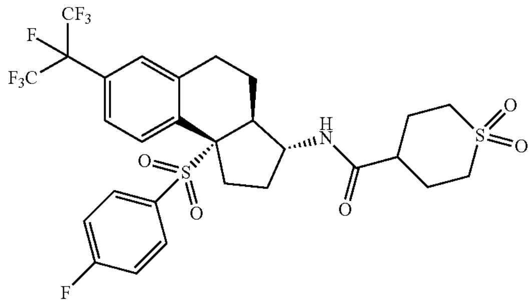 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)C1CCS(=O)(=O)CC1] | 674.0 (M + H)$^+$ | 2.14 | A |
| 150 | 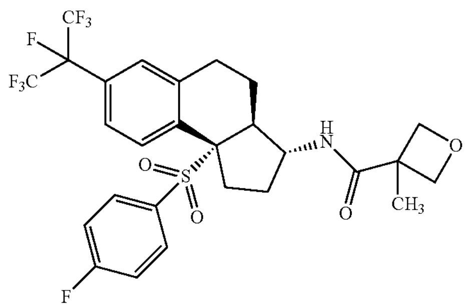 [SMILES: CC1(C(=O)N[C@@H]2CC[C@@]3(S(=O)(=O)c4ccc(F)cc4)c4ccc(C(F)(C(F)(F)F)C(F)(F)F)cc4CC[C@@H]23)COC1] | 612.3 (M + H)$^+$ | 2.21 | A |
| 151 | 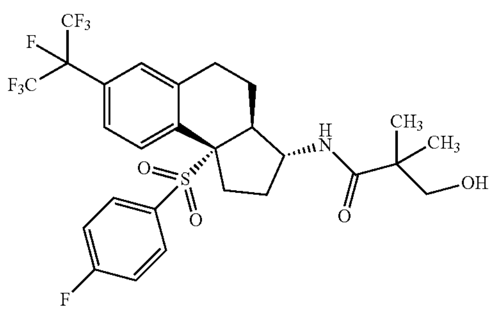 [SMILES: CC(C)(CO)C(=O)N[C@@H]1CC[C@@]2(S(=O)(=O)c3ccc(F)cc3)c3ccc(C(F)(C(F)(F)F)C(F)(F)F)cc3CC[C@@H]12] | 614.1 (M + H)$^+$ | 2.21 | A |
| 152 | 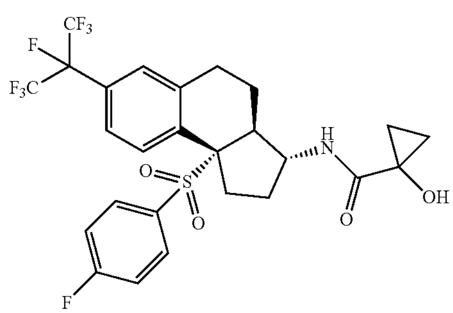 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)C1(O)CC1] | 598.0 (M + H)$^+$ | 2.15 | A |
| 153 | 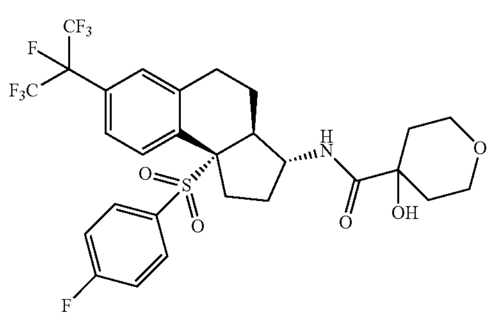 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)C1(O)CCOCC1] | 642.0 (M + H)$^+$ | 2.07 | A |

TABLE 8-continued
| Ex. number | Structure | LCMS m/z observed | HPLC $t_R$ (min) | HPLC method |
|---|---|---|---|---|
| 154 | 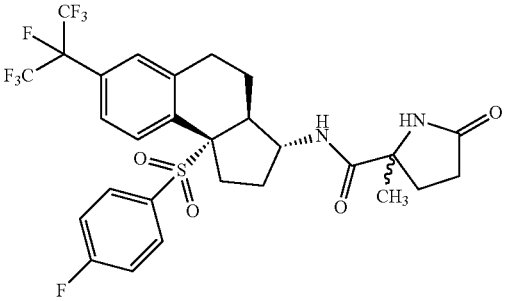 Diastereomeric mixture | 639.1 (M + H)+ | 2.07 | A |
| 155 | 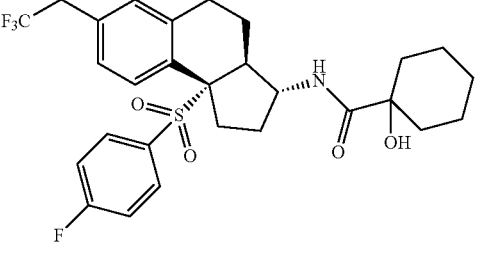 | 640.3 (M + H)+ | 2.38 | A |
| 156 | 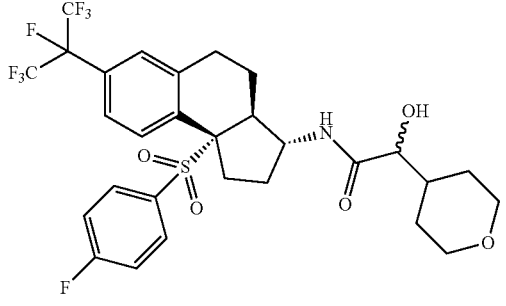 Diastereomeric mixture | 656.3 (M + H)+ | 2.13 | A |
| 157 | 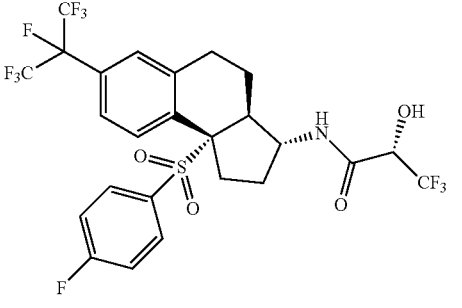 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)[C@H](O)C(F)(F)F] | 640.0 (M + H)+ | 2.28 | A |

TABLE 8-continued

| Ex. number | Structure | LCMS m/z observed | HPLC $t_R$ (min) | HPLC method |
|---|---|---|---|---|
| 158 | 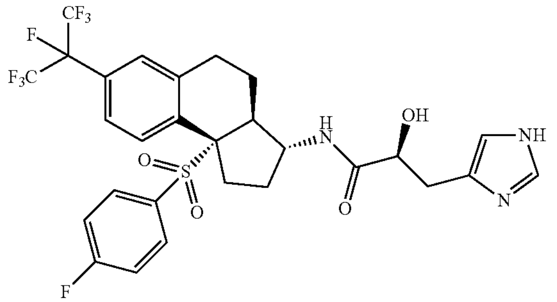 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)[C@@H](O)Cc1c[nH]cn1] | 652.2 (M + H)+ | 1.78 | A |
| 159 | 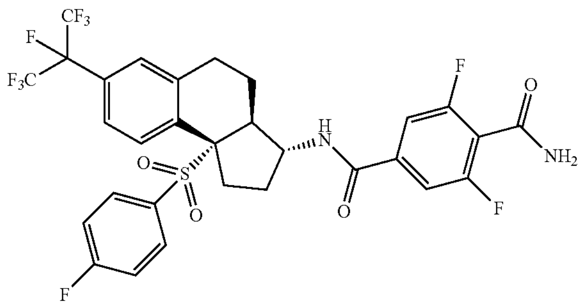 [SMILES: NC(=O)c1c(F)cc(C(=O)N[C@@H]2CC[C@@]3(S(=O)(=O)c4ccc(F)cc4)c4ccc(C(F)(C(F)(F)F)C(F)(F)F)cc4CC[C@@H]23)cc1F] | 697.1 (M + H)+ | 2.22 | A |
| 160 | Diastereomeric mixture | 662.9 (M + H)+ | 1.81 | A |
| 161 | 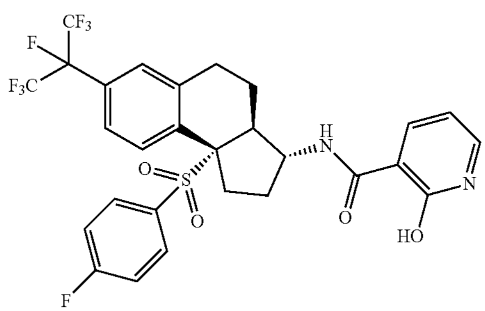 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)c1cccnc1O] | 634.9 (M + H)+ | 2.11 | A |
| 162 | 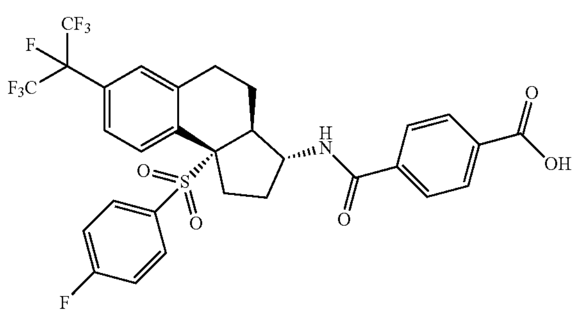 [SMILES: O=C(O)c1ccc(C(=O)N[C@@H]2CC[C@@]3(S(=O)(=O)c4ccc(F)cc4)c4ccc(C(F)(C(F)(F)F)C(F)(F)F)cc4CC[C@@H]23)cc1] | 661.9 (M + H)+ | 2.27 | A |

TABLE 8-continued
| Ex. number | Structure | LCMS m/z observed | HPLC $t_R$ (min) | HPLC method |
|---|---|---|---|---|
| 163 | 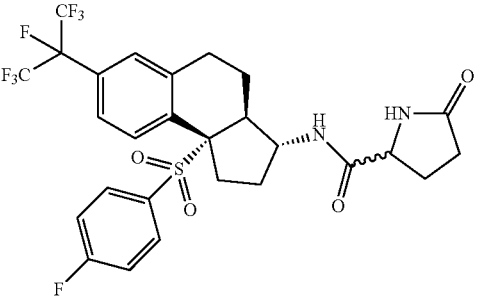<br>Diastereomeric mixture | 625.2 $(M + H)^+$ | 1.99 | A |
| 164 | 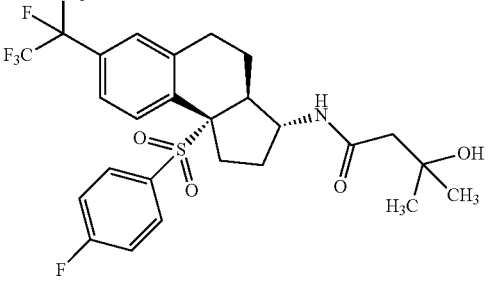 | 614.3 $(M + H)^+$ | 2.28 | A |
| 165 | 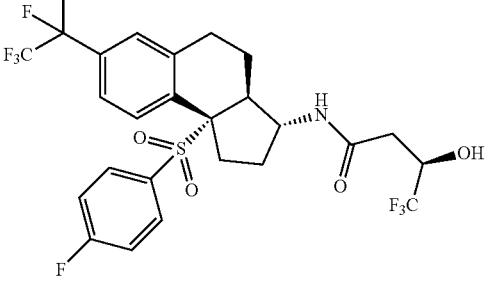 | 654.2 $(M + H)^+$ | 2.27 | A |
| 166 | 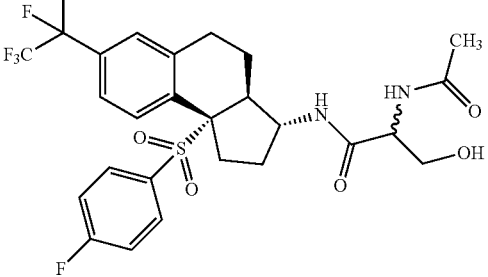<br>Diastereomeric mixture | 643.2 $(M + H)^+$ | 1.92 | A |

TABLE 8-continued

| Ex. number | Structure | LCMS m/z observed | HPLC $t_R$ (min) | HPLC method |
|---|---|---|---|---|
| 167 | Diastereomeric mixture | 600.3 (M + H)+ | 2.18 | A |
| 168 | 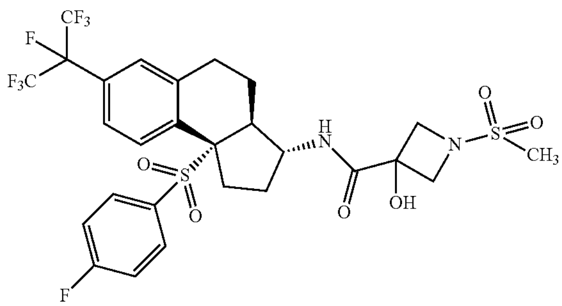 [SMILES: CS(=O)(=O)N1CC(O)(C(=O)N[C@@H]2CC[C@@]3(S(=O)(=O)c4ccc(F)cc4)c4ccc(C(F)(C(F)(F)F)C(F)(F)F)cc4CC[C@@H]23)C1] | 691.2 (M + H)+ | 2.16 | A |
| 169 | 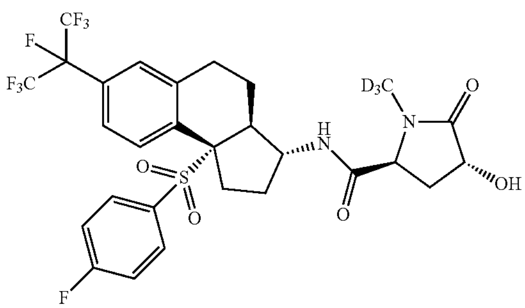 [SMILES: [2H]C([2H])([2H])N1C(=O)[C@H](O)C[C@H]1C(=O)N[C@@H]1CC[C@@]2(S(=O)(=O)c3ccc(F)cc3)c3ccc(C(F)(C(F)(F)F)C(F)(F)F)cc3CC[C@@H]12] | 658.1 (M + H)+ | 2.12 | A |
| 170 | 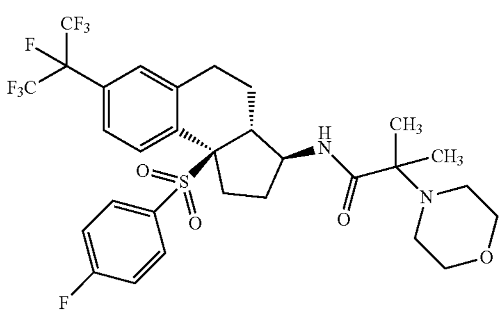 [SMILES: CC(C)(C(=O)N[C@H]1CC[C@]2(S(=O)(=O)c3ccc(F)cc3)c3ccc(C(F)(C(F)(F)F)C(F)(F)F)cc3CC[C@H]12)N1CCOCC1] | 669.1 (M + H)+ | 0.91 | A |
| 171 | 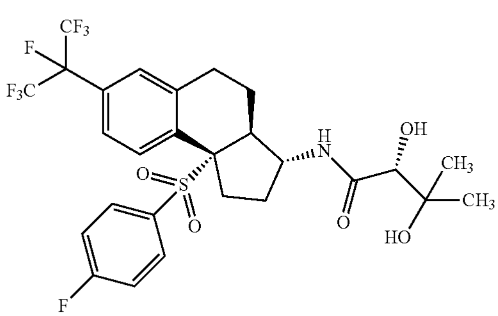 [SMILES: CC(C)(O)[C@@H](O)C(=O)N[C@@H]1CC[C@@]2(S(=O)(=O)c3ccc(F)cc3)c3ccc(C(F)(C(F)(F)F)C(F)(F)F)cc3CC[C@@H]12] | 630.1 (M + H)+ | 1.07 | A |

TABLE 8-continued
| Ex. number | Structure | LCMS m/z observed | HPLC $t_R$ (min) | HPLC method |
|---|---|---|---|---|
| 172 | 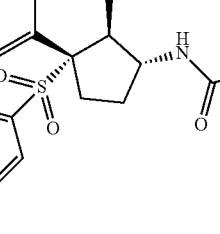 | 624.1 (M + H)+ | 2.24 | C |
| 173 | 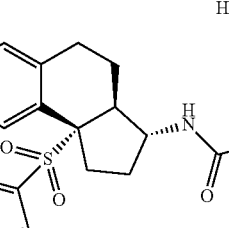 | 682.2 (M + H)+ | 2.26 | C |
| 174 | 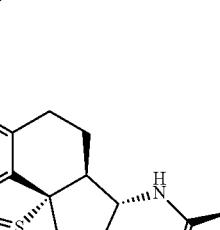 | 626.5 (M + H)+ | 1.07 | A |
| 175 | 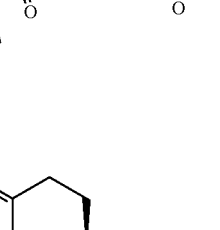 | 626.5 (M + H)+ | 1.07 | A |
| 176 | 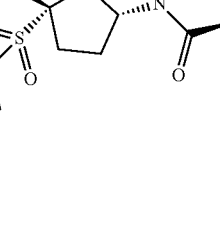 | 625.2 (M + H)+ | 2.03 | C |

TABLE 8-continued

| Ex. number | Structure | LCMS m/z observed | HPLC $t_R$ (min) | HPLC method |
|---|---|---|---|---|
| 177 | 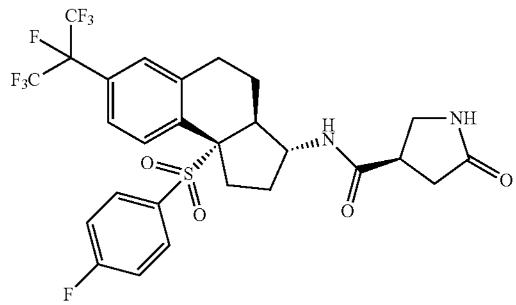 [SMILES: O=C1C[C@@H](C(=O)N[C@@H]2CC[C@@]3(S(=O)(=O)c4ccc(F)cc4)c4ccc(C(F)(C(F)(F)F)C(F)(F)F)cc4CC[C@@H]23)CN1] | 625.2 (M + H)+ | 2.02 | C |
| 178 | 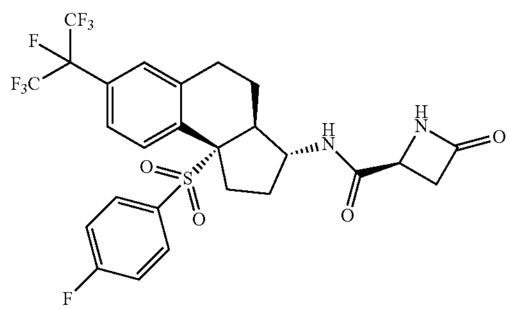 [SMILES: O=C1C[C@@H](C(=O)N[C@@H]2CC[C@@]3(S(=O)(=O)c4ccc(F)cc4)c4ccc(C(F)(C(F)(F)F)C(F)(F)F)cc4CC[C@@H]23)N1] | 611.0 (M + H)+ | 2.14 | C |
| 179 | Homochiral from peak 1 | 639.1 (M + H)+ | 2.08 | C |
| 180 | Homochiral from peak 2 | 639.1 (M + H)+ | 2.11 | C |

TABLE 8-continued
| Ex. number | Structure | LCMS m/z observed | HPLC $t_R$ (min) | HPLC method |
|---|---|---|---|---|
| 181 | 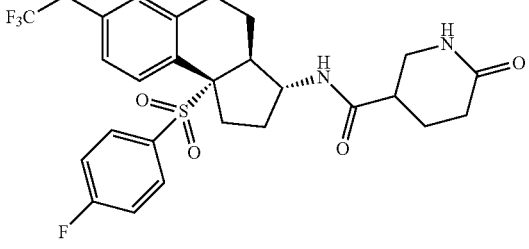<br>Homochiral from peak 1 | 639.3 (M + H)+ | 2.06 | C |
| 182 | 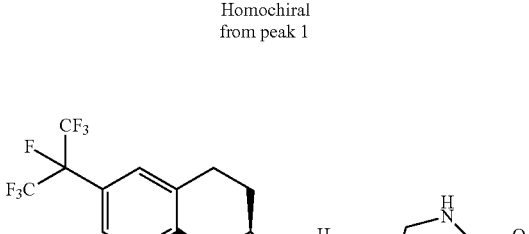<br>Homochiral from peak 2 | 639.3 (M + H)+ | 2.06 | C |
| 183 | 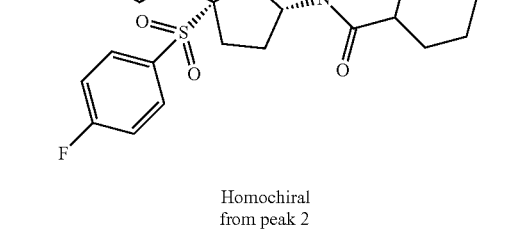 | 649.0 (M + H)+ | 2.23 | C |
| 184 | 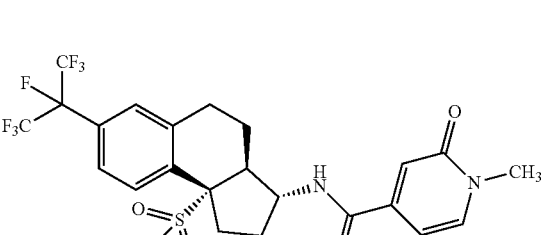<br>Diastereomeric mixture | 690.1 (M + H)+ | 2.11 | C |

TABLE 8-continued

| Ex. number | Structure | LCMS m/z observed | HPLC t$_R$ (min) | HPLC method |
|---|---|---|---|---|
| 185 | 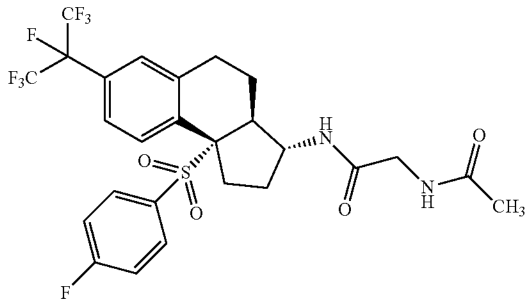 [SMILES: CC(=O)NCC(=O)N[C@@H]1CC[C@@]2(S(=O)(=O)c3ccc(F)cc3)c3ccc(C(F)(C(F)(F)F)C(F)(F)F)cc3CC[C@@H]12] | 613.3 (M + H)$^+$ | 2.10 | C |
| 186 | 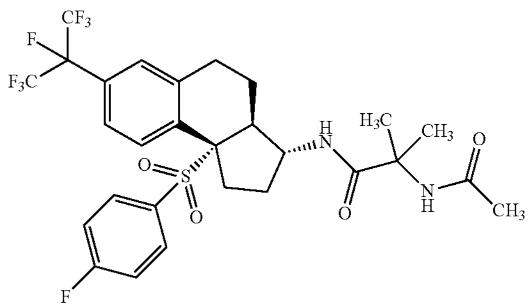 [SMILES: CC(=O)NC(C)(C)C(=O)N[C@@H]1CC[C@@]2(S(=O)(=O)c3ccc(F)cc3)c3ccc(C(F)(C(F)(F)F)C(F)(F)F)cc3CC[C@@H]12] | 641.3 (M + H)$^+$ | 2.16 | B |
| 187 | 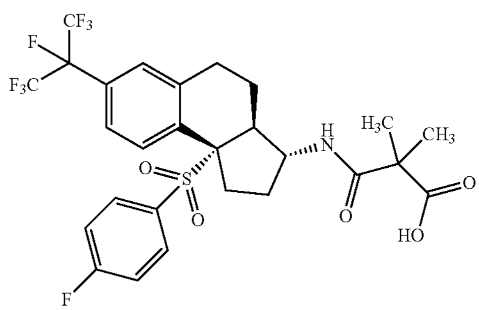 [SMILES: CC(C)(C(=O)O)C(=O)N[C@@H]1CC[C@@]2(S(=O)(=O)c3ccc(F)cc3)c3ccc(C(F)(C(F)(F)F)C(F)(F)F)cc3CC[C@@H]12] | 628.1 (M + H)$^+$ | 2.34 | C |
| 188 | 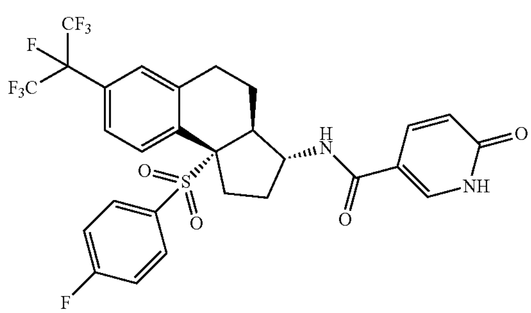 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)c1ccc(=O)[nH]c1] | 635.1 (M + H)$^+$ | 2.20 | C |
| 189 | 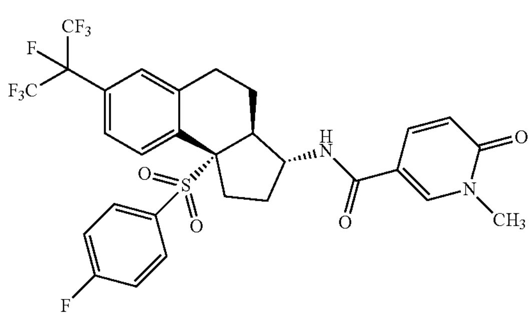 [SMILES: Cn1cc(C(=O)N[C@@H]2CC[C@@]3(S(=O)(=O)c4ccc(F)cc4)c4ccc(C(F)(C(F)(F)F)C(F)(F)F)cc4CC[C@@H]23)ccc1=O] | 649.3 (M + H)$^+$ | 2.20 | C |

TABLE 8-continued

| Ex. number | Structure | LCMS m/z observed | HPLC $t_R$ (min) | HPLC method |
|---|---|---|---|---|
| 190 | 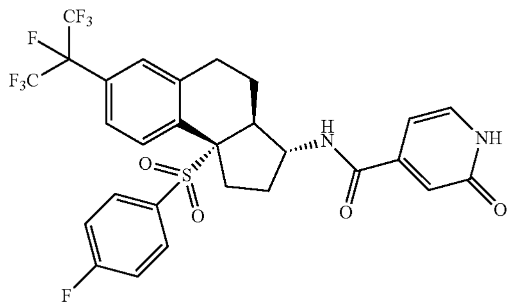 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)c1cc[nH]c(=O)c1] | 635.1 (M + H)+ | 2.20 | C |

Example 191

(1s,4s)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-4-hydroxycyclohexane-1-carboxylic acid

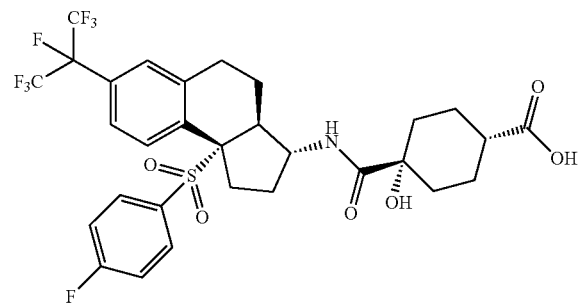 [SMILES: O=C(O)[C@H]1CC[C@](O)(C(=O)N[C@@H]2CC[C@@]3(S(=O)(=O)c4ccc(F)cc4)c4ccc(C(F)(C(F)(F)F)C(F)(F)F)cc4CC[C@@H]23)CC1]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114; 25 mg, 0.040 mmol) and (1s,4s)-4-(ethoxycarbonyl)-1-hydroxycyclohexanecarboxylic acid (22 mg, 0.100 mmol) in DMF (1 mL) was treated with DIEA (84 µL, 0.478 mmol) and HATU (38 mg, 0.100 mmol) and the mixture was stirred at rt. After 3 h, the mixture was diluted with EtOAc, washed sequentially with 10% aqueous LiCl (once) and brine (twice), dried and concentrated. The residue was dissolved in THF (3 mL) and 1 M aqueous NaOH (2.1 mL, 2.1 mmol) was added. MeOH was added until the mixture was homogenous. After stirring overnight at rt, the mixture was concentrated and the residue was dissolved in EtOAc and treated with 1 M aqueous HCl (3 mL). The organic phase was separated, washed with brine, dried and concentrated. The residue was purified by preparative HPLC (Method E, gradient 40-80% B, 19 min; then Method F, gradient 30-70% B, 27 min) to provide (1s,4s)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-4-hydroxycyclohexane-1-carboxylic acid (9.7 mg, 35% yield). LCMS m/z 684.1 (M+H)+; HPLC $t_R$ 2.11 min (Method C). $^1$H NMR (500 MHz, DMSO-d$_6$) δ 7.93 (br d, J=8.5 Hz, 1H), 7.62-7.56 (m, 1H), 7.54-7.48 (m, 1H), 7.36-7.29 (m, 3H), 7.29-7.22 (m, 2H), 4.04-3.93 (m, 1H), 3.07-2.97 (m, 1H), 2.91-2.81 (m, 1H), 2.70-2.60 (m, 1H), 2.35-2.24 (m, 1H), 2.23-2.13 (m, 1H), 2.03-1.87 (m, 3H), 1.87-1.48 (m, 9H), 1.26 (br s, 1H).

The Examples in Table 9 were prepared using the procedures used to prepare Example 191, or similar procedures, from the appropriate carboxylic acid and amine starting materials.

TABLE 9

| Ex. number | Structure | LCMS m/z observed | HPLC $t_R$ (min) | HPLC method |
|---|---|---|---|---|
| 192 | 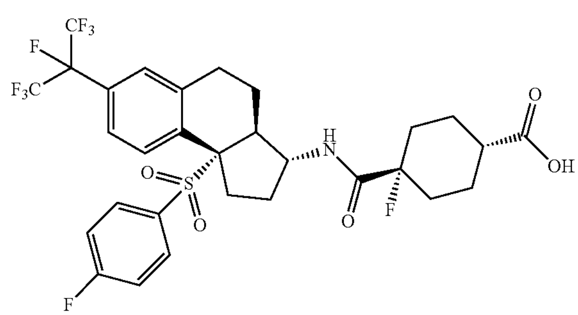 | 686.3 (M + H)+ | 2.28 | C |

TABLE 9-continued

| Ex. number | Structure | LCMS m/z observed | HPLC $t_R$ (min) | HPLC method |
|---|---|---|---|---|
| 193 | 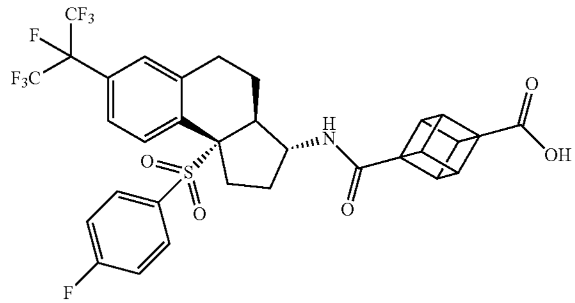 [SMILES: O=C(O)C12C3C4C1C1C2C3C41C(=O)N[C@@H]1CC[C@@]2(S(=O)(=O)c3ccc(F)cc3)c3ccc(C(F)(C(F)(F)F)C(F)(F)F)cc3CC[C@@H]12] | 688.0 (M + H)⁺ | 2.25 | C |
| 194 | 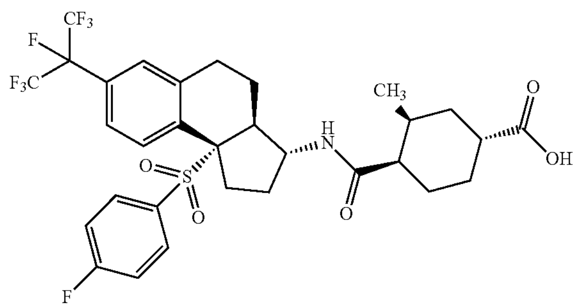 [SMILES: C[C@H]1C[C@H](C(=O)O)CC[C@H]1C(=O)N[C@@H]1CC[C@@]2(S(=O)(=O)c3ccc(F)cc3)c3ccc(C(F)(C(F)(F)F)C(F)(F)F)cc3CC[C@@H]12] | 681.9 (M + H)⁺ | 2.21 | C |

Example 195

N-((3R,3aS,9bS)-9b-((4-fluorophenyl)sulfonyl)-7-(perfluoropropan-2-yl)-2,3,a3a4,59b-hexahydro-1H-cyclopenta[a]naphthalen-3-yl)-4-hydroxypiperidine-4-carboxamide

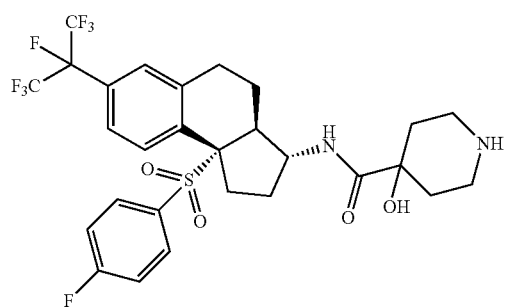 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)C1(O)CCNCC1]

A mixture of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114, 110 mg, 0.175 mmol), 1-(tert-butoxycarbonyl)-4-hydroxypiperidine-4-carboxylic acid (64.5 mg, 0.263 mmol), DMF (3 mL), DIEA (306 µL, 1.75 mmol) and HATU (100 mg, 0.263 mmol) was stirred at rt. After 1 h the mixture was diluted with EtOAc and water and the layers were separated. The organic phase was washed sequentially with saturated aqueous Na₂CO₃, 10% aqueous LiCl and brine, then was dried and concentrated. The residue was dissolved in DCM (5 mL) and treated with HCl (4 M in 1,4-dioxane; 394 µL, 1.58 mmol). After standing overnight at rt, the mixture was concentrated under vacuum. A sample of the residue (19.6 mg) was purified by preparative HPLC (Method E, gradient 30-70% B, 20 min) to provide N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxypiperidine-4-carboxamide (15.9 mg, 86% yield). LCMS m/z 641.2 (M+H)⁺; HPLC $t_R$ 1.81 min (Method C). ¹H NMR (500 MHz, DMSO-d₆) δ 8.00 (br d, J=8.5 Hz, 1H), 7.63-7.56 (m, 1H), 7.52 (br d, J=8.2 Hz, 1H), 7.32 (br s, 3H), 7.29-7.21 (m, 2H), 4.04-3.92 (m, 1H), 3.07-2.97 (m, 1H), 2.93-2.79 (m, 4H), 2.70-2.60 (m, 1H), 2.34-2.24 (m, 1H), 2.04-1.85 (m, 6H), 1.55-1.39 (m, 2H), 1.31-1.19 (m, 1H), 1.00 (d, J=6.4 Hz, 1H).

The Examples in Table 10 were prepared using the procedures used to prepare Example 195, or similar procedures, from the appropriate carboxylic acid and amine starting materials.

TABLE 10

| Ex. number | Structure | LCMS m/z observed | HPLC $t_R$ (min) | HPLC method |
|---|---|---|---|---|
| 196 | 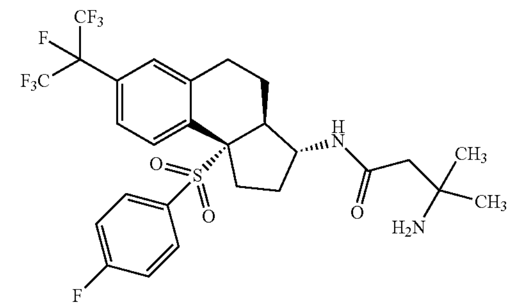 [SMILES: CC(C)(N)CC(=O)N[C@@H]1CC[C@@]2(S(=O)(=O)c3ccc(F)cc3)c3ccc(C(F)(C(F)(F)F)C(F)(F)F)cc3CC[C@@H]12] | 613.1 (M + H)+ | 0.88 | A |
| 197 | 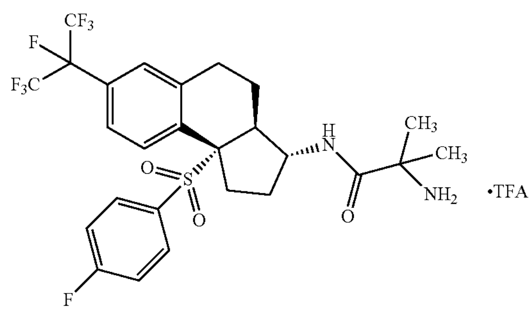 [SMILES: CC(C)(N)C(=O)N[C@@H]1CC[C@@]2(S(=O)(=O)c3ccc(F)cc3)c3ccc(C(F)(C(F)(F)F)C(F)(F)F)cc3CC[C@@H]12] | 599.1 (M + H)+ | 0.87 | A |
| 198 | 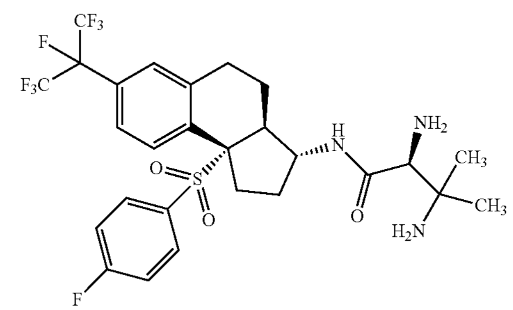 [SMILES: CC(C)(N)[C@H](N)C(=O)N[C@@H]1CC[C@@]2(S(=O)(=O)c3ccc(F)cc3)c3ccc(C(F)(C(F)(F)F)C(F)(F)F)cc3CC[C@@H]12] | 628.1 (M + H)+ | 0.88 | A |
| 199 | 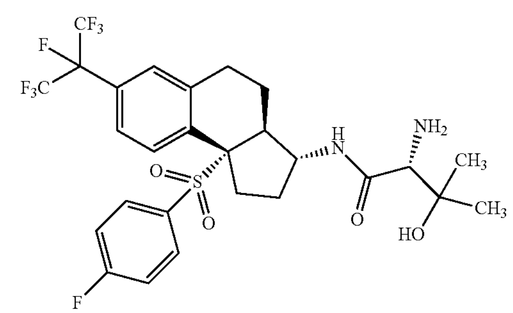 [SMILES: CC(C)(O)[C@@H](N)C(=O)N[C@@H]1CC[C@@]2(S(=O)(=O)c3ccc(F)cc3)c3ccc(C(F)(C(F)(F)F)C(F)(F)F)cc3CC[C@@H]12] | 629.1 (M + H)+ | 1.09 | A |
| 200 | 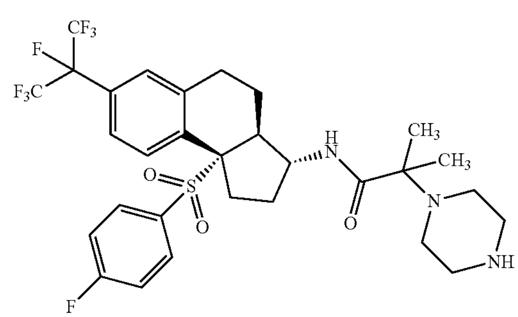 [SMILES: CC(C)(C(=O)N[C@@H]1CC[C@@]2(S(=O)(=O)c3ccc(F)cc3)c3ccc(C(F)(C(F)(F)F)C(F)(F)F)cc3CC[C@@H]12)N1CCNCC1] | 668.1 (M + H)+ | 0.96 | A |

Example 201

N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)methanesulfonamide

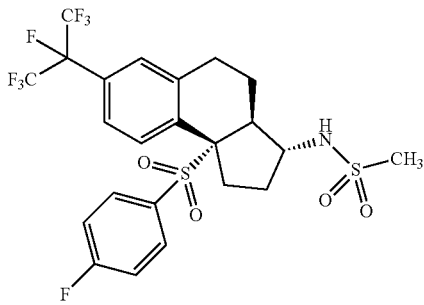 [SMILES: CS(=O)(=O)N[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114; 40 mg, 0.078 mmol) in DCM (2 mL) was treated with methanesulfonyl chloride (11.6 mg, 0.101 mmol) and TEA (11 µL, 0.078 mmol) at rt and stirred for 2 h. The mixture was diluted with water and saturated aqueous NaHCO₃ and extracted with EtOAc. The organic layer was dried and concentrated, and the residue was purified by preparative HPLC (Method B, gradient 41-81% B, 20 min) to provide N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)methanesulfonamide (6.8 mg, 15% yield). LCMS m/z 592.1 (M+H)$^+$; HPLC $t_R$ 1.10 min (Method A). $^1$H NMR (500 MHz, DMSO-d$_6$) δ 7.53-7.43 (m, 3H), 7.39-7.25 (m, 5H), 3.19-3.15 (m, 1H), 3.03-2.96 (m, 1H), 2.93-2.90 (m, 3H), 2.83-2.76 (m, 1H), 2.70-2.61 (m, 1H), 2.21-2.13 (m, 1H), 2.12-2.03 (m, 3H), 1.90-1.82 (m, 1H), 1.40-1.32 (m, 1H).

Example 202

2-hydroxy-2-methylpropyl ((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamate

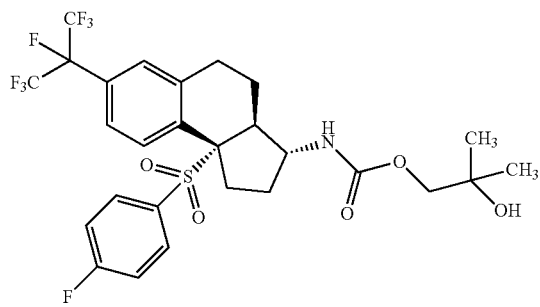 [SMILES: CC(C)(O)COC(=O)N[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114 trifluoroacetate; 40 mg, 0.078 mmol) in DCM (2 mL) was stirred on an ice-water bath, treated with phosgene (42.4 mg, 0.086 mmol) and TEA (43 µL, 0.312 mmol) and stirred at 0° C. for 0.5 h. The mixture was warmed to rt and concentrated, and the residue was dissolved in DCM (4 mL) and treated with 2-methylpropane-1,2-diol (35.1 mg, 0.390 mmol) and TEA (43 µL, 0.312 mmol). The mixture was stirred at rt for 5 h, then was diluted with water and saturated aqueous NaHCO₃ and extracted with EtOAc. The organic layer was dried and concentrated, and the residue was purified by preparative HPLC (Method B, gradient 40-100% B, 20 min) to provide 2-hydroxy-2-methylpropyl ((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamate (2.1 mg, 4% yield). LCMS m/z 630.2 (M+H)$^+$; HPLC $t_R$ 2.34 min (Method B). $^1$H NMR (500 MHz, DMSO-d$_6$) δ 7.51 (s, 1H), 7.43 (br d, J=7.6 Hz, 1H), 7.37-7.24 (m, 5H), 3.75 (s, 2H), 3.73-3.60 (m, 1H), 3.07-2.95 (m, 1H), 2.92-2.80 (m, 1H), 2.70-2.60 (m, 1H), 2.21 (ddd, J=14.3, 11.0, 7.0 Hz, 1H), 2.06-1.91 (m, 3H), 1.87-1.75 (m, 1H), 1.36-1.21 (m, 2H), 1.12 (s, 6H).

Example 203

1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(2-hydroxy-2-methylpropyl)urea

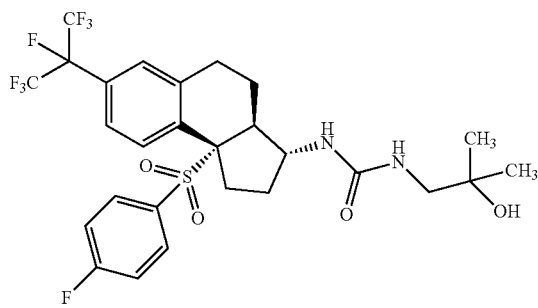 [SMILES: CC(C)(O)CNC(=O)N[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114 trifluoroacetate; 50 mg, 0.097 mmol) in DCM (2 mL) was stirred on an ice-water bath and treated with phosgene (53.0 mg, 0.107 mmol) and TEA (54 µL, 0.390 mmol) and stirred at 0° C. for 30 min. The mixture was warmed to rt and concentrated, and the residue was dissolved in DCM (4 mL). The mixture was treated 1-amino-2-methylpropan-2-ol (43.4 mg, 0.487 mmol) and TEA (54 µL, 0.390 mmol), and stirred at rt for 2 h. The mixture was diluted with water and saturated aqueous NaHCO₃ and extracted with EtOAc. The organic layer was dried and concentrated, and the residue was purified by preparative HPLC (Method B, gradient 39-79% B, 20 min) to provide 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(2-hydroxy-2-methylpropyl)urea (11.4 mg, 18% yield). LCMS m/z 629.1 (M+H)$^+$; HPLC $t_R$ 1.06 min (Method A). $^1$H NMR (500 MHz, DMSO-d$_6$) δ 7.51-7.46 (m, 2H), 7.36-7.31 (m, 1H), 7.30-7.22 (m, 4H), 6.41-6.37 (m, 1H), 5.92-5.85 (m, 1H), 4.56-4.52 (m, 1H), 3.90-3.82 (m, 1H), 3.52-3.45 (m, 1H), 3.06-2.98 (m, 1H), 2.97-2.92 (m, 2H), 2.70-2.60 (m, 2H), 2.23-2.15 (m, 1H), 2.08-2.02 (m, 1H), 2.01-1.91 (m, 2H), 1.79-1.69 (m, 1H), 1.31-1.23 (m, 1H), 1.07-1.03 (m, 6H).

The Examples in Table 11 were prepared using the procedures used to prepare Example 203, or similar procedures, from the appropriate carboxylic acid and amine starting materials.

TABLE 11

| Ex. number | Structure | LCMS m/z observed | HPLC $t_R$ (min) | HPLC method |
|---|---|---|---|---|
| 204 | 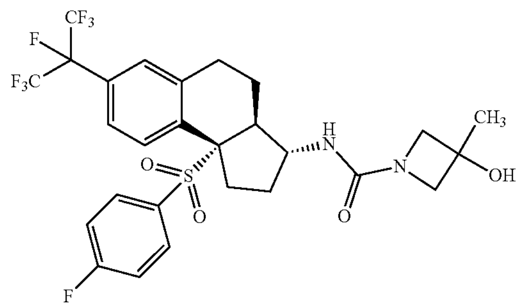 [SMILES: CC1(O)CN(C(=O)N[C@@H]2CC[C@@]3(S(=O)(=O)c4ccc(F)cc4)c4ccc(C(F)(C(F)(F)F)C(F)(F)F)cc4CC[C@@H]23)C1] | 627.2 (M + H)+ | 2.08 | C |
| 205 | 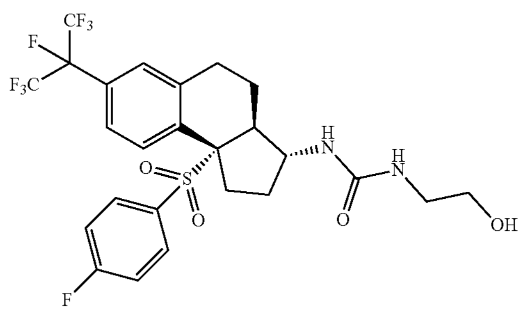 [SMILES: O=C(NCCO)N[C@@H]1CC[C@@]2(S(=O)(=O)c3ccc(F)cc3)c3ccc(C(F)(C(F)(F)F)C(F)(F)F)cc3CC[C@@H]12] | 601.1 (M + H)+ | 1.01 | A |
| 206 | 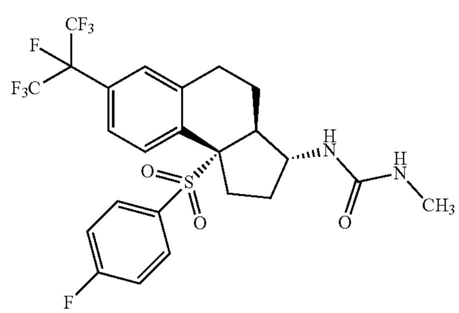 [SMILES: CNC(=O)N[C@@H]1CC[C@@]2(S(=O)(=O)c3ccc(F)cc3)c3ccc(C(F)(C(F)(F)F)C(F)(F)F)cc3CC[C@@H]12] | 571.1 (M + H)+ | 1.05 | A |
| 207 | 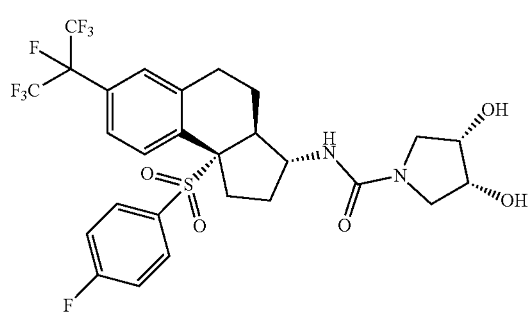 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)N1C[C@@H](O)[C@@H](O)C1] | 643.1 (M + H)+ | 0.99 | A |

Examples 208 and 209

2-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-N-methylacetamide and 2,2'-(((3R,3aS,9bS)-9b-((4-fluorophenyl)sulfonyl)-7-perfluoropropan-2-yl)-2,3,3a,4,5,9b-hexahydro-1H-cyclopenta[a]naphthalen-3-yl)azanediyl)bis(N-methylacetamide)

Example 208

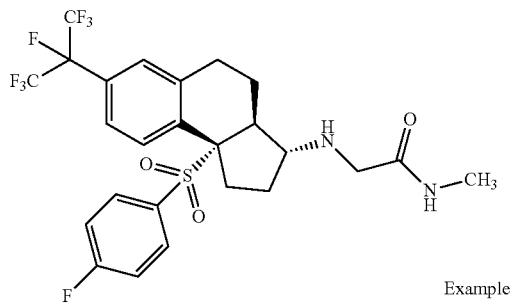

Example 209

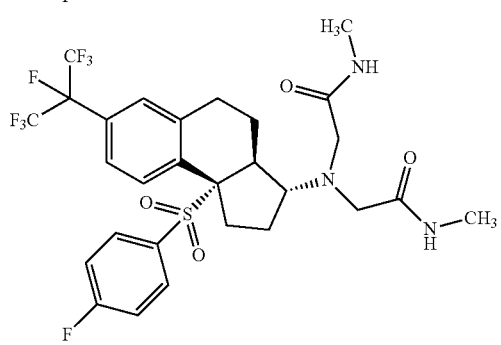

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114 trifluoroacetate; 26.4 mg, 0.042 mmol) in DMF (1 mL) was treated with 2-chloro-N-methylacetamide (5.9 mg, 0.055 mmol) and DIEA (95 μL, 0.546 mmol). The reaction was stirred at rt for 3 h, then at 80° C. Two additional portions of 2-chloro-N-methylacetamide (10 mg, 0.093 mmol) were added after 3 h and after heating overnight. The mixture was cooled to rt and subjected to preparative LCMS (Method E, gradient 40-80% B, 22 min) to provide 2-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-N-methylacetamide (Example 208; 9.1 mg, 35% yield). LCMS m/z 585.1 (M+H)$^+$; HPLC $t_R$ 1.89 min (Method A). $^1$H NMR (500 MHz, DMSO-$d_6$) δ 7.83 (br d, J=4.3 Hz, 1H), 7.50-7.41 (m, 2H), 7.30 (s, 1H), 7.28-7.16 (m, 4H), 3.77 (br s, 1H), 3.74 (br s, 1H), 3.24-3.10 (m, 2H), 3.00 (br dd, J=14.3, 4.0 Hz, 1H), 2.85-2.75 (m, 1H), 2.75-2.67 (m, 1H), 2.63 (d, J=4.6 Hz, 3H), 2.23-2.06 (m, 2H), 1.97-1.85 (m, 2H), 1.75-1.59 (m, 1H), 1.21-1.12 (m, 1H).

A second product was isolated and purified again by preparative LCMS (Method F, gradient 40-65% B, 25 min) to provide 2,2'-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)azanediyl)bis(N-methylacetamide) (Example 209; 4.4 mg, 16% yield). LCMS m/z 656.4 (M+H)$^+$; HPLC $t_R$ 1.89 min (Method A).

The Examples in Table 12 were prepared using procedures used to prepare Examples 208 and 209, or similar procedures.

TABLE 12

| Ex. number | Structure | LCMS m/z observed | HPLC $t_R$ (min) | HPLC method |
|---|---|---|---|---|
| 210 | 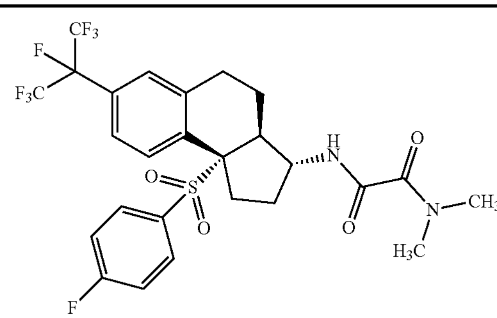 | 599.3 (M + H)$^+$ | 1.95 | A |
| 211 | 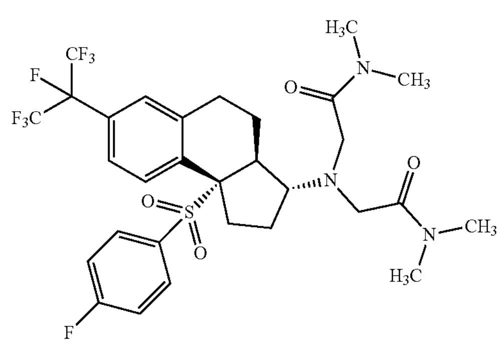 [SMILES: CN(C)C(=O)CN(CC(=O)N(C)C)[C@@H]1CC[C@@]2(S(=O)(=O)c3ccc(F)cc3)c3ccc(C(F)(C(F)(F)F)C(F)(F)F)cc3CC[C@@H]12] | 684.0 (M + H)$^+$ | 2.26 | B |

TABLE 12-continued

| Ex. number | Structure | LCMS m/z observed | HPLC $t_R$ (min) | HPLC method |
|---|---|---|---|---|
| 212 | 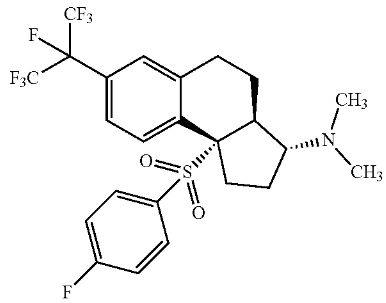 [SMILES: CN(C)[C@@H]1CC[C@@]2(S(=O)(=O)c3ccc(F)cc3)c3ccc(C(F)(C(F)(F)F)C(F)(F)F)cc3CC[C@@H]12] | 542.1 (M + H)⁺ | 1.82 | A |
| 213 | 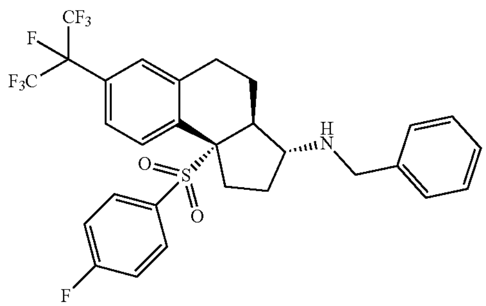 [SMILES: O=S(=O)(c1ccc(F)cc1)[C@@]12CC[C@@H](NCc3ccccc3)[C@@H]1CCc1cc(C(F)(C(F)(F)F)C(F)(F)F)ccc12] | 604.1 (M + H)⁺ | 2.03 | A |

Example 214

3-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2,2-dimethylpropan-1-ol

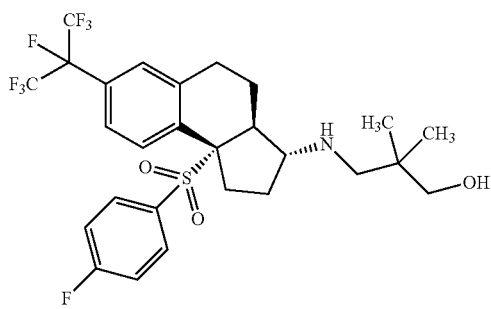 [SMILES: CC(C)(CO)CN[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 20.0 mg, 0.039 mmol) in DCM (1 mL) was treated with DIEA (14 µL, 0.078 mmol) and 3-hydroxy-2,2-dimethylpropanal (39.8 mg, 0.390 mmol) and stirred at rt. After 45 min the mixture was treated with sodium triacetoxyborohydride (33.0 mg, 0.156 mmol) and stirred at rt overnight. The mixture was treated with a drop of saturated aqueous NaHCO₃, concentrated and purified by preparative HPLC (Method E, gradient 48-88% B, 20 min) to provide 3-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2,2-dimethylpropan-1-ol (7.2 mg, 30% yield). LCMS m/z 600.2 (M+H)⁺; HPLC $t_R$ 1.91 min (Method C). ¹H NMR (500 MHz, DMSO-d₆) δ 7.48 (s, 2H), 7.36-7.20 (m, 5H), 3.25-3.14 (m, 2H), 2.98 (br dd, J=10.8, 3.5 Hz, 1H), 2.82 (q, J=7.2 Hz, 1H), 2.73-2.66 (m, 1H), 2.61 (br d, J=15.6 Hz, 1H), 2.48-2.32 (m, 2H), 2.22-2.06 (m, 2H), 2.03-1.82 (m, 3H), 1.75-1.60 (m, 1H), 1.35-1.17 (m, 1H), 0.82 (2s, 6H).

Example 215

(3R,3aS,9bS)-9b-((4-fluorophenyl)sulfonyl)-7-(perfluoropropan-2-yl)-N-phenyl-2,3,3a,4,5,9b-hexahydro-1H-cyclopenta[a]naphthalen-3-amine A mixture of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114 trifluoroacetate; 20 mg, 0.032 mmol), bromobenzene (10.0 mg, 0.064 mmol) and toluene (1 mL) was purged with nitrogen for 2 min. Palladium(II) acetate (1.4 mg, 6.37 µmol), BINAP (6.0 mg, 9.56 µmol) and sodium tert-butoxide (12.3 mg, 0.127 mmol) were added and the mixture was heated at 105° C. under nitrogen overnight. The mixture was cooled to rt, diluted with ethyl acetate and washed with brine. The organic phase was dried and concentrated, and the residue was purified by preparative HPLC (Method F, gradient 52-92% B, 19 min; then Method E, gradient 58-98% B, 20 min) to provide (3R,3aS,9bS)-9b-((4-fluorophenyl)sulfonyl)-7-(perfluoropropan-2-yl)-N-phenyl-2,3,3a,4,5,9b-hexahydro-1H-cyclopenta[a]naphthalen-3-amine (3.2 mg, 17% yield). LCMS m/z 590.2 (M+H)$^+$; HPLC $t_R$ 2.55 min (Method C). $^1$H NMR (500 MHz, DMSO-$d_6$) δ 7.54-7.41 (m, 2H), 7.36 (br s, 1H), 7.33-7.20 (m, 4H), 7.06 (br t, J=7.5 Hz, 2H), 6.62 (br d, J=7.9 Hz, 2H), 6.51 (br t, J=7.2 Hz, 1H), 5.82 (br d, J=7.6 Hz, 1H), 3.69-3.57 (m, 1H), 3.11-2.90 (m, 2H), 2.63 (br d, J=16.2 Hz, 1H), 2.33-2.21 (m, 1H), 2.20-2.06 (m, 2H), 2.00 (br t, J=12.2 Hz, 1H), 1.77-1.65 (m, 1H), 1.39-1.25 (m, 1H).

Example 216

(3R,3 aR,9bS)-9b-((4-fluorophenyl)sulfonyl)-N-(2-hydroxy-2-methylpropyl)-5-methyl-7-(perfluoropropan-2-yl)-2,3,3a,4,5,9b-hexahydro-1H-cyclopenta[c]quinoline-3-carboxamide

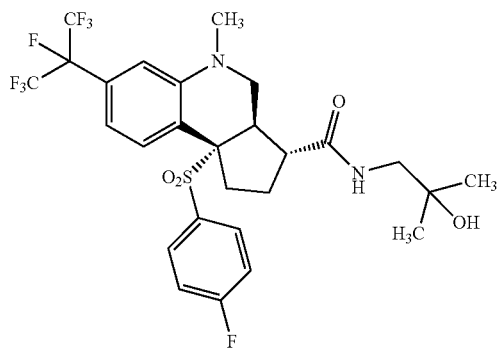 [SMILES: CN1C[C@H]2[C@H](C(=O)NCC(C)(C)O)CC[C@@]2(S(=O)(=O)c2ccc(F)cc2)c2ccc(C(F)(C(F)(F)F)C(F)(F)F)cc21]

Step A: (3R,3aR,9bS)-9b-((4-fluorophenyl)sulfonyl)-N-(2-hydroxy-2-methylpropyl)-7-(perfluoropropan-2-yl)-2,3,3a,4,5,9b-hexahydro-1H-cyclopenta[c]quinoline-3-carboxamide

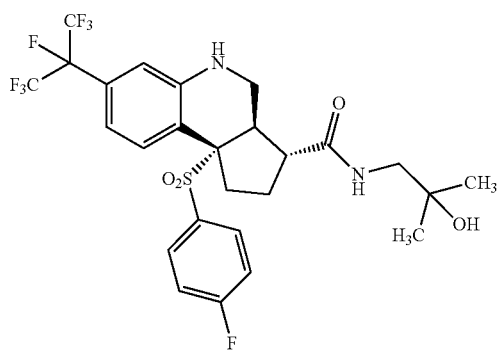 [SMILES: CC(C)(O)CNC(=O)[C@@H]1CC[C@@]2(S(=O)(=O)c3ccc(F)cc3)c3ccc(C(F)(C(F)(F)F)C(F)(F)F)cc3NC[C@@H]12]

A solution of (3R,3aR,9bS)-9b-((4-fluorophenyl)sulfonyl)-7-(perfluoropropan-2-yl)-2,3,3a,4,5,9b-hexahydro-1H-cyclopenta[c]quinoline-3-carboxylic acid hydrochloride (Intermediate 16; 50 mg, 0.092 mmol) in DMF (920 μL) was treated with 1-amino-2-methylpropan-2-ol (8.2 mg, 0.092 mmol), DIEA (64 μL, 0.37 mmol), and HATU (53 mg, 0.14 mmol). The mixture was stirred at rt for 30 min, then was purified by preparative HPLC (Method E, gradient 45-90% B, 20 min) to provide (3R,3aR,9bS)-9b-((4-fluorophenyl)sulfonyl)-N-(2-hydroxy-2-methylpropyl)-7-(perfluoropropan-2-yl)-2,3,3a,4,5,9b-hexahydro-1H-cyclopenta[c]quinoline-3-carboxamide (14 mg, 48% yield). LCMS m/z 615.0 (M+1)$^+$; HPLC $t_R$ 0.99 min (Method A). $^1$H NMR (500 MHz, DMSO-$d_6$) δ 7.82 (br t, J=5.8 Hz, 1H), 7.64 (br dd, J=8.2, 5.2 Hz, 2H), 7.42 (br t, J=8.5 Hz, 2H), 7.32 (d, J=8.2 Hz, 1H), 6.83 (s, 1H), 6.74 (br d, J=7.9 Hz, 1H), 6.62 (br s, 1H), 4.39 (s, 1H), 3.29-3.12 (m, 1H), 3.09-3.00 (m, 1H), 3.00-2.87 (m, 3H), 2.65-2.54 (m, 2H), 2.32 (br t, J=4.9 Hz, 1H), 1.79-1.63 (m, 1H), 1.60 (br d, J=10.1 Hz, 1H), 1.01 (d, J=2.4 Hz, 6H).

Step B: (3R,3aR,9bS)-9b-((4-fluorophenyl)sulfonyl)-N-(2-hydroxy-2-methylpropyl)-5-methyl-7-(perfluoropropan-2-yl)-2,3,3a,4,5,9b-hexahydro-1H-cyclopenta[c]quinoline-3-carboxamide

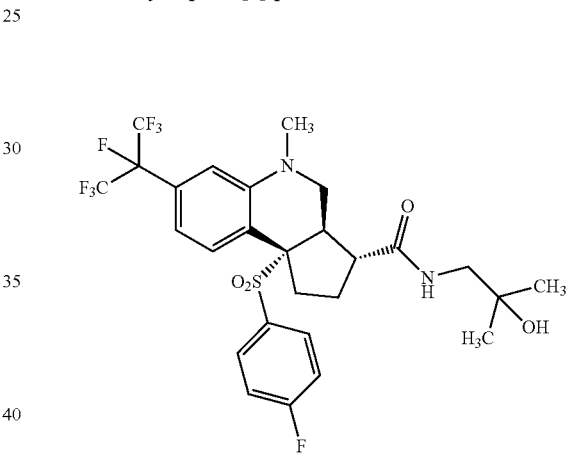

A solution of (3R,3aR,9bS)-9b-((4-fluorophenyl)sulfonyl)-N-(2-hydroxy-2-methylpropyl)-7-(perfluoropropan-2-yl)-2,3,3a,4,5,9b-hexahydro-1H-cyclopenta[c]quinoline-3-carboxamide (30 mg, 0.049 mmol) in MeOH (0.5 mL) was treated with formaldehyde (40 mg, 0.49 mmol), acetic acid (56 μL, 0.98 mmol) and sodium cyanoborohydride (31 mg, 0.49 mmol). The mixture was stirred at rt for 30 min, then was purified by preparative HPLC (Method E, gradient 45-90% B, 20 min) to provide (3R,3aR,9bS)-9b-((4-fluorophenyl)sulfonyl)-N-(2-hydroxy-2-methylpropyl)-5-methyl-7-(perfluoropropan-2-yl)-2,3,3a,4,5,9b-hexahydro-1H-cyclopenta[c]quinoline-3-carboxamide (11 mg, 36% yield). LCMS m/z 629.0 (M+1)$^+$; HPLC $t_R$ 1.04 min (Method A). $^1$H NMR (500 MHz, DMSO-$d_6$) δ 7.82 (br t, J=5.8 Hz, 1H), 7.55 (t, J=6.4 Hz, 2H), 7.46-7.31 (m, 3H), 6.89 (br d, J=8.5 Hz, 1H), 6.66 (s, 1H), 3.07-2.90 (m, 4H), 2.74 (s, 3H), 2.72-2.55 (m, 4H), 2.48-2.28 (m, 1H), 1.77-1.61 (m, 2H), 1.03 (s, 6H).

The Examples in Table 13 were prepared using procedures used to prepare Example 216 or similar procedures.

TABLE 13
| Ex. number | Structure | LCMS m/z observed | HPLC $t_R$ (min) | HPLC method |
|---|---|---|---|---|
| 217 | 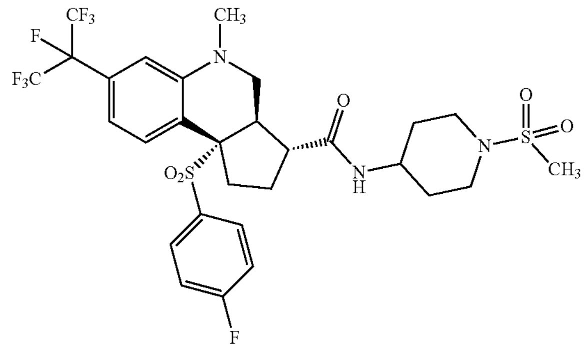 [SMILES: CN1C[C@H]2[C@H](C(=O)NC3CCN(S(C)(=O)=O)CC3)CC[C@@]2(S(=O)(=O)c2ccc(F)cc2)c2ccc(C(F)(C(F)(F)F)C(F)(F)F)cc21] | 718.0 (M + H)+ | 1.05 | A |
| 218 | 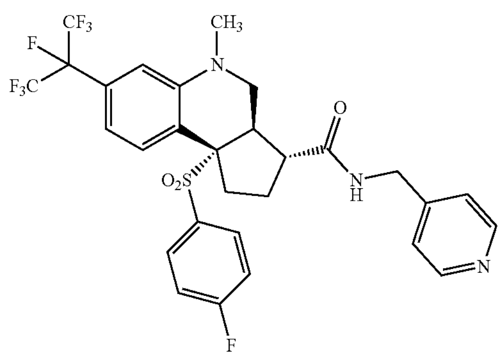 [SMILES: CN1C[C@H]2[C@H](C(=O)NCc3ccncc3)CC[C@@]2(S(=O)(=O)c2ccc(F)cc2)c2ccc(C(F)(C(F)(F)F)C(F)(F)F)cc21] | 648.0 (M + H)+ | 0.91 | A |
Example 219
N-((3R,3 aS,9bS)-9b-((4-fluorophenyl)sulfonyl)-7-perfluoropropan-2-yl)-2,3,3a,4,5,9b-hexahydro-1H-cyclopenta[c]quinolin-3-yl)-pyridin-4-yl)acetamide
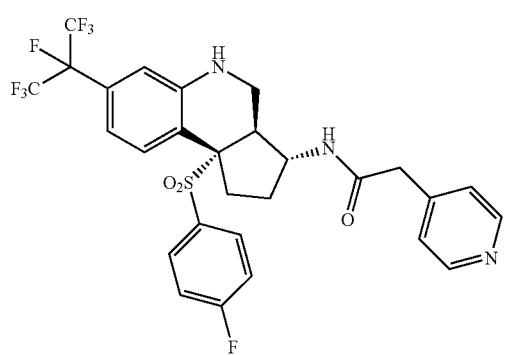 [SMILES: O=C(Cc1ccncc1)N[C@@H]1CC[C@@]2(S(=O)(=O)c3ccc(F)cc3)c3ccc(C(F)(C(F)(F)F)C(F)(F)F)cc3NC[C@@H]12]
Step A: (3R,3 aS,9bS)-9b-((4-fluorophenyl)sulfonyl)-7-(perfluoropropan-2-yl)-2,3,3a,4,5,9b-hexahydro-1H-cyclopenta[c]quinolin-3-amine bis-trifluoroacetate
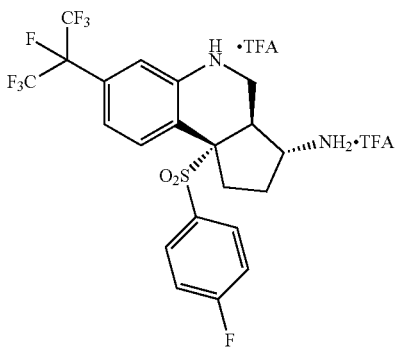

A solution of (3R,3aR,9bS)-5-(tert-butoxycarbonyl)-9b-((4-fluorophenyl)sulfonyl)-7-(perfluoropropan-2-yl)-2,3,3a,4,5,9b-hexahydro-1H-cyclopenta[c]quinoline-3-carboxylic acid (Intermediate 15; 1.0 g, 1.9 mmol) in toluene (20 mL) was stirred on an ice-water bath and treated with triethylamine (1.1 mL, 7.8 mmol). The mixture was stirred at 0° C. for 5 min, then diphenyl phosphorazidate (1.8 mL, 7.8 mmol) was added and the mixture was allowed to warm to rt and stirred for 1 h. The mixture was treated with water and extracted with EtOAc. The organic phase was washed with brine, dried and concentrated. The residue was suspended in 2-(trimethylsilyl)ethanol (6.0 mL, 42 mmol) and stirred at 80° C. for 3 h. The mixture was cooled to rt, diluted with water, and extracted with EtOAc. The organic phase was washed with brine, dried and concentrated. The residue was subjected to column chromatography on silica gel, eluting with EtOAc-hexanes, to provide tert-butyl (3R,3 aS,9bS)-9b-((4-fluorophenyl)sulfonyl)-7-(perfluoropropan-2-yl)-3-(((2-(trimethylsilyl)ethoxy)carbonyl)amino)-1,2,3,3a,4,9b-hexahydro-5H-cyclopenta[c]quinoline-5-carboxylate. This material was dissolved in DCM (8 mL) and treated with TFA (5 mL). The mixture was stirred at rt for 2 h, then was concentrated. The residue was dissolved in EtOAc, washed with brine, dried and concentrated to provide (3R,3aS,9bS)-9b-((4-fluorophenyl)sulfonyl)-7-(perfluoropropan-2-yl)-2,3,3a,4,5,9b-hexahydro-1H-cyclopenta[c]quinolin-3-amine bis-trifluoroacetate (1.0 g, 87% yield), used without further purification. LCMS m/z 515.0 (M+1)$^+$; HPLC $t_R$ 0.85 min (Method A).

Step B: N-((3R,3aS,9bS)-9b-((4-fluorophenyl)sulfonyl)-7-(perfluoropropan-2-yl)-2,3,3a,4,5,9b-hexahydro-1H-cyclopenta[c]quinolin-3-yl)-2-(pyridin-4-yl)acetamide

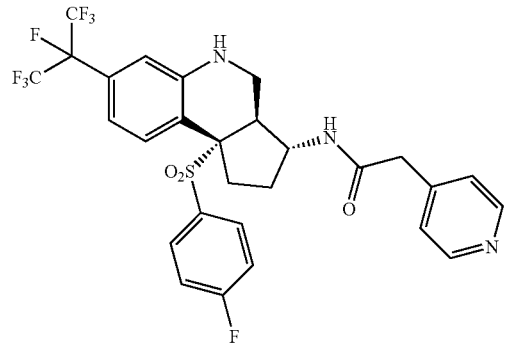 [SMILES: O=C(Cc1ccncc1)N[C@@H]1CC[C@@]2(S(=O)(=O)c3ccc(F)cc3)c3ccc(C(F)(C(F)(F)F)C(F)(F)F)cc3NC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[c]quinolin-3-amine bis-trifluoroacetate (50 mg, 0.097 mmol) was dissolved in DMF (970 μL) and treated with 2-(pyridin-4-yl)acetic acid (53 mg, 0.39 mmol), DIEA (100 μL, 0.58 mmol), and HATU (55 mg, 0.15 mmol). The mixture was stirred at room temperature for 30 min, then was purified by preparative HPLC (Method E, gradient 45-90% B, 20 min) to provide N-((3R,3aS,9bS)-9b-((4-fluorophenyl)sulfonyl)-7-(perfluoropropan-2-yl)-2,3,3a,4,5,9b-hexahydro-1H-cyclopenta[c]quinolin-3-yl)-2-(pyridin-4-yl)acetamide (11 mg, 17% yield). LCMS m/z 634.1 (M+1)$^+$; HPLC $t_R$ 0.84 min (Method B). $^1$H NMR (500 MHz, DMSO-d$_6$) δ 8.54-8.47 (m, 2H), 8.44 (br d, J=8.2 Hz, 1H), 7.62-7.52 (m, 2H), 7.39 (br t, J=8.5 Hz, 2H), 7.34-7.25 (m, 3H), 6.82-6.68 (m, 2H), 6.50 (s, 1H), 3.86 (br t, J=8.9 Hz, 1H), 3.49 (br s, 1H), 3.11 (br dd, J=12.2, 4.0 Hz, 1H), 3.02-2.86 (m, 1H), 2.82-2.67 (m, 1H), 2.60 (br s, 1H), 2.56 (s, 1H), 2.38-2.18 (m, 1H), 1.85 (br dd, J=12.5, 7.3 Hz, 1H), 1.56-1.45 (m, 1H).

The Examples in Table 14 were prepared using procedures used to prepare Example 219 or similar procedures.

TABLE 14

| Ex. number | Structure | LCMS m/z observed | HPLC $t_R$ (min) | HPLC method |
|---|---|---|---|---|
| 220 | 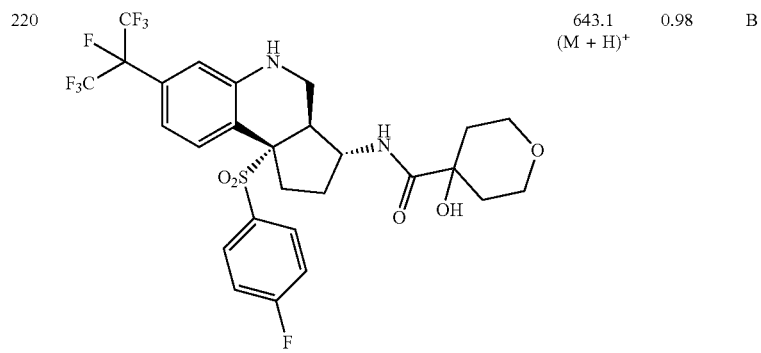 | 643.1 (M + H)$^+$ | 0.98 | B |

| Ex. number | Structure | LCMS m/z observed | HPLC $t_R$ (min) | HPLC method |
|---|---|---|---|---|
| 221 | 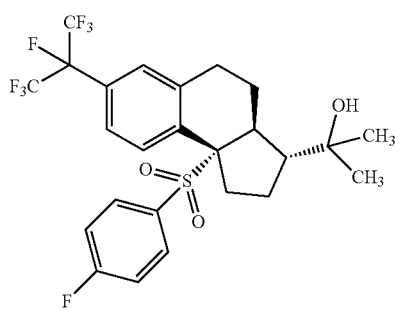 | 615.3 (M + H)$^+$ | 1.01 | B |

Example 222

2-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)propan-2-ol A mixture of (3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxylic acid (Intermediate 14; 20 mg, 0.037 mmol), BOP (19.6 mg, 0.044 mmol), and DCM (1 mL) was treated with DIEA (19 µL, 0.111 mmol). The solution obtained was stirred at rt for 1.5 h. The mixture was filtered through a pad of silica gel, the solids were rinsed with EtOAc and the combined filtrate were concentrated. The residue was dissolved in THF (2 mL) and cooled on an ice-water bath. The solution was treated dropwise with methylmagnesium bromide (3 M in diethyl ether; 31 µL, 0.092 mmol) and the mixture was stirred at rt for 3 days. The mixture was treated with saturated aqueous NH$_4$Cl (1 mL) and extracted with EtOAc (2×1 mL). The combined organic phases were dried and concentrated. The residue was purified by preparative HPLC (Method E, gradient 46-90% B, 20 min) to provide 2-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)propan-2-ol (4.1 mg, 20% yield). LCMS m/z 579.1 (M+H)$^+$; HPLC $t_R$ 2.46 min (Method C). $^1$H NMR (500 MHz, DMSO-d$_6$) δ 7.52-7.41 (m, 2H), 7.36-7.16 (m, 5H), 3.03-2.80 (m, 2H), 2.67-2.56 (m, 1H), 2.35-2.24 (m, 1H), 2.19-2.06 (m, 1H), 2.04-1.93 (m, 1H), 1.90-1.78 (m, 2H), 1.68-1.59 (m, 1H), 1.31-1.21 (m, 2H), 1.19-1.12 (m, 6H).

Examples 223 and 224

N-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)methyl)-2-hydroxy-2-methylpropanamide and N-(((3R,3aS,9bS)-9b-((4-aminophenyl)sulfonyl)-7-(perfluoropropan-2-yl)-2,3,3a,4,5,9b-hexahydro-1H-cyclopenta[a]naphthalen-3-yl)methyl)-2-hydroxy-2-methylpropanamide trifluoroacetate Example 223

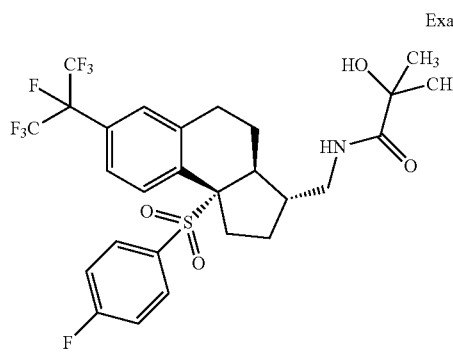

Example 224

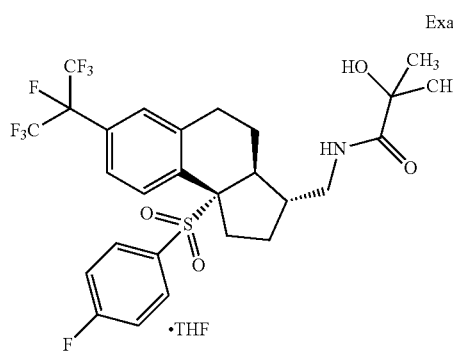

197

Step A: ((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)methanol

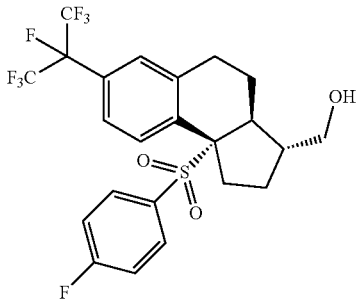 [SMILES: O=S(=O)(c1ccc(F)cc1)[C@@]12CC[C@@H](CO)[C@@H]1CCc1cc(C(F)(C(F)(F)F)C(F)(F)F)ccc12]

A mixture of (3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxylic acid hydrochloride (Intermediate 14 hydrochloride; 100 mg, 0.184 mmol) in DCM (2 mL) was treated with BOP (98 mg, 0.221 mmol) and DIEA (129 μL, 0.737 mmol) at rt. The solution obtained was stirred for 3 h. NaBH$_4$ (14.0 mg, 0.369 mmol) was added, followed by ethanol (1 mL). The mixture was stirred at rt for 3 days, then was treated with saturated aqueous NH$_4$Cl (6 mL). The mixture was extracted with EtOAc (3×2 mL) and the combined organic phases were dried and concentrated. The residue was subjected to column chromatography on silica gel to provide ((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)methanol (80 mg, 82% yield). LCMS m/z 570.1 (M+H+MeCN)$^+$; HPLC t$_R$ 1.35 min (Method D).

Step B: N-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)methyl)-2-hydroxy-2-methylpropanamide and N-(((3R,3aS,9bS)-9b-((4-aminophenyl)sulfonyl)-7-(perfluoropropan-2-yl)-2,3,3a,4,5,9b-hexahydro-1H-cyclopenta[a]naphthalen-3-yl)methyl)-2-hydroxy-2-methylpropanamide trifluoroacetate

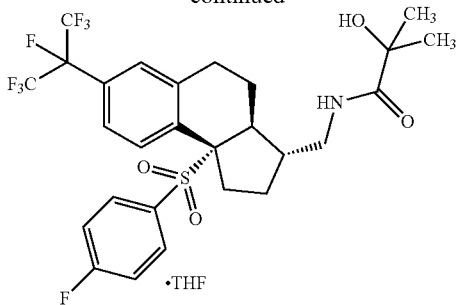

A solution of ((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)methanol (80 mg, 0.151 mmol) in DCM (4 mL) was stirred on an ice-water bath and treated with methanesulfonyl chloride (23 μL, 0.303 mmol). DIEA (106 μL, 0.606 mmol) was then added dropwise and the mixture was stirred at 0° C. After 2 h the mixture was treated with aqueous ammonia. The mixture was extracted with EtOAc, and the combined organic phases were dried and concentrated. The residue was dissolved in DMF (0.5 mL) and treated with sodium azide (49.2 mg, 0.757 mmol). The mixture was stirred at rt for several days, then was diluted with water and extracted with EtOAc. The organic phase was dried and concentrated, and the residue was subjected to column chromatography on silica gel. The isolated azide intermediate (40 mg) was dissolved in MeOH (2 mL). Palladium on carbon (20 mg, 0.019 mmol) and 1 M aqueous HCl (72 μL, 0.072 mmol) were added, and the mixture was stirred at rt under a hydrogen atmosphere (balloon pressure) for 4 h. The mixture was filtered and the filtrate was concentrated. The residue was dissolved in DCM (1 mL) and treated with DIEA (101 μL, 0.578 mmol), 2-hydroxy-2-methylpropanoic acid (15.0 mg, 0.145 mmol), and BOP (63.9 mg, 0.145 mmol). The mixture was stirred at rt for 4 h, concentrated, and the residue was subjected preparative HPLC (Method F, gradient 42-82% B, 25 min) to provide N-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)methyl)-2-hydroxy-2-methylpropanamide (Example 223; 6 mg, 11% yield). LCMS m/z 614.4 (M+H)$^+$; HPLC t$_R$ 2.30 min (Method C). $^1$H NMR (500 MHz, DMSO-d$_6$) δ 7.92-7.87 (m, 1H), 7.52-7.44 (m, 2H), 7.30-7.23 (m, 3H), 7.23-7.16 (m, 2H), 5.39-5.35 (m, 1H), 3.36-3.28 (m, 1H), 3.27-3.20 (m, 1H), 3.07-3.00 (m, 1H), 2.79-2.73 (m, 1H), 2.59-2.51 (m, 1H), 2.20-2.06 (m, 2H), 2.02-1.94 (m, 1H), 1.80-1.65 (m, 3H), 1.29-1.23 (m, 6H), 1.17-1.04 (m, 1H).

Also isolated was N-(((3R,3aS,9bS)-9b-((4-aminophenyl)sulfonyl)-7-(perfluoropropan-2-yl)-2,3,3a,4,5,9b-hexahydro-1H-cyclopenta[a]naphthalen-3-yl)methyl)-2-hydroxy-2-methylpropanamide trifluoroacetate (Example 224; 18.8 mg, 35% yield). LCMS m/z 611.4 (M+H)$^+$; HPLC t$_R$ 2.01 min (Method C). $^1$H NMR (500 MHz, DMSO-d$_6$) δ 7.85-7.80 (m, 1H), 7.52-7.48 (m, 1H), 7.47-7.43 (m, 1H), 7.23-7.19 (m, 1H), 6.38-6.31 (m, 2H), 6.13-6.07 (m, 2H), 5.46-5.43 (m, 1H), 3.33-3.25 (m, 1H), 3.24-3.18 (m, 1H), 3.02-2.93 (m, 1H), 2.65-2.56 (m, 1H), 2.49-2.42 (m, 1H), 2.11-2.00 (m, 2H), 1.96-1.87 (m, 1H), 1.75-1.61 (m, 3H), 1.28-1.22 (m, 6H), 1.09-0.97 (m, 1H).

Examples 225 and 226

1-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethan-1-amine (two single diastereomers)

Example 225

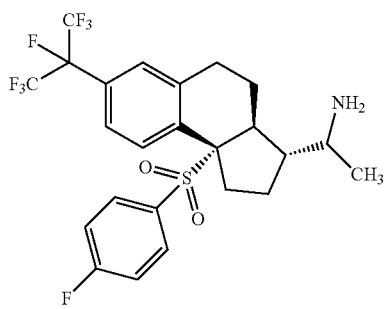

Homochiral from peak 1

Example 226

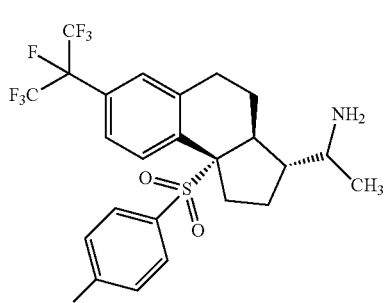

Homochiral from peak 2

Step A: (3R,3aS,9bS)-9b-((4-fluorophenyl)sulfonyl)-N-methoxy-N-methyl-7-(perfluoropropan-2-yl)-2,3,3a,4,5,9b-hexahydro-1H-cyclopenta[a]naphthalene-3-carboxamide

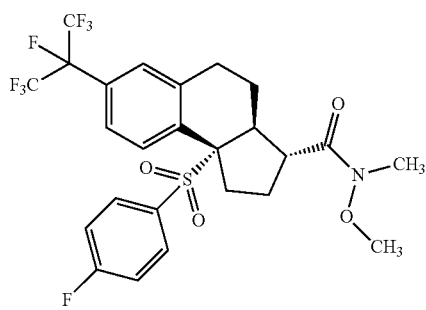 [SMILES: CON(C)C(=O)[C@@H]1CC[C@@]2(S(=O)(=O)c3ccc(F)cc3)c3ccc(C(F)(C(F)(F)F)C(F)(F)F)cc3CC[C@@H]12]

A mixture of (3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxylic acid (Intermediate 14, 300 mg, 0.553 mmol), N,O-dimethylhydroxylamine hydrochloride (64.7 mg, 0.664 mmol), DIEA (386 μL, 2.21 mmol), and DCM (5 mL) was treated with BOP (294 mg, 0.664 mmol). The solution obtained was stirred at rt for 1.5 h. Saturated aqueous NaHCO₃ (5 mL) was added, and the aqueous layer was separated and extracted with EtOAc (3×3 mL). The combined organic phases were dried and concentrated, and the residue was subjected to column chromatography on silica gel (12 g), eluting with EtOAc-hexanes (gradient from 0-100%) to provide (3R,3aS,9bS)-9b-((4-fluorophenyl)sulfonyl)-N-methoxy-N-methyl-7-(perfluoropropan-2-yl)-2,3,3a,4,5,9b-hexahydro-1H-cyclopenta[a]naphthalene-3-carboxamide (255 mg, 79% yield). LCMS m/z 586.3 (M+H)⁺; HPLC $t_R$ 1.42 min (Method D).

Step B: 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethan-1-one

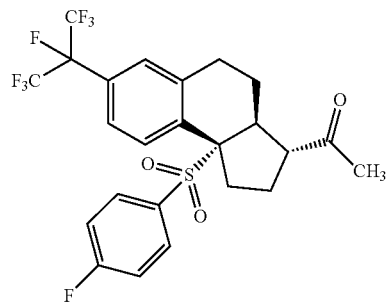

A solution of (3R,3aS,9bS)-9b-((4-fluorophenyl)sulfonyl)-N-methoxy-N-methyl-7-(perfluoropropan-2-yl)-2,3,3a,4,5,9b-hexahydro-1H-cyclopenta[a]naphthalene-3-carboxamide (255 mg, 0.436 mmol) in THF (5 mL) was cooled on an ice-water bath and treated dropwise with methylmagnesium bromide (3 M in diethyl ether; 726 μL, 2.18 mmol). The mixture was stirred at rt for 1 h, then was cooled again to 0° C. and treated with saturated aqueous NH₄Cl (3 mL). The mixture was extracted with EtOAc (3×4 mL) and the combined organic phases were dried and concentrated. The residue was subjected to column chromatography on silica gel (4 g), eluting with EtOAc-hexanes (gradient from 0-100%), to provide 1-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethan-1-one (220 mg, 93% yield). LCMS m/z 541.2 (M+H)⁺; HPLC $t_R$ 1.44 min (Method D). ¹H NMR (400 MHz, CDCl₃) δ 7.63-7.50 (m, 1H), 7.50-7.42 (m, 1H), 7.23-7.12 (m, 3H), 6.99-6.88 (m, 2H), 3.53-3.33 (m, 2H), 2.78-2.65 (m, 1H), 2.51-2.36 (m, 2H), 2.32-2.20 (m, 5H), 2.19-2.08 (m, 1H), 1.81-1.67 (m, 1H), 1.20-1.06 (m, 1H).

Step C: 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethan-1-amine (two single diastereomers)

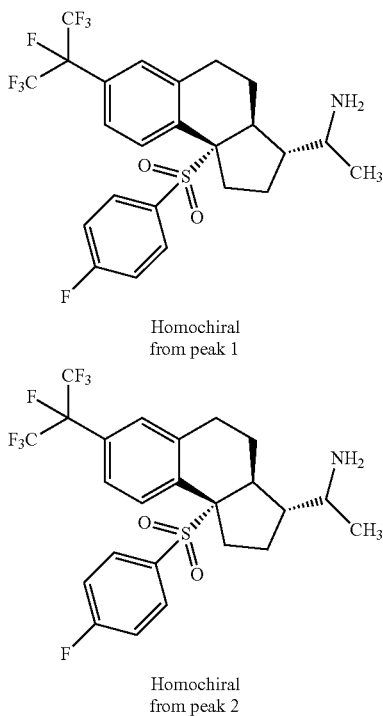

Homochiral
from peak 1

Homochiral
from peak 2

A mixture of 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethan-1-one (200 mg, 0.370 mmol), ammonium acetate (285 mg, 3.70 mmol), methanol (5 mL), and DCM (1.5 mL) was sonicated, then cooled on an ice-water bath. Sodium cyanoborohydride (93 mg, 1.48 mmol) was added, and the mixture was stirred at 0° C. for 1 h, then overnight at rt. The mixture was concentrated and the residue was mixed with EtOAc (2 mL) and water (3 mL), then treated with $K_2CO_3$ to make the pH basic. The aqueous layer was separated and extracted with EtOAc (3×1 mL). The combined organic phases were dried and concentrated. The residue was separated by preparative chiral SFC on a Lux Cellulose-4 column (30×250 mm, 5 m) at 50° C.; eluting with $CO_2$-MeOH (80:20) with 0.1% aqueous $NH_4OH$ at 160 mL/min and 100 bars. Peak 1 eluted with $t_R$ 2.85 min, and peak 2 eluted with $t_R$ 3.55 min.

Peak 1 (Example 225, 74 mg): LCMS m/z 520.0 (M+H)$^+$; HPLC $t_R$ 1.87 min (Method C). $^1$H NMR (500 MHz, DMSO-$d_6$) δ 7.55-7.45 (m, 2H), 7.33-7.27 (m, 2H), 7.26 (s, 1H), 7.18 (br t, J=8.5 Hz, 2H), 3.13-3.03 (m, 1H), 3.03-2.95 (m, 1H), 2.94-2.85 (m, 1H), 2.60-2.54 (m, 1H), 2.33-2.22 (m, 1H), 2.21-2.10 (m, 1H), 1.96-1.90 (m, 1H), 1.82-1.69 (m, 3H), 1.21-1.11 (m, 1H), 1.08 (d, J=6.3 Hz, 3H).

Peak 2 (Example 226, 110 mg): LCMS m/z 520.0 (M+H)$^+$; HPLC $t_R$ 1.89 min (Method C). $^1$H NMR (500 MHz, DMSO-$d_6$) δ 7.58-7.42 (m, 2H), 7.33-7.20 (m, 3H), 7.19-7.08 (m, 2H), 3.26-3.15 (m, 1H), 3.14-3.05 (m, 1H), 2.86-2.72 (m, 1H), 2.58-2.53 (m, 1H), 2.26-2.06 (m, 2H), 1.94-1.80 (m, 4H), 1.27-1.19 (m, 3H), 1.18-1.09 (m, 1H).

The absolute configurations of the 1-aminoethyl substituents were not determined.

Examples 227 and 228

(4R)-4-fluoro-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(2-hydroxy-2-methylpropyl)-5-oxopyrrolidine-2-carboxamide (2 single diastereomers)

Example 227

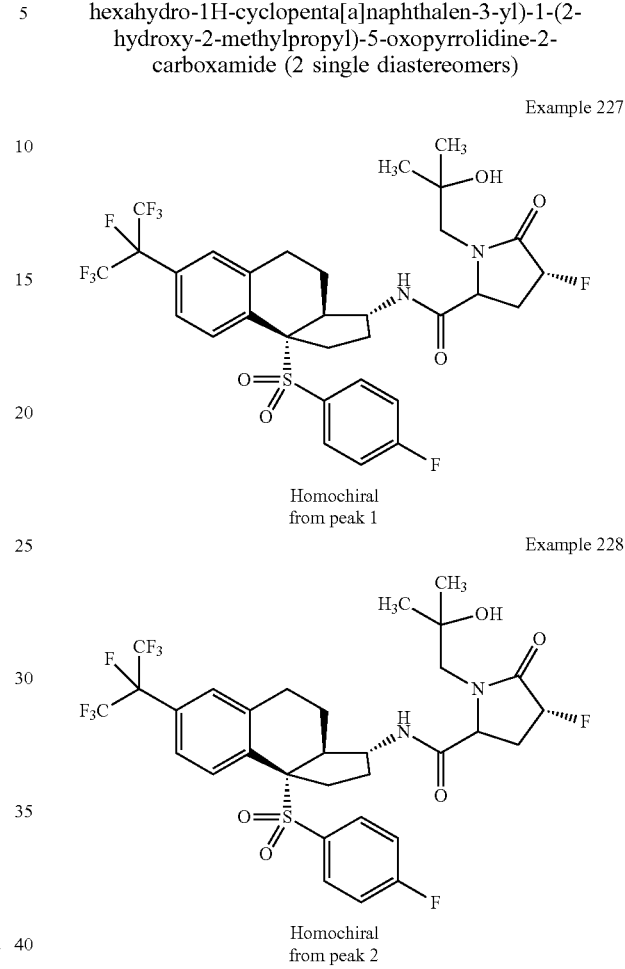

Homochiral
from peak 1

Example 228

Homochiral
from peak 2

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 50 mg, 0.097 mmol), (2S,4R)-4-fluoro-5-oxopyrrolidine-2-carboxylic acid (Intermediate 20; 15.8 mg, 0.107 mmol), HATU (40.7 mg, 0.107 mmol) and DIEA (51 μL, 0.292 mmol) in DMF (1.5 mL) was stirred at rt for 1 h. The mixture was diluted with EtOAc, submitted to standard aqueous washes, dried and concentrated. The residue was treated with 2,2-dimethyloxirane (35.1 mg, 0.487 mmol), $K_2CO_3$ (26.9 mg, 0.195 mmol) and tert-butanol (1 mL) and the mixture was stirred in a sealed vial at 110° C. for 2 h. After cooling to rt, the mixture was purified by preparative HPLC (Method E, gradient 39-79% B, 20 min) to provide two separated diastereomers of (4R)-4-fluoro-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(2-hydroxy-2-methylpropyl)-5-oxopyrrolidine-2-carboxamide.

Peak 1 (Example 227, 1.6 mg, 2.3% yield): LCMS m/z 715.2 (M+H)$^+$; HPLC $t_R$ 2.16 min (Method C). $^1$H NMR (500 MHz, DMSO-$d_6$) δ 8.53-8.43 (m, 1H), 7.53-7.42 (m, 2H), 7.36 (s, 1H), 7.28 (br d, J=6.7 Hz, 4H), 5.32-5.13 (m, 1H), 4.57-4.49 (m, 1H), 4.04-3.94 (m, 1H), 3.60 (br d, J=13.7 Hz, 1H), 3.09-3.00 (m, 1H), 2.93-2.75 (m, 2H), 2.72-2.63 (m, 2H), 2.56 (s, 1H), 2.33-2.24 (m, 1H), 2.08-

1.97 (m, 3H), 1.95-1.87 (m, 1H), 1.81 (s, 1H), 1.26 (br d, J=11.9 Hz, 1H), 1.12 (s, 3H), 1.02 (s, 3H).

Peak 2 (Example 228, 6.5 mg, 9.3% yield): LCMS m/z 715.2 (M+H)+; HPLC $t_R$ 2.14 min (Method C). $^1$H NMR (500 MHz, DMSO-$d_6$) δ 8.70-8.60 (m, 1H), 7.52-7.34 (m, 3H), 7.26 (d, J=6.7 Hz, 4H), 5.35-5.13 (m, 1H), 4.67-4.56 (m, 1H), 3.99-3.91 (m, 1H), 3.08-2.95 (m, 1H), 2.92-2.81 (m, 1H), 2.75-2.54 (m, 4H), 2.42-2.20 (m, 3H), 2.14-2.00 (m, 2H), 1.96 (br s, 1H), 1.88 (s, 1H), 1.33-1.22 (m, 1H), 1.14 (s, 3H), 1.09 (s, 3H).

The absolute configurations at the 2-position of the pyrrolidinone ring were not determined.

Example 229

N-((3R,3aS,9bS)-9b-((4-fluorophenyl)sulfonyl)-7-(perfluoropropan-2-yl)-2,3,3a,4,59b-hexahydro-1H-cyclopenta[a]naphthalen-3-yl)-2-(2-hydroxy-2-methylpropyl)-3-oxopyrazolidin-1-carboxamide

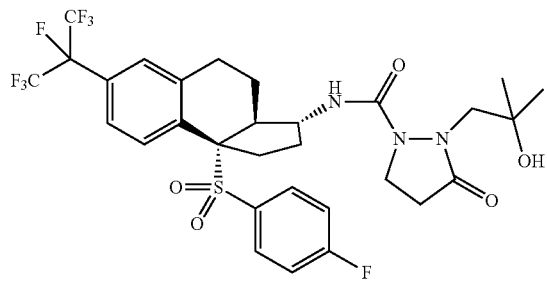 [SMILES: CC(C)(O)CN1C(=O)CCN1C(=O)N[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 100 mg, 0.195 mmol) in DCM (5 mL) was cooled in a dry ice-acetone bath and treated dropwise with phosgene (38.5 mg, 0.390 mmol), then with DIEA (136 μL, 0.779 mmol). The mixture was stirred at −78° C. for 20 min, then was warmed to rt and concentrated. The residue was dissolved in DCM (5 mL) and treated with DIEA (136 μL, 0.779 mmol) and pyrazolidin-3-one hydrochloride (23.9 mg, 0.195 mmol). The mixture was stirred at rt for 2 h, then was washed sequentially with 0.5 M aqueous HCl, water and brine, dried and concentrated. The residue was mixed with 2,2-dimethyloxirane (111 μL, 1.28 mmol) and K$_2$CO$_3$ (35.4 mg, 0.256 mmol) in tert-BuOH (1 mL) and heated in a sealed vial at 110° C. for 4 h. The mixture was cooled to rt and purified by preparative HPLC (Method E, gradient 45-90% B, 20 min) to provide N-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-(2-hydroxy-2-methylpropyl)-3-oxopyrazolidin-1-carboxamide (3.6 mg, 2.6% yield). LCMS m/z 698.3 (M+H)+; HPLC $t_R$ 2.23 min (Method D). $^1$H NMR (500 MHz, DMSO-$d_6$) δ 7.95 (s, 1H), 7.61-7.47 (m, 2H), 7.36-7.20 (m, 5H), 6.59 (br d, J=8.2 Hz, 1H), 4.01-3.89 (m, 2H), 3.76 (br t, J=9.9 Hz, 1H), 3.04-2.95 (m, 1H), 2.93-2.85 (m, 3H), 2.74 (s, 1H), 2.66 (br d, J=14.6 Hz, 1H), 2.56 (s, 1H), 2.32-2.22 (m, 1H), 2.04-1.90 (m, 3H), 1.82 (br d, J=8.2 Hz, 1H), 1.33-1.23 (m, 1H), 1.17 (s, 6H).

Examples 230 and 231

1-(acetyl-d$_3$)-3-(2-(((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-oxoethyl)azetidin-3-yl acetate-d$_3$ and 2-(1-(acetyl-d$_3$)-3-hydroxyazetidin-3-yl)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)acetamide Example 230

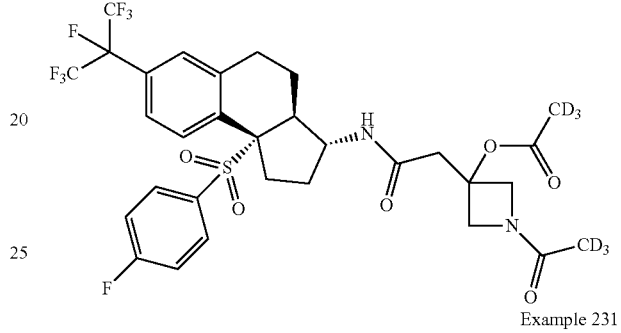

Example 231

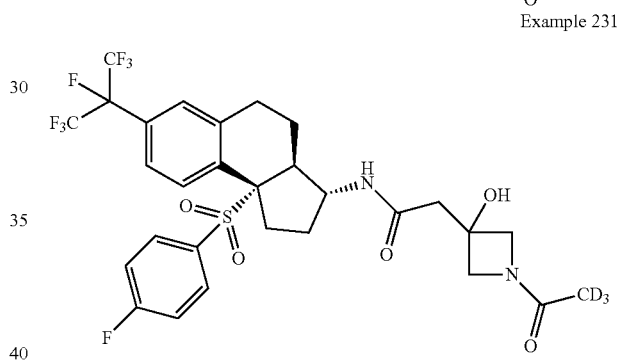

Part A: N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-(3-hydroxyazetidin-3-yl)acetamide hydrochloride

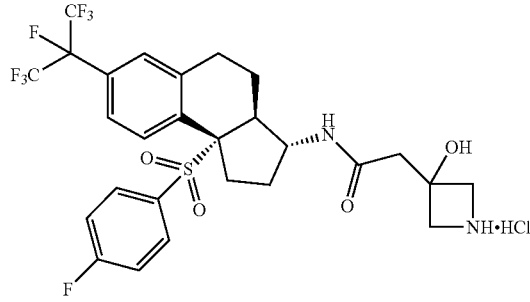

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 40 mg, 0.078 mmol) in DMF (1 mL) was treated with 2-(1-(tert-butoxycarbonyl)-3-hydroxyazetidin-3-yl)acetic acid (23.4 mg, 0.101 mmol), DIEA (109 μL, 0.623 mmol) and HATU (38.5 mg, 0.101 mmol). The mixture was stirred at rt for 3 h, then was partitioned between EtOAc and water. The organic phase was washed with saturated aqueous Na$_2$CO$_3$, 10% aqueous LiCl and brine, then was dried and concentrated to give crude tert-butyl 3-(2-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-oxoethyl)-3-hydroxyazetidine-1-carboxylate. LCMS m/z 727.2 (M+H)$^+$; HPLC t$_R$ 1.09 min (Method A). The residue was dissolved in DCM (5 mL) and treated with HCl (4 M in 1,4-dioxane; 1.2 mL, 4.67 mmol). The mixture was stirred at rt overnight, then was concentrated to provide crude N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-(3-hydroxyazetidin-3-yl)acetamide hydrochloride, which was used without further purification. LCMS m/z 627.1 (M+H)$^+$; HPLC t$_R$ 0.80 min (Method A).

Part B: 1-(acetyl-d$_3$)-3-(2-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-oxoethyl)azetidin-3-yl acetate-d$_3$ and 2-(1-(acetyl-d$_3$)-3-hydroxyazetidin-3-yl)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)acetamide

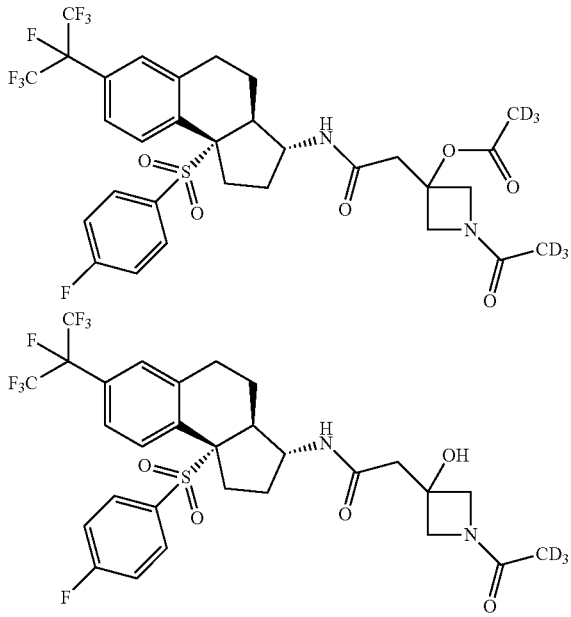

A solution of crude N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-(3-hydroxyazetidin-3-yl)acetamide hydrochloride (24.4 mg, 0.039 mmol) in DMF (1 mL) was treated with DIEA (102 μL, 0.585 mmol) and acetic anhydride-d$_6$ (25.3 mg, 0.234 mmol). The reaction was stirred at rt. After 1 h, additional acetic anhydride-d$_6$ (25.3 mg, 0.234 mmol) and DIEA (102 μL, 0.585 mmol) were added. After 3 h, the mixture was purified by preparative HPLC (Method E, gradient 30-80% B, 19 min) to provide 1-(acetyl-d$_3$)-3-(2-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-oxoethyl)azetidin-3-yl acetate-d$_3$ (Example 230; 2.6 mg, 9% yield). LCMS m/z 717.4 (M+H)$^+$; HPLC t$_R$ 2.12 min (Method C). $^1$H NMR (500 MHz, DMSO-d$_6$) δ 8.36 (br t, J=7.8 Hz, 1H), 7.51-7.41 (m, 2H), 7.35 (br s, 1H), 7.28 (br s, 4H), 4.41 (br t, J=8.7 Hz, 1H), 4.25 (br d, J=10.1 Hz, 1H), 4.14 (br dd, J=10.7, 4.0 Hz, 1H), 3.97-3.86 (m, 2H), 3.00 (br dd, J=7.3, 3.7 Hz, 1H), 2.93-2.84 (m, 2H), 2.83-2.74 (m, 1H), 2.65 (br d, J=14.3 Hz, 1H), 2.28-2.16 (m, 1H), 2.09-1.89 (m, 3H), 1.85-1.77 (m, 1H), 1.28-1.21 (m, 1H).

Also isolated was 2-(1-(acetyl-d$_3$)-3-hydroxyazetidin-3-yl)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)acetamide (Example 231; 1.7 mg, 5% yield). LCMS m/z 672.2 (M+H)$^+$; HPLC t$_R$ 2.14 min (Method C). $^1$H NMR (500 MHz, DMSO-d$_6$) δ 8.09 (br s, 1H), 7.48 (br s, 2H), 7.39-7.28 (m, 3H), 7.28-7.21 (m, 2H), 4.28-4.20 (m, 1H), 4.02-3.89 (m, 3H), 3.67 (br d, J=7.4 Hz, 1H), 3.09-2.99 (m, 1H), 2.89-2.79 (m, 1H), 2.74-2.63 (m, 1H), 2.55 (s, 2H), 2.24 (ddd, J=14.4, 10.7, 6.9 Hz, 1H), 2.15-1.92 (m, 3H), 1.90-1.78 (m, 1H), 1.37-1.25 (m, 1H).

Example 232

1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(2-hydroxyethyl-2,2-d$_2$)urea

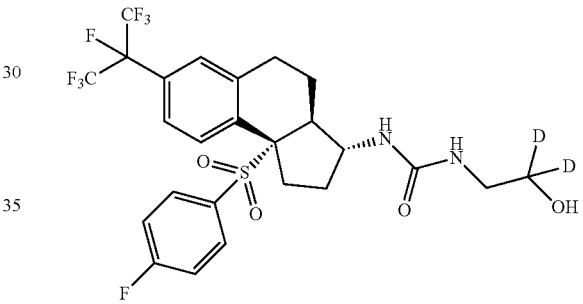

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 100 mg, 0.195 mmol) in DCM (3 mL) was stirred on an ice-water bath and treated with phosgene (123 μL, 0.234 mmol), then with TEA (109 μL, 0.779 mmol). The mixture was stirred 0° C. for 0.5 h, then was warmed to rt for 0.5 h. The mixture was concentrated and the residue was dissolved in DCM (4 mL) and treated with methyl glycinate (17.4 mg, 0.195 mmol) and TEA (109 μL, 0.779 mmol), and stirred at rt for 16 h. The mixture was diluted with water and saturated aqueous NaHCO$_3$ and extracted with EtOAc. The organic layer was dried and concentrated to give methyl (((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)glycinate, which was used without further purification. LCMS m/z 629.1 (M+H)$^+$; HPLC t$_R$ 1.05 min (Method A).

This material was dissolved in THF (4 mL) and MeOH (1 mL) and treated with sodium borodeuteride (51.6 mg, 1.363 mmol). After 16 h at rt, the mixture was diluted with water and saturated aqueous NaHCO$_3$ and extracted with EtOAc. The organic layer was dried and concentrated, and the residue was purified by preparative HPLC (Method F, gradient 50-72% B, 25 min) to provide 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(2-hydroxyethyl-2,2-d$_2$)urea (5.6 mg, 4.8% yield). LCMS m/z 603.1 (M+H)$^+$; HPLC t$_R$ 1.01 min (Method A). $^1$H NMR (500 MHz, DMSO-$d_6$) δ 7.48-7.42 (m, 2H), 7.32-7.19 (m, 5H), 6.27-6.21 (m, 1H), 3.83 (br s, 1H), 3.64-3.55 (m, 2H), 3.12-3.05 (m, 2H), 3.03-2.96 (m, 1H), 2.71-2.60 (m, 2H), 2.21-2.12 (m, 1H), 2.07-2.01 (m, 2H), 2.01-1.92 (m, 1H), 1.77-1.68 (m, 1H), 1.31-1.22 (m, 2H).

Example 233

N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-hydroxy-2-(4-hydroxytetrahydro-2H-pyran-4-yl)acetamide (mixture of diastereomers)

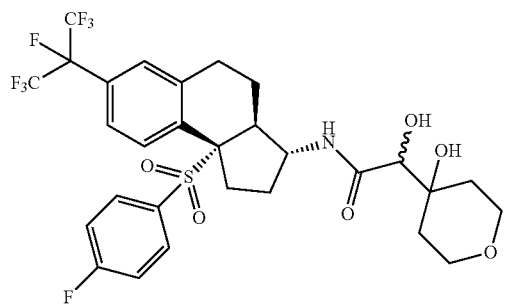 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)C(O)C1(O)CCOCC1]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 80 mg, 0.156 mmol) and 2-(tetrahydro-4H-pyran-4-ylidene)acetic acid (28.8 mg, 0.203 mmol) in DMF (2 mL) was treated with HATU (77 mg, 0.203 mmol) and TEA (65 µL, 0.467 mmol) and stirred at rt for 3 h. The mixture was diluted with water and saturated aqueous NaHCO$_3$ and extracted with EtOAc. The organic layer was dried and concentrated to give N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-(tetrahydro-4H-pyran-4-ylidene)acetamide which was used without further purification. LCMS m/z 638.1 (M+H)$^+$; HPLC $t_R$ 1.13 min (Method A).

This material was dissolved in acetone (4 mL) and water (0.4 mL) and treated with OsO$_4$ (2.5% in tert-butanol, 196 µL, 0.016 mmol) and 4-methylmorpholine 4-oxide (27.4 mg, 0.234 mmol). After stirring overnight, the mixture was treated with saturated aqueous Na$_2$S$_2$O$_3$ stirred at rt for 1 h. The mixture was diluted with water and extracted with EtOAc. The organic layer was dried and concentrated, and the residue was purified by preparative HPLC (Method E, gradient 39-79% B, 20 min) to provide a mixture of diastereomers of N-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-hydroxy-2-(4-hydroxytetrahydro-2H-pyran-4-yl)acetamide (20.3 mg, 19% yield). LCMS m/z 673.1 (M+H)$^+$; HPLC $t_R$ 1.05 min (Method A). $^1$H NMR (500 MHz, DMSO-$d_6$) δ 8.05-7.94 (m, 2H), 7.55-7.47 (m, 4H), 7.33-7.18 (m, 11H), 5.92-5.83 (m, 1H), 4.76-4.71 (m, 1H), 4.07-3.98 (m, 2H), 3.85-3.78 (m, 2H), 3.71-3.54 (m, 6H), 3.07-2.95 (m, 2H), 2.91-2.81 (m, 3H), 2.66-2.56 (m, 3H), 2.31-2.22 (m, 2H), 2.08-1.65 (m, 14H), 1.43-1.20 (m, 7H).

The Examples in Table 15 were prepared using procedures used to prepare Example 233 or similar procedures.

TABLE 15

| Ex. number | Structure | LCMS m/z observed | HPLC $t_R$ (min) | HPLC method |
|---|---|---|---|---|
| 234 | (structure; Diastereomeric mixture) | 630.1 (M + H)$^+$ | 1.02 | A |
| 235 | (structure) | 642.2 (M + H)$^+$ | 2.01 | C |

TABLE 15-continued
| Ex. number | Structure | LCMS m/z observed | HPLC $t_R$ (min) | HPLC method |
|---|---|---|---|---|
| 236 | 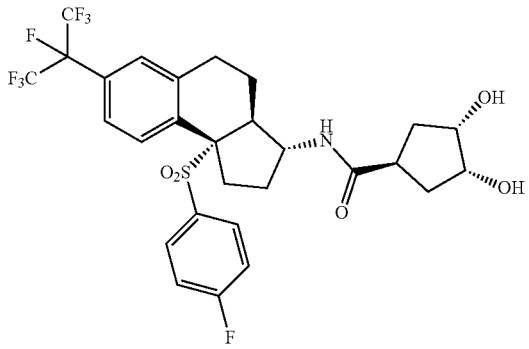 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)[C@@H]1C[C@@H](O)[C@@H](O)C1] | 642.2 (M + H)+ | 2.05 | C |
| 237 | 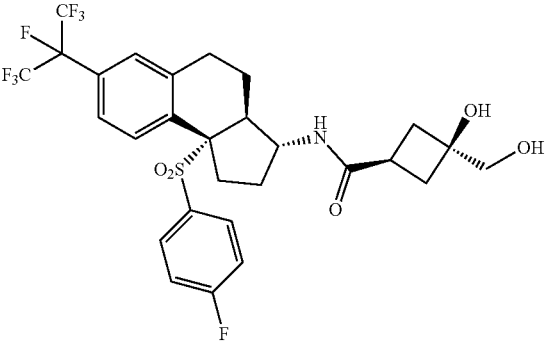 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)[C@H]1C[C@](O)(CO)C1] | 642.2 (M + H)+ | 1.0 | A |
| 238 | 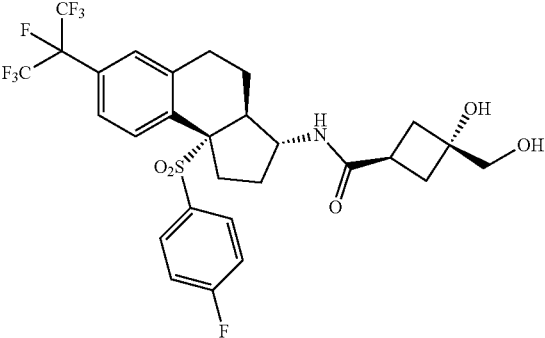 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)[C@H]1C[C@@](O)(CO)C1] | 642.2 (M + H)+ | 1.0 | A |

Example 239

1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(pyridin-4-yl)pyrrolidin-2-one (mixture of two diastereomers)

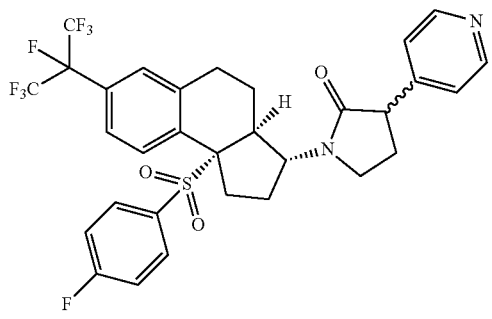

Diastereomeric mixture

Part A: ethyl 2-(pyridin-4-yl)pent-4-enoate (racemic)

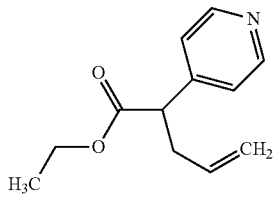

A solution of ethyl 2-(pyridin-4-yl)acetate (460 μL, 3.03 mmol) in THF (10 mL) was cooled on a dry ice-acetone bath and treated with 3-bromoprop-1-ene (290 μL, 3.3 mmol) and lithium bis(trimethylsilyl)amide (1.0 M in THF; 6 mL, 6.00 mmol). The mixture was stirred at −78° C. for 2 h, then was warmed to rt. Celite was added and the mixture was concentrated. The residue was subjected to column chromatography on silica gel, eluting with EtOAc-hexanes, to provide ethyl 2-(pyridin-4-yl)pent-4-enoate (250 mg, 40% yield). LCMS m/z 206.1 (M+1)$^+$; HPLC t$_R$ 0.57 min (Method A). $^1$H NMR (499 MHz, CDCl$_3$) δ 8.58 (d, J=5.1 Hz, 2H), 7.34-7.16 (m, 2H), 5.86-5.63 (m, 1H), 5.14-4.91 (m, 2H), 4.27-4.06 (m, 2H), 3.66-3.56 (m, 1H), 2.88-2.70 (m, 1H), 2.57-2.47 (m, 1H), 1.38-1.17 (m, 3H).

Part B: racemic ethyl 4-oxo-2-(pyridin-4-yl)butanoate

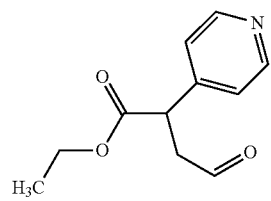

A solution of ethyl 2-(pyridin-4-yl)pent-4-enoate (250 mg, 1.2 mmol) in a mixture of 1,4-dioxane (9 mL) and water (3 mL) was treated with 2,6-lutidine (280 μL, 2.4 mmol), OsO$_4$ (2.5% in water, 770 μL, 0.061 mmol) and sodium periodate (1.0 g, 4.9 mmol). The mixture was stirred at rt overnight, then was diluted with EtOAc and washed 3 times with water. The organic layer was dried and concentrated to provide racemic ethyl 4-oxo-2-(pyridin-4-yl)butanoate, used without further purification. LCMS m/z 208.1 (M+1)$^+$; HPLC t$_R$ 0.43 min (Method A).

Part C: 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(pyridin-4-yl)pyrrolidin-2-one (mixture of 2 diastereomers)

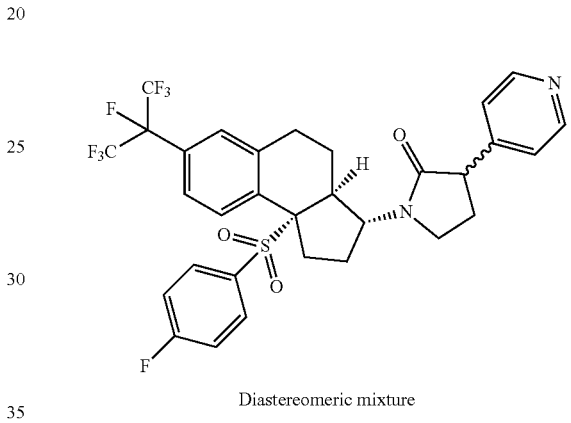

Diastereomeric mixture

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 60 mg, 0.12 mmol) in 1,2-dichloroethane (2.3 mL) was treated with ethyl 4-oxo-2-(pyridin-4-yl)butanoate (48 mg, 0.23 mmol) and sodium triacetoxyborohydride (50 mg, 0.23 mmol). The mixture was stirred at rt for 30 min, then for 2 h at 60° C. The mixture was cooled to rt and purified by preparative HPLC (Method E, gradient 45-90% B, 20 min) to provide a mixture of diastereomers of 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(pyridin-4-yl)pyrrolidin-2-one (3.4 mg, 4% yield). LCMS m/z 659.1 (M+1)$^+$; HPLC t$_R$ 0.92 min (Method A). $^1$H NMR (500 MHz, DMSO-d$_6$) δ 8.84-8.51 (m, 2H), 7.75-7.42 (m, 4H), 7.42-7.17 (m, 5H), 4.47-4.26 (m, 1H), 4.07-3.90 (m, 1H), 3.82-3.39 (m, 1H), 3.26-2.98 (m, 2H), 2.77-2.57 (m, 4H), 2.49-2.21 (m, 2H), 2.14-2.03 (m, 1H), 2.03-1.75 (m, 2H), 1.41-1.16 (m, 2H).

Example 240

3-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)oxazolidin-2-one

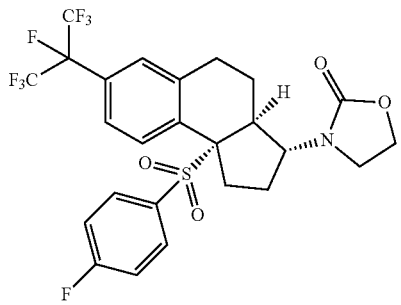 [SMILES: O=C1OCCN1[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 30 mg, 0.058 mmol) in DCM (3 mL) was treated with DIEA (31 μL, 0.175 mmol) and 2-chloroethyl carbonochloridate (8.4 mg, 0.058 mmol) and stirred at rt for 2 h. The mixture was concentrated and the residue was dissolved in DMF (1 mL) and treated with NaH (mineral oil dispersion; 7.0 mg, 0.175 mmol). The mixture was stirred at rt for 1.5 h, treated with water and purified by preparative HPLC (Method E, gradient 40-80% B, 20 min) to provide 3-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)oxazolidin-2-one (12.2 mg, 36% yield). LCMS m/z 584.0 (M+H)$^+$; HPLC $t_R$ 1.05 min (Method A). $^1$H NMR (500 MHz, DMSO-$d_6$) δ 7.59-7.46 (m, 2H), 7.34-7.17 (m, 3H), 6.94-6.81 (m, 1H), 6.49 (br d, J=8.9 Hz, 1H), 4.41-4.31 (m, 2H), 4.13-3.98 (m, 1H), 3.85-3.72 (m, 1H), 3.60 (br d, J=7.9 Hz, 1H), 3.17-3.00 (m, 1H), 2.97 (s, 1H), 2.56 (s, 1H), 2.34-2.03 (m, 3H), 1.88-1.72 (m, 2H), 1.30-1.13 (m, 1H).

Examples 241 and 242

5-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-methylimidazolidine-2,4-dione (two single diastereomers)

Example 241

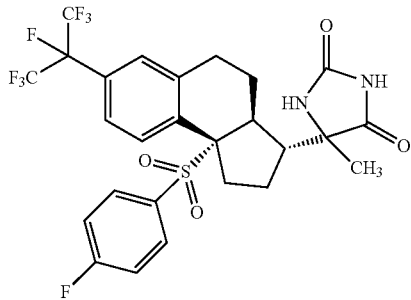

Homochiral
from peak 1

Example 242

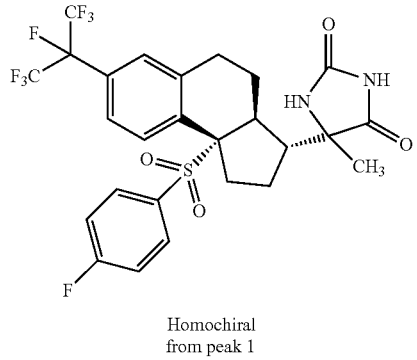

Homochiral
from peak 1

A mixture of (NH$_4$)$_2$CO$_3$ (14.2 mg, 0.148 mmol), sodium cyanide (3.6 mg, 0.074 mmol), 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethan-1-one (Examples 225 and 226, Part B; 20 mg, 0.037 mmol), 95% ethanol (0.6 mL), and water (0.2 mL) was stirred at 85° C. under a nitrogen atmosphere for 1 day. The mixture was cooled, diluted with EtOAc (3 mL), dried and concentrated. The residue was separated by preparative chiral SFC on a Lux Cellulose-4 column (30×250 mm, 5 m) at 50° C., eluting with CO$_2$-MeOH (83:17) at 160 mL/min and 100 bars. Peak 1 eluted with $t_R$ 2.40 min, and peak 2 eluted with $t_R$ 3.30 min.

Peak 1 (Example 241, 12 mg, 52% yield): LCMS m/z 628.1 (M+NH$_4$)$^+$; HPLC $t_R$ 1.27 min (Method D). $^1$H NMR (400 MHz, MeOH-$d_4$) δ 7.62-7.55 (m, 1H), 7.54-7.46 (m, 1H), 7.24 (s, 1H), 7.22-7.13 (m, 2H), 7.11-7.04 (m, 2H), 3.29-3.22 (m, 1H), 2.75 (dt, J=11.5, 7.2 Hz, 1H), 2.46 (dt, J=16.0, 3.6 Hz, 1H), 2.34 (dt, J=11.2, 7.7 Hz, 1H), 2.27-2.10 (m, 2H), 2.10-1.96 (m, 2H), 1.66-1.49 (m, 1H), 1.45 (s, 3H), 1.23-1.08 (m, 1H).

Peak 2 (Example 242, 6 mg, 26% yield): LCMS m/z 628.2 (M+NH$_4$)$^+$; HPLC $t_R$ 1.28 min (Method D). $^1$H NMR (400 MHz, MeOH-$d_4$) δ 7.43 (s, 1H), 7.42-7.37 (m, 1H), 7.32 (dd, J=8.6, 5.1 Hz, 2H), 7.28 (s, 1H), 7.08 (t, J=8.7 Hz, 2H), 3.24-3.12 (m, 1H), 3.05-2.95 (m, 1H), 2.60-2.52 (m, 1H), 2.40-2.31 (m, 1H), 2.28-2.00 (m, 4H), 1.78-1.68 (m, 1H), 1.56-1.51 (m, 3H), 0.93-0.82 (m, 1H).

The absolute configurations at the 5-position of the imidazolidinedione ring were not determined.

Example 243

(R)-3-((3R,3aS,9bS)-9b-((4-fluorophenyl)sulfonyl)-7-(perfluoropropan-2-yl)-2,33a,4,59b-hexahydro-1H-cyclopenta[a]naphthalen-3-yl)-5-(2-hydroxy-2-methylpropyl)imidazolidine-2,4-dione

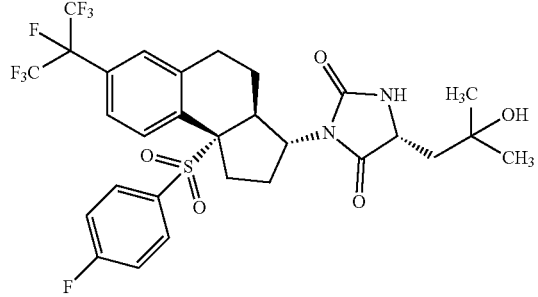 [SMILES: CC(C)(O)C[C@H]1NC(=O)N([C@@H]2CC[C@@]3(S(=O)(=O)c4ccc(F)cc4)c4ccc(C(F)(C(F)(F)F)C(F)(F)F)cc4CC[C@@H]23)C1=O]

Step A: tert-butyl (R)-3-((tert-butoxycarbonyl)amino)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-4-oxobutanoate

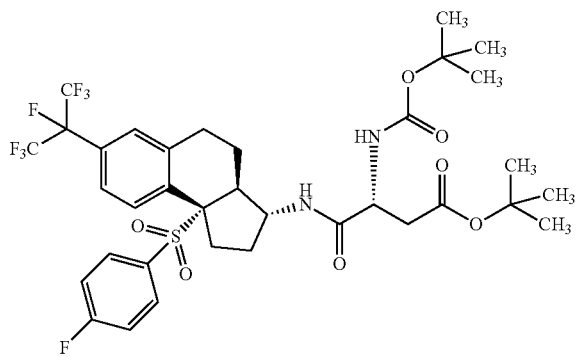 [SMILES: CC(C)(C)OC(=O)C[C@@H](NC(=O)OC(C)(C)C)C(=O)N[C@@H]1CC[C@@]2(S(=O)(=O)c3ccc(F)cc3)c3ccc(C(F)(C(F)(F)F)C(F)(F)F)cc3CC[C@@H]12]

A solution of (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine (Example 114; 200 mg, 0.390 mmol) and (R)-4-(tert-butoxy)-2-((tert-butoxycarbonyl)amino)-4-oxobutanoic acid (113 mg, 0.390 mmol) in DMF (2 mL) was treated with HATU (222 mg, 0.584 mmol) and TEA (217 µL, 1.56 mmol). The mixture was stirred at rt overnight, then was partitioned between EtOAc (40 mL) and water (30 mL). The organic layer was washed sequentially with water (30 mL) and brine (30 mL), dried and concentrated. The residue was subjected to column chromatography on silica gel, eluting with EtOAc-hexanes (gradient from 0-100%) to give tert-butyl (R)-3-((tert-butoxycarbonyl)amino)-4-(((3R,3aS,9bS)-9b-((4-fluorophenyl)-sulfonyl)-7-(perfluoropropan-2-yl)-2,3,3a,4,5,9b-hexahydro-1H-cyclopenta[a]naphthalen-3-yl)amino)-4-oxobutanoate as a white solid (225 mg, 74% yield). LCMS m/z 785.4 (M+H)+; HPLC $t_R$ 1.23 min (Method A). $^1$H NMR (500 MHz, DMSO-$d_6$) δ 7.76 (br d, J=8.2 Hz, 1H), 7.63 (br d, J=8.5 Hz, 1H), 7.55-7.47 (m, 1H), 7.15 (br s, 3H), 6.92 (t, J=8.5 Hz, 2H), 5.71 (br d, J=8.7 Hz, 1H), 4.68-4.47 (m, 1H), 4.39-4.25 (m, 1H), 3.39-3.23 (m, 1H), 2.99 (br d, J=5.1 Hz, 1H), 2.81-2.64 (m, 2H), 2.54-2.45 (m, 1H), 2.43-2.33 (m, 1H), 2.20-2.02 (m, 3H), 1.53-1.46 (m, 18H), 1.35-1.28 (m, 2H).

Step B: methyl 2-((R)-1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2,5-dioxoimidazolidin-4-yl)acetate

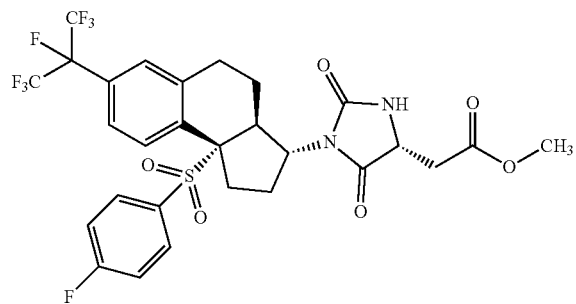 [SMILES: COC(=O)C[C@H]1NC(=O)N([C@@H]2CC[C@@]3(S(=O)(=O)c4ccc(F)cc4)c4ccc(C(F)(C(F)(F)F)C(F)(F)F)cc4CC[C@@H]23)C1=O]

A solution of tert-butyl (R)-3-((tert-butoxycarbonyl)amino)-4-(((3R,3aS,9bS)-9b-((4-fluorophenyl)-sulfonyl)-7-(perfluoropropan-2-yl)-2,3,3a,4,5,9b-hexahydro-1H-cyclopenta[a]naphthalen-3-yl)amino)-4-oxobutanoate (220 mg, 0.280 mmol) in DCM (5 mL) was treated with HCl (4 M in 1,4-dioxane; 170 µL, 5.60 mmol). The mixture was stirred at rt for 4 hr, then was concentrated. The residue was dissolved in MeOH (5 mL) and treated with thionyl chloride (250 µL) and the mixture was stirred at rt overnight. The mixture was concentrated, and the residue was dissolved in DCM (10 mL). The solution was cooled on an ice-water bath and treated with triphosgene (40.6 mg, 0.137 mmol) and pyridine (457 µL, 5.65 mmol). The mixture was allowed to warm to rt over 30 min, stirred 30 min more at rt, then was heated at 50° C. overnight. The mixture was concentrated and the residue was purified by preparative HPLC (Method G, gradient 0-100% B, 10 min) to provide methyl 2-((R)-1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2,5-dioxoimidazolidin-4-yl)acetate as a white solid (60 mg, 26% yield). LCMS m/z 669.2 (M+H)+; HPLC $t_R$ 1.08 min (Method A).

Step C: (R)-3-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-(2-hydroxy-2-methylpropyl)imidazolidine-2,4-dione

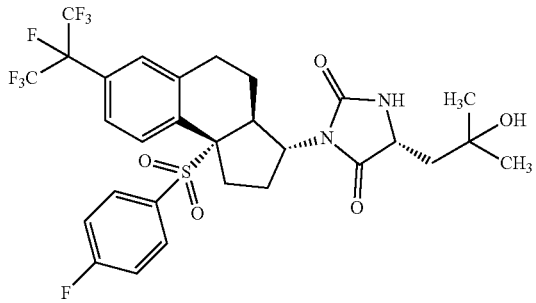 [SMILES: CC(C)(O)C[C@H]1NC(=O)N([C@@H]2CC[C@@]3(S(=O)(=O)c4ccc(F)cc4)c4ccc(C(F)(C(F)(F)F)C(F)(F)F)cc4CC[C@@H]23)C1=O]

A solution of methyl 2-((R)-1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2,5-dioxoimidazolidin-4-yl)acetate (30 mg, 0.045 mmol) in THF (1 mL) was cooled on an ice-water bath and treated with methyllithium (1.0 M in THF; 135 µL, 0.135 mmol). The mixture was stirred at 0° C. for 2 h, then was treated with a few drops of saturated aqueous NH$_4$Cl. The mixture was partitioned between EtOAc (25 mL) and water (20 mL). The organic layer was separated, washed with brine (15 mL), dried and concentrated. The residue was purified by preparative HPLC (Method E, gradient 42-82% B, 20 min) to provide (R)-3-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-(2-hydroxy-2-methylpropyl)imidazolidine-2,4-dione (5.9 mg, 19% yield). LCMS m/z 669.3 (M+H)+; HPLC $t_R$ 2.24 min (Method C). $^1$H NMR (500 MHz, DMSO-$d_6$) δ 7.89 (s, 1H), 7.58-7.42 (m, 5H), 7.38-7.29 (m, 2H), 4.58 (s, 1H), 4.13 (br d, J=8.9 Hz, 1H), 4.00 (br d, J=7.9 Hz, 1H), 3.49-3.40 (m, 1H), 3.02-2.90 (m, 1H), 2.79-2.65 (m, 1H), 2.38-2.23 (m, 2H), 1.97-1.79 (m, 2H), 1.77-1.65 (m, 1H), 1.55 (dd, J=14.2, 9.3 Hz, 1H), 1.34 (br dd, J=13.6, 6.3 Hz, 1H), 1.16 (s, 6H).

Example 244

(3R,3aS,9bS)—N-((1s,3S)-3-acetamidocyclobutyl)-9b-((4-fluorophenyl)sulfonyl)-7-(perfluoropropan-2-yl)-2,3,3a4,5,9b-hexahydro-1H-cyclopenta[a]naphthalene-3-carboxamide

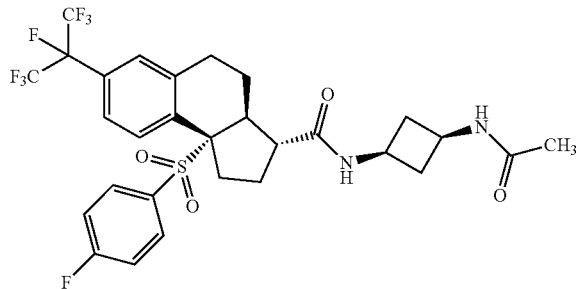 [SMILES: CC(=O)N[C@H]1C[C@@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1]

A solution of (3R,3aS,9bS)—N-((1s,3S)-3-aminocyclobutyl)-9b-((4-fluorophenyl)sulfonyl)-7-(perfluoropropan-2-yl)-2,3,3a,4,5,9b-hexahydro-1H-cyclopenta[a]naphthalene-3-carboxamide (Example 110; 25 mg, 0.041 mmol) in DMF (410 L) was treated with DIEA (29 μL, 0.16 mmol) and acetyl chloride (6 μL, 0.082 mmol). The mixture was stirred at rt for 30 min, then was purified by preparative HPLC (Method E, gradient 45-90% B, 20 min) to provide (3R,3aS,9bS)—N-((1s,3S)-3-acetamidocyclobutyl)-9b-((4-fluorophenyl)sulfonyl)-7-(perfluoropropan-2-yl)-2,3,3a,4,5,9b-hexahydro-1H-cyclopenta[a]naphthalene-3-carboxamide (12 mg, 43% yield). LCMS m/z 653.1 (M+1)$^+$; HPLC $t_R$ 1.00 min (Method A). $^1$H NMR (500 MHz, DMSO-$d_6$) δ 8.11 (br d, J=7.0 Hz, 1H), 8.09 (br d, J=7.6 Hz, 1H), 7.49-7.37 (m, 3H), 7.37-7.20 (m, 4H), 3.84 (br s, 2H), 3.59-3.48 (m, 2H), 3.23-3.09 (m, 2H), 3.02-2.95 (m, 1H), 2.64-2.55 (m, 1H), 2.46-2.38 (m, 1H), 2.32-2.11 (m, 3H), 2.01-1.94 (m, 1H), 1.91-1.83 (m, 2H), 1.82-1.70 (m, 4H).

Example 245

1-(acetyl-d$_3$)-N-((3R,3aS,9bS)-9b-((4-fluorophenyl)sulfonyl)-7-(perfluoropropan-2-)-2,3,3a,4,5,9b-hexahydro-1H-cyclopenta[a]naphthalen-3-yl)-4-hydroxypiperidine-4-carboxamide

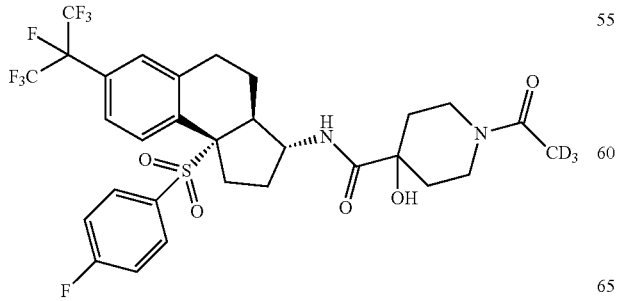

A solution of N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxypiperidine-4-carboxamide (Example 195; 23.4 mg, 0.0365 mmol) in DMF (1 mL) was treated with acetic anhydride-d$_6$ (19.7 mg, 0.183 mmol) and DIEA (960 μL, 0.548 mmol). The mixture was stirred at rt for 2 h, then was purified by preparative HPLC (Method E, gradient 40-80% B, 20 min) to provide 1-(acetyl-d$_3$)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxypiperidine-4-carboxamide (18.8 mg, 74% yield). LCMS m/z 686.2 (M+1)$^+$; HPLC $t_R$ 2.02 min (Method B). $^1$H NMR (500 MHz, DMSO-$d_6$) δ 8.02 (br d, J=5.8 Hz, 1H), 7.62-7.55 (m, 1H), 7.55-7.48 (m, 1H), 7.32 (br s, 3H), 7.28-7.20 (m, 2H), 5.60 (s, 1H), 4.21 (br d, J=11.3 Hz, 1H), 4.05-3.93 (m, 1H), 3.67 (br d, J=12.8 Hz, 1H), 3.52-3.41 (m, 1H), 3.38-3.22 (m, 1H), 3.10-2.96 (m, 1H), 2.94-2.77 (m, 2H), 2.72-2.58 (m, 1H), 2.30 (dt, J=14.5, 7.1 Hz, 1H), 2.05-1.80 (m, 4H), 1.80-1.67 (m, 1H), 1.59-1.41 (m, 2H), 1.31-1.18 (m, 1H).

Examples 246 and 247

N—((S)-1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethyl)-1H-imidazole-5-carboxamide trifluoroacetate (single diastereomer) and 2-((S)-1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethyl)guanidine trifluoroacetate (single diastereomer)

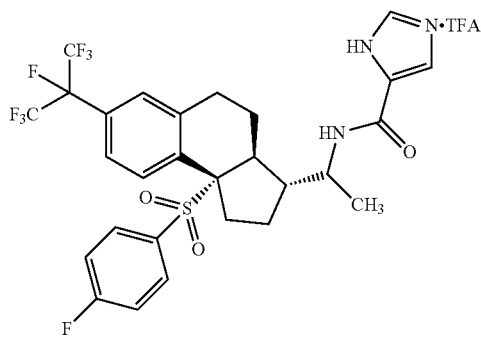

Homochiral
from peak 1

219
-continued

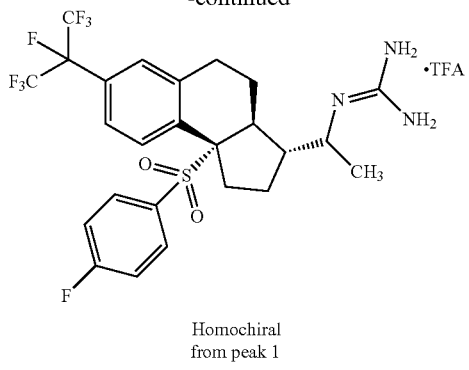

Homochiral
from peak 1

A mixture of a single diastereomer of 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethan-1-amine (Example 225; 16 mg, 0.030 mmol), 1H-imidazole-4-carboxylic acid (4.3 mg, 0.038 mmol), HATU (14.6 mg, 0.038 mmol), DIEA (210 μL, 0.118 mmol), and anhydrous DMF (0.3 mL) was sonicated and then stirred at rt for 22 h. The mixture was purified by preparative HPLC (Method F, gradient 31-80% B, 20 min) to provide a single diastereomer of N-(1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethyl)-1H-imidazole-4-carboxamide trifluoroacetate (Example 246; 3.4 mg, 15% yield). LCMS m/z 636.2 (M+H)$^+$; HPLC $t_R$ 1.95 min (Method C). $^1$H NMR (500 MHz, DMSO-d$_6$) δ 8.06-7.95 (m, 2H), 7.82-7.75 (m, 1H), 7.53-7.49 (m, 1H), 7.48-7.43 (m, 1H), 7.28-7.21 (m, 2H), 7.20-7.10 (m, 3H), 4.30-4.22 (m, 1H), 3.10 (br dd, J=14.2, 5.6 Hz, 1H), 2.88-2.81 (m, 1H), 2.46-2.39 (m, 1H), 2.20-2.10 (m, 2H), 2.04-1.96 (m, 2H), 1.88-1.79 (m, 2H), 1.57-1.48 (m, 1H), 1.20-1.15 (m, 2H), 1.15-1.07 (m, 1H).

Also isolated was a single diastereomer of 2-(1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethyl)-1,1,3,3-tetramethylguanidine trifluoroacetate (Example 247; 2.3 mg, 10% yield). LCMS m/z 639.9 (M+H)$^+$; HPLC $t_R$ 2.13 min (Method C). $^1$H NMR (500 MHz, DMSO-d$_6$) δ 7.46-7.39 (m, 2H), 7.35-7.31 (m, 1H), 7.31-7.28 (m, 1H), 7.26-7.00 (m, 3H), 3.75-3.67 (m, 1H), 3.09-3.01 (m, 1H), 2.95-2.91 (m, 12H), 2.81-2.72 (m, 1H), 2.64-2.57 (m, 1H), 2.27-2.13 (m, 1H), 2.04-1.94 (m, 2H), 1.91-1.76 (m, 2H), 1.38-1.13 (m, 5H).

220
Example 248

2-amino-N—((S)-1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethyl)-2-methylpropanamide (single diastereomer)

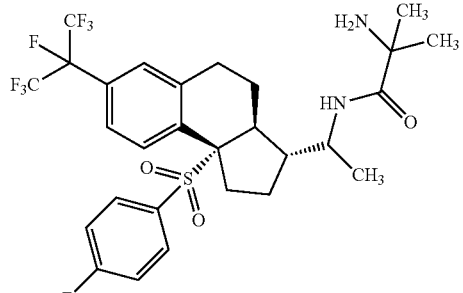

Homochiral
from peak 2

A stirred solution of a single diastereomer of 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethan-1-amine (Example 226; 8 mg, 0.015 mmol) and 2-((tert-butoxycarbonyl)amino)-2-methylpropanoic acid (6.0 mg, 0.030 mmol) in DMF (0.3 mL) was treated with BOP (13.1 mg, 0.030 mmol) and DIEA (10 μL, 0.059 mmol). The mixture was stirred at rt for 2 h, then was treated with 10% aqueous LiCl (3 mL) and extracted with EtOAc (3×1 mL). The combined organic phases were dried and concentrated. The residue was dissolved in 1,2-dichloroethane (1 mL) and treated with TFA (0.5 mL). The mixture was stirred at rt for 1 h, then was concentrated. The residue was purified by preparative HPLC (Method E, gradient 42-85% B, 20 min) to provide a single diastereomer of 2-amino-N-(1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethyl)-2-methylpropanamide (7.8 mg, 82% yield). LCMS m/z 627.2 (M+H)$^+$; HPLC $t_R$ 2.14 min (Method C). $^1$H NMR (500 MHz, DMSO-d$_6$) δ 7.43-7.39 (m, 1H), 7.37-7.32 (m, 1H), 7.29-7.24 (m, 1H), 7.19-7.15 (m, 4H), 4.10-4.03 (m, 1H), 3.04-2.98 (m, 1H), 2.78-2.71 (m, 1H), 2.60-2.54 (m, 1H), 2.22-2.07 (m, 2H), 1.98-1.71 (m, 7H), 1.30-1.27 (m, 3H), 1.26-1.21 (m, 4H), 1.17-1.12 (m, 3H).

The Examples in Table 16 were prepared using procedures used to prepare Examples 244 through 248 or similar procedures, starting from the appropriate Example amine and an appropriate carboxylic acid, acyl chloride or acid anhydride.

TABLE 16

| Ex. number | Structure | LCMS m/z observed | HPLC $t_R$ (min) | HPLC method |
|---|---|---|---|---|
| 249 | ![structure] | 653.1 (M + H)$^+$ | 1.00 | A |

TABLE 16-continued
| Ex. number | Structure | LCMS m/z observed | HPLC $t_R$ (min) | HPLC method |
|---|---|---|---|---|
| 250 | 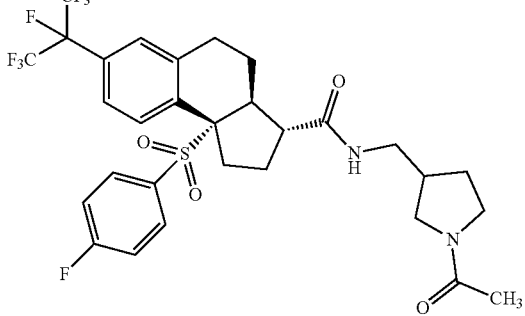 Homochiral from peak 2 | 667.2 (M + H)⁺ | 1.01 | A |
| 251 | 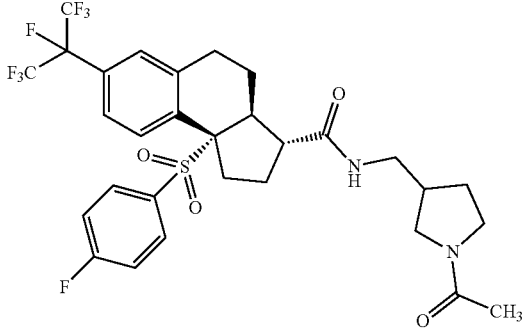 Homochiral from peak 1 | 667.2 (M + H)⁺ | 1.01 | A |
| 252 | 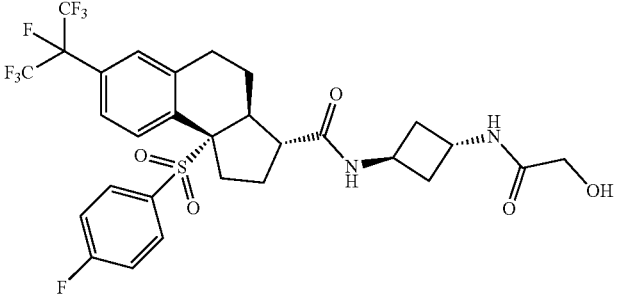 [SMILES: O=C(CO)N[C@H]1C[C@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1] | 669.0 (M + H)⁺ | 0.98 | A |
| 253 | 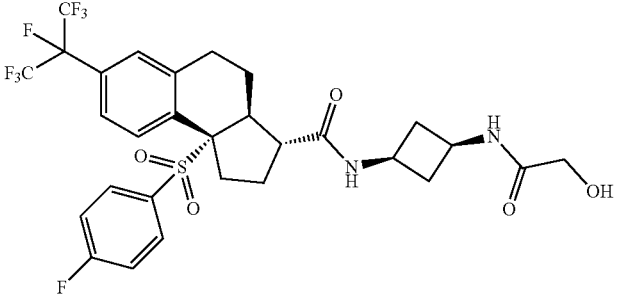 [SMILES: O=C(CO)N[C@H]1C[C@@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1] | 669.1 (M + H)⁺ | 0.97 | A |

TABLE 16-continued

| Ex. number | Structure | LCMS m/z observed | HPLC $t_R$ (min) | HPLC method |
|---|---|---|---|---|
| 254 | Homochiral from peak 1 | 683.3 (M + H)+ | 0.99 | A |
| 255 | Homochiral from peak 2 | 683.2 (M + H)+ | 0.99 | A |
| 256 | 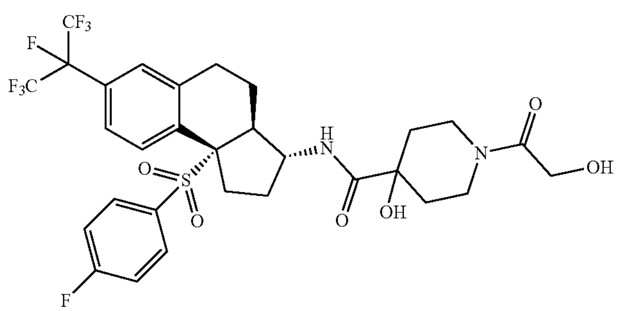 [SMILES: O=C(CO)N1CCC(O)(C(=O)N[C@@H]2CC[C@@]3(S(=O)(=O)c4ccc(F)cc4)c4ccc(C(F)(C(F)(F)F)C(F)(F)F)cc4CC[C@@H]23)CC1] | 699.2 (M + H)+ | 1.98 | C |
| 257 | Homochiral from peak 2 | 636.1 (M + H)+ | 2.00 | C |

TABLE 16-continued
| Ex. number | Structure | LCMS m/z observed | HPLC $t_R$ (min) | HPLC method |
|---|---|---|---|---|
| 258 | 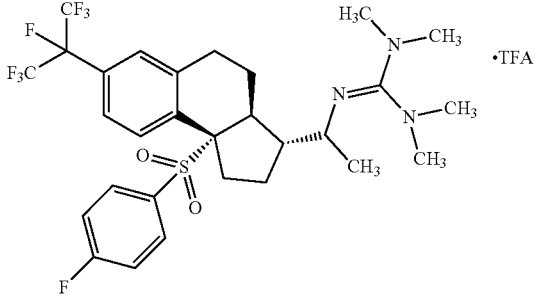 Homochiral from peak 2 | 640.3 (M + H)+ | 2.20 | C |
| 259 | 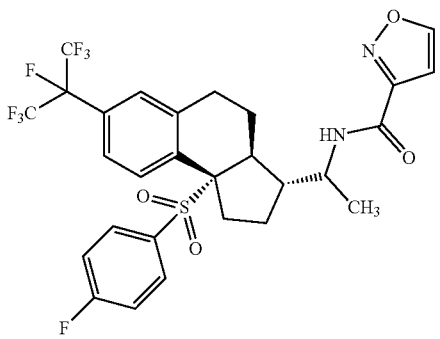 Homochiral from peak 1 | 637.2 (M + H)+ | 2.45 | C |
| 260 | 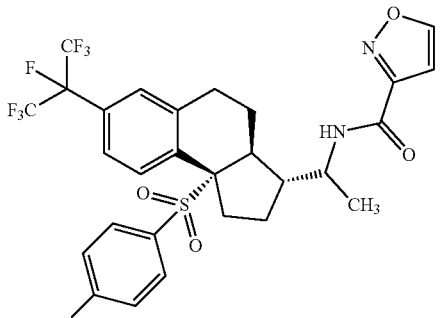 Homochiral from peak 2 | 637.4 (M + H)+ | 2.59 | C |
| 261 | 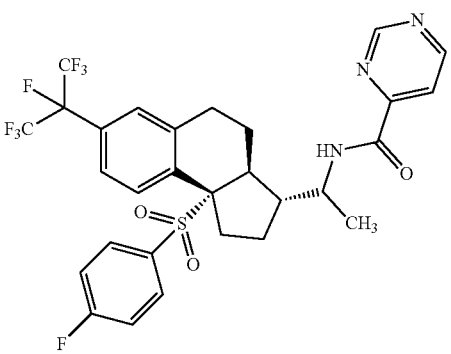 Homochiral from peak 1 | 648.2 (M + H)+ | 2.57 | C |

TABLE 16-continued
| Ex. number | Structure | LCMS m/z observed | HPLC $t_R$ (min) | HPLC method |
|---|---|---|---|---|
| 262 | 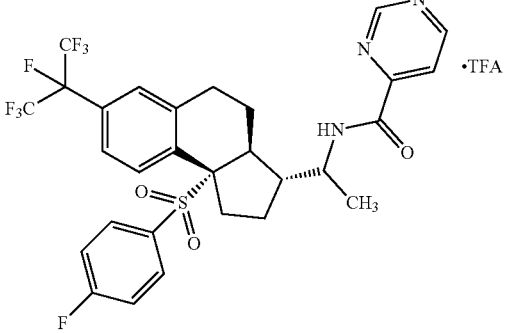 Homochiral from peak 2 | 648.2 (M + H)+ | 2.46 | C |
| 263 | 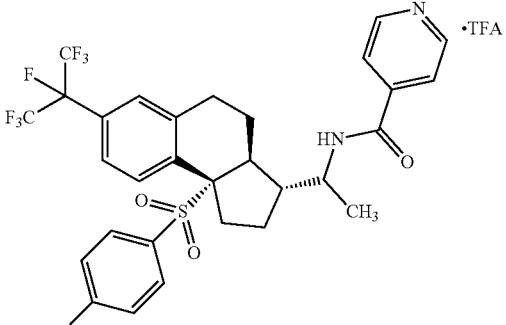 Homochiral from peak 1 | 647.3 (M + H)+ | 2.05 | C |
| 264 | 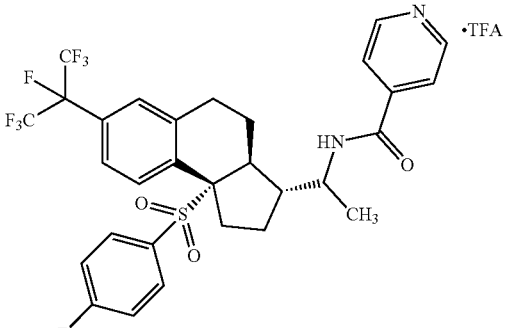 Homochiral from peak 2 | 647.2 (M + H)+ | 2.08 | C |
| 265 | 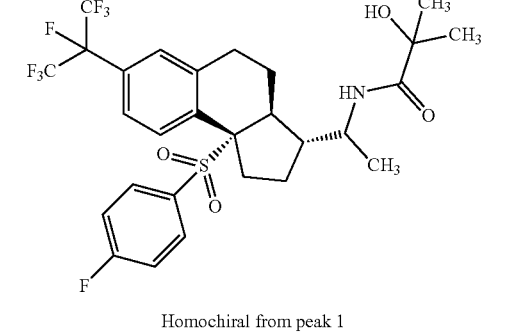 Homochiral from peak 1 | 628.2 (M + H)+ | 2.33 | C |

TABLE 16-continued

| Ex. number | Structure | LCMS m/z observed | HPLC $t_R$ (min) | HPLC method |
|---|---|---|---|---|
| 266 | Homochiral from peak 2 | 628.4 (M + H)$^+$ | 2.49 | C |
| 267 | Homochiral from peak 1 | 671.1 (M + H)$^+$ | 2.32 | C |
| 268 | Homochiral from peak 2 | 671.1 (M + H)$^+$ | 2.19 | C |
| 269 | Homochiral from peak 2 | 614.3 (M + H)$^+$ | 2.28 | C |

| Ex. number | Structure | LCMS m/z observed | HPLC $t_R$ (min) | HPLC method |
|---|---|---|---|---|
| 270 | 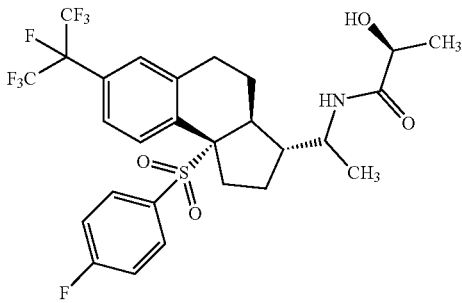<br>Homochiral from peak 2 | 614.2 (M + H)⁺ | 2.27 | C |
| 271 | 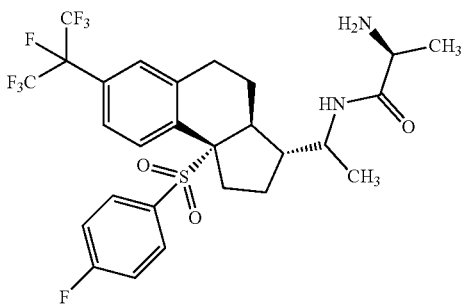<br>Homochiral from peak 2 | 613.2 (M + H)⁺ | 1.98 | C |

Example 272

N-(1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethyl)-1-methyl-1H-pyrazole-4-sulfonamide

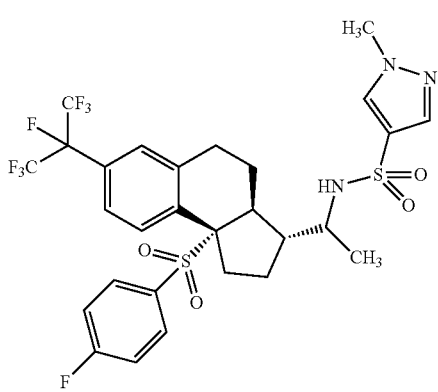

Homochiral from peak 1

A stirred solution of a single diastereomer of 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethan-1-amine (Example 225; 8 mg, 0.015 mmol) in DMSO (0.3 mL) was treated with 1-methyl-1H-pyrazole-4-sulfonyl chloride (5.3 mg, 0.030 mmol) and DIEA (10 µL, 0.059 mmol). The mixture was stirred at rt for 2 h, then was purified by preparative HPLC (Method E, gradient 43-83% B, 20 min) to provide N-(1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)ethyl)-1-methyl-1H-pyrazole-4-sulfonamide (4.3 mg, 41% yield). LCMS m/z 686.2 (M+H)⁺; HPLC $t_R$ 2.36 min (Method C). ¹H NMR (500 MHz, DMSO-$d_6$) δ 8.26-8.21 (m, 1H), 7.74 (s, 1H), 7.54 (d, J=8.5 Hz, 2H), 7.52-7.47 (m, 1H), 7.22 (s, 1H), 7.18-7.13 (m, 3H), 3.90-3.86 (m, 5H), 3.37-3.30 (m, 1H), 3.13-3.06 (m, 1H), 2.86-2.78 (m, 1H), 2.28-2.18 (m, 1H), 2.18-2.08 (m, 1H), 1.81-1.72 (m, 2H), 1.71-1.62 (m, 1H), 1.57-1.46 (m, 1H), 1.08-0.97 (m, 1H), 0.91-0.85 (m, 3H).

The Examples in Table 17 were prepared using procedures used to prepare Example 272 or similar procedures, starting from the appropriate Example amine and an appropriate sulfonyl chloride.

TABLE 17
| Ex. number | Structure | LCMS m/z observed | HPLC $t_R$ (min) | HPLC method |
|---|---|---|---|---|
| 273 | 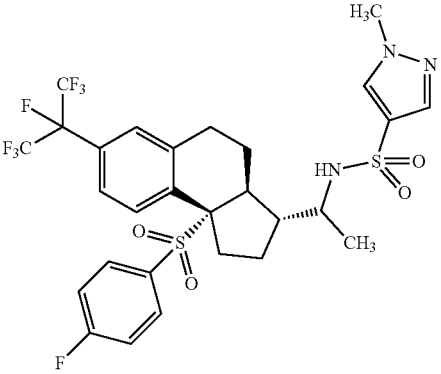<br>Homochiral from peak 2 | 686.2 (M + H)+ | 2.38 | C |
| 274 | 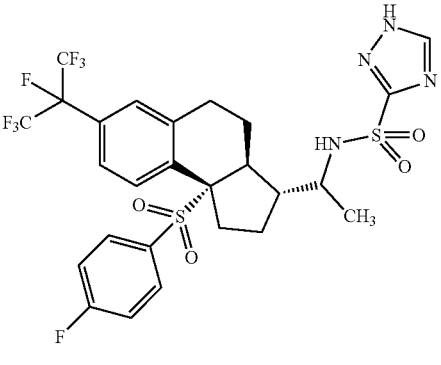<br>Homochiral from peak 1 | 673.1 (M + H)+ | 2.24 | C |
| 275 | 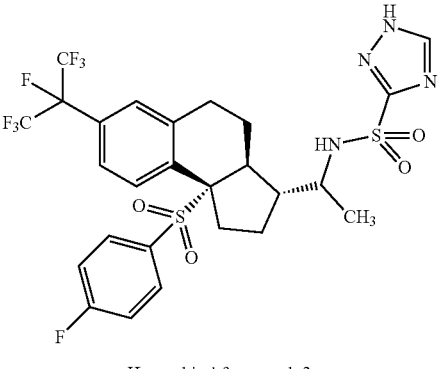<br>Homochiral from peak 2 | 673.1 (M + H)+ | 2.24 | C |
| 276 | 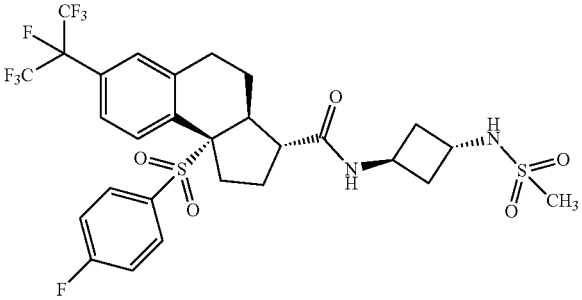 [SMILES: CS(=O)(=O)N[C@H]1C[C@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1] | 689.1 (M + H)+ | 1.03 | A |

TABLE 17-continued
| Ex. number | Structure | LCMS m/z observed | HPLC $t_R$ (min) | HPLC method |
|---|---|---|---|---|
| 277 | 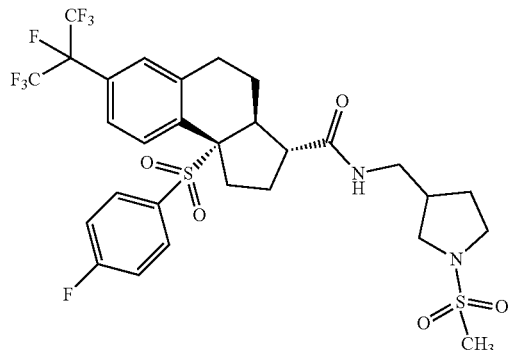 Homochiral from peak 1 | 703.2 (M + H)+ | 1.04 | A |
| 278 | 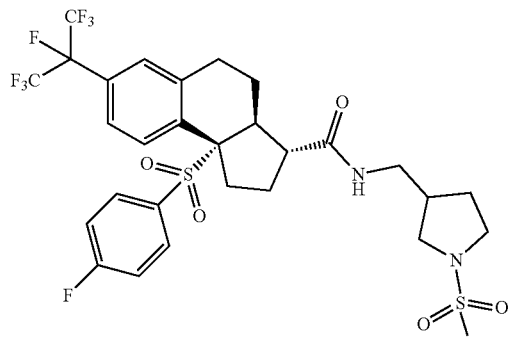 Homochiral from peak 2 | 703.2 (M + H)+ | 1.05 | A |
| 279 | 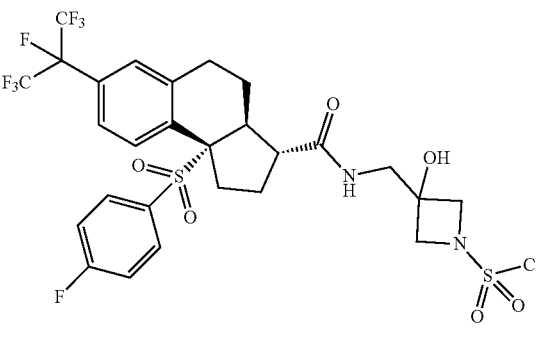 | 705.1 (M + H)+ | 2.13 | C |

Example 280

(3R,3aS,9bS)-9b-((4-fluorophenyl)sulfonyl)-7-(perfluoropropan-2-yl)-N-((1s,3S)-3-(sulfamoylamino)cyclobutyl)-2,3,3a,4,5 0.9b-hexahydro-1H-cyclopenta[a]naphthalene-3-carboxamide

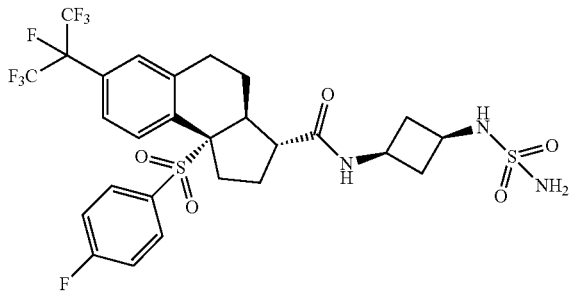 [SMILES: NS(=O)(=O)N[C@H]1C[C@@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1]

A solution of (3R,3aS,9bS)—N-((1s,3S)-3-aminocyclobutyl)-9b-((4-fluorophenyl)sulfonyl)-7-(perfluoropropan-2-yl)-2,3,3a,4,5,9b-hexahydro-1H-cyclopenta[a]naphthalene-3-carboxamide hydrochloride (Example 110; 25 mg, 0.041 mmol) in DMF (410 μL) was treated with DIEA (29 μL, 0.16 mmol) and sulfuric diamide (20 mg, 0.20 mmol). The mixture was stirred at rt for 30 min, then was purified by preparative HPLC (Method E, gradient 45-90% B, 20 min) to provide (3R,3aS,9bS)-9b-((4-fluorophenyl)sulfonyl)-7-(perfluoropropan-2-yl)-N-((1s,3S)-3-(sulfamoylamino)cyclobutyl)-2,3,3a,4,5,9b-hexahydro-1H-cyclopenta[a]naphthalene-3-carboxamide (3.8 mg, 13% yield). LCMS m/z 690.1 (M+1)$^+$; HPLC $t_R$ 1.02 min (Method B). $^1$H NMR (500 MHz, DMSO-$d_6$) δ 8.17-8.06 (m, 1H), 7.53-7.18 (m, 6H), 6.55-6.41 (m, 1H), 3.88-3.73 (m, 1H), 3.60-3.47 (m, 1H), 3.47-3.29 (m, 1H), 3.22-3.08 (m, 1H), 3.03-2.90 (m, 2H), 2.77-2.62 (m, 2H), 2.50-2.34 (m, 2H), 2.34-2.08 (m, 2H), 2.03-1.88 (m, 2H), 1.88-1.72 (m, 4H), 1.32-1.15 (m, 1H).

The Examples in Table 18 were prepared using procedures used to prepare Example 280 or similar procedures, starting from the appropriate Example amine.

TABLE 18

| Ex. number | Structure | LCMS m/z observed | HPLC $t_R$ (min) | HPLC method |
|---|---|---|---|---|
| 281 | 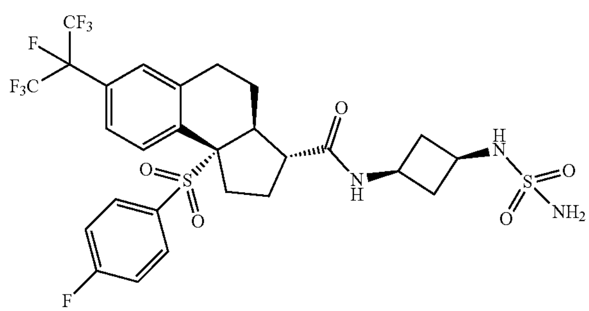 [SMILES: NS(=O)(=O)N[C@H]1C[C@@H](NC(=O)[C@@H]2CC[C@@]3(S(=O)(=O)c4ccc(F)cc4)c4ccc(C(F)(C(F)(F)F)C(F)(F)F)cc4CC[C@@H]23)C1] | 690.1 (M + H)$^+$ | 1.00 | A |
| 282 | 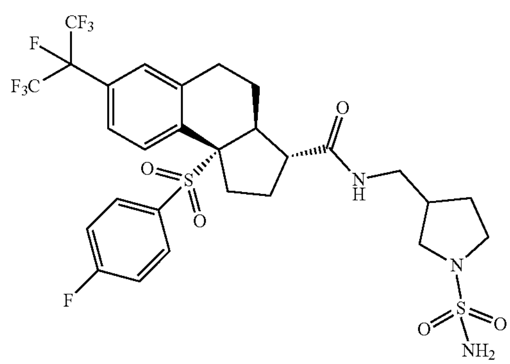 | 704.2 (M + H)$^+$ | 1.02 | A |

Homochiral from peak 1

TABLE 18-continued

| Ex. number | Structure | LCMS m/z observed | HPLC $t_R$ (min) | HPLC method |
|---|---|---|---|---|
| 283 | 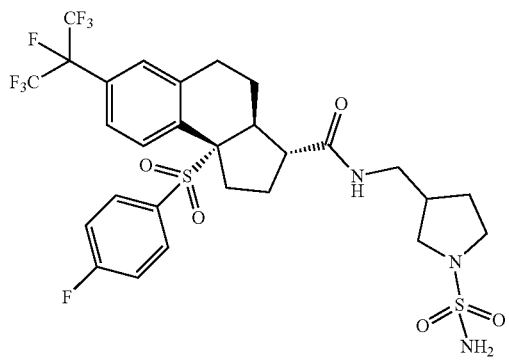 Homochiral from peak 2 | 704.2 (M + H)+ | 1.02 | A |

Example 284

1-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-methyl-1-oxopropan-2-yl dihydrogen phosphate

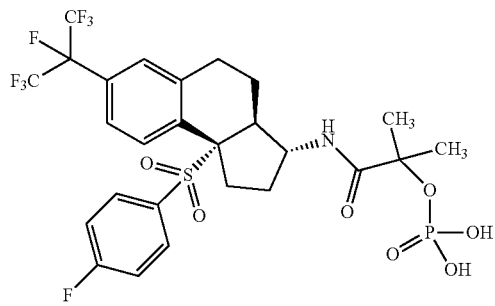 [SMILES: CC(C)(OP(=O)(O)O)C(=O)N[C@@H]1CC[C@@]2(S(=O)(=O)c3ccc(F)cc3)c3ccc(C(F)(C(F)(F)F)C(F)(F)F)cc3CC[C@@H]12]

Step A: dibenzyl (1-(((3R,3aS,9bS)-9b-((4-fluorophenyl)sulfonyl)-perfluoropropan-2-yl)-2,3,3a,4,5 0.9b-hexahydro-1H-cyclopenta[a]naphthalen-3-yl)amino)-2-methyl-1-oxopropan-2-yl) phosphate

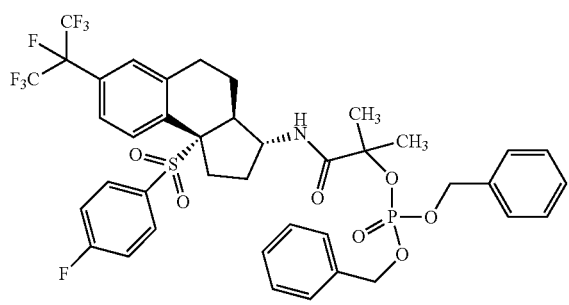 [SMILES: CC(C)(OP(=O)(OCc1ccccc1)OCc1ccccc1)C(=O)N[C@@H]1CC[C@@]2(S(=O)(=O)c3ccc(F)cc3)c3ccc(C(F)(C(F)(F)F)C(F)(F)F)cc3CC[C@@H]12]

A solution of N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-hydroxy-2-methylpropanamide (Example 137; 400 mg, 0.667 mmol) and 5-methyl-1H-tetrazole (337 mg, 4.00 mmol) in DCM (13.3 mL) was purged with nitrogen and cooled in an ice-water bath, then was treated with dibenzyl diisopropylphosphoramidite (732 μL, 2.00 mmol) and the mixture was stirred at 0° C. for 5 min, then at rt for 2 h. The mixture was cooled again in an ice-water bath and treated with 30% aqueous hydrogen peroxide (750 μL, 7.34 mmol). After 1 h, the mixture was partitioned between DCM and saturated aqueous NaHCO$_3$. The organic phase was washed with brine, dried and concentrated. The residue was subjected to column chromatography on silica gel (24 g), eluting with EtOAc-hexanes (gradient from 0-100%), to provide dibenzyl (1-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-methyl-1-oxopropan-2-yl) phosphate as a white solid (500 mg, 87% yield). LCMS m/z 860.4 (M+H)+, HPLC $t_R$ 1.24 min (method A). $^1$H NMR (499 MHz, MeOH-d$_4$) δ 7.73 (d, J=8.5 Hz, 1H), 7.55 (br d, J=9.3 Hz, 1H), 7.45-7.31 (m, 10H), 7.26 (s, 1H), 7.25-7.20 (m, 2H), 7.00 (t, J=8.8 Hz, 2H), 5.24-5.14 (m, 4H), 4.24-4.16 (m, 1H), 3.25-3.16 (m, 1H), 2.99 (ddd, J=11.9, 5.9, 4.0 Hz, 1H), 2.58 (dt, J=16.1, 3.7 Hz, 1H), 2.53-2.45 (m, 1H), 2.19-2.12 (m, 1H), 2.12-1.97 (m, 2H), 1.87-1.79 (m, 1H), 1.76 (s, 3H), 1.71 (s, 3H), 1.35-1.26 (m, 1H).

Step B: 1-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-methyl-1-oxopropan-2-yl dihydrogen phosphate

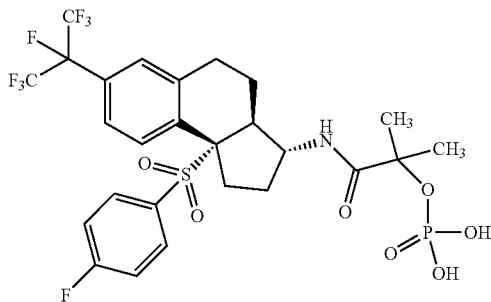 [SMILES: CC(C)(OP(=O)(O)O)C(=O)N[C@@H]1CC[C@@]2(S(=O)(=O)c3ccc(F)cc3)c3ccc(C(F)(C(F)(F)F)C(F)(F)F)cc3CC[C@@H]12]

A solution of dibenzyl (1-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-methyl-1-oxopropan-2-yl) phosphate (450 mg, 0.523 mmol) in MeOH-EtOAc (2:1, 20.9 mL) was treated with palladium on carbon (195 mg) and stirred under a hydrogen atmosphere (balloon pressure). After 3 h, the mixture was filtered, the solids were washed with methanol and the filtrates were concentrated. The residue was stirred at rt overnight in MeCN, and the solid was collected, washed with cold MeCN and dried to provide 1-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-methyl-1-oxopropan-2-yl dihydrogen phosphate as a white solid (330 mg, 88% yield). LCMS m/z 680.2 (M+H)$^+$, HPLC $t_R$ 1.02 min (method A). $^1$H NMR (499 MHz, MeOH-$d_4$) δ 7.61 (d, J=8.4 Hz, 1H), 7.52 (br d, J=8.0 Hz, 1H), 7.36-7.28 (m, 3H), 7.11 (t, J=8.8 Hz, 2H), 4.21-4.13 (m, 1H), 3.24 (ddd, J=14.6, 7.3, 5.2 Hz, 1H), 3.04 (dt, J=10.9, 6.3 Hz, 1H), 2.64 (dt, J=16.1, 4.2 Hz, 1H), 2.38 (ddd, J=14.5, 9.3, 7.4 Hz, 1H), 2.21-2.06 (m, 3H), 2.06-1.97 (m, 1H), 1.73 (s, 3H), 1.69 (s, 3H), 1.40-1.30 (m, 1H).

Example 285

1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carbonyl)-2-(methyl-$d_3$)pyrazolidin-3-one

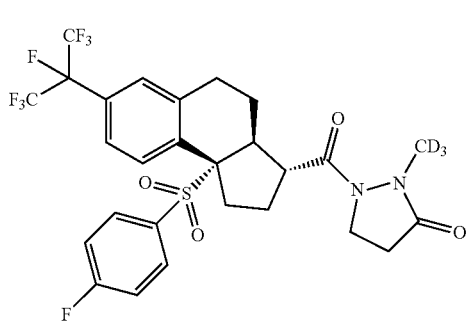 [SMILES: [2H]C([2H])([2H])N1C(=O)CCN1C(=O)[C@@H]1CC[C@@]2(S(=O)(=O)c3ccc(F)cc3)c3ccc(C(F)(C(F)(F)F)C(F)(F)F)cc3CC[C@@H]12]

A solution of 1-((3R,3aS,9bR)-9b-((4-fluorophenyl)sulfonyl)-7-(perfluoropropan-2-yl)-2,3,3a,4,5,9b-hexahydro-1H-cyclopenta[a]naphthalene-3-carbonyl)pyrazolidin-3-one (Example 75; 30 mg, 0.049 mmol) in MeCN (1 mL) was treated with iodomethane-$d_3$ (71 mg, 0.49 mmol) and Cs$_2$CO$_3$ (18 mg, 0.054 mmol). The mixture was stirred at 40° C. for 2 h, then purified by preparative HPLC (Method E, gradient 45-90% B, 20 min) to provide 1-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalene-3-carbonyl)-2-(methyl-$d_3$)pyrazolidin-3-one (2 mg, 5% yield). LCMS m/z 628.1 (M+1)$^+$; HPLC $t_R$ 2.26 min (Method C). $^1$H NMR (500 MHz, DMSO-$d_6$) δ 7.60-7.13 (m, 7H), 4.02-3.80 (m, 2H), 3.26-3.12 (m, 1H), 3.12-2.95 (m, 1H), 2.95-2.81 (m, 2H), 2.77-2.65 (m, 1H), 2.35-2.13 (m, 2H), 2.09-1.79 (m, 3H), 1.33-1.14 (m, 1H), 1.06-0.90 (m, 1H).

The Examples in Table 19 were prepared using procedures used to prepare Example 285 or similar procedures, starting from the appropriate Example starting material and an appropriate alkyl halide.

TABLE 19

| Ex. number | Structure | LCMS m/z observed | HPLC $t_R$ (min) | HPLC method |
|---|---|---|---|---|
| 286 | ![structure] | 639.3 (M + H)$^+$ | 2.07 | C |

TABLE 19-continued

| Ex. number | Structure | LCMS m/z observed | HPLC $t_R$ (min) | HPLC method |
|---|---|---|---|---|
| 287 | 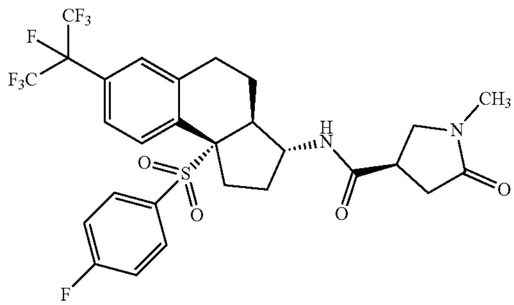 | 639.3 (M + H)+ | 2.08 | C |
| 288 | 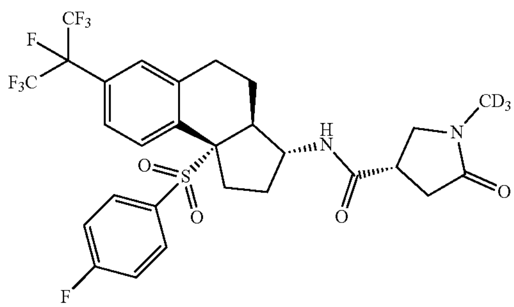 | 642.3 (M + H)+ | 2.06 | C |

Example 289

(S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(2-hydroxyethyl-2,2-d₂)-5-oxopyrrolidine-3-carboxamide

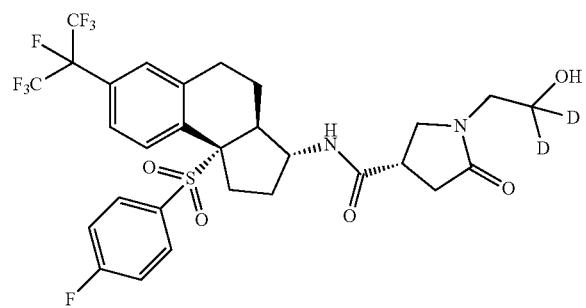 [SMILES: [2H]C([2H])(O)CN1C[C@@H](C(=O)N[C@@H]2CC[C@@]3(S(=O)(=O)c4ccc(F)cc4)c4ccc(C(F)(C(F)(F)F)C(F)(F)F)cc4CC[C@@H]23)CC1=O]

Part A: ethyl 2-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)acetate

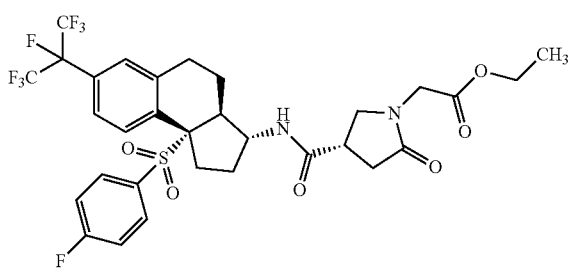 [SMILES: CCOC(=O)CN1C[C@@H](C(=O)N[C@@H]2CC[C@@]3(S(=O)(=O)c4ccc(F)cc4)c4ccc(C(F)(C(F)(F)F)C(F)(F)F)cc4CC[C@@H]23)CC1=O]

A solution of (3S)—N-((3R,3aS)-9b-((4-fluorophenyl)sulfonyl)-7-(perfluoropropan-2-yl)-2,3,3a,4,5,9b-hexahydro-1H-cyclopenta[a]naphthalen-3-yl)-5-oxopyrrolidine-3-carboxamide (Example 176; 30 mg, 0.048 mmol) in DMF (0.5 mL) was treated with Cs₂CO₃ (47.0 mg, 0.144 mmol) and ethyl 2-bromoacetate (16.0 mg, 0.096 mmol). The mixture was stirred at 75° C. for 3 h. After cooling to rt, the mixture was partitioned between EtOAc (30 mL) and water (20 mL). The organic layer was washed sequentially with water (3×10 mL) and brine (15 mL), dried and concentrated. The residue was subjected to silica gel chromatography, eluting with EtOAc-hexanes (gradient from 0-100%), to give ethyl 2-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)acetate as a beige solid (20 mg, 59% yield). LCMS m/z 711.3 (M+1)+; HPLC $t_R$ 1.05 min (Method A). ¹H NMR (499 MHz, CDCl₃) δ 7.73 (d, J=8.5 Hz, 1H), 7.52 (br d, J=8.3 Hz, 1H), 7.25 (br d, J=8.0 Hz, 1H), 7.18-7.08 (m, 3H), 6.94 (br t, J=8.5 Hz, 2H), 4.40-4.29 (m, 1H), 4.25 (q, J=7.2 Hz, 2H), 4.19-4.03 (m, 2H), 3.86-3.66 (m, 2H), 3.25 (dt, J=15.1, 7.6 Hz, 2H), 2.86-2.77 (m, 3H), 2.55-2.41 (m, 2H), 2.26-2.15 (m, 1H), 2.11-1.99 (m, 2H), 1.67-1.53 (m, 1H), 1.32 (t, J=7.2 Hz, 4H).

Part B: (S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(2-hydroxyethyl-2,2-d₂)-5-oxopyrrolidine-3-carboxamide Example 290

N-((3R³aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxy-1-methyl-piperidine-4-carboxamide

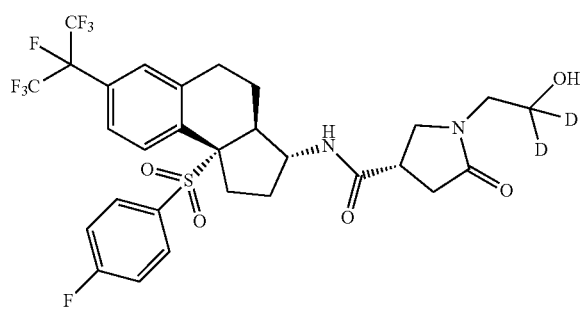 [SMILES: [2H]C([2H])(O)CN1C[C@@H](C(=O)N[C@@H]2CC[C@@]3(S(=O)(=O)c4ccc(F)cc4)c4ccc(C(F)(C(F)(F)F)C(F)(F)F)cc4CC[C@@H]23)CC1=O]

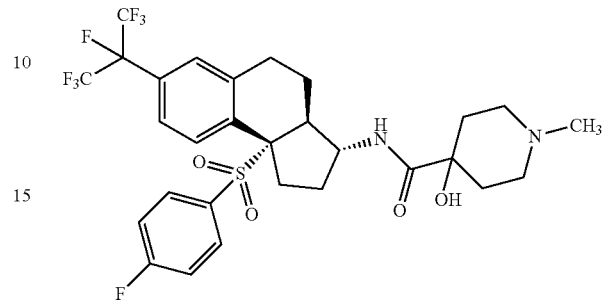

A solution of ethyl 2-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)acetate (20 mg, 0.028 mmol) in THF (0.5 mL) and DMF (0.5 mL) was treated with NaBD₄ (5.9 mg, 0.141 mmol) and stirred at rt overnight. The mixture was treated with saturated aqueous NH₄Cl (1 mL) and partitioned between EtOAc (30 mL) and water (20 mL). The organic layer was washed with brine (15 mL), dried and concentrated. The residue was purified by preparative HPLC (Method F, gradient 34-74% B, 20 min) to provide (S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(2-hydroxyethyl-2,2-d₂)-5-oxopyrrolidine-3-carboxamide (4.9 mg, 26% yield). LCMS m/z 671.3 (M+1)⁺; HPLC $t_R$ 1.97 min (Method C). ¹H NMR (500 MHz, DMSO-d₆) δ 8.33 (br d, J=7.6 Hz, 1H), 7.53-7.39 (m, 2H), 7.34 (s, 1H), 7.29-7.20 (m, 4H), 3.92 (br d, J=7.9 Hz, 1H), 3.57 (br s, 1H), 3.46-3.36 (m, 1H), 3.29-3.11 (m, 3H), 3.09-2.97 (m, 1H), 2.83 (br d, J=6.7 Hz, 1H), 2.64 (br d, J=15.9 Hz, 1H), 2.50-2.44 (m, 2H), 2.30-2.17 (m, 1H), 2.10-1.93 (m, 3H), 1.83 (br s, 1H), 1.24 (br d, J=10.4 Hz, 1H).

A solution of N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxypiperidine-4-carboxamide (Example 195; 23.4 mg, 0.0365 mmol) in DCM (1 mL) was treated with 37% aqueous formaldehyde (41 μL, 0.548 mmol) and stirred at rt. After 1.5 h, the mixture was treated with sodium triacetoxyborohydride (30.9 mg, 0.146 mmol), and the mixture was stirred at rt for 2 h. A drop of saturated aqueous Na₂CO₃ was added and the mixture was concentrated. The residue was purified by preparative HPLC (Method E, gradient 30-70% B, 20 min) to provide N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxy-1-methylpiperidine-4-carboxamide (14.6 mg, 59% yield). LCMS m/z 655.1 (M+H)⁺; HPLC $t_R$ 1.85 min (Method C). ¹H NMR (500 MHz, DMSO-d₆) δ 7.94 (br d, J=8.5 Hz, 1H), 7.62-7.56 (m, 1H), 7.55-7.48 (m, 1H), 7.32 (br s, 3H), 7.29-7.21 (m, 2H), 4.03-3.93 (m, 1H), 3.08-2.97 (m, 1H), 2.91-2.81 (m, 1H), 2.71-2.61 (m, 1H), 2.36-2.25 (m, 1H), 2.24-2.18 (m, 2H), 2.17 (s, 3H), 2.03-1.87 (m, 7H), 1.87-1.74 (m, 1H), 1.53-1.37 (m, 2H), 1.31-1.18 (m, 1H).

The Example in Table 20 was prepared using the procedures used to prepare Example 290, or similar procedures, from the appropriate Example starting material and an appropriate carbonyl compound.

TABLE 20

| Ex. number | Structure | LCMS m/z observed | HPLC $t_R$ (min) | HPLC method |
|---|---|---|---|---|
| 291 | ![structure] | 697.2 (M + H)⁺ | 1.85 | C |

Example 292

(S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(2-hydroxy-2-methylpropyl)-5-oxopyrrolidine-3-carboxamide

Example 294

(S)-1-(2-cyanoethyl)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-oxopyrrolidine-3-carboxamide

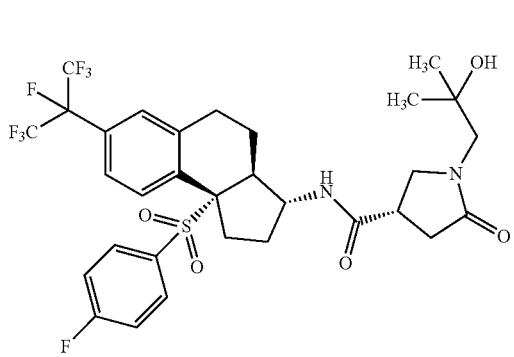 [SMILES: CC(C)(O)CN1C[C@@H](C(=O)N[C@@H]2CC[C@@]3(S(=O)(=O)c4ccc(F)cc4)c4ccc(C(F)(C(F)(F)F)C(F)(F)F)cc4CC[C@@H]23)CC1=O]

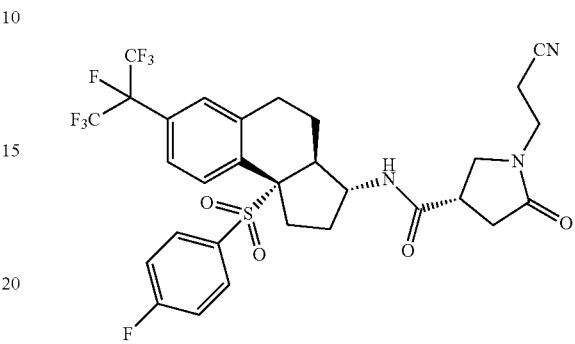

A mixture of (S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-oxopyrrolidine-3-carboxamide (Example 176; 25 mg, 0.040 mmol), $Cs_2CO_3$ (13.0 mg, 0.040 mmol), IPA (0.8 mL) and 2,2-dimethyloxirane (28.9 mg, 0.400 mmol) was heated in a sealed vial at 100° C. After 1 h, the mixture was cooled to rt and purified by preparative HPLC (Method F, gradient 37-77% B, 20 min) to provide (S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(2-hydroxy-2-methylpropyl)-5-oxopyrrolidine-3-carboxamide (8.8 mg, 30% yield). LCMS m/z 697.1 (M+H)$^+$; HPLC $t_R$ 2.05 min (Method C). $^1$H NMR (500 MHz, DMSO-$d_6$) δ 9.80-9.70 (m, 1H), 8.38-8.21 (m, 1H), 7.46 (br d, J=6.4 Hz, 2H), 7.34 (s, 1H), 7.29-7.20 (m, 4H), 4.60 (d, J=3.1 Hz, 1H), 3.94 (br s, 1H), 3.82-3.65 (m, 1H), 3.51 (br s, 1H), 3.21-2.95 (m, 4H), 2.83 (br s, 1H), 2.66 (br s, 1H), 2.49-2.41 (m, 2H), 2.23 (dt, J=6.7, 3.7 Hz, 1H), 2.10-1.92 (m, 3H), 1.84 (br d, J=9.5 Hz, 1H), 1.24 (br d, J=11.0 Hz, 1H), 1.11-0.98 (m, 6H).

The Example in Table 21 was prepared using the procedures used to prepare Example 292, or similar procedures, from the appropriate Example starting material.

A mixture of (S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-oxopyrrolidine-3-carboxamide (Example 176; 15 mg, 0.024 mmol), $Cs_2CO_3$ (7.8 mg, 0.024 mmol), DMF (0.5 mL) and acrylonitrile (2.6 mg, 0.048 mmol) was heated in a sealed vial at 60° C. for 5 h. The mixture was cooled to rt and purified by preparative HPLC (Method E, gradient 37-77% B, 20 min) to provide (S)-1-(2-cyanoethyl)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-oxopyrrolidine-3-carboxamide (6.9 mg, 42% yield). LCMS m/z 678.3 (M+H)$^+$; HPLC $t_R$ 2.13 min (Method C). $^1$H NMR (500 MHz, DMSO-$d_6$) δ 8.35 (br d, J=7.6 Hz, 1H), 7.54-7.42 (m, 2H), 7.35 (s, 1H), 7.27 (br d, J=7.0 Hz, 4H), 3.95 (br s, 1H), 3.69-3.58 (m, 1H), 3.18 (br d, J=6.7 Hz, 1H), 3.08-2.98 (m, 1H), 2.84 (br d, J=6.4 Hz, 1H), 2.74 (t, J=6.6 Hz, 2H), 2.69-2.61 (m, 1H), 2.51 (br s, 5H), 2.24 (dt, J=6.7, 3.7 Hz, 1H), 2.10-1.93 (m, 3H), 1.86 (br d, J=8.5 Hz, 1H), 1.25 (br d, J=11.0 Hz, 1H).

TABLE 20

| Ex. number | Structure | LCMS m/z observed | HPLC $t_R$ (min) | HPLC method |
|---|---|---|---|---|
| 293 | 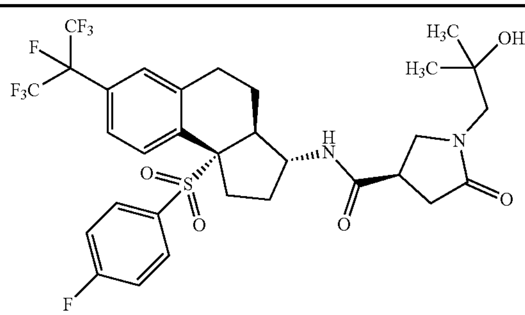 | 697.3 (M + H)$^+$ | 2.04 | C |

Example 295

3-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)propanoic acid

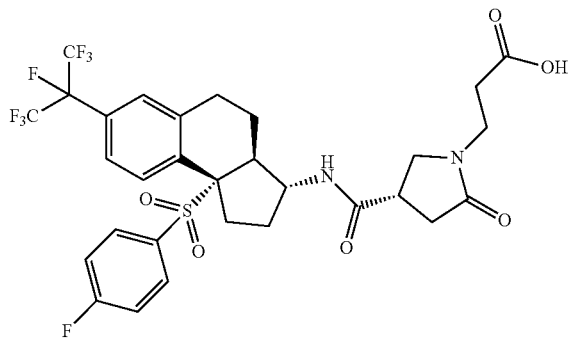 [SMILES: O=C(O)CCN1C[C@@H](C(=O)N[C@@H]2CC[C@@]3(S(=O)(=O)c4ccc(F)cc4)c4ccc(C(F)(C(F)(F)F)C(F)(F)F)cc4CC[C@@H]23)CC1=O]

Step A: methyl 3-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)propanoate

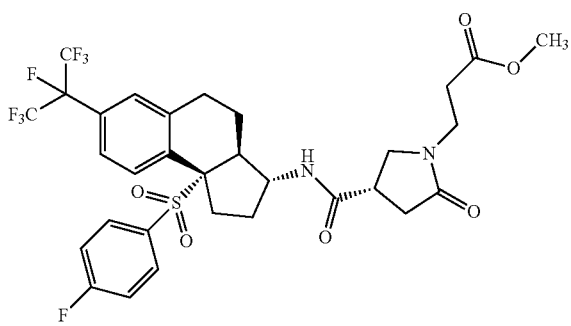 [SMILES: COC(=O)CCN1C[C@@H](C(=O)N[C@@H]2CC[C@@]3(S(=O)(=O)c4ccc(F)cc4)c4ccc(C(F)(C(F)(F)F)C(F)(F)F)cc4CC[C@@H]23)CC1=O]

A mixture of (S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-oxopyrrolidine-3-carboxamide (Example 176; 20 mg, 0.032 mmol), $Cs_2CO_3$ (31.3 mg, 0.096 mmol), DMF (0.5 mL) and methyl acrylate (5.5 mg, 0.064 mmol) was heated in a sealed vial at 85° C. for 1 h. The mixture was cooled to rt and partitioned between EtOAc (30 mL) and water (10 mL). The organic layer was washed sequentially with water (3×10 mL) and brine (15 mL), dried and concentrated. The residue was subjected to column chromatography on silica gel, eluting with MeOH-DCM (gradient from 0-10%), to give methyl 3-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)propanoate as a yellow solid (19 mg, 83% yield). LCMS m/z 711.3 (M+H)$^+$; HPLC $t_R$ 1.02 min (Analytical HPLC Method A). $^1$H NMR (500 MHz, DMSO-$d_6$) δ 7.75 (d, J=8.5 Hz, 1H), 7.52 (s, 1H), 7.16 (s, 4H), 6.95 (br d, J=8.1 Hz, 2H), 4.36 (br dd, J=7.9, 2.8 Hz, 1H), 3.73 (s, 4H), 3.68 (d, J=8.6 Hz, 1H), 3.65-3.60 (m, 2H), 3.31-3.10 (m, 2H), 2.83-2.68 (m, 3H), 2.64 (br d, J=2.5 Hz, 2H), 2.48 (s, 2H), 2.25-2.15 (m, 1H), 2.12-2.03 (m, 2H), 1.59 (br s, 1H), 1.34-1.22 (m, 1H).

Step B: 3-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)propanoic acid

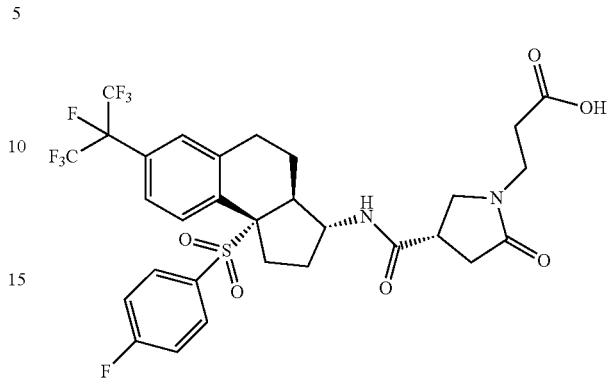

A mixture of 3-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)propanoate (10 mg, 0.014 mmol), THF (0.5 mL), water (0.5 mL) and LiOH hydrate (0.89 mg, 0.021 mmol) was stirred at rt for 5 h. The mixture was concentrated and purified by preparative HPLC (Method F, gradient 35-75% B, 20 min) to provide 3-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)propanoic acid (5.4 mg, 55% yield). LCMS m/z 697.1 (M+H)$^+$; HPLC $t_R$ 1.92 min (Method C). $^1$H NMR (500 MHz, DMSO-$d_6$) δ 8.33 (br d, J=7.6 Hz, 1H), 7.51-7.41 (m, 2H), 7.34 (s, 1H), 7.29-7.21 (m, 4H), 3.98-3.89 (m, 1H), 3.44-3.31 (m, 2H), 3.16-3.09 (m, 1H), 3.01 (br d, J=5.5 Hz, 1H), 2.83 (br d, J=6.4 Hz, 1H), 2.64 (br d, J=15.9 Hz, 1H), 2.51 (br s, 2H), 2.47-2.38 (m, 4H), 2.23 (br s, 1H), 2.09-1.93 (m, 3H), 1.84 (br d, J=8.2 Hz, 1H), 1.23 (br d, J=10.4 Hz, 1H).

Example 296

(S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(3-hydroxypropyl)-5-oxopyrrolidine-3-carboxamide

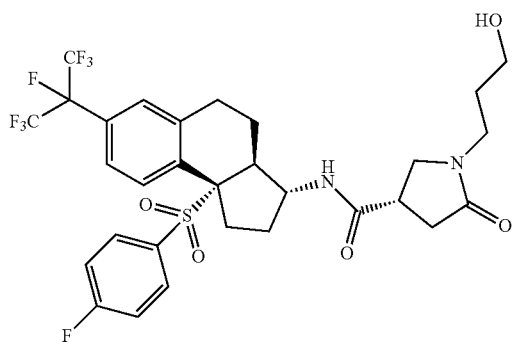 [SMILES: O=C(N[C@@H]1CC[C@@]2(S(=O)(=O)c3ccc(F)cc3)c3ccc(C(F)(C(F)(F)F)C(F)(F)F)cc3CC[C@@H]12)[C@H]1CC(=O)N(CCCO)C1]

A solution of methyl 3-((S)-4-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)carbamoyl)-2-oxopyrrolidin-1-yl)propanoate (Example 295, Step A; 10 mg, 0.014 mmol) in THF (0.5 mL) was treated with LiBH$_4$ (2.0 M in THF; 14 μL, 0.028 mmol). The mixture was stirred at rt for 2 h. The mixture was treated with saturated aqueous NH₄Cl (1 mL) and partitioned between EtOAc (20 mL) and water (15 mL). The organic layer was washed sequentially with water (10 mL) and brine (15 mL), dried and concentrated. The residue was purified by preparative HPLC (Method E, gradient 35-75% B, 20 min) to provide (S)—N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(3-hydroxypropyl)-5-oxopyrrolidine-3-carboxamide (5.0 mg, 50% yield). LCMS m/z 683.1 (M+H)$^+$; HPLC $t_R$ 2.92 min (Method C). $^1$H NMR (500 MHz, DMSO-d₆) δ 8.31 (br d, J=7.3 Hz, 1H), 7.53-7.41 (m, 2H), 7.35 (s, 1H), 7.27 (br d, J=7.0 Hz, 4H), 4.51 (t, J=5.0 Hz, 1H), 4.04-3.88 (m, 1H), 3.55-3.32 (m, 2H), 3.25-3.08 (m, 3H), 3.06-2.97 (m, 1H), 2.83 (br d, J=6.7 Hz, 1H), 2.65 (br d, J=15.9 Hz, 1H), 2.50-2.40 (m, 2H), 2.31-2.17 (m, 1H), 2.09-1.92 (m, 3H), 1.85 (br d, J=8.9 Hz, 1H), 1.59 (br t, J=6.7 Hz, 2H), 1.25 (br d, J=10.7 Hz, 1H).

The Example in Table 22 was prepared using the procedures used to prepare Examples 295 and 296, or similar procedures, from the appropriate Example starting material.

TABLE 22

| Ex. number | Structure | LCMS m/z observed | HPLC $t_R$ (min) | HPLC method |
|---|---|---|---|---|
| 297 | 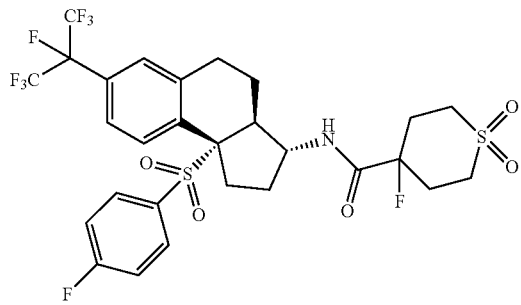 | 685.4 (M + H)$^+$ | 2.04 | C |

Examples 298 and 299

4-fluoro-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)tetrahydro-2H-thiopyran-4-carboxamide 1,1-dioxide and N-((3R,3aS,9bS)-9b-((4-fluorophenyl)sulfonyl)-7-(perfluoropropan-2-yl)-2,3,3a4,5,9b-hexahydro-1H-cyclopenta[a]naphthalen-3-yl)-3,6-dihydro-2H-thiopyran-4-carboxamide 1,1-dioxide Example 298

Example 299

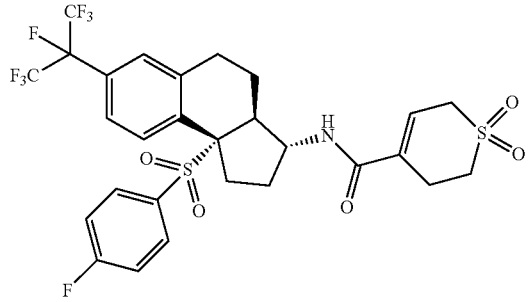

Following the procedure of Example 118, (3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-amine trifluoroacetate (Example 114 trifluoroacetate; 39.5 mg, 0.063 mmol) was converted into N-((3R,3aS,9bS)-9b-((4-fluorophenyl)sulfonyl)-7-(perfluoropropan-2-yl)-2,3,3a, 4,5,9b-hexahydro-1H-cyclopenta[a]naphthalen-3-yl)-4-hydroxytetrahydro-2H-thiopyran-4-carboxamide 1,1-dioxide (Example 123). Without purification, the crude material was dissolved in DCM (3 mL) and treated with DAST (42 µL, 0.315 mmol). The mixture was stirred at rt for 30 min, then stored in a freezer overnight. The mixture was treated with saturated aqueous NaHCO₃ (1.5 mL) and extracted with EtOAc (2×1 mL). The combined organic phases were dried and concentrated. The residue was purified by preparative HPLC (Method E, gradient 53-78% B, 25 min; then Method F, gradient 40-80% B, 19 min) to provide 4-fluoro-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)tetrahydro-2H-thiopyran-4-carboxamide 1,1-dioxide (Example 298; 2.5 mg, 6% yield). LCMS m/z 692.1 (M+H)$^+$; HPLC $t_R$ 2.24 min (Method B). $^1$H NMR (500 MHz, DMSO-d₆) δ 8.51 (br d, J=5.8 Hz, 1H), 7.60-7.55 (m, 1H), 7.54-7.49 (m, 1H), 7.37-7.23 (m, 5H), 4.01-3.92 (m, 1H), 3.20 (br d, J=16.2 Hz, 1H), 3.04-2.98 (m, 1H), 2.65 (br d, J=15.3 Hz, 1H), 2.60-2.23 (m, J=19.5 Hz, 8H), 2.04-1.83 (m, 4H), 1.32-1.20 (m, 2H).

Also obtained was N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3,6-dihydro-2H-thiopyran-4-carboxamide 1,1-dioxide (Example 299; 5.5 mg, 13% yield). LCMS m/z 672.1 (M+H)$^+$; HPLC $t_R$ 2.09 min (Method C). $^1$H NMR (500 MHz, DMSO-$d_6$) δ 8.23 (br d, J=7.3 Hz, 1H), 7.50 (s, 2H), 7.39-7.22 (m, 5H), 6.44 (br s, 1H), 3.99 (quin, J=7.7 Hz, 1H), 3.91 (br s, 2H), 3.31-3.22 (m, 1H), 3.09-2.93 (m, 2H), 2.87 (br s, 2H), 2.72-2.60 (m, 1H), 2.32-2.20 (m, 1H), 2.10-1.93 (m, 3H), 1.93-1.82 (m, 1H), 1.34-1.18 (m, 2H).

Example 300

N-((3R,3aS,9bS)-7-(perfluoropropan-2-yl)-9b-(phenylsulfonyl)-2,3,3a,4,5,9b-hexahydro-1H-cyclopenta[a]naphthalen-3-yl)tetrahydro-2H-thiopyran-4-carboxamide 1,1-dioxide

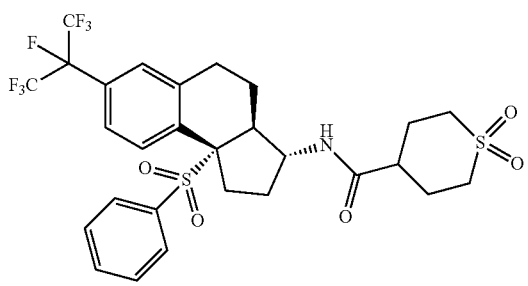 [SMILES: O=C(N[C@@H]1CC[C@@]2(S(=O)(=O)c3ccccc3)c3ccc(C(F)(C(F)(F)F)C(F)(F)F)cc3CC[C@@H]12)C1CCS(=O)(=O)CC1]

A solution of N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)tetrahydro-2H-thiopyran-4-carboxamide 1,1-dioxide (Example 149; 60 mg, 0.089 mmol) in THF (3 mL) was stirred on an ice-water bath and treated with bis(tricyclohexylphosphine)nickel(II) chloride (6.2 mg, 8.9 mol), then with lithium tri-tert-butoxyaluminum hydride (1.0 M in THF; 891 µL, 0.891 mmol). The mixture was heated with stirring at 65° C. for 16 h, then was cooled to rt. The mixture was filtered, and the filtrate was treated with 1 M aqueous HCl and extracted with EtOAc. The organic layer was dried and concentrated, and the residue was purified by preparative HPLC (Method E, gradient 54-78% B, 20 min) to provide N-((3R,3aS,9bS)-7-(perfluoropropan-2-yl)-9b-(phenylsulfonyl)-2,3,3a,4,5,9b-hexahydro-1H-cyclopenta[a]naphthalen-3-yl)tetrahydro-2H-thiopyran-4-carboxamide 1,1-dioxide (2.4 mg, 4% yield). LCMS m/z 556.1 (M+H)$^+$; HPLC $t_R$ 1.05 min (Method A).

The Examples in Table 23 were prepared using the procedures used to prepare Example 1, or similar procedures, from the appropriate carboxylic acid and amine starting materials.

TABLE 23

| Ex. number | Structure | LCMS m/z observed | HPLC $t_R$ (min) | HPLC method |
|---|---|---|---|---|
| 301 | Diastereomeric mixture | 577.0 (M + H)$^+$ | 0.80 | A |
| 302 | Diastereomeric mixture | 617.1 (M + H)$^+$ | 0.79 | A |

TABLE 23-continued

| Ex. number | Structure | LCMS m/z observed | HPLC $t_R$ (min) | HPLC method |
|---|---|---|---|---|
| 303 | 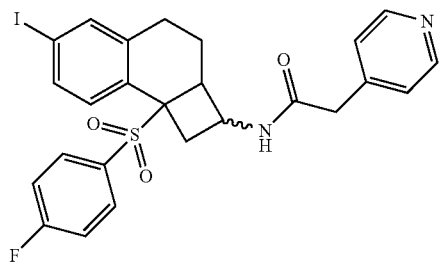 Diastereomeric mixture | 576.9 $(M + H)^+$ | 0.80, 0.82 | A |
| 304 | 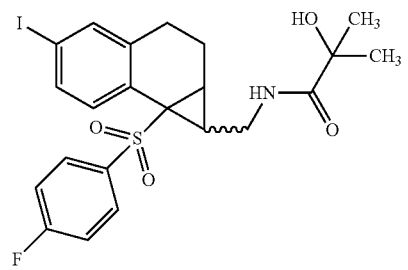 Diastereomeric mixture | 544.1 $(M + H)^+$ | 0.94 | A |

General RORγ Gal4 Reporter Assay

Inverse agonist activity of potential ligands to RORγ was measured by inhibition of luminescence in a Gal4-luciferase reporter assay in Jurkat cells.

Jurkat cells stably over-expressing the RORγ receptor, Jurkat pEx/Gal/hRORγ CLBD/HYG pG5luc/blast, were plated at a concentration of 10,000 cells/well in a 384-well solid white cell culture plate (Perkin Elmer #6007899) in assay buffer RPMI 1640 (Gibco 11875-085 1L) containing 0.1% BSA, 100×HEPES (Gibco 15360-080), 100 mM sodium pyruvate (Gibco 11360-040), 50 mg/mL Hygromycin B (Invitrogen 10687-010) and 10 mg/mL blasticidin (Invitrogen R210-01). 100 nL of test compound in a 3-fold serial dilution, with final concentrations ranging from 40 µM to 0.67 nM, were added to the cells which were then incubated overnight.

The following day, cells were lysed with 10 µL of Steady-Glo Luciferase Assay System (Promega Cat. No. EZ550), and analyzed immediately. $IC_{50}$ values were determined. The $IC_{50}$ value is defined as the concentration of test compound needed to reduce luciferase activity by 50% and is calculated using the four parameter logistic equation to fit the normalized data.

$IC_{50}$ values for compounds of the invention in the RORγ Gal4 reporter assay are provided below.

| Example # | RORγ Gal4, $IC_{50}$ (µm) |
|---|---|
| 1 | 2.845 |
| 2 | 1.788 |
| 3 | 0.026 |
| 4 | 0.019 |
| 5 | 2.914 |
| 6 | 1.545 |
| 7 | 3.337 |
| 8 | 0.007 |
| 9 | 1.919 |

-continued

| Example # | RORγ Gal4, $IC_{50}$ (µm) |
|---|---|
| 10 | 0.061 |
| 11 | 0.034 |
| 12 | 0.031 |
| 13 | 0.033 |
| 14 | 0.017 |
| 15 | 0.017 |
| 16 | 0.012 |
| 17 | 0.061 |
| 18 | 0.250 |
| 19 | 0.082 |
| 20 | 0.070 |
| 21 | 0.043 |
| 22 | 0.039 |
| 23 | 0.013 |
| 24 | 0.047 |
| 25 | 0.021 |
| 26 | 0.082 |
| 27 | 0.048 |
| 28 | 0.009 |
| 29 | 0.014 |
| 30 | 0.005 |
| 31 | 0.014 |
| 32 | 0.019 |
| 33 | 0.025 |
| 34 | 0.008 |
| 35 | 0.008 |
| 36 | 0.011 |
| 37 | 0.013 |
| 38 | 0.020 |
| 39 | 0.019 |
| 40 | 0.014 |
| 41 | 0.034 |
| 42 | 0.034 |
| 43 | 0.181 |
| 44 | 0.026 |
| 45 | 0.044 |
| 46 | 0.033 |
| 47 | 0.027 |
| 48 | 0.394 |
| 49 | 0.023 |

| Example # | RORγ Gal4, IC$_{50}$ (μm) |
|---|---|
| 50 | 0.010 |
| 51 | 0.004 |
| 52 | 0.012 |
| 53 | 0.004 |
| 54 | 0.003 |
| 55 | 0.005 |
| 56 | 0.008 |
| 57 | 0.010 |
| 58 | 0.006 |
| 59 | 0.016 |
| 60 | 0.007 |
| 61 | 0.010 |
| 62 | 0.009 |
| 63 | 0.021 |
| 64 | 0.037 |
| 65 | 0.013 |
| 66 | 0.015 |
| 67 | 0.073 |
| 68 | 0.009 |
| 69 | 0.006 |
| 70 | 0.006 |
| 71 | 0.004 |
| 72 | 0.004 |
| 73 | 0.009 |
| 74 | 0.043 |
| 75 | 0.033 |
| 76 | 0.001 |
| 77 | 0.004 |
| 78 | 0.493 |
| 79 | 0.272 |
| 80 | 0.421 |
| 81 | 3.435 |
| 82 | 0.018 |
| 83 | 0.009 |
| 84 | 0.005 |
| 85 | 0.014 |
| 86 | 0.033 |
| 87 | 0.029 |
| 88 | 0.037 |
| 89 | 0.025 |
| 90 | 0.048 |
| 91 | 0.040 |
| 92 | 0.041 |
| 93 | 0.027 |
| 94 | 0.419 |
| 95 | 0.026 |
| 96 | 0.013 |
| 97 | 0.018 |
| 98 | 0.022 |
| 99 | 0.014 |
| 100 | 0.053 |
| 101 | 0.007 |
| 102 | 0.033 |
| 103 | 0.031 |
| 104 | 1.024 |
| 105 | 0.042 |
| 106 | 0.188 |
| 107 | 0.088 |
| 108 | 0.130 |
| 109 | 0.138 |
| 110 | 0.101 |
| 111 | 0.445 |
| 112 | 0.212 |
| 113 | 0.128 |
| 114 | 0.421 |
| 115 | 0.561 |
| 116 | 2.519 |
| 117 | 2.556 |
| 118 | 0.021 |
| 119 | 0.009 |
| 120 | 0.005 |
| 121 | 0.776 |
| 122 | 0.005 |
| 123 | 0.002 |
| 124 | 0.007 |
| 125 | 0.015 |
| 126 | 0.024 |
| 127 | 0.019 |
| 128 | 0.533 |
| 129 | 3.707 |
| 130 | 0.013 |
| 131 | 0.007 |
| 132 | 0.005 |
| 133 | 0.009 |
| 134 | 0.006 |
| 135 | 0.006 |
| 136 | 0.007 |
| 137 | 0.006 |
| 138 | 0.009 |
| 139 | 0.024 |
| 140 | 0.184 |
| 141 | 0.007 |
| 142 | 0.261 |
| 143 | 0.034 |
| 144 | 0.040 |
| 145 | 0.011 |
| 146 | 0.013 |
| 147 | 0.009 |
| 148 | 0.010 |
| 149 | 0.009 |
| 150 | 0.009 |
| 151 | 0.010 |
| 152 | 0.004 |
| 153 | 0.068 |
| 154 | 0.004 |
| 155 | 0.001 |
| 156 | 0.004 |
| 157 | 0.013 |
| 158 | 0.014 |
| 159 | 0.003 |
| 160 | 0.008 |
| 161 | 0.016 |
| 162 | 0.022 |
| 163 | 0.008 |
| 164 | 0.002 |
| 165 | 0.006 |
| 166 | 0.006 |
| 167 | 0.007 |
| 168 | 0.028 |
| 169 | 0.012 |
| 170 | 0.002 |
| 171 | 0.009 |
| 172 | 0.015 |
| 173 | 0.009 |
| 174 | 0.005 |
| 175 | 0.004 |
| 176 | 0.008 |
| 177 | 0.011 |
| 178 | 0.009 |
| 179 | 0.007 |
| 180 | 0.008 |
| 181 | 0.003 |
| 182 | 0.003 |
| 183 | 0.006 |
| 184 | 0.003 |
| 185 | 0.005 |
| 186 | 0.002 |
| 187 | 0.027 |
| 188 | 0.009 |
| 189 | 0.009 |
| 190 | 0.023 |
| 191 | 0.054 |
| 192 | 0.024 |
| 193 | 0.097 |
| 194 | 0.032 |
| 195 | 0.026 |
| 196 | 0.048 |
| 197 | 0.030 |
| 198 | 0.017 |
| 199 | 0.018 |
| 200 | 0.063 |
| 201 | 0.007 |
| 202 | 0.009 |
| 203 | 0.003 |

| Example # | RORγ Gal4, IC$_{50}$ (μm) |
|---|---|
| 204 | 0.009 |
| 205 | 0.003 |
| 206 | 0.004 |
| 207 | 0.012 |
| 208 | 0.016 |
| 209 | 0.166 |
| 210 | 0.107 |
| 211 | 0.204 |
| 212 | 0.160 |
| 213 | 0.075 |
| 214 | 0.042 |
| 215 | 0.008 |
| 216 | 3.000 |
| 217 | 0.082 |
| 218 | 0.113 |
| 219 | 0.070 |
| 220 | 0.610 |
| 221 | 0.045 |
| 222 | 0.026 |
| 223 | 0.006 |
| 224 | 0.158 |
| 225 | 0.132 |
| 226 | 0.222 |
| 227 | 0.006 |
| 228 | 0.013 |
| 229 | 0.005 |
| 230 | 0.035 |
| 231 | 0.065 |
| 232 | 0.017 |
| 233 | 0.002 |
| 234 | 0.002 |
| 235 | 0.009 |
| 236 | 0.004 |
| 237 | 0.003 |
| 238 | 0.006 |
| 239 | 0.128 |
| 240 | 0.009 |
| 241 | 0.051 |
| 242 | 0.035 |
| 243 | 0.070 |
| 244 | 0.007 |
| 245 | 0.002 |
| 246 | 0.037 |
| 247 | 0.767 |
| 248 | 0.073 |
| 249 | 0.079 |
| 250 | 0.011 |
| 251 | 0.014 |
| 252 | 0.159 |
| 253 | 0.019 |
| 254 | 0.007 |
| 255 | 0.009 |
| 256 | 0.004 |
| 257 | 0.027 |
| 258 | 0.344 |
| 259 | 0.312 |
| 260 | 0.083 |
| 261 | 0.034 |
| 262 | 0.087 |
| 263 | 0.022 |
| 264 | 0.082 |
| 265 | 0.016 |
| 266 | 0.003 |
| 267 | 0.015 |
| 268 | 0.021 |
| 269 | 0.009 |
| 270 | 0.004 |
| 271 | 0.045 |
| 272 | 0.027 |
| 273 | 0.026 |
| 274 | 0.062 |
| 275 | 0.065 |
| 276 | 0.052 |
| 277 | 0.006 |
| 278 | 0.007 |
| 279 | 0.019 |
| 280 | 0.022 |
| 281 | 0.058 |
| 282 | 0.018 |
| 283 | 0.006 |
| 284 | 0.234 |
| 285 | 0.060 |
| 286 | 0.003 |
| 287 | 0.015 |
| 288 | 0.003 |
| 289 | 0.008 |
| 290 | 0.012 |
| 291 | 0.002 |
| 292 | 0.011 |
| 293 | 0.010 |
| 294 | 0.004 |
| 295 | 0.146 |
| 296 | 0.004 |
| 297 | 0.003 |
| 298 | 0.007 |
| 299 | 0.005 |
| 300 | 0.017 |
| 301 | 6.531 |
| 302 | 0.151 |
| 303 | 0.153 |
| 304 | 7.025 |

What is claimed is:
1. A compound of the formula

$R^1$ is, independently at each occurrence, selected from hydrogen, $CD_3$, halo, $OCF_3$, CN, $S(O)_p(C_1-C_6)$alkyl, $S(O)(NR^g)(C_1-C_6)$alkyl, —$S(O)_p(C_1-C_6)$alkyl-OH, $S(O)(NR^g)(C_1-C_6)$alkyl-OH, -thioalkoxyalkoxy, $NR^{11}R^{11}$, $C_{1-6}$ alkyl substituted with 0-3 $R^{1a}$, O—$C_{1-6}$ alkyl substituted with 0-3 $R^{1a}$, —$(CR^{1b}R^{1c})_r$-3-14 membered carbocycle substituted with 0-3 $R^{1a}$ and —$(CR^{1b}R^{1c})_r$-5-10 membered heterocycle comprising carbon atoms and 1-4 heteroatoms selected from N, O, $S(O)_p$ and $S(O)(NR^g)$, substituted with 0-3 $R^{1a}$;

$R^{1a}$ is, independently at each occurrence, hydrogen, =O, halo, $CF_3$, $OCF_3$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$S(O)(NR^g)R^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_p R^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, $S(O)_p$ and $S(O)(NR^g)$, substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, CN or $C_{1-4}$ alkyl;

$R^2$ is, independently at each occurrence, hydrogen, $C_{1-6}$ alkyl substituted with 0-3 $R^{2a}$, $=CR^{2a}R^{2a}$, $C_{2-6}$ alkenyl substituted with 0-3 $R^{2a}$, $-(CR^{2e}R^{2f})_rOR^{2b}$, $-(CR^{2e}R^{2f})_rC(O)R^{2b}$, $-(CR^{2e}R^{2f})_rC(O)OR^{2b}$, $-(CR^{2e}R^{2f})_rOC(O)OR^{2b}$, $-(CR^{2e}R^{2f})_rOC(O)NR^{11}R^{11}$, $-(CR^{2e}R^{2f})_rNR^{2b}C(O)NR^{11}R^{11}$, $-(CR^{2e}R^{2f})_rC(O)NR^{11}R^{11}$, $-(CR^{2e}R^{2f})_rS(O)_pR^c$, $-(CR^{2e}R^{2f})_rS(O)(NR^g)R^c$, $-(CR^{2e}R^{2f})_rS(O)_pNR^{11}R^{11}$, $-(CR^{2e}R^{2f})_rNR^{2b}C(O)R^{2c}$, $-(CR^{2e}R^{2f})_rNR^{2b}C(O)R^{2c}$, $-(CR^{2e}R^{2f})_r NR^{11}R^{11}$, $-(CR^{2e}R^{2f})_rNR^{2b}S(O)_pR^c$, $-(CR^{2e}R^{2f})_rNR^{2b}S(O)_pNR^{11}R^{11}$, $-(CR^{2e}R^{2f})_r$-3-10 membered carbocycle substituted with 0-3 $R^{2a}$ or $-(CR^{2e}R^{2f})_r$-4-10 membered heterocycle comprising carbon atoms, and 1-4 heteroatoms selected from N, O, S(O)$_p$ and S(O)(NR$^g$) substituted with 0-3 $R^{2a}$; or one $R^2$ together with an $R^2$ on an adjacent carbon combine to form a fused ring substituted with 0-3 $R^{2a}$, wherein the fused ring is selected from 3-10 membered carbocycle substituted with 0-3 $R^{2a}$, or 3-7 membered heterocycle comprising carbon atoms and 1-4 heteroatoms selected from N, O, P(O), S(O)$_p$ and S(O)(NR$^g$), substituted with 0-3 $R^{2a}$;

$R^{2a}$ is, independently at each occurrence, hydrogen, $=O$, halo, $OCF_3$, CN, $NO_2$, $-(CR^{2e}R^{2f})_r-OR^b$, $-(CR^{2e}R^{2f})_r-S(O)_pR^b$, $-(CR^{2e}R^{2f})_r-S(O)(NR^g)R^b$, $-(CR^{2e}R^{2f})_r-C(O)R^b$, $-(CR^{2e}R^{2f})_r-C(O)OR^b$, $-(CR^{2e}R^{2f})_r-OC(O)R^b$, $-(CR^{2e}R^{2f})_r-OC(O)NR^{11}R^{11}$, $-(CR^{2e}R^{2f})_r-OC(O)OR^c$, $-(CR^{2e}R^{2f})_r-NR^{11}R^{11}$, $-(CR^{2e}R^{2f})_r-C(O)NR^{11}R^{11}$, $-(CR^{2e}R^{2f})_r-NR^bC(O)R^c$, $-(CR^{2e}R^{2f})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})_r$-3-14 membered carbocycle substituted with 0-3 $R^a$, or $-(CR^{2e}R^{2f})_r$-4-7 membered heterocycle comprising carbon atoms, and 1-4 heteroatoms selected from N, O, S(O)$_p$ and S(O)(NR$^g$), substituted with 0-4 $R^a$;

$R^{2b}$ is, independently at each occurrence, hydrogen, $CF_3$, $-(CR^{2e}R^{2f})_qOR^b$, $-(CR^{2e}R^{2f})_qS(O)_pR^b$, $-(CR^{2e}R^{2f})_qS(O)(NR^g)R^b$, $-(CR^{2e}R^{2f})_r-C(O)R^c$, $-(CR^{2e}R^{2f})_q-C(O)OR^b$, $-(CR^{2e}R^{2f})_qOC(O)R^b$, $-(CR^{2e}R^{2f})_qNR^{11}R^{11}$, $-(CR^{2e}R^{2f})_r-C(O)NR^{11}R^{11}$, $-(CR^{2e}R^{2f})_qNR^bC(O)R^c$, $-(CR^{2e}R^{2f})_qNR^bC(O)OR^c$, $-(CR^{2e}R^{2f})_qNR^bC(O)NR^{11}R^{11}$, $-(CR^{2e}R^{2f})_qS(O)NR^{11}R^{11}$, $-(CR^{2e}R^{2f})_qNR^bS(O)R^e$, $C_{1-6}$ alkyl substituted with 0-2 $R^a$, $C_{1-6}$ haloalkyl, $-(CR^{2e}R^{2f})_r$-3-14 membered carbocycle substituted with 0-3 $R^a$, or $-(CR^{2e}R^{2f})_r$-5-7 membered heterocycle comprising carbon atoms and 1-4 heteroatoms selected from N, O, S(O)$_p$ and S(O)(NR$^g$), substituted with 0-4 $R^a$, $R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or $-(CR^{2e}R^{2f})_r$-5-10 membered heterocycle containing 1-4 heteroatoms selected from N, O, S(O)$_p$ and S(O)(NR$^g$), substituted with 0-4 $R^a$;

$R^{2e}$ and $R^{2f}$ are, independently at each occurrence, hydrogen, halogen or $C_{1-6}$ alkyl;

$R^3$ is, independently at each occurrence, selected from hydrogen, halo, $N_3$, CN, $-(CR^{1b}R^{1c})_r-OR^{3b}$, $-(CR^{1b}R^{1c})_r-NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, S(O)$_p$ and S(O)(NR$^g$), substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O, S(O)$_p$ and S(O)(NR$^g$), both optionally substituted with 0-3 $R^{3a}$;

$R^{3a}$ is, independently at each occurrence, hydrogen, $=O$, halo, $OCF_3$, $OCHF_2$, $CF_3$, $CHF_2$, CN, $NO_2$, $-(CR^{1b}R^{1c})_r-OR^b$, $-(CR^{1b}R^{1c})_r-S(O)_pR^b$, $-(CR^{1b}R^{1c})_r-S(O)(NR^g)R^b$, $-(CR^{1b}R^{1c})_r-C(O)R^b$, $-(CR^{1b}R^{1c})_r-C(O)OR^b$, $-(CR^{1b}R^{1c})_r-OC(O)R^b$, $-(CR^{1b}R^{1c})_r-NR^{11}R^{11}$, $-(CR^{1b}R^{1c})_r-C(O)NR^{11}R^{11}$, $-(CR^{1b}R^{1c})_r-NR^bC(O)R^c$, $-(CR^{1b}R^{1c})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CR^{1b}R^{1c})_r$-3-14 membered carbocycle substituted with 0-3 $R^a$, or $-(CR^{1b}R^{1c})_r$-5-10 membered heterocycle comprising carbon atoms and 1-4 heteroatoms selected from N, O, S(O)$_p$ and S(O)(NR$^g$), substituted with 0-3 $R^a$;

$R^{3b}$ is, independently at each occurrence, hydrogen, $CF_3$, $-(CR^{1b}R^{1c})_qOR^b$, $-(CR^{1b}R^{1c})_q$ $S(O)_pR^b$, $-(CR^{1b}R^{1c})_qS(O)(NR^g)R^b$, $-(CR^{1b}R^{1c})_r-C(O)R^{3d}$, $-(CR^{1b}R^{1c})_r-C(O)OR^b$, $-(CR^{1b}R^{1c})_qOC(O)R^b$, $-(CR^{1b}R^{1c})_aNR^{11}R^{11}$, $-(CR^{1b}R^{1c})_r-C(O)NR^{11}R^{11}$, $-(CR^{1b}R^{1c})_qNR^bC(O)R^{3c}$, $-(CR^{1b}R^{1c})_qNR^bC(O)OR^c$, $-(CR^{1b}R^{1c})_qNR^bC(O)NR^{11}R^{11}$, $-(CR^{1b}R^{1c})_qS(O)_2NR^{11}R^{11}$, $-(CR^{1b}R^{1c})_qNR^bS(O)_2R^c$, $C_{1-6}$ alkyl substituted with 0-3 $R^a$, $C_{1-6}$ haloalkyl, $-(CR^{1b}R^{1c})_r$-3-14 membered carbocycle substituted with 0-3 $R^a$, or $-(CR^{1b}R^{1c})_r$-5-7 membered heterocycle comprising carbon atoms and 1-4 heteroatoms selected from N, O, S(O)$_p$ and S(O)(NR$^g$), substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, halo, $C(=O)C_{1-4}$ alkyl, $C(=O)OC_{1-4}$ alkyl, $C_{1-6}$ alkyl or $C_{1-6}$ haloalkyl, or $R^4$ and $R^5$ taken together are $=O$, or together with the carbon atom to which they are attached form a 3- to 6-membered spirocarbocyclyl ring or a spiroheterocyclyl ring;

$R^6$ and $R^7$ are independently hydrogen, $C(=O)C_{1-4}$ alkyl, $C(=O)OC_{1-4}$ alkyl, $C_{1-6}$ alkyl or $C_{1-6}$ haloalkyl; or $R^6$ and $R^7$ taken together are $=O$, or together with the carbon atom to which they are attached form a 3- to 6-membered spirocarbocyclyl ring or a spiroheterocyclyl ring;

$R^{11}$ is, independently at each occurrence, hydrogen, $C_{1-6}$ alkyl substituted with 0-3 $R^f$, $CF_3$, $-(CR^{1b}R^{1c})_r-C_{3-10}$ cycloalkyl substituted with 0-3 $R^f$, $-(CR^{1b}R^{1c})_r$-phenyl substituted with 0-3 $R^d$, or $-(CR^{1b}R^{1c})_r$-5-7 membered heterocycle comprising carbon atoms and 1-4 heteroatoms selected from N, O, S(O)$_p$ and S(O)(NR$^g$), substituted with 0-4 $R^d$;

or one $R^{11}$ and a second $R^{11}$, both attached to the same nitrogen atom, combine to form a heterocycle comprising carbon atoms and 1-4 heteroatoms selected from N, O, S(O)$_p$ and S(O)(NR$^g$), substituted with 0-4 $R^d$;

$R^a$ is, independently at each occurrence, hydrogen, $=O$, halo, $OCF_3$, $CF_3$, $CHF_2$, CN, $NO_2$, $-(CR^{1b}R^{1c})_r-OR^b$, $-(CR^{1b}R^{1c})_r-S(O)_pR^b$, $-(CR^{1b}R^{1c})_r-S(O)$ (NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —(CR$^{1b}$R$^{1c}$)$_r$—O(CR$^{1b}$R$^{1c}$O)$_t$P(O)(OR$^b$)$_2$, —(CR$^{1b}$R$^{1c}$)$_r$-O(CR$^{1b}$R$^{1c}$O)$_t$S(O)$_2$OR$^b$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$-C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C(O)R$^e$, —NR$^e$R$^e$, —NR$^e$C(O)OR$^e$, C(O)NR$^e$R$^e$, —NR$^e$C(O)R$^c$, CO$_2$H, CO$_2$R$^c$, —NR$^e$SO$_2$R$^c$, SO$_2$R$^c$, SO(NR$^g$)R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, S(O)$_p$ and S(O)(NR$^g$), substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), SO(NR$^g$)(C$_{1-6}$ alkyl), CO$_2$H, CO$_2$(C$_{1-6}$ alkyl), OH, C$_{3-6}$ cycloalkyl, CF$_3$, O(C$_{1-6}$ alkyl): or an optionally substituted —(CR$^{1b}$R$^{1c}$)$_r$-5-10 membered heterocycle comprising carbon atoms and 1-4 heteroatoms selected from N, O, S(O)$_p$ and S(O)(NR$^g$), phenyl or C$_{3-6}$ cycloalkyl, each group optionally substituted with halo, CN, CF$_3$, C$_{1-6}$ alkyl or O(C$_{1-6}$ alkyl);

R$^g$ is, independently at each occurrence, hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(O) and S(O)$_p$ substituted with 0-4 R$^f$;

m is 0, 1, 2 or 3;
p is, independently at each occurrence, 0, 1, or 2;
g is, independently at each occurrence, 2 or 3; and
r is 0, 1, 2, 3, or 4;

or a stereoisomer or pharmaceutically-acceptable salt thereof.

2. A compound according to claim 1 wherein

R$^1$ is halo, phenyl substituted with 0-3 R$^{1a}$, C$_{1-6}$ alkyl substituted with 0-3 R$^{1a}$, or O—C$_{1-6}$ alkyl substituted with 0-3 R$^{1a}$;

R$^{1a}$ is, independently at each occurrence, hydrogen, CF$_3$, halo, C$_{1-6}$ alkyl substituted with 0-3 R$^a$, —(CR$^{1b}$R$^{1c}$)$_r$—OR$^b$, or —(CR$^{1b}$R$^{1c}$)$_r$-phenyl substituted with 0-3 R$^a$;

R$^{1b}$ and R$^{1c}$ are, independently at each occurrence, hydrogen, halogen or C$_{1-6}$ alkyl;

R$^{1d}$ is, independently at each occurrence, hydrogen, CD$_3$, halo, CF$_3$, CN or C$_1$-C$_4$ alkyl;

R$^2$ is hydrogen, —S(O)$_2$R$^{2c}$, C$_{1-6}$ alkyl substituted with 0-3 R$^{2a}$, —C(O)OR$^{2b}$, —C(O)R$^{2b}$, —C(O)NR$^{11}$R$^{11}$, —NR$^{2b}$C(O)NR$^{11}$R$^{11}$, —NR$^{2b}$C(O)R$^{2c}$ NR$^{2b}$C(O)OR$^{2c}$, NR$^{11}$R$^{11}$, —NR$^{2b}$S(O)$_p$R$^c$, NR$^{2b}$S(O)$_p$NR$^{11}$R$^{11}$, or a 5-7 membered heterocycle comprising carbon atoms and 1-4 heteroatoms selected from N, O, P(O), S(O)$_p$ and S(O)(NR$^g$), substituted with 0-4 R$^a$;

R$^{2a}$ is, independently at each occurrence, hydrogen or C$_{1-6}$ alkyl substituted with 0-3 R$^a$;

R$^{2b}$ is hydrogen, C$_{1-6}$ alkyl substituted with 0-2 R$^a$, C$_{3-6}$ cycloalkyl substituted with 0-3 R$^a$, —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$, or —(CR$^{2e}$R$^{2f}$)$_r$-phenyl substituted with 0-3 R$^a$;

R$^{2c}$ is C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;

R$^3$ is, independently at each occurrence, hydrogen, halo, N$_3$, CN, OR$^{3b}$, —NH$_2$, —NH(C$_{1-6}$ alkyl), N(C$_{1-6}$ alkyl)$_2$, C$_{1-6}$ alkyl substituted with 0-3 R$^{3a}$, or C$_{3-10}$ cycloalkyl substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—S(O)(NR$^g$)R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, S(O)$_p$ and S(O)(NR$^g$), substituted with 0-3 R$^a$; and R$^{3b}$ is, independently at each occurrence, hydrogen, C$_{1-6}$ alkyl substituted with 0-3 R$^a$ or phenyl substituted with 0-3 R$^a$;

or a stereoisomer or pharmaceutically-acceptable salt thereof.

3. A compound according to claim 2 of the formula

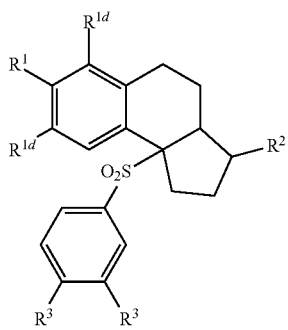

wherein
R$^1$ is C$_{1-6}$ alkyl substituted with 0-3 R$^{1a}$ or O—C$_{1-6}$ alkyl substituted with 0-3 R$^{1a}$;
R$^{1a}$ is, independently at each occurrence, hydrogen, CF$_3$, halo or C$_{1-6}$ alkyl substituted with 0-3 R$^a$;
R$^{1d}$ is, independently at each occurrence, hydrogen, halo, or CN;
R$^2$ is C$_{1-6}$ alkyl substituted with 0-3 R$^{2a}$, —C(O)OR$^{2b}$, —C(O)R$^{2b}$, —C(O)NR$^{11}$R$^{11}$, —NR$^{2b}$C(O)NR$^{11}$R$^{11}$, —R$^{2b}$C(O)R$^{2c}$ NR$^{2b}$C(O)OR$^{2c}$ NR$^{11}$R$^{11}$, —NR$^{2b}$S(O)$_p$R$^c$, or NR$^{2b}$S(O)$_p$NR$^{11}$R$^{11}$;
R$^{2a}$ is, independently at each occurrence, hydrogen or C$_{1-6}$ alkyl substituted with 0-3 R$^a$;
R$^{2b}$ is hydrogen, C$_{1-6}$ alkyl substituted with 0-2 R$^a$, C$_{3-6}$ cycloalkyl substituted with 0-3 R$^a$, —(CR$^{2e}$R$^{2f}$)$_r$-5-7 membered heterocycle comprising carbon atoms and 1-4 heteroatoms selected from N, O, S(O)$_p$ and S(O)(NR$^g$), substituted with 0-4 R$^a$, or
—(CR$^{2e}$R$^{2f}$)$_r$-phenyl substituted with 0-3 R$^a$;
R$^{2c}$ is C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)$_r$-5-10 membered heterocycle containing 1-4 heteroatoms selected from N, O, S(O)$_p$ and S(O)(NR$^g$), substituted with 0-4 R$^a$;
R$^3$ is, independently at each occurrence, hydrogen, halo, cyclopropyl or C$_{1-6}$ alkyl;
or a stereoisomer or pharmaceutically-acceptable salt thereof.

4. A compound according to claim 2 of the formula

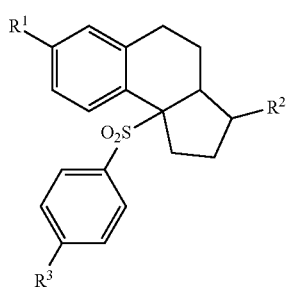

wherein
R$^1$ is C$_{1-6}$ alkyl substituted with 0-3 R$^{1a}$ or O—C$_{1-6}$ alkyl substituted with 0-3 R$^{1a}$;
R$^2$ is —C(O)NR$^{11}$R$^{11}$, —(CH$_2$)$_{0-1}$NHC(O)NR$^{11}$R$^{11}$ or —(CH$_2$)$_{0-1}$NHC(O)R$^{2c}$;

R$^{2c}$ is C$_{1-4}$ alkyl substituted with 0-3 R$^a$, C$_{3-6}$ cycloalkyl substituted with 0-3 R$^a$ or 5-10 membered heterocycle containing 1-2 heteroatoms selected from N, O and S(O)$_2$, substituted with 0-3 R$^a$;
R$^3$ is, independently at each occurrence, hydrogen or halo;
R$^{11}$ is, independently at each occurrence, hydrogen, C$_{1-6}$ alkyl substituted with 0-2 R$^f$, C$_{4-6}$ cycloalkyl substituted with 0-2 R$^f$, -CH$_2$-C$_{4-6}$ cycloalkyl substituted with 0-2 R$^f$, 5-6 membered heterocycle comprising carbon atoms and 1-2 heteroatoms selected from N, O and S(O)$_2$, substituted with 0-1 R$^d$, -CH$_2$-5-6 membered heterocycle comprising carbon atoms and 1-2 heteroatoms selected from N, O and S(O)$_2$, substituted with 0-2 R$^d$;
or one R$^{11}$ and a second R$^{11}$, both attached to the same nitrogen atom, combine to form a heterocycle comprising carbon atoms and 1-2 heteroatoms selected from N, O and S(O)$_2$, substituted with 0-2 R$^d$;
R$^a$ is, independently at each occurrence, hydrogen, =O, halo, CF$_3$, OH, CH$_2$OH, S(O)$_2$CH$_3$, —C(O)CH$_3$, NHC(O)CH$_3$, —OP(O)(OH)$_2$, C$_{1-2}$ alkyl substituted with 0-1 R$^f$ or pyridyl;
R$^d$ is, independently at each occurrence, hydrogen, —OH, —C(O)CH$_3$, CO$_2$H, CO$_2$R$^c$ or SO$_2$R$^c$;
R$^f$ is, independently at each occurrence, hydrogen, CO$_2$H, CN or OH;
or a stereoisomer or pharmaceutically-acceptable salt thereof.

5. A compound selected from the following:
1-(4-((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carbonyl)piperazin-1-yl)ethan-1-one,
(3R, 3 aS,9bS)-N-((1,1-dioxidotetrahydrothiophen-3-yl)methyl)-9b-((4-fluorophenyl)sulfonyl)-7-(perfluoropropan-2-yl)-2,3,3a,4,5,9b-hexahydro-1H-cyclopenta[a]naphthalene-3-carboxamide (diastereomeric mixture),
methyl 4-((3R,3 aS,9bS)-9b-((4-fluorophenyl)sulfonyl)-7-(perfluoropropan-2-yl)-2,3,3a,4, 5,9b-hexahydro-1H-cyclopenta[a]naphthalene-3-carboxamido)tetrahydro-2H-thiopyran-4-carboxylate 1,1-dioxide,
(3R,3 aS,9bS)-N-(2,3-dihydroxy-3-methylbutyl)-9b-((4-fluorophenyl)sulfonyl)-7-(perfluoropropan-2-yl)-2,3,3a,4,5,9b-hexahydro-1H-cyclopenta[a]naphthalene-3-carboxamide,
(3R,3 aS,9bS)-9b-((4-fluorophenyl)sulfonyl)-N-(2-hydroxy-2-methylpropyl)-7-(perfluoropropan-2-yl)-2,3,3a,4,5,9b-hexahydro-1H-cyclopenta[a]naphthalene-3-carboxamide,
(3R,3 aS,9bS)-9b-((4-fluorophenyl)sulfonyl)-N-((1r,4R)-4-hydroxycyclohexyl)-7-(perfluoropropan-2-yl)-2,3,3a,4,5,9b-hexahydro-1H-cyclopenta[a]naphthalene-3-carboxamide,
(1,1-dioxidothiomorpholino)((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)methanone,
(3R,3 aS, 9bS)-9b-((4-fluorophenyl)sulfonyl)-N—((R)-2-hydroxypropyl)-7-(perfluoropropan-2-yl)-2,3,3a,4,5,9b-hexahydro-1H-cyclopenta[a]naphthalene-3-carboxamide,
(3R,3 aS,9bS)-9b-((4-fluorophenyl)sulfonyl)-N-((1-hydroxycyclopentyl)methyl)-7-(perfluoropropan-2-yl)-2,3,3a,4,5,9b-hexahydro-1H-cyclopenta[a]naphthalene-3-carboxamide, (3R,3aS,9bS)-9b-((4-fluorophenyl)sulfonyl)-N-((1-hydroxycyclobutyl)methyl)-7-(perfluoropropan-2-yl)-2,3,3a,4,5,9b-hexahydro-1H-cyclopenta[a]naphthalene-3-carboxamide, (3R,3aS,9bS)-9b-((4-fluorophenyl)sulfonyl)-N-((1-hydroxycyclopropyl)methyl)-7-(perfluoropropan-2-yl)-2,3,3a,4,5,9b-hexahydro-1H-cyclopenta[a]naphthalene-3-carboxamide, (3R,3aS, 9bS)-9b-((4-fluorophenyl)sulfonyl)-N-((4-hydroxytetrahydro-2H-pyran-4-yl)methyl)-7-(perfluoropropan-2-yl)-2,3,3a,4,5,9b-hexahydro-H-cyclopenta[a]naphthalene-3-carboxamide, (3R,3aS,9bS)-9b-((4-fluorophenyl)sulfonyl)-N-(1-(methylsulfonyl)piperidin-4-yl)-7-(perfluoropropan-2-yl)-2,3,3a,4,5,9b-hexahydro-1H-cyclopenta[a]naphthalene-3-carboxamide, 3-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxamido)methyl)cyclobutane-1-carboxylic acid (homochiral, from peak 1), 3-(((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxamido)methyl)cyclobutane-1-carboxylic acid (homochiral, from peak 2), (1S,3R)-3-((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxamido)cyclopentane-1-carboxylic acid, 3-((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carboxamido)cyclohexane-1-carboxylic acid (homochiral, from peak 2), 1-((3R,3aS,9bS)-9b-((4-fluorophenyl)sulfonyl)-7-(perfluoropropan-2-yl)-2,3,3a,4,5,9b-hexahydro-1H-cyclopenta[a]naphthalene-3-carbonyl)piperidine-4-carboxylic acid, (S)-1-(2-cyanoethyl)-N-((3R,3aS, 9bS)-9b-((4-fluorophenyl)sulfonyl)-7-(perfluoropropan-2-yl)-2,3,3a,4,5,9b-hexahydro-1H-cyclopenta[a]naphthalen-3-yl)-5-oxopyrrolidine-2-carboxamide, N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)acetamide-2,2,2-d3, N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-(pyridin-4-yl)acetamide, N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxytetrahydro-2H-thiopyran-4-carboxamide 1,1-dioxide, N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxy-1-(methylsulfonyl)piperidine-4-carboxamide, 1-acetyl-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)piperidine-4-carboxamide, N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxytetrahydro-2H-pyran-4-carboxamide, (2S,4R)-4-fluoro-N-((3R,3aS, 9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(methyl-d$_3$)-5-oxopyrrolidine-2-carboxamide, N-((3R, 3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-methyltetrahydro-2H-thiopyran-4-carboxamide 1,1-dioxide (homochiral, from peak 1), N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-methyltetrahydro-2H-thiopyran-4-carboxamide 1,1-dioxide (homochiral, from peak 3), N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-hydroxy-2-methylpropanamide, (R)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-hydroxypropanamide, N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)tetrahydro-2H-thiopyran-4-carboxamide 1,1-dioxide, N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-3-methyloxetane-3-carboxamide, N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-3-hydroxy-2,2-dimethylpropanamide, N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-1-hydroxycyclopropane-1-carboxamide, N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-methyl-5-oxopyrrolidine-2-carboxamide, N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-1-hydroxycyclohexane-1-carboxamide, N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-hydroxy-2-(tetrahydro-2H-pyran-4-yl)acetamide, (S)-3,3,3-trifluoro-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-hydroxypropanamide, N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-hydroxy-3-(pyridin-4-yl)propanamide, N-((3R,3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-3-hydroxy-3-methylbutanamide, (R)-4,4,4-trifluoro-N-((3R,3aS, 9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-hydroxybutanamide, 2-acetamido-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-hydroxypropanamide, N-((3R, 3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-methyl-2-morpholinopropanamide, (1s,3S)-N-((3R,3aS)-9b-((4-fluorophenyl)sulfonyl)-7-(perfluoropropan-2-yl)-2,3,3a,4,5,9b-hexahydro-1H-cyclopenta[a]naphthalen-3-yl)-3-hydroxy-3-methylcyclobutane-1-carboxamide, N-((3R, 3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-5-oxopyrrolidine-3-carboxamide, N-((3R, 3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-oxopiperidine-4-carboxamide (homochiral, from peak 2), N-((3R,3 aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-6-oxopiperidine-3-carboxamide (homochiral, from peak 1), N-((3R,3 aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-6-oxopiperidine-3-carboxamide (homochiral, from peak 2), N-((3R,3 aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-1-methyl-2-oxo-1,2-dihydropyridine-4-carboxamide, N-((3R,3 aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-(3-hydroxy-1,1-dioxidotetrahydrothiophen-3-yl)acetamide, 2-acetamido-N-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)acetamide, 2-acetamido-N-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-2-methylpropanamide, 1-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(2-hydroxy-2-methylpropyl)urea, 1-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(2-hydroxyethyl)urea, (3S,4R)-N-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3,4-dihydroxypyrrolidine-1-carboxamide, N-(((3R,3 aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)methyl)-2-hydroxy-2-methylpropanamide trifluoroacetate, 1-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-3-(2-hydroxyethyl-2,2-d2)urea, N-((3R, 3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-2-hydroxy-2-(4-hydroxytetrahydro-2H-pyran-4-yl)acetamide, (1r,3R,4S)-N-((3R,3aS)-9b-((4-fluorophenyl)sulfonyl)-7-(perfluoropropan-2-yl)-2,3,3a,4,5,9b-hexahydro-1H-cyclopenta[a]naphthalen-3-yl)-3,4-dihydroxycyclopentane-1-carboxamide, (1r,3R,4S)-N-((3R,3aS)-9b-((4-fluorophenyl)sulfonyl)-7-(perfluoropropan-2-yl)-2,3,3a,4,5,9b-hexahydro-1H-cyclopenta[a]naphthalen-3-yl)-3,4-dihydroxycyclopentane-1-carboxamide, (1s,3S)-N-((3R,3aS)-9b-((4-fluorophenyl)sulfonyl)-7-(perfluoropropan-2-yl)-2,3,3a,4,5,9b-hexahydro-1H-cyclopenta[a]naphthalen-3-yl)-3-hydroxy-3-(hydroxymethyl)cyclobutane-1-carboxamide, (1r,3R)-N-((3R,3 aS)-9b-((4-fluorophenyl)sulfonyl)-7-(perfluoropropan-2-yl)-2,3,3a,4, 5,9b-hexahydro-1H-cyclopenta[a]naphthalen-3-yl)-3-hydroxy-3-(hydroxymethyl)cyclobutane-1-carboxamide, 1-(acetyl-d$_3$)-N-((3R, 3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-4-hydroxypiperidine-4-carboxamide, N-((3R, 3aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-4-hydroxy-1-(2-hydroxyacetyl)piperidine-4-carboxamide, (3R,3 aS,9bS)-9b-((4-fluorophenyl)sulfonyl)-N-((1-(methylsulfonyl)pyrrolidin-3-yl)methyl)-7-(perfluoropropan-2-yl)-2,3,3a,4,5,9b-hexahydro-1H-cyclopenta[a]naphthalene-3-carboxamide (homochiral, from peak 1), (3R,3 aS,9bS)-9b-((4-fluorophenyl)sulfonyl)-N-((1-(methylsulfonyl)pyrrolidin-3-yl)methyl)-7-(perfluoropropan-2-yl)-2,3,3a,4,5,9b-hexahydro-1H-cyclopenta[a]naphthalene-3-carboxamide (homochiral, from peak 2), 1-(((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)amino)-2-methyl-1-oxopropan-2-yl dihydrogen phosphate, (S)-N-((3R,3aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)-1-(methyl-d3)-5-oxopyrrolidine-3-carboxamide, N-((3R,3 aS,9bS)-9b-((4-fluorophenyl)sulfonyl)-7-(perfluoropropan-2-yl)-2,3,3a,4, 5,9b-hexahydro-1H-cyclopenta[a]naphthalen-3-yl)-4-hydroxy-1-(oxetan-3-yl)piperidine-4-carboxamide, (S)-1-(2-cyanoethyl)-N-((3R,3 aS, 9bS)-9b-((4-fluorophenyl)sulfonyl)-7-(perfluoropropan-2-yl)-2,3,3a,4,5, 9b-hexahydro-1H-cyclopenta[a]naphthalen-3-yl)-5-oxopyrrolidine-3-carboxamide, and 4-fluoro-N-((3R,3 aS,9bS)-9b-((4-fluorophenyl)sulfonyl)-7-(perfluoropropan-2-yl)-2,3,3a,4,5,9b-hexahydro-1H-cyclopenta[a]naphthalen-3-yl)tetrahydro-2H-thiopyran-4-carboxamide 1,1-dioxide, or a stereoisomer or pharmaceutically acceptable salt thereof.

6. A pharmaceutical composition comprising one or more A compounds according to claim 1, and a pharmaceutically acceptable carrier or diluent.

* * * * *